United States Patent
Kimura et al.

(10) Patent No.: US 7,618,960 B2
(45) Date of Patent: Nov. 17, 2009

(54) MORPHOLINE TYPE CINNAMIDE COMPOUND

(75) Inventors: Teiji Kimura, Tsukuba (JP); Koki Kawano, Tsukuba (JP); Eriko Doi, Tsukuba (JP); Noritaka Kitazawa, Tsukuba (JP); Mamoru Takaishi, Tsukuba (JP); Koichi Ito, Tsukuba (JP); Toshihiko Kaneko, Tsukuba (JP); Takeo Sasaki, Tsukuba (JP); Nobuaki Sato, Tsukuba (JP); Takehiko Miyagawa, Tsukuba (JP); Hiroaki Hagiwara, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 353 days.

(21) Appl. No.: 11/594,130

(22) Filed: Nov. 8, 2006

(65) Prior Publication Data

US 2007/0117798 A1    May 24, 2007

(30) Foreign Application Priority Data

| Nov. 24, 2005 | (JP) | ............................. 2005-337952 |
| Jul. 28, 2006 | (JP) | ............................. 2006-205591 |

(51) Int. Cl.
C07D 498/04 (2006.01)
A61K 31/5375 (2006.01)

(52) U.S. Cl. ................. 514/230.5; 514/235.8; 544/105; 544/139

(58) Field of Classification Search .................. 544/105, 544/139; 514/230.5, 235.8
See application file for complete search history.

(56) References Cited

U.S. PATENT DOCUMENTS

| 4,910,200 | A | 3/1990 | Curtze et al. |
| 5,281,626 | A | 1/1994 | Oinuma et al. |
| 5,563,162 | A | 10/1996 | Oku et al. |
| 5,985,856 | A | 11/1999 | Stella et al. |
| 6,235,728 | B1 | 5/2001 | Golik et al. |
| 6,306,870 | B1 | 10/2001 | Bombrun et al. |
| 7,053,087 | B1 | 5/2006 | Beatch et al. |
| 7,138,414 | B2 | 11/2006 | Schoenafinger et al. |
| 7,300,936 | B2 | 11/2007 | Parker et al. |
| 2001/0051642 | A1 | 12/2001 | Ahn |
| 2002/0128263 | A1 | 9/2002 | Mutel et al. |
| 2003/0195201 | A1 | 10/2003 | Bo et al. |
| 2003/0208082 | A1 | 11/2003 | Mutel et al. |
| 2003/0225070 | A1 | 12/2003 | Mutel et al. |
| 2004/0034096 | A1 | 2/2004 | Jolidon et al. |
| 2004/0038969 | A1 | 2/2004 | Doherty et al. |
| 2004/0063770 | A1 | 4/2004 | Ahn et al. |
| 2004/0087798 | A1 | 5/2004 | Yamada |
| 2004/0127494 | A1 | 7/2004 | Parker et al. |
| 2004/0127555 | A1 | 7/2004 | Snow et al. |
| 2004/0152743 | A1 | 8/2004 | Schoenafinger et al. |
| 2004/0192743 | A1 | 9/2004 | Mjalli et al. |
| 2004/0235864 | A1 | 11/2004 | Graczyk et al. |
| 2005/0070538 | A1 | 3/2005 | Cheng et al. |
| 2005/0131043 | A1 | 6/2005 | Mutel et al. |
| 2005/0187277 | A1 | 8/2005 | Mjalli et al. |
| 2006/0004013 | A1 | 1/2006 | Kimura et al. |
| 2007/0117798 | A1 | 5/2007 | Kimura et al. |
| 2007/0117839 | A1 | 5/2007 | Kimura et al. |
| 2007/0219181 | A1 | 9/2007 | Kimura et al. |
| 2008/0070902 | A1 | 3/2008 | Kimura et al. |
| 2008/0085894 | A1 | 4/2008 | Parker et al. |
| 2008/0096892 | A1 | 4/2008 | Cheng et al. |
| 2008/0280948 | A1 | 11/2008 | Baumann et al. |
| 2009/0048213 | A1 | 2/2009 | Kimura et al. |

FOREIGN PATENT DOCUMENTS

| DE | 3 541 716 A1 | 5/1987 |
| EP | 0 219 756 A1 | 4/1987 |
| EP | 0 973 768 B1 | 7/2003 |
| EP | 1 757 591 A1 | 2/2007 |
| EP | 1 808 432 A1 | 7/2007 |
| EP | 1 953 131 A1 | 8/2008 |
| EP | 1 953 158 A1 | 8/2008 |
| GE | P 2006 3920 B | 5/2006 |

(Continued)

OTHER PUBLICATIONS

Official Action dated Jul. 4, 2008, which issued in corresponding Russian Patent Application No. 2006146070.

(Continued)

*Primary Examiner*—Kahsay T Habte
(74) *Attorney, Agent, or Firm*—Birch, Stewart, Kolasch & Birch, LLP

(57) ABSTRACT

The present invention relates to a compound represented by the formula (I):

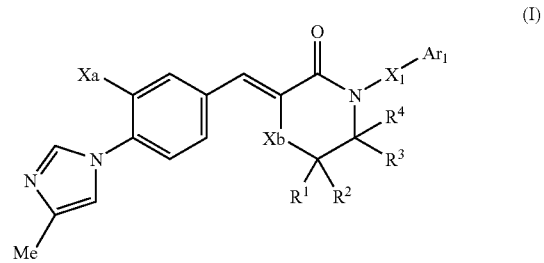

(I)

or a pharmacologically acceptable salt thereof, wherein $R^1$, $R^2$, $R^3$, and $R^4$ are the same or different and each represent a hydrogen atom or a C1-6 alkyl group; $X_1$ represents a C1-6 alkylene group that may be substituted; $X_a$ represents a methoxy group or a fluorine atom; $X_b$ represents an oxygen atom or a methylene group, provided that $X_b$ is only an oxygen atom when $X_a$ is a methoxy group; and $Ar_1$ represents an aryl group, pyridinyl group, aryloxy group, or pyridinyloxy group that may have a substituent such as a halogen atom; and to use of the compound or salt as a pharmaceutical agent.

16 Claims, No Drawings

FOREIGN PATENT DOCUMENTS

| | | | |
|---|---|---|---|
| JP | 3-206042 A | 9/1991 |
| JP | 8-283219 A | 10/1996 |
| JP | 10-510512 A | 10/1998 |
| JP | 11-228548 A | 8/1999 |
| JP | 3176365 B2 | 4/2001 |
| JP | 2001-508767 A | 7/2001 |
| JP | 2001-527083 A | 12/2001 |
| JP | 2003-206280 A | 7/2003 |
| JP | 2004-531519 A | 10/2004 |
| JP | 2005-518371 A | 6/2005 |
| JP | 2005-526807 A | 9/2005 |
| JP | 2005-531596 A | 10/2005 |
| JP | 2005-533092 A | 11/2005 |
| JP | 7-2780 A | 12/2005 |
| JP | 2006-502247 A | 1/2006 |
| JP | 2007-504282 T | 3/2007 |
| RU | 2001126135 A | 7/2003 |
| WO | WO-91/12237 A1 | 8/1991 |
| WO | WO-96/10559 A1 | 4/1996 |
| WO | WO-97/43287 A1 | 11/1997 |
| WO | WO-98/03166 A1 | 1/1998 |
| WO | WO-98/24785 A1 | 6/1998 |
| WO | WO-00/07993 A1 | 2/2000 |
| WO | WO-00/50391 A1 | 8/2000 |
| WO | WO-00/51981 A1 | 9/2000 |
| WO | WO-01/68585 A1 | 9/2001 |
| WO | WO-01/81312 A2 | 11/2001 |
| WO | WO-03/053912 A1 | 7/2003 |
| WO | WO-03/082292 A1 | 10/2003 |
| WO | WO-03/101927 A1 | 12/2003 |
| WO | WO-2004/007455 A1 | 1/2004 |
| WO | WO-2005/020921 A2 | 3/2005 |
| WO | WO-2005/115990 A1 | 8/2005 |
| WO | WO-2006/046575 A1 | 5/2006 |
| WO | WO-2006/112550 A2 | 10/2006 |
| WO | WO-2007/034282 A2 | 3/2007 |
| WO | WO-2007/060810 A1 | 5/2007 |
| WO | WO-2007/102580 A1 | 9/2007 |
| WO | WO-2008/013213 A1 | 1/2008 |
| WO | WO-2008/097538 A1 | 8/2008 |
| WO | WO-2008/137139 A1 | 11/2008 |
| WO | WO-2008/156580 A1 | 12/2008 |
| WO | WO-2009/020580 A1 | 2/2009 |

OTHER PUBLICATIONS

Official Action issued on Nov. 14, 2008, in corresponding Russian Patent Application No. 2006146070.
T. A. Comery, The Journal of Neuroscience, Sep. 28, 2005, 25(39): 8898-8902.
T. A. Comery et al., Society for Neuroscience Annual Meeting (2003), Abstracts, Program No. 525.21.
J. G. Varnes et al., Bioorganic & Medicinal Chemistry Letters, 14 (2004) 1645-1649.
H. Stark et al., Pharmazie 52 (1997), vol. 6, pp. 419-423.
M. Kajbaf et al., Journal of Chromatography, 575 (1992) 75-85.
S. L. Marcus, Cancer Research, 45, 112-115, Jan. 1995.
H. L. Yale, J. Med. Chem., 1966, 9(1), 42-46.
Guiroy, Acta Neuropathol (1991) 82:87-92.
Ross, J. Med. Chem., 1973, vol. 16, No. 4, 347-352.
Office Action dated Sep. 16, 2008, that issued in connection with copending U.S. Appl. No. 11/594,150.
Office Action dated Jul. 11, 2008, that issued in connection with copending U.S. Appl. No. 11/136,355.
S. M. Catalano et al., "The Role of Amyloid-Beta Derived Diffusible Ligands (ADDLs) in Alzheimer's Disease," Current Topics in Medicinal Chemistry, vol. 6, 597-608 (2006).
Gong et al., PNAS, vol. 100, No. 18, pp. 10417-10422, (Sep. 2003).
Hock et al., Neuron, vol. 38, pp. 547-554, (May 2003).
Jarrett et al., Biochemistry, vol. 32, No. 18, pp. 4693-4697, (1993).
Glenner et al., Biochemical and Biophysical Research Communications, vol. 120, No. 3, pp. 885-890, (May 1984).
Masters et al., Proc. Natl. Acad. Sci. USA, vol. 82, No. 12, pp. 4245-4249, (Jun. 1985).
Gouras et al., American Journal of Pathology, vol. 156, No. 1, pp. 15-20, (Jan. 2000).
Scheuner et al., Nature Medicine, vol. 2, No. 8, pp. 864-870, (Aug. 1996).
Shearman et al., Biochemistry, vol. 39, No. 30, pp. 8698-8704, (Aug. 2000).
Lewis et al., Biochemistry, vol. 42, No. 24, pp. 7580-7586, (Jun. 2003).
Lanz et al., The Journal of Pharmacology and Experimental Therapeutics, vol. 309, No. 1, pp. 49-55, (Apr. 2004).
Wong et al., The Journal of Biological Chemistry, vol. 279, No. 13, pp. 12876-12882, (Mar. 2004).
Forman et al., The Journal of Biological Chemistry, vol. 272, No. 51, pp. 32247-32253, (Dec. 1997).
Blass et al., Journal of Neuroscience Research, vol. 66, No. 5, 851-856, (2001).
Evin et al., Molecular Neuroscience, vol. 13, No. 5, pp. 719-723, (2002).
Yasuhara et al., Neuroscience Letters, vol. 171, Nos. 1 & 2, pp. 63-66, (1994).
Teller et al., Nature Medicine, vol. 2, No. 1, pp. 93-95, (1996).
Tokuda et al., Annals Neurology, vol. 41, No. 2, pp. 271-273, (1997).
Hayashi et al., Brain Research, vol. 789, No. 2, pp. 307-314, (1998).
Barelli et al., Molecular Medicine, vol. 3, No. 10, pp. 695-707, (1997).
Calhoun et al., PNAS, vol. 96, No. 24, pp. 14088-14093, (1999).
Dermaut et al., Brain, vol. 124, No. 12, pp. 2383-2392, (2001).
Cras et al., Acta Neuropathol, vol. 96, No. 3, pp. 253-260, (1998).
Herzig et al., Nature Neuroscience, vol. 7, No. 9, pp. 954-960, (2004).
Van Duinen et al., Proc. Natl. Acad. Sci., vol. 84, No. 16, pp. 5991-5994, (1987).
Levy et al., Science, vol. 248, No. 4959, pp. 1124-1126, (1990).
Laws et al., Neurobiology of Aging, vol. 23, No. 1, pp. 55-58, (2002).
Vaucher et al., Experimental Neurology, vol. 175, No. 2, pp. 398-406, (2002).
Morgan et al., Nature, vol. 408, No. 6815, pp. 982-985, (2000).
Moran et al., Proc. Natl. Acad. Sci., vol. 92, No. 12, pp. 5341-5345, (1995).
Koisinaho et al., PNAS, vol. 99, No. 3, pp. 1610-1615, (2002).
Zhang et al., Journal of Neuroscience, vol. 17, No. 20, pp. 7655-7661, (1997).
Sadowski et al., Neurochemical Research, vol. 29, No. 6, pp. 1257-1266, (2004).
O'Riordan et al., Neurology, vol. 59, No. 7, pp. 1108-1110, (2002).
Gehrmann et al., GLIA, vol. 15, No. 2, pp. 141-151, (1995).
Reynolds et al., Experimental Neurology, vol. 155, No. 1, pp. 31-41, (1999).
Smith et al., NeuroMolecular Medicine, vol. 4, Nos. 1 & 2, pp. 59-72, (2003).
Matsubara-Tsutsui et al., American Journal of Medical Genetics, vol. 114, No. 3, pp. 292-298, (2002).
Kirkitadze et al., Journal of Neuroscience Research, vol. 69, No. 5, pp. 567-577, (2002).
Evert et al., Journal of Neuroscience, vol. 21, No. 5, pp. 5389-5396, (2001).
Mann et al., Neuroscience Letters, vol. 109, Nos. 1 & 2, pp. 68-75, (1990).
Primavera et al., Journal of Alzheimer's Disease, vol. 1, No. 3, pp. 183-193, (1999).
Giasson et al., NeuroMolecular Medicine, vol. 4, Nos. 1 & 2, pp. 49-58, (2003).
Masliah et al., PNAS, vol. 98, No. 21, pp. 12245-12250, (2001).
Barrachina et al., Neurochemistry International, vol. 46, No. 3, pp. 253-260, (2005).
Schmidt et al., Acta Neuropathol, vol. 95, No. 2, pp. 117-122, (1998).
Ito et al., Neuropathology and Applied Neurobiology, vol. 17, No. 5, pp. 365-373, (1991).
Rosso et al., Annals of the New York Academy of Science, vol. 920, pp. 115-119, (2000).

Tolnay et al., Neuropathology and Applied Neurobiology, vol. 25, No. 4, pp. 295-305, (1999).
Jin et al., American Journal o Pathology, vol. 164, No. 3, pp. 975-985, (2004).
Sasaki et al., Acta Neuropathol., vol. 97, No. 5, pp. 463-468, (1999).
Tamaoka et al., J. Neurol., vol. 247, No. 8, pp. 633-635, (2000).
Hamilton et al., Acta Neuropathol, vol. 107, No. 6, pp. 515-522, (2004).
Turner et al., Neurochemical Research, vol. 29, No. 12, pp. 2281-2286, (2004).
Weller et al., Journal of Neuropathology and Experimental Neurology, vol. 57, No. 10, pp. 885-894, (1998).
Silverberg et al., The Lancet Neurology, vol. 2, No. 8, pp. 506-511, (2003).
Weller et al., Annals of the New York Academy of Science, vol. 903, pp. 110-117, (2000).
Yow et al., Neuropathology and Applied Neurology, vol. 28, pp. 149, (2002).
Weller et al., Annals of the New York Academy of Science, vol. 977, pp. 162-168, (2002).
Smith et al., Ann. Neurol., vol. 49, No. 1, pp. 125-129, (2001).
Crook et al., Nature Medicine, vol. 4, No. 4, pp. 452-455, (1998).
Atwood et al., Brain Research Reviews, vol. 43, No. 1, pp. 164-178, (2003).
Lowenson et al., Trends in Cardiovascular Medicine, vol. 4, No. 1, pp. 3-8, (1994).
Singleton et al., Brain, vol. 123, No. 12, pp. 2467-2474, (2000).
Gattaz et al., J. Neural. Transm., vol. 111, No. 5, pp. 591-601, (2004).
Assini et al., Neurology, vol. 63, No. 5, pp. 828-831, (2004).
De Meyer et al., Circulation Research, vol. 90, No. 11, pp. 1197-1204, (2002).
Masahiko Kato et al., Chem. Pharm. Bull., 42 (12), 2546-2555 (1994).
Search Report issued May 27, 2009, in connection with Georgia Patent Application No. AP 2006 010709 (with English translation).
The International Search Report for International Appl. No. PCT/JP2008/053887, mailed Sep. 19, 2008.
An Office Action from Russian Patent Appl. No. 2008125426/04(030920), date Jun. 1, 2009.
An Office Action from U.S. Appl. No. 11/715,440, dated Jul. 16, 2009.
An Office Action from U.S. Appl. No. 12/200,731, dated Jul. 30, 2009.

MORPHOLINE TYPE CINNAMIDE COMPOUND

BACKGROUND OF THE INVENTION (1) Field of the Invention

The present invention relates to a morpholine type cinamide compound and a pharmaceutical agent comprising the compound as an active ingredient. More specifically, the present invention relates to a nonpeptidic two cyclic cinamide compound and an amyloid-β (hereinafter referred to as Aβ) production inhibitor which comprises the compound as an active ingredient and is particularly effective for treatment of a neurodegenerative disease caused by Aβ such as Alzheimer's disease or Down's syndrome.

(2) Description of Related Art

Alzheimer's disease is a disease characterized by degeneration and loss of neurons as well as formation of senile plaques and neurofibrillary degeneration. Currently, Alzheimer's disease is treated only with symptomatic treatment using a symptom improving agent typified by an acetylcholinesterase inhibitor, and a fundamental remedy to inhibit progression of the disease has not yet been developed. It is necessary to develop a method for controlling the cause of the onset of pathology in order to create a fundamental remedy for Alzheimer's disease.

It is assumed that Aβ-proteins as metabolites of amyloid precursor proteins (hereinafter referred to as APP) are highly involved in degeneration and loss of neurons and onset of symptoms of dementia (see Klein W L, and seven others, Alzheimer's disease-affected brain: Presence of oligomeric Aβ ligands (ADDLs) suggests a molecular basis for reversible memory loss, Proceeding National Academy of Science USA 2003, Sep. 2; 100(18), p. 10417-10422; and Nitsch R M, and sixteen others, Antibodies against β-amyloid slow cognitive decline in Alzheimer's disease, Neuron, 2003, May 22; 38, p. 547-554, for example). An Aβ-protein has, as main components, Aβ40 consisting of 40 amino acids and Aβ42 in which the number of amino acids is increased by two at the C-terminal. The Aβ40 and Aβ42 are known to have high aggregability (see Jarrett J T, and two others, The carboxy terminus of the β amyloid protein is critical for the seeding of amyloid formation: Implications for the pathogenesis of Alzheimer's disease, Biochemistry, 1993, 32(18), p. 4693-4697, for example) and to be main components of senile plaques (see Jarrett J T, and two others, The carboxy terminus of the β amyloid protein is critical for the seeding of amyloid formation: Implications for the pathogenesis of Alzheimer's disease, Biochemistry, 1993, 32(18), p. 4693-4697; Glenner G G, and one other, Alzheimer's disease: initial report of the purification and characterization of a novel cerebrovascular amyloid protein, Biochemical and biophysical research communications, 1984, May 16, 120(3), p. 885-890; and Masters C L, and five others, Amyloid plaque core protein in Alzheimer disease and Down syndrome, Proceeding National Academy of Science USA, 1985, June, 82(12), p. 4245-4249, for example). Further, it is known that the Aβ40 and Aβ42 are increased by mutation in APP and presenilin genes which is observed in familial Alzheimer's disease (see Gouras G K, and eleven others, Intraneuronal Aβ42 accumulation in human brain, American Journal of Pathology, 2000, January, 156(1), p. 15-20; Scheuner D, and twenty others, Secreted amyloid β-protein similar to that in the senile plaques of Alzheimer's disease is increased in vivo by the presenilin 1 and 2 and APP mutations linked to familial Alzheimer's disease, Nature Medicine, 1996, August, 2(8), p. 864-870; and Forman M S, and four others, Differential effects of the swedish mutant amyloid precursor protein on β-amyloid accumulation and secretion in neurons and nonneuronal cells, The Journal of Biological Chemistry, 1997, Dec. 19, 272(51), p. 32247-32253, for example). Accordingly, a compound that reduces production of Aβ40 and Aβ42 has been expected as a progression inhibitor or prophylactic agent for Alzheimer's disease.

Aβ is produced by cleaving APP by β-secretase and subsequently by γ-secretase. For this reason, attempts have been made to create γ-secretase and β-secretase inhibitors in order to reduce Aβ production. Many of these secretase inhibitors already known are, for example, peptides and peptide mimetics such as L-685,458 (see Shearman M S, and nine others, L-685,458, an Aspartyl Protease Transition State Mimic, Is a Potent Inhibitor of Amyloid β-Protein Precursor γ-Secretase Activity, Biochemistry, 2000, Aug. 1, 39(30), p. 8698-8704, for example) and LY-411575 (see Shearman M S, and six others, Catalytic Site-Directed γ-Secretase Complex Inhibitors Do Not Discriminate Pharmacologically between Notch S3 and β-APP Cleavages, Biochemistry, 2003, Jun. 24, 42(24), p. 7580-7586; Lanz T A, and three others, Studies of Aβ pharmacodynamics in the brain, cerebrospinal fluid, and plasma in young (plaque-free) Tg2576 mice using the γ-secretase inhibitor N2-[(2S)-2-(3,5-difluorophenyl)-2-hydroxyethanoyl]-N1-[(7S)-5-methyl-6-oxo-6,7-dihydro-5H-dibenzo[b,d]azepin-7-yl]-L-alaninamide (LY-411575), The journal of pharmacology and experimental therapeutics, 2004, April, 309(1), p. 49-55; and Wong G T, and twelve others, Chronic treatment with the γ-secretase inhibitor LY-411,575 inhibits β-amyloid peptide production and alters lymphopoiesis and intestinal cell differentiation, The journal of biological chemistry, 2004, Mar. 26, 279(13), p. 12876-12882, for example).

BRIEF SUMMARY OF THE INVENTION

As described above, a compound that inhibits production of Aβ40 and Aβ42 from APP has been expected as a therapeutic or prophylactic agent for a disease caused by Aβ which is typified by Alzheimer's disease. However, a nonpeptidic compound having high efficacy which inhibits production of Aβ40 and Aβ42 has not yet been known. Accordingly, there is a need for a novel low-molecular-weight compound that inhibits production of Aβ40 and Aβ42.

As a result of extensive studies, the present inventors have found a nonpeptidic morpholine type cinamide compound that inhibits production of Aβ40 and Aβ42 from APP for the first time, and thus found a prophylactic or therapeutic agent for a disease caused by Aβ which is typified by Alzheimer's disease. This finding has led to the accomplishment of the present invention.

Specifically, the present invention relates to

1) A compound represented by the formula (I):

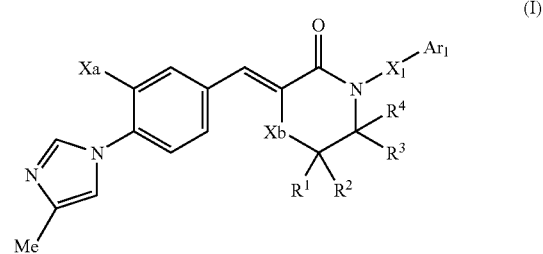

or a pharmacologically acceptable salt thereof, wherein (a) $R^1$, $R^2$, $R^3$, and $R^4$ are the same or different and each represent a hydrogen atom or a C1-6 alkyl group;

$X_1$ represents a C1-6 alkylene group, wherein the C1-6 alkylene group may be substituted with 1 to 3 hydroxyl groups or C1-6 alkyl groups, wherein the C1-6 alkyl groups may be substituted with 1 to 3 hydroxyl groups, or a C3-13 cycloalkyl group formed by two C1-6 alkyl groups together bonded to the same carbon atom of the C1-6 alkylene group;

$X_a$ represents a methoxy group or a fluorine atom;

$X_b$ represents an oxygen atom or a methylene group, provided that $X_b$ is only an oxygen atom when $X_a$ is a methoxy group; and $Ar_1$ represents an aryl group, pyridinyl group, aryloxy group, or pyridinyloxy group that may be substituted with 1 to 3 substituents selected from Substituent Group A1;

(b) $Ar_1$—$X_1$— represents a C3-8 cycloalkyl group condensed with a benzene ring, wherein one methylene group on the C3-8 cycloalkyl group may be substituted with an oxygen atom, the C3-8 cycloalkyl group may be substituted with 1 to 3 hydroxyl groups and/or C1-6 alkyl groups, and the benzene ring may be substituted with 1 to 3 substituents selected from Substituent Group A1; and $R^1$, $R^2$, $R^3$, $R^4$, $X_a$, and $X_b$ are as defined in (a);

(c) one of $R^1$ and $R^2$ and one of $R^3$ and $R^4$ are the same or different and each represent a hydrogen atom or a C1-6 alkyl group; the other of $R^1$ and $R^2$ and the other of $R^3$ and $R^4$, together with the carbon atoms to which they are respectively bonded, form a C3-8 cycloalkyl group, wherein the C3-8 cycloalkyl group may be substituted with 1 to 3 substituents selected from Substituent Group A1; and $X_1$, $X_a$, $X_b$, and $Ar_1$ are as defined in (a) or (b);

(d) $Ar_1$—$X_1$— and $R^4$, together with the nitrogen atom to which $Ar_1$—$X_1$— is bonded and the carbon atom to which $R^4$ is bonded, form a 4- to 8-membered nitrogen-containing heterocyclic group that may be substituted with an aryl group or pyridinyl group, wherein one methylene group on the 4- to 8-membered nitrogen-containing heterocyclic group may be substituted with a methylene group substituted with 1 or 2 substituents selected from Substituent Group A1, a vinylene group that may be substituted with 1 or 2 substituents selected from Substituent Group A1, an oxygen atom, or an imino group that may be substituted with a substituent selected from Substituent Group A1, and the aryl group or pyridinyl group may be substituted with 1 to 3 substituents selected from Substituent Group A1; $X_b$ represents an oxygen atom; and $R^1$, $R^2$, $R^3$, and $X_a$ are as defined in (a) and (b);

(e) $R^1$ and $R^2$, together with the carbon atom to which they are bonded, form a C3-8 cycloalkyl group; and $R^3$, $R^4$, $X_1$, $X_a$, $X_b$, and $Ar_1$ are as defined in (a) and (b); or (f) $R^3$ and $R^4$, together with the carbon atom to which they are bonded, form a C3-8 cycloalkyl group; and $R^1$, $R^2$, $X_1$, $X_a$, $X_b$, and $Ar_1$ are as defined in (a) and (b)

(Substituent Group A1: (1) a halogen atom, (2) a hydroxyl group, (3) a cyano group, (4) a C3-8 cycloalkyl group, (5) a C3-8 cycloalkoxy group, (6) a C1-6 alkyl group, wherein the C1-6 alkyl group may be substituted with 1 to 5 halogen atoms or one to three C1-6 alkoxy groups, (7) an amino group that may be substituted with one or two C1-6 alkyl groups, wherein the C1-6 alkyl groups may be substituted with 1 to 5 halogen atoms, (8) a C1-6 alkoxy group, wherein the C1-6 alkoxy group may be substituted with 1 to 5 halogen atoms, and (9) a carbamoyl group that may be substituted with one or two C1-6 alkyl groups, wherein the C1-6 alkyl groups may be substituted with 1 to 3 halogen atoms);

2) The compound or pharmacologically acceptable salt thereof according to 1) above, wherein the compound is represented by the formula (I-a):

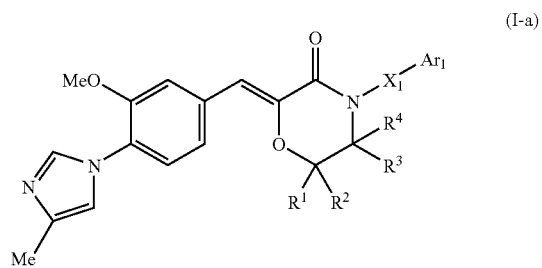

wherein $R^1$, $R^2$, $R^3$, $R^4$, $X_1$, and $Ar_1$ are as defined in 1) above;

3) The compound or pharmacologically acceptable salt thereof according to 1) above, wherein the compound is represented by the formula (II):

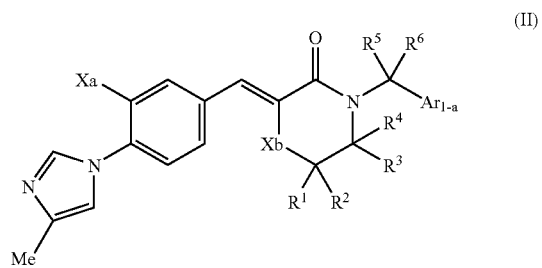

wherein $R^1$, $R^2$, $R^3$, $R^4$, $X_a$, and $X_b$ are as defined in 1) above; $R^5$ and $R^6$ are the same or different and each represent a hydrogen atom or a C1-6 alkyl group, wherein the C1-6 alkyl group may be substituted with 1 to 3 hydroxyl groups; and $Ar_{1-a}$ represent a phenyl group or pyridinyl group that may be substituted with 1 to 3 substituents selected from Substituent Group A1 as defined in 1) above;

4) The compound or pharmacologically acceptable salt thereof according to 3) above, wherein the compound is represented by the formula (II-a):

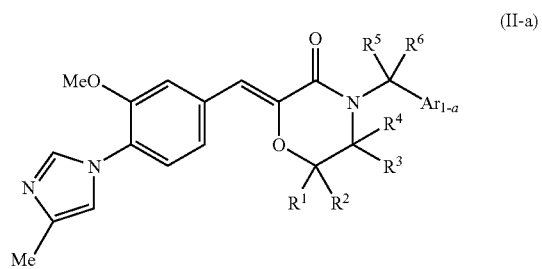

wherein $R^1$, $R^2$, $R^3$, and $R^4$ are as defined in 1) above; and $R^5$, $R^6$, and $Ar_{1-a}$ are as defined in 3) above;

5) The compound or pharmacologically acceptable salt thereof according to 3) above, wherein the compound is represented by the formula (II-b):

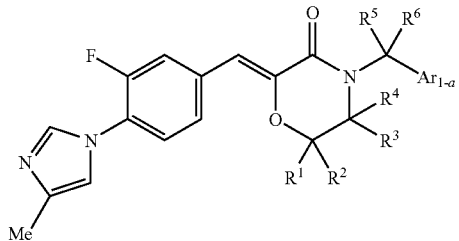

(II-b)

wherein $R^1$, $R^2$, $R^3$, and $R^4$ are as defined in 1) above; and $R^5$, $R^6$, and $Ar_{1-a}$ are as defined in 3) above;

6) The compound or pharmacologically acceptable salt thereof according to 3) above, wherein the compound is represented by the formula (II-c):

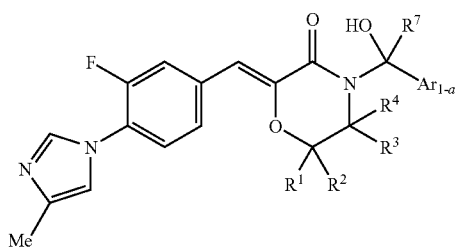

(II-c)

wherein $R^1$, $R^2$, $R^3$, and $R^4$ are as defined in 1) above; $R^7$ represents a hydrogen atom or a C1-6 alkyl group; and $Ar_{1-a}$ is as defined in 3) above;

7) The compound or pharmacologically acceptable salt thereof according to 3) above, wherein the compound is represented by the formula (II-d):

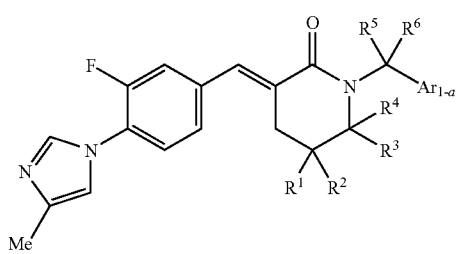

(II-d)

wherein $R^1$, $R^2$, $R^3$, and $R^4$ are as defined in 1) above; and $R^5$, $R^6$, and $Ar_{1-a}$ are as defined in 3) above;

8) The compound or pharmacologically acceptable salt thereof according to 3) above, wherein the compound is represented by the formula (II-e):

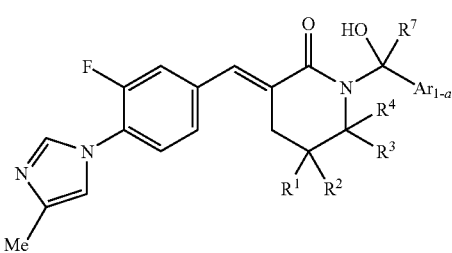

(II-e)

wherein $R^1$, $R^2$, $R^3$, and $R^4$ are as defined in 1) above; $Ar_{1-a}$ is as defined in 3) above; and $R^7$ is as defined in 6) above;

9) The compound or pharmacologically acceptable salt thereof according to 1) above, wherein the compound is represented by the formula (I-b):

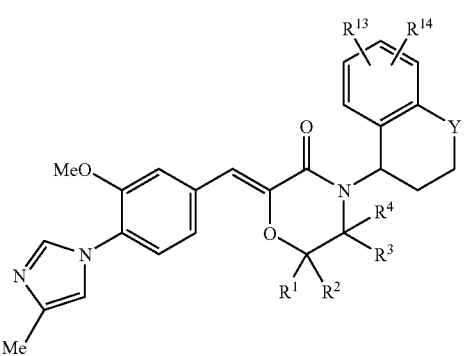

(I-b)

wherein $R^1$, $R^2$, $R^3$, and $R^4$ are as defined in 1) above; $R^{13}$ and $R^{14}$ are the same or different and each represent a hydrogen atom or a substituent selected from Substituent Group A1 as defined in 1) above; and Y represents a methylene group or an oxygen atom;

10) The compound or pharmacologically acceptable salt thereof according to 9) above, wherein $R^{13}$ and $R^{14}$ are the same or different and each represent a hydrogen atom, a halogen atom, or a C1-6 alkoxy group;

11) The compound or pharmacologically acceptable salt thereof according to 1) above, wherein the compound is represented by the formula (I-c):

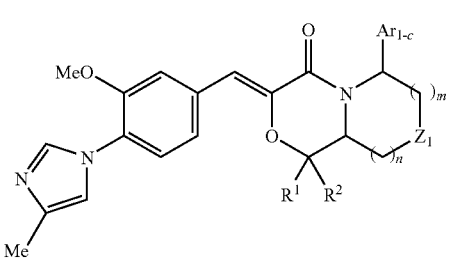

(I-c)

wherein $R^1$ and $R^2$ are as defined in 1) above; $Ar_{1-c}$ represents a phenyl group or pyridinyl group that may be substituted with 1 to 3 substituents which are the same or different and selected from Substituent Group A1; $Z_1$ represents a methylene group or vinylene group that may be substituted with 1 or 2 substituents selected from Substituent Group A1 as defined in 1) above, an oxygen atom, or an imino group that may be substituted with a substituent selected from Substituent Group A1;

and n and m are the same or different and each represent an integer of 0 to 2;

12) The compound or pharmacologically acceptable salt thereof according to 11) above, wherein $Z_1$ represents a methylene group, wherein the methylene group may be substituted with 1 or 2 substituents which are the same or different and selected from the group consisting of a C1-6 alkyl group and a hydroxyl group; and n and m each represent 1;

13) The compound or pharmacologically acceptable salt thereof according to 11) above, wherein $Z_1$ represents an oxygen atom, and n and m represent an integer of 1;

14) The compound or pharmacologically acceptable salt thereof according to 1) above, wherein $Ar_1$ represents an aryl group or pyridinyl group, or an aryl group or pyridinyl group substituted with 1 to 3 halogen atoms;

15) The compound or pharmacologically acceptable salt thereof according to 1) above, wherein $Ar_1$ represents a phenyl group or pyridinyl group, or a phenyl group or pyridinyl group substituted with 1 to 3 halogen atoms;

16) The compound or pharmacologically acceptable salt thereof according to 1) above, wherein the compound is selected from the following group:

1) (Z)-2-[1-[3-methoxy-4-(4-methyl-1H-imidazol-1-yl)phenyl]methylidene]-4-(3,4,5-trifluorobenzyl)morpholin-3-one,
2) (Z)-2-[1-[3-methoxy-4-(4-methyl-1H-imidazol-1-yl)phenyl]methylidene]-4-(2,3,4-trifluorobenzyl)morpholin-3-one,
3) (Z)-(S)-2-[1-[3-methoxy-4-(4-methyl-1H-imidazol-1-yl)phenyl]methylidene]-6-methyl-4-(3,4,5-trifluorobenzyl)morpholin-3-one,
4) (Z)-(R)-2-[1-[3-methoxy-4-(4-methyl-1H-imidazol-1-yl)phenyl]methylidene]-6-methyl-4-(3,4,5-trifluorobenzyl)morpholin-3-one,
5) (Z)-(S)-2-[1-[3-methoxy-4-(4-methyl-1H-imidazol-1-yl)phenyl]methylidene]-6-methyl-4-(2,3,4-trifluorobenzyl)morpholin-3-one,
6) (Z)-(R)-2-[1-[3-methoxy-4-(4-methyl-1H-imidazol-1-yl)phenyl]methylidene]-6-methyl-4-(2,3,4-trifluorobenzyl)morpholin-3-one,
7) (Z)-4-[(S)-1-(4-fluorophenyl)ethyl]-2-[1-[3-methoxy-4-(4-methyl-1H-imidazol-1-yl)phenyl]methylidene]-6,6-dimethylmorpholin-3-one,
8) (Z)-(R)-4-[(S)-1-(4-fluorophenyl)ethyl]-2-[1-[3-methoxy-4-(4-methyl-1H-imidazol-1-yl)phenyl]methylidene]-6-methylmorpholin-3-one,
9) (Z)-(S)-4-[(S)-1-(4-fluorophenyl)ethyl]-2-[1-[3-methoxy-4-(4-methyl-1H-imidazol-1-yl)phenyl]methylidene]-6-methylmorpholin-3-one,
10) (Z)-2-[1-[3-methoxy-4-(4-methyl-1H-imidazol-1-yl)phenyl]methylidene]-4-[(S)-1-(3,4,5-trifluorophenyl)ethyl]morpholin-3-one,
11) (Z)-2-[1-[3-methoxy-4-(4-methyl-1H-imidazol-1-yl)phenyl]methylidene]-4-[(R)-1-(3,4,5-trifluorophenyl)ethyl]morpholin-3-one,
12) (Z)-4-[(S)-chroman-4-yl]-2-[1-[3-methoxy-4-(4-methyl-1H-imidazol-1-yl)phenyl]methylidene]-6,6-dimethylmorpholin-3-one,
13) (Z)-(S)-4-[(S)-chroman-4-yl]-2-[1-[3-methoxy-4-(4-methyl-1H-imidazol-1-yl)phenyl]methylidene]-6-methylmorpholin-3-one,
14) (Z)-(R)-4-[(S)-chroman-4-yl]-2-[1-[3-methoxy-4-(4-methyl-1H-imidazol-1-yl)phenyl]methylidene]-6-methylmorpholin-3-one,
15) (Z)-(6S,9aR)-6-(4-fluorophenyl)-3-{1-[3-methoxy-4-(4-methyl-1H-imidazol-1-yl)benzylidene]hexahydropyrido[2,1-c][1,4]oxazin-4-one,
16) (Z)-(6R,9aS)-6-(4-fluorophenyl)-3-{1-[3-methoxy-4-(4-methyl-1H-imidazol-1-yl)benzylidene]hexahydropyrido[2,1-c][1,4]oxazin-4-one,
17) (Z)-(S)-4-[(S)-1-(6-chloropyridin-3-yl)ethyl]-2-[1-[3-methoxy-4-(4-methyl-1H-imidazol-1-yl)phenyl]methylidene]-6-methylmorpholin-3-one,
18) (Z)-(S)-4-[(R)-1-(6-chloropyridin-3-yl)ethyl]-2-[1-[3-methoxy-4-(4-methyl-1H-imidazol-1-yl)phenyl]methylidene]-6-methylmorpholin-3-one,
19) (Z)-(S)-4-[(S)-1-(5-chloropyridin-2-yl)ethyl]-2-[1-[3-methoxy-4-(4-methyl-1H-imidazol-1-yl)phenyl]methylidene]-6-methylmorpholin-3-one,
20) (Z)-(S)-4-[(R)-1-(5-chloropyridin-2-yl)ethyl]-2-[1-[3-methoxy-4-(4-methyl-1H-imidazol-1-yl)phenyl]methylidene]-6-methylmorpholin-3-one,
21) (Z)-(S)-4-[(S)-1-(2,6-difluoropyridin-3-yl)ethyl]-2-[1-[3-methoxy-4-(4-methyl-1H-imidazol-1-yl)phenyl]methylidene]-6-methylmorpholin-3-one,
22) (Z)-(S)-4-[(R)-1-(2,6-difluoropyridin-3-yl)ethyl]-2-[1-[3-methoxy-4-(4-methyl-1H-imidazol-1-yl)phenyl]methylidene]-6-methylmorpholin-3-one,
23) (Z)-(S)-4-[(S)-1-(2,3-difluoropyridin-4-yl)ethyl]-2-[1-[3-methoxy-4-(4-methyl-1H-imidazol-1-yl)phenyl]methylidene]-6-methylmorpholin-3-one,
24) (Z)-(S)-4-[(R)-1-(2,3-difluoropyridin-4-yl)ethyl]-2-[1-[3-methoxy-4-(4-methyl-1H-imidazol-1-yl)phenyl]methylidene]-6-methylmorpholin-3-one,
25) (Z)-(S)-4-[(1R,2R)-2-hydroxy-1-(3,4,5-trifluorophenyl)propyl]-2-[1-[3-methoxy-4-(4-methyl-1H-imidazol-1-yl)phenyl]methylidene]-6-methylmorpholin-3-one,
26) (Z)-4-[(1R,2R)-2-hydroxy-1-(3,4,5-trifluorophenyl)propyl]-2-[1-[3-methoxy-4-(4-methyl-1H-imidazol-1-yl)phenyl]methylidene]-6,6-dimethylmorpholin-3-one,
27) (Z)-4-[(R)-1-(4-fluorophenyl)-2-hydroxyethyl]-2-[1-[3-methoxy-4-(4-methyl-1H-imidazol-1-yl)phenyl]methylidene]-6,6-dimethylmorpholin-3-one,
28) (Z)-(6R)-4-[(1R,2R)-2-hydroxy-1-(3,4,5-trifluorophenyl)propyl]-2-[1-[3-methoxy-4-(4-methyl-1H-imidazol-1-yl)phenyl]methylidene]-6-methylmorpholin-3-one,
29) (Z)-4-[(1R,2R)-2-hydroxy-1-(3,4,5-trifluorophenyl)propyl]-2-[1-[3-methoxy-4-(4-methyl-1H-imidazol-1-yl)phenyl]methylidene]morpholin-3-one,
30) (Z)-4-[(1R,2R)-1-(3,4-difluorophenyl)-2-hydroxypropyl]-2-[1-[3-methoxy-4-(4-methyl-1H-imidazol-1-yl)phenyl]methylidene]morpholin-3-one,
31) (Z)-(S)-4-[(1R,2R)-1-(4-fluorophenyl)-2-hydroxypropyl]-2-[1-[3-methoxy-4-(4-methyl-1H-imidazol-1-yl)phenyl]methylidene]-6-methylmorpholin-3-one,
32) (Z)-4-[(1R,2R)-1-(4-fluorophenyl)-2-hydroxypropyl]-2-[1-[3-methoxy-4-(4-methyl-1H-imidazol-1-yl)phenyl]methylidene]-6,6-dimethylmorpholin-3-one,
33) (Z)-(S)-4-[(1R,2R)-1-(3,4-difluorophenyl)-2-hydroxypropyl]-2-[1-[3-methoxy-4-(4-methyl-1H-imidazol-1-yl)phenyl]methylidene]-6-methylmorpholin-3-one,
34) (Z)-4-[(1R,2R)-1-(3,4-difluorophenyl)-2-hydroxypropyl]-2-[1-[3-methoxy-4-(methylimidazol-1-yl)phenyl]methylidene]-6,6-dimethylmorpholin-3-one,
35) (Z)-(S)-4-[(S)-2-hydroxy-1-methyl-1-(3,4,5-trifluorophenyl)ethyl]-2-[1-[3-methoxy-4-(4-methyl-1H-imidazol-1-yl)phenyl]methylidene]-6-methylmorpholin-3-one,
36) (Z)-(6S)-2-[1-[3-methoxy-4-(4-methyl-1H-imidazol-1-yl)phenyl]methylidene]-6-methyl-4-[(S)-1-(3,4,5-trifluorophenyl)ethyl]morpholin-3-one, 37) (Z)-(6S)-4-[1-(4-fluorophenyl)-1-methylethyl]-2-[1-[3-methoxy-4-(4-methyl-1H-imidazol-1-yl)phenyl]methylidene]-6-methylmorpholin-3-one,
38) (Z)-(6S)-4-[1-(4-fluorophenyl)cyclopropyl]-2-[1-[3-methoxy-4-(4-methyl-1H-imidazol-1-yl)phenyl]methylidene]-6-methylmorpholin-3-one,
39) (Z)-(6S,9aR)-3-{1-[3-methoxy-4-(4-methyl-1H-imidazol-1-yl)benzylidene]-6-(3,4,5-trifluorophenyl)hexahydropyrido[2,1-c][1,4]oxazin-4-one,
40) (Z)-(6S,9aR)-6-(3,4-difluorophenyl)-3-{1-[3-methoxy-4-(4-methyl-1H-imidazol-1-yl)benzylidene]hexahydropyrido[2,1-c][1,4]oxazin-4-one,
41) (Z)-(6S,9aR)-6-(2,6-difluoropyridin-3-yl)-3-{1-[3-methoxy-4-(4-methyl-1H-imidazol-1-yl)benzylidene]hexahydropyrido[2,1-c][1,4]oxazin-4-one,
42) (Z)-(S)-4-[(S)-1-(5-fluoropyridin-2-yl)ethyl]-2-[1-[3-methoxy-4-(4-methyl-1H-imidazol-1-yl)phenyl]methylidene]-6-methylmorpholin-3-one,
43) (Z)-(S)-4-[(S)-1-(2-chloropyridin-4-yl)ethyl]-2-[1-[3-methoxy-4-(4-methyl-1H-imidazol-1-yl)phenyl]methylidene]-6-methylmorpholin-3-one,
44) (Z)-(S)-4-[(S)-1-(2-chloro-3-fluoropyridin-4-yl)ethyl]-2-[1-[3-methoxy-4-(4-methyl-1H-imidazol-1-yl)phenyl]methylidene]-6-methylmorpholin-3-one,
45) (Z)-(S)-4-[(S)-1-(2,6-difluoropyridin-4-yl)ethyl]-2-[1-[3-methoxy-4-(4-methyl-1H-imidazol-1-yl)phenyl]methylidene]-6-methylmorpholin-3-one,
46) (Z)-4-[(S)-1-(2-chloropyridin-4-yl)ethyl]-2-[1-[3-methoxy-4-(4-methyl-1H-imidazol-1-yl)phenyl]methylidene]-6,6-dimethylmorpholin-3-one,
47) (Z)-4-[(S)-1-(2,6-difluoropyridin-3-yl)ethyl]-2-[1-[3-methoxy-4-(4-methyl-1H-imidazol-1-yl)phenyl]methylidene]-6,6-dimethylmorpholin-3-one,
48) (Z)-4-[(S)-1-(6-fluoropyridin-3-yl)ethyl]-2-[1-[3-methoxy-4-(4-methyl-1H-imidazol-1-yl)phenyl]methylidene]-6,6-dimethylmorpholin-3-one,
49) (Z)-4-[(S)-1-(6-chloropyridin-3-yl)ethyl]-2-[1-[3-methoxy-4-(4-methyl-1H-imidazol-1-yl)phenyl]methylidene]-6,6-dimethylmorpholin-3-one,
50) (Z)-4-[(S)-1-(2,3-difluoropyridin-4-yl)ethyl]-2-[1-[3-methoxy-4-(4-methyl-1H-imidazol-1-yl)phenyl]methylidene]-6,6-dimethylmorpholin-3-one,
51) (Z)-4-[(S)-1-(5-chloropyridin-2-yl)ethyl]-2-[1-[3-methoxy-4-(4-methyl-1H-imidazol-1-yl)phenyl]methylidene]-6,6-dimethylmorpholin-3-one,
52) (Z)-(R)-4-[(S)-1-(2,6-difluoropyridin-3-yl)ethyl]-2-[1-[3-methoxy-4-(4-methyl-1H-imidazol-1-yl)phenyl]methylidene]-6-methylmorpholin-3-one,
53) (Z)-(S)-4-(4-fluorobenzyl)-2-[1-[3-fluoro-4-(4-methyl-1H-imidazol-1-yl)phenyl]methylidene]-6-methylmorpholin-3-one,
54) (Z)-2-[1-[3-fluoro-4-(4-methyl-1H-imidazol-1-yl)phenyl]methylidene]-4-[(S)-1-(4-trifluorophenyl)ethyl]-6,6-dimethylmorpholin-3-one,
55) (Z)-4-[(S)-chroman-4-yl]-2-[1-[3-fluoro-4-(4-methyl-1H-imidazol-1-yl)phenyl]methylidene]-6,6-dimethylmorpholin-3-one,
56) (Z)-(S)-4-[(S)-chroman-4-yl]-2-[1-[3-fluoro-4-(4-methyl-1H-imidazol-1-yl)phenyl]methylidene]-6-methylmorpholin-3-one,
57) (Z)-(S)-2-[1-[3-fluoro-4-(4-methyl-1H-imidazol-1-yl)phenyl]methylidene]-4-[(1R,2R)-2-hydroxy-1-(3,4,5-trifluorophenyl)propyl]-6-methylmorpholin-3-one,
58) (Z)-(S)-4-[(1R,2R)-1-(3,4-difluorophenyl)-2-hydroxypropyl]-2-[1-[3-fluoro-4-(4-methyl-1H-imidazol-1-yl)phenyl]methylidene]-6-methylmorpholin-3-one,
59) (Z)-(S)-2-[1-[3-fluoro-4-(4-methyl-1H-imidazol-1-yl)phenyl]methylidene]-4-[(1R,2R)-1-(4-fluorophenyl)-2-hydroxypropyl]-6-methylmorpholin-3-one,
60) (Z)-2-[1-[3-fluoro-4-(4-methyl-1H-imidazol-1-yl)phenyl]methylidene]-4-[(1R,2R)-2-hydroxy-1-(3,4,5-trifluorophenyl)propyl]-6,6-dimethylmorpholin-3-one,
61) (Z)-4-[(1R,2R)-1-(3,4-difluorophenyl)-2-hydroxypropyl]-2-[1-[3-fluoro-4-(4-methyl-1H-imidazol-1-yl)phenyl]methylidene]-6,6-dimethylmorpholin-3-one,
62) 1-[1-(2,4-difluorophenyl)ethyl]-3-{1-[3-fluoro-4-(4-methyl-1H-imidazol-1-yl)phenyl]-(E)-methylidene}piperidin-2-one,
63) (E)-(S)-3-{1-[3-fluoro-4-(4-methyl-1H-imidazol-1-yl)phenyl]methylidene}-1-[(1R,2R)-2-hydroxy-1-(3,4,5-trifluorophenyl)propyl]-5-methylpiperidin-2-one,
64) (E)-3-{1-[3-fluoro-4-(4-methyl-1H-imidazol-1-yl)phenyl]methylidene}-1-[(1R,2R)-2-hydroxy-1-(3,4,5-trifluorophenyl)propyl]piperidin-2-one,
65) (E)-3-{1-[3-fluoro-4-(4-methyl-1H-imidazol-1-yl)phenyl]methylidene}-1-[(2R,3R)-3-hydroxy-1,1-dimethylindane-2-yl]piperidin-2-one,
66) (E)-3-{1-[3-fluoro-4-(4-methyl-1H-imidazol-1-yl)phenyl]methylidene}-1-[(S)-2-hydroxy-1-methyl-1-(3,4,5-trifluorophenyl)ethyl]piperidin-2-one,
67) (E)-3-{1-[3-fluoro-4-(4-methyl-1H-imidazol-1-yl)phenyl]methylidene}-1-[1-(4-fluorophenyl)-1-methylethyl]piperidin-2-one,
68) (E)-(R)-3-[(1-[3-fluoro-4-(4-methyl-1H-imidazol-1-yl)phenyl]methylidene}-1-[(1R,2R)-2-hydroxy-1-(3,4,5-trifluorophenyl)propyl]-5-methylpiperidin-2-one,
69) (E)-(S)-1-[(1R,2R)-1-(3,4-difluorophenyl)-2-hydroxypropyl]-3-{1-[3-fluoro-4-(4-methyl-1H-imidazol-1-yl)phenyl]methylidene}-5-methylpiperidin-2-one,
70) (Z)-(6S,8aR)-3-{1-[3-methoxy-4-(4-methyl-1H-imidazol-1-yl)benzylidene]-6-(3,4,5-trifluorophenyl)tetrahydropyrrolo[2,1-c][1,4]oxazin-4-one,
71) (6S,9aR)-6-(4-chlorophenyl)-3-{1-[3-methoxy-4-(4-methyl-1H-imidazol-1-yl)phenyl]-(Z)-methylidene}hexahydropyrido[2,1-c][1,4]oxazin-4-one,
72) (6R,9aR)-3-{1-[3-methoxy-4-(4-methyl-1H-imidazol-1-yl)phenyl]-(Z)-methylidene}-6-(3,4,5-trifluorophenyl)-tetrahydro[1,4]oxazino[3,4-c][1,4]oxazin-4-one,
73) (6R,9aR)-6-(3,4-difluorophenyl)-3-{1-[3-methoxy-4-(4-methyl-1H-imidazol-1-yl)phenyl]-(Z)-methylidene}-tetrahydro[1,4]oxazino[3,4-c][1,4]oxazin-4-one,
74) (6R,9aR)-6-(4-fluorophenyl)-3-{1-[3-methoxy-4-(4-methyl-1H-imidazol-1-yl)phenyl]-(Z)-methylidene}-tetrahydro[1,4]oxazino[3,4-c][1,4]oxazin-4-one and
75) (6R,9aR)-6-(4-chlorophenyl)-3-{1-[3-methoxy-4-(4-methyl-1H-imidazol-1-yl)phenyl]-(Z)-methylidene}-tetrahydro[1,4]oxazino[3,4-c]oxazin-4-one;
17) A pharmaceutical agent comprising the compound or pharmacologically acceptable salt thereof according to any of 1) to 16) above as an active ingredient;
18) The pharmaceutical agent according to 17) above for preventing or treating a disease caused by amyloid-β; and
19) The pharmaceutical agent according to 18) above, wherein the disease, caused by amyloid-β is Alzheimer's disease, senile dementia, Down's syndrome, or amyloidosis.

The compound of the general formula (I) or pharmacologically acceptable salt thereof according to the present invention and the prophylactic or therapeutic agent for a disease caused by Aβ according to the present invention are novel inventions that have not yet been described in any documents.

DETAILED DESCRIPTION OF THE INVENTION

Meanings of symbols, terms, and the like used in the present specification will be explained, and the present invention will be described in detail below.

In the present specification, a structural formula of a compound may represent a certain isomer for convenience. However, the present invention includes all isomers and isomer mixtures such as geometric isomers which can be generated from the structure of a compound, optical isomers based on asymmetric carbon, stereoisomers, and tautomers. The present invention is not limited to the description of a chemical formula for convenience, and may include any one of the isomers or mixtures thereof. Accordingly, the compound of the present invention may have an asymmetric carbon atom in the molecule, and exist as an optically active compound or racemate, and the present invention includes each of the optically active compound and the racemate without limitations. Although crystal polymorphs of the compound may be present, the compound is not limited thereto as well and may be present as a single crystal form or a mixture of single crystal forms. The compound may be an anhydride or hydrate.

The "disease caused by Aβ" refers to a wide variety of diseases such as Alzheimer's disease (see Klein W L, and seven others, Alzheimer's disease-affected brain: Presence of oligomeric Aβ ligands (ADDLs) suggests a molecular basis for reversible memory loss, Proceeding National Academy of Science USA, 2003, Sep. 2, 100(18), p. 10417-10422; Nitsch R M, and sixteen others, Antibodies against β-amyloid-slow cognitive decline in Alzheimer's disease, Neuron, 2003, May 22, 38(4), p. 547-554; Jarrett J T, and two others, The carboxy terminus of the β amyloid protein is critical for the seeding of amyloid formation: Implications for the pathogenesis of Alzheimer's disease, Biochemistry, 1993, May 11, 32(18), p. 4693-4697; Glenner G G, and one other, Alzheimer's disease: initial report of the purification and characterization of a novel cerebrovascular amyloid protein, Biochemical and biophysical research communications, 1984, May 16, 120(3), p. 885-890; Masters C L, and six others, Amyloid plaque core protein in Alzheimer disease and Down syndrome, Proceeding National Academy of Science USA, 1985, June, 82(12), p. 4245-4249; Gouras G K, and eleven others, Intraneuronal Aβ42 accumulation in human brain, American journal of pathology, 2000, January, 156(1), p. 15-20; Scheuner D, and twenty others, Secreted amyloid β-protein similar to that in the senile plaques of Alzheimer's disease is increased in vivo by the presenilin 1 and 2 and APP mutations linked to familial Alzheimer's disease, Nature Medicine, 1996, August, 2(8), p. 864-870; and Forman M S, and four others, Differential effects of the swedish mutant amyloid precursor protein on β-amyloid accumulation and secretion in neurons and non-neuronal cells, The journal of biological chemistry, 1997, Dec. 19, 272(51), p. 32247-32253, for example), senile dementia (see Blass J P, Brain metabolism and brain disease: Is metabolic deficiency the proximate cause of Alzheimer dementia? Journal of Neuroscience Research, 2001; Dec. 1, 66(5); p. 851-856, for example), frontotemporal dementia (see Evin G, and eleven others, Alternative transcripts of presenilin-1 associated with frontotemporal dementia, Neuroreport, 2002, Apr. 16, 13(5), p. 719-723, for example), Pick's disease (see Yasuhara O, and three others, Accumulation of amyloid precursor protein in brain lesions of patients with Pick disease, Neuroscience Letters, 1994, Apr. 25, 171 (1-2), p. 63-66, for example), Down's syndrome (see Teller J K, and ten others, Presence of soluble amyloid β-peptide precedes amyloid plaque formation in Down's syndrome, Nature Medicine, 1996, January, 2(1), p. 93-95; and Tokuda T, and six others, Plasma levels of amyloid β proteins Aβ1-40 and Aβ1-42(43) are elevated in Down's syndrome, Annals of Neurology, 1997, February, 41(2), p. 271-273, for example), cerebral angiopathy (see Hayashi Y, and nine others, Evidence for presenilin-1 involvement in amyloid angiopathy in the Alzheimer's disease-affected brain, Brain Research, 1998, Apr. 13, 789(2), p. 307-314; Barelli H, and fifteen others, Characterization of new polyclonal antibodies specific for 40 and 42 amino acid-long amyloid β peptides: their use to examine the cell biology of presenilins and the immunohistochemistry of sporadic Alzheimer's disease and cerebral amyloid angiopathy cases, Molecular Medicine, 1997, October, 3(10), p. 695-707; Calhoun M E, and ten others, Neuronal overexpression of mutant amyloid precursor protein results in prominent deposition of cerebrovascular amyloid, Proceeding National Academy of Science USA, 1999, Nov. 23, 96(24), p. 14088-14093; and Dermaut B, and ten others, Cerebral amyloid angiopathy is a pathogenic lesion in Alzheimer's Disease due to a novel presenilin-1 mutation, Brain, 2001, December, 124(12), p. 2383-2392, for example), hereditary cerebral hemorrhage with amyloidosis (Dutch type) (see Cras P, and nine others, Presenile Alzheimer dementia characterized by amyloid angiopathy and large amyloid core type senile plaques in the APP 692Ala-->Gly mutation, Acta Neuropathologica (Berl), 1998, September, 96(3), p. 253-260; Herzig M C, and fourteen others, Aβ is targeted to the vasculature in a mouse model of hereditary cerebral hemorrhage with amyloidosis, Nature Neuroscience, 2004, September, 7(9), p. 954-960; van Duinen S G, and five others, Hereditary cerebral hemorrhage with amyloidosis in patients of Dutch origin is related to Alzheimer disease, Proceeding National Academy of Science USA, 1987, August, 84(16), p. 5991-5994; and Levy E, and eight others, Mutation of the Alzheimer's disease amyloid gene in hereditary cerebral hemorrhage, Dutch type, Science, 1990, Jun. 1, 248(4959), p. 1124-1126, for example), cognitive impairment (see Laws S M, and seven others, Association between the presenilin-1 mutation Glu318Gly and complaints of memory impairment, Neurobiology of Aging, 2002, January-February, 23(1), p. 55-58, for example), memory disorder and learning disability (see Vaucher E, and five others, Object recognition memory and cholineraic parameters in mice expressing human presenilin 1 transgenes, Experimental Neurology, 2002 June, 175(2), p. 398-406; Morgan D, and fourteen others, Aβ peptide vaccination prevents memory loss in an animal model of Alzheimer's disease, Nature, 2000 Dec. 21-28, 408(6815), p. 982-985; and Moran P M, and three others, Age-related learning deficits in transgenic mice expressing the 751-amino acid isoform of human β-amyloid precursor protein, Proceeding National Academy of Science USA, 1995, Jun. 6, 92(12), p. 5341-5345, for example), amyloidosis, cerebral ischemia (see Laws S M, and seven others, Association between the presenilin-1 mutation Glu318Gly and complaints of memory impairment, Neurobiology of Aging, 2002, January-February, 23(1), p. 55-58; Koistinaho M, and ten others, β-amyloid precursor protein transgenic mice that harbor diffuse Aβ deposits but do not form plaques show increased ischemic vulnerability: Role of inflammation, Proceeding National Academy of Science USA, 2002, Feb. 5, 99(3), p. 1610-1615; and Zhang F, and four others, Increased susceptibility to ischemic brain damage in transgenic mice overexpressing the amyloid precursor protein, The journal of neuroscience, 1997, Oct. 15, 17(20), p. 7655-7661, for example), vascular dementia (see Sadowski M, and six others, Links between the pathology of Alzheimer's disease and vascular dementia, Neurochemical Research, 2004, June, 29(6), p. 1257-1266, for example), ophthalmoplegia (see O'Riordan S, and seven others, Presenilin-1 mutation (E280G), spastic paraparesis, and cranial MRI white-matter abnormalities, Neurology, 2002, Oct. 8, 59(7), p. 1108-1110, for example), multiple sclerosis (see Gehrmann J, and four others, Amyloid precursor protein (APP) expression in multiple sclerosis lesions, Glia, 1995, October, 15(2), p. 141-51; and Reynolds W F, and six others, Myeloperoxidase polymorphism is associated with gender specific risk for Alzheimer's disease, Experimental Neurology, 1999, January, 155(1), p. 31-41, for example), head injury, cranial trauma (see Smith D H, and four others, Protein accumulation in traumatic brain injury, NeuroMolecular Medicine, 2003, 4(1-2), p. 59-72, for example), apraxia (see Matsubara-Tsutsui M, and seven others, Molecular evidence of presenilin 1 mutation in familial early onset dementia, American journal of Medical Genetics, 2002, Apr. 8, 114(3), p. 292-298, for example), prion disease, familial amyloid neuropathy, triplet repeat disease (see Kirkitadze M D, and two others, Paradigm shifts in Alzheimer's disease and other neurodegenerative disorders: the emerging role of oligomeric assemblies, Journal of Neuroscience Research, 2002, Sep. 1, 69(5), p. 567-577; Evert B O, and eight others, Inflammatory genes are upreglulated in expanded ataxin-3-expressing cell lines and spinocerebellar ataxia type 3 brains, The Journal of Neuroscience, 2001, Aug. 1, 21(15), p. 5389-5396; and Mann D M, and one other, Deposition of amyloid (A4) protein within the brains of persons with dementing disorders other than Alzheimer's disease and Down's syndrome, Neuroscience Letters, 1990, Feb. 5, 109(1-2), p. 68-75, for example), Parkinson's disease (see Primavera J, and four others, Brain accumulation of amyloid-β in Non-Alzheimer Neurodegeneration, Journal of Alzheimer's Disease, 1999, October, 1(3), p. 183-193, for example), Lewy body dementia (see Giasson B I, and two others, Interactions of amyloidogenic proteins. NeuroMolecular Medicine, 2003, 4(1-2), p. 49-58; Masliah E, and six others, β-amyloid peptides enhance α-synuclein accumulation and neuronal deficits in a trancgenic mouse model linking Alzheimer's disease and Parkinson's disease, Proceeding National Academy of Science USA, 2001, Oct. 9, 98(21), p. 12245-12250; Barrachina M, and six others, Amyloid-β deposition in the cerebral cortex in Dementia with Lewy bodies is accompanied by a relative increase in AβPP mRNA isoforms containing the Kunitz protease inhibitor, Neurochemistry International, 2005, February, 46(3), p. 253-260; and Primavera J, and four others, Brain accumulation of amyloid-β in Non-Alzheimer Neurodegeneration, Journal of Alzheimer's Disease, 1999, October, 1(3), p. 183-193, for example), parkinsonism-dementia complex (see Schmidt M L, and six others, Amyloid plaques in Guam amyotrophic lateral sclerosis/parkinsonism-dementia complex contain species of Aβ similar to those found in the amyloid plaques of Alzheimer's disease and pathological aging, Acta Neuropathologica (Berl), 1998, February, 95(2), p. 117-122; and Ito H, and three others, Demonstration of β amyloid protein-containing neurofibrillary tangles in parkinsonism-dementia complex on Guam, Neuropathology and applied neurobiology, 1991, October, 17(5), p. 365-373, for example), frontotemporal dementia and parkinsonism linked to chromosome 17 (see Rosso S M, and three others, Coexistent tau andamyloid pathology in hereditary frontotemporal dementia with tau mutations, Annals of the New York academy of sciences, 2000, 920, p. 115-119, for example), dementia with argyrophilic grains (see Tolnay M, and four others, Low amyloid (Aβ) plaque load and relative predominance of diffuse plaques distinguish argyrophilic grain disease from Alzheimer's disease, Neuropathology and applied neurobiology, 1999, August, 25(4), p. 295-305, for example), Niemann-Pick disease (see Jin L W, and three others, Intracellular accumulation of amyloidogenic fragments of amyloid-β precursor protein in neurons with Niemann-Pick type C defects is associated with endosomal abnormalities, American Journal of Pathology, 2004, March, 164(3), p. 975-985, for example), amyotrophic lateral sclerosis (see Sasaki S, and one other, Immunoreactivity of β-amyloid precursor protein in amyotrophic lateral sclerosis, Acta Neuropathologica (Berl), 1999, May, 97(5), p. 463-468; Tamaoka A, and four others, Increased amyloid β protein in the skin of patients with amyotrophic lateral sclerosis, Journal of neurology, 2000, August, 247(8), p. 633-635; Hamilton R L, and one other, Alzheimer disease pathology in amyotrophic lateral sclerosis, Acta Neuropathologica, 2004, June, 107(6), p. 515-522; and Turner B J, and six others, Brain β-amyloid accumulation in transgenic mice expressing mutant superoxide dismutase 1, Neurochemical Research, 2004, December, 29(12), p. 2281-2286, for example), hydrocephalus (see Weller RO, Pathology of cerebrospinal fluid and interstitial fluid of the CNS: Significance for Alzheimer disease, prion disorders and multiple sclerosis, Journal of Neuropathology and Experimental Neurology, 1998, October, 57(10), p. 885-894; Silverberg GD, and four others, Alzheimer's disease, normal-pressure hydrocephalus, and senescent changes in CSF circulatory physiology: a hypothesis, Lancet neurology, 2003, August, 2(8), p. 506-511; Weller RO, and three others, Cerebral amyloid angiopathy: Accumulation of Aβ in interstitial fluid drainage pathways in Alzheimer's disease, Annals of the New York academy of sciences, 2000, April, 903, p. 110-117; Yow HY, and one other, A role for cerebrovascular disease in determining the pattern of β-amyloid deposition in Alzheimer's disease, Neurology and applied neurobiology, 2002, 28, p. 149; and Weller R O, and four others, Cerebrovascular disease is a major factor in the failure of elimination of Aβ from the aging human brain, Annals of the New York academy of sciences, 2002, November, 977, p. 162-168, for example), paraparesis (see O'Riordan S, and seven others, Presenilin-1 mutation (E280G), spastic paraparesis, and cranial MRI white-matter abnormalities, Neurology, 2002, Oct. 8, 59(7), p. 1108-1110; Matsubara-Tsutsui M, and seven others, Molecular evidence of presenilin 1 mutation in familial early onset dementia, American journal of Medical Genetics, 2002, Apr. 8, 114(3), p. 292-298; Smith M J, and eleven others, Variable phenotype of Alzheimer's disease with spastic paraparesis, Annals of Neurology, 2001, 49(1), p. 125-129; and Crook R, and seventeen others, A variant of Alzheimer's disease with spastic pararesis and unusual plaques due to deletion of exon 9 of presenilin 1, Nature Medicine, 1998, April; 4(4), p. 452-455, for example), progressive supranuclear palsy (see Barrachina M, and six others, Amyloid-β deposition in the cerebral cortex in Dementia with Lewy bodies is accompanied by a relative increase in AβPP mRNA isoforms containing the Kunitz protease inhibitor, Neurochemistry International, 2005, February, 46(3), p. 253-260; and Primavera J, and four others, Brain accumulation of amyloid-β in Non-Alzheimer Neurodegeneration, Journal of Alzheimer's Disease, 1999, October, 1(3), p. 183-193, for example), intracerebral hemorrhage (see Atwood C S, and three others, Cerebrovascular requirement for sealant, anticoagulant and remodeling molecules that allow for the maintenance of vascular integrity and blood supply, Brain Research Reviews, 2003, September, 43(1), p. 164-78; and Lowenson J D, and two others, Protein aging: Extracellular amyloid formation and intracellular repair, Trends in cardiovascular medicine, 1994, 4(1), p. 3-8, for example), convulsion (see Singleton A B, and thirteen others, Pathology of early-onset Alzheimer's disease cases bearing the Thr113-114ins presenilin-1 mutation, Brain, 2000, December, 123(Pt 12), p. 2467-2474, for example), mild cognitive impairment (see Gattaz W F, and four others, Platelet phospholipase A2 activity in Alzheimer's disease and mild cognitive impairment, Journal of Neural Transmission, 2004, May, 111(5), p. 591-601; and Assini A, and fourteen others, Plasma levels of amyloid β-protein 42 are increased in women with mild cognitive impairment, Neurology, 2004, Sep. 14, 63(5), p. 828-831, for example), and arteriosclerosis (see De Meyer G R, and eight others, Platelet phagocytosis and processing of β-amyloid precursor protein as a mechanism of macrophage activation in atherosclerosis, Circulation Research, 2002, Jun. 14, 90(11), p. 1197-1204, for example).

The "C1-6 alkylene group" refers to an alkylene group having 1 to 6 carbon atoms. Preferable examples of the group include a methylene group, ethylene group, propylene group, butylene group, and pentylene group.

The "C1-6 alkyl group" refers to an alkyl group having 1 to 6 carbon atoms. Preferable examples of the group include linear or branched alkyl groups such as a methyl group, ethyl group, n-propyl group, i-propyl group, n-butyl group, i-butyl group, tert-butyl group, n-pentyl group, i-pentyl group, neopentyl group, n-hexyl group, 1-methylpropyl group, 1,2-dimethylpropyl group, 1-ethylpropyl group, 1-methyl-2-ethylpropyl group, 1-ethyl-2-methylpropyl group, 1,1,2-trimethylpropyl group, 1-methylbutyl group, 2-methylbutyl group, 1,1-dimethylbutyl group, 2,2-dimethylbutyl group, 2-ethylbutyl group, 1,3-dimethylbutyl group, 2-methylpentyl group, and 3-methylpentyl group.

The "C3-13 cycloalkyl group" refers to a cyclic alkyl group having 3 to 13 carbon atoms. Preferable examples of the group include a cyclopropyl group, cyclobutyl group, cyclopentyl group, cyclohexyl group, cycloheptyl group, cyclooctyl group, cyclononanyl group, cyclodecanyl group, cycloundecanyl group, cyclododecanyl group, and cyclotridecanyl group.

The "aryl group" refers to a "6- to 14-membered cyclic aromatic hydrocarbon group" or a "5- to 14-membered aromatic heterocyclic group". The "6- to 14-membered cyclic aromatic hydrocarbon group" used herein refers to a monocyclic, bicyclic, or tricyclic aromatic hydrocarbon group having 6 to 14 carbon atoms. Preferable examples of the group include 6- to 14-membered monocyclic, bicyclic, or tricyclic aromatic hydrocarbon groups such as a phenyl group, indenyl group, naphthyl group, azulenyl group, heptalenyl group, biphenyl group, fluorenyl group, phenalenyl group, phenanthrenyl group, and anthracenyl group. The "5- to 14-membered aromatic heterocyclic group" refers to a monocyclic, bicyclic, or tricyclic aromatic heterocyclic group having 5 to 14 carbon atoms. Preferable examples of the group include (1) nitrogen-containing aromatic heterocyclic groups such as a pyrrolyl group, pyridyl group, pyridazinyl group, pyrimidinyl group, pyrazinyl group, pyrazolinyl group, imidazolyl group, indolyl group, isoindolyl group, indolizinyl group, purinyl group, indazolyl group, quinolyl group, isoquinolyl group, quinolizinyl group, phthalazinyl group, naphthyridinyl group, quinoxalinyl group, quinazolinyl group, cinnolinyl group, pteridinyl group, imidazotriazinyl group, pyrazinopyridazinyl group, acridinyl group, phenanthridinyl group, carbazolyl group, perimidinyl group, phenanthrolinyl group, and phenacyl group, (2) sulfur-containing aromatic heterocyclic groups such as a thienyl group and benzothienyl group, (3) oxygen-containing aromatic heterocyclic groups such as a furyl group, pyranyl group, cyclopentapyranyl group, benzofuranyl group, and isobenzofuranyl group, and (4) aromatic heterocyclic groups containing two or more hetero atoms selected from the group consisting of a nitrogen atom, sulfur atom, and oxygen atom such as a thiazolyl group, isothiazolyl group, benzothiazolinyl group, benzothiadiazolyl group, phenothiazinyl group, isoxazolyl group, furazanyl group, phenoxazinyl group, pyrazoloxazolyl group, imidazothiazolyl group, thienofuryl group, furopyrrolyl group, and pyridooxazinyl group.

The "aryloxy group" refers to a group in which a hydrogen atom on the aromatic hydrocarbon ring of the "6- to 14-membered cyclic aromatic hydrocarbon group" or a hydrogen atom on the aromatic heterocycle of the "5- to 14-membered aromatic heterocyclic group" is substituted with an oxygen atom.

The "C3-8 cycloalkyl group condensed with a benzene ring" may be, for example, a group of the formula:

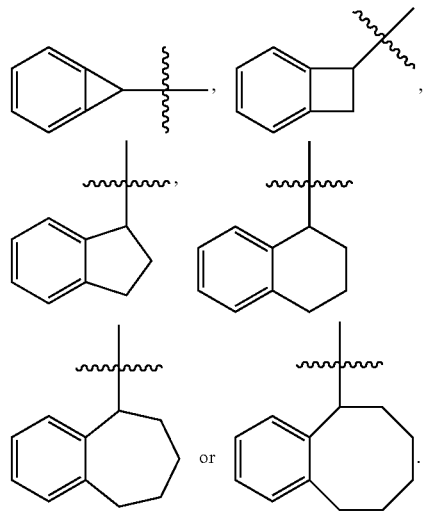

The benzene ring may be substituted with 1 to 3 substituents selected from Substituent Group A1; one methylene group on the C3-8 cycloalkyl group may be substituted with an oxygen atom; and the C3-8 cycloalkyl group may be substituted with 1 to 3 hydroxyl groups and/or C1-6 alkyl groups.

The "4- to 8-membered nitrogen-containing heterocyclic group formed by $Ar_1$—$X_1$— and $R^4$ together with the nitrogen atom to which $Ar_1$—$X_1$— is bonded and the carbon atom to which $R^4$ is bonded" may be, for example, a group of the formula:

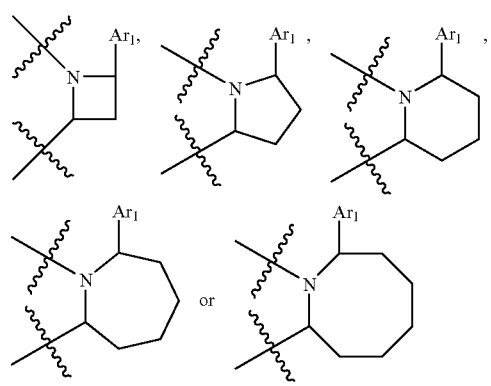

The 4- to 8-membered nitrogen-containing heterocyclic group may be substituted with an aryl group or pyridinyl group, wherein the aryl group or pyridinyl group may be substituted with 1 to 3 substituents selected from Substituent Group A1. In addition, one methylene group on the 4- to 8-membered nitrogen-containing heterocyclic group may be substituted with a methylene group substituted with 1 or 2 substituents selected from Substituent Group A1, a vinylene group that may be substituted with 1 or 2 substituents selected from Substituent Group A1, an oxygen atom, or an imino group that may be substituted with a substituent selected from Substituent Group A1.

The 4- to 8-membered nitrogen-containing heterocyclic group having one methylene group that may be substituted with a methylene group substituted with 1 or 2 substituents selected from Substituent Group A1, a vinylene group that may be substituted with 1 or 2 substituents selected from Substituent Group A1, an oxygen atom, or an imino group that may be substituted with a substituent selected from Substituent Group A1 may be, for example, a group specifically represented by the formula:

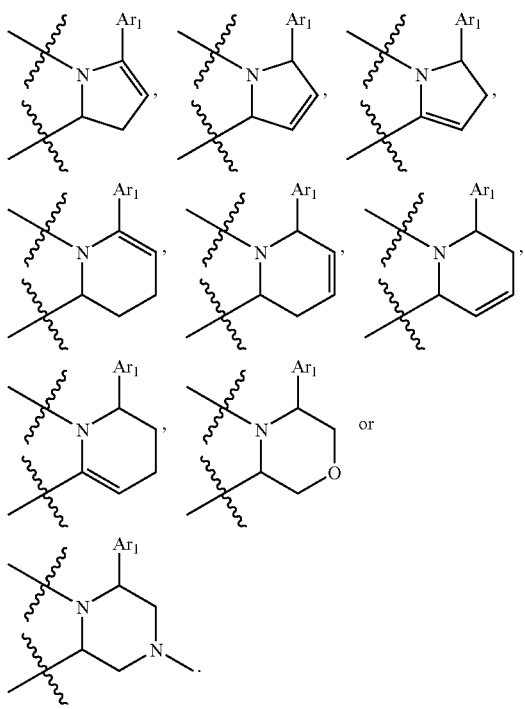

The "C1-6 acyl group" used herein refers to an acyl group having 1 to 6 carbon atoms. Preferable examples of the group include a formyl group, acetyl group, propionyl group, butyryl group, isobutyryl group, pentanoyl group, and hexanoyl group.

The "C3-8 cycloalkyl group formed by $R^1$ and $R^2$ together with the carbon atom to which they are bonded" or the "C3-8 cycloalkyl group formed by $R^3$ and $R^4$ together with the carbon atom to which they are bonded" may be, for example, a group specifically represented by the formula:

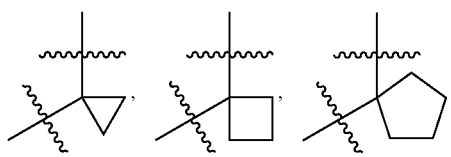

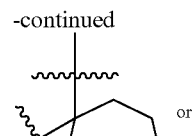

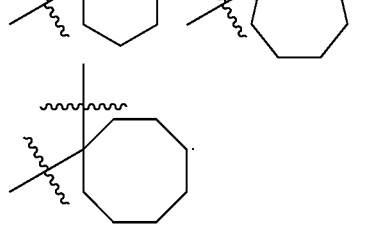

The "C1-6 alkylene group, wherein the C1-6 alkylene group may be substituted with 1 to 3 hydroxyl groups or C1-6 alkyl groups, wherein the C1-6 alkyl groups may be substituted with 1 to 3 hydroxyl groups, or a C3-13 cycloalkyl group formed by two C1-6 alkyl groups together bonded to the same carbon atom of the C1-6 alkylene group" may be, for example, a group specifically represented by the formula:

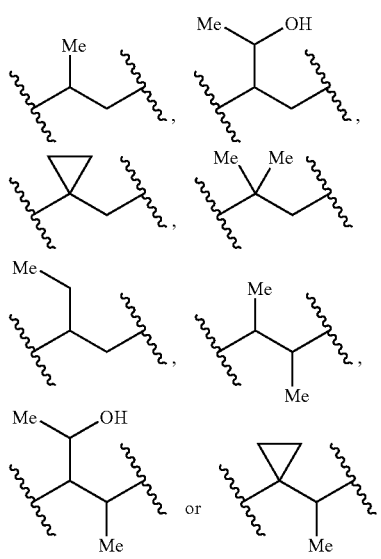

Substituent Groups A1 refers to the following groups.

Substituent Group A1: (1) a halogen atom, (2) a hydroxyl group, (3) a cyano group, (4) a C3-8 cycloalkyl group, (5) a C3-8 cycloalkoxy group, (6) a C1-6 alkyl group, wherein the C1-6 alkyl group may be substituted with 1 to 5 halogen atoms or one to three C1-6 alkoxy groups, (7) an amino group that may be substituted with one or two C1-6 alkyl groups, wherein the C1-6 alkyl groups may be substituted with 1 to 5 halogen atoms, (8) a C1-6 alkoxy group, wherein the C1-6 alkoxy group may be substituted with 1 to 5 halogen atoms, and (9) a carbamoyl group that may be substituted with one or two C1-6 alkyl groups, wherein the C1-6 alkyl groups may be substituted with 1 to 3 halogen atoms.

The "halogen atom" used herein refers to a fluorine atom, chlorine atom, bromine atom, iodine atom, or the like, and is preferably a fluorine atom, chlorine atom, or bromine atom.

The "C3-8 cycloalkyl group" refers to a cyclic alkyl group having 3 to 8 carbon atoms. Preferable examples of the group include a cyclopropyl group, cyclobutyl group, cyclopentyl group, cyclohexyl group, cycloheptyl group, and cyclooctyl group.

The "C3-8 cycloalkoxy group" refers to a cyclic alkyl group having 3 to 8 carbon atoms in which one hydrogen atom is substituted with an oxygen atom. Preferable examples of the group include a cyclopropoxy group, cyclobutoxy group, cyclopentoxy group, cyclohexoxy group, cycloheptyloxy group, and cyclooctyloxy group.

The "C1-6 alkyl group" is as defined above, and specific examples of the group are as described above.

The "C1-6 alkoxy group" refers to an alkyl group having 1 to 6 carbon atoms in which a hydrogen atom is substituted with an oxygen atom. Preferable examples of the group include a methoxy group, ethoxy group, n-propoxy group, i-propoxy group, n-butoxy group, i-butoxy group, sec-butoxy group, tert-butoxy group, n-pentoxy group, i-pentoxy group, sec-pentoxy group, tert-pentoxy group, n-hexoxy group, i-hexoxy group, 1,2-dimethylpropoxy group, 2-ethylpropoxy group, 1-methyl-2-ethylpropoxy group, 1-ethyl-2-methylpropoxy group, 1,1,2-trimethylpropoxy group, 1,1,2-trimethylpropoxy group, 1,1-dimethylbutoxy group, 2,2-dimethylbutoxy group, 2-ethylbutoxy group, 1,3-dimethylbutoxy group, 2-methylpentoxy group, 3-methylpentoxy group, and hexyloxy group.

The "amino group that may be substituted with one or two C1-6 alkyl group" refers to an amino group in which one or two hydrogen atoms are substituted with one or two alkyl groups having 1 to 6 carbon atoms. Preferable examples of the group include a methylamino group, dimethylamino group, ethylamino group, diethylamino group, n-propylamino group, and di-n-propylamino group.

The "carbamoyl group that may be substituted with one or two C1-6 alkyl group" refers to a carbamoyl group in which one or two hydrogen atoms are substituted with one or two alkyl groups having 1 to 6 carbon atoms. Preferable examples of the group include a methylcarbamoyl group, dimethylcarbamoyl group, ethylcarbamoyl group, diethylcarbamoyl group, n-propylcarbamoyl group, and di-n-propylcarbamoyl group.

In the present specification, there are no specific limitations to the "pharmacologically acceptable salt" insofar as it is a pharmacologically acceptable salt formed with a compound of the general formula (I) that is a prophylactic or therapeutic agent for a disease caused by Aβ. Preferable specific examples of the salt include hydrohalides (such as hydrofluorides, hydrochlorides, hydrobromides, and hydroiodides), inorganic acid salts (such as sulfates, nitrates, perchlorates, phosphates, carbonates, and bicarbonates), organic carboxylates (such as acetates, oxalates, maleates, tartrates, fumarates, and citrates), organic sulfonates (such as methanesulfonates, trifluoromethanesulfonates, ethanesulfonates, benzenesulfonates, toluenesulfonates, and camphorsulfonates), amino acid salts (such as aspartates and glutamates), quaternary amine salts, alkali metal salts (such as sodium salts and potassium salts), and alkali earth metal salts (such as magnesium salts and calcium salts).

Next, the compound of the formula (I) of the present invention will be described.

In the compound of the formula (I) or pharmacologically acceptable salt thereof, preferably, (a) $R^1$, $R^2$, $R^3$, and $R^4$ are the same or different and each represent a hydrogen atom or a C1-6 alkyl group;

$X_1$ represents a C1-6 alkylene group, wherein the C1-6 alkylene group may be substituted with 1 to 3 hydroxyl groups or C1-6 alkyl groups, wherein the C1-6 alkyl groups may be substituted with 1 to 3 hydroxyl groups, or a C3-13 cycloalkyl group formed by two C1-6 alkyl groups together bonded to the same carbon atom of the C1-6 alkylene group;

$X_a$ represents a methoxy group or a fluorine atom;

$X_b$ represents an oxygen atom or a methylene group, provided that $X_b$ is only an oxygen atom when $X_a$ is a methoxy group; and $Ar_1$ represents an aryl group, pyridinyl group, aryloxy group, or pyridinyloxy group that may be substituted with 1 to 3 substituents selected from Substituent Group A1;

(b) $Ar_1$—$X_1$— represents a C3-8 cycloalkyl group condensed with a benzene ring, wherein one methylene group on the C3-8 cycloalkyl group may be substituted with an oxygen atom, the C3-8 cycloalkyl group may be substituted with 1 to 3 hydroxyl groups and/or C1-6 alkyl groups, and the benzene ring may be substituted with 1 to 3 substituents selected from Substituent Group A1; and $R^1$, $R^2$, $R^3$, $R^4$, $X_a$, and $X_b$ are as defined in (a);

(c) one of $R^1$ and $R^2$ and one of $R^3$ and $R^4$ are the same or different and each represent a hydrogen atom or a C1-6 alkyl group; the other of $R^1$ and $R^2$ and the other of $R^3$ and $R^4$, together with the carbon atoms to which they are respectively bonded, form a C3-8 cycloalkyl group, wherein the C3-8 cycloalkyl group may be substituted with 1 to 3 substituents selected from Substituent Group A1; and $X_1$, $X_a$, $X_b$, and $Ar_1$ are as defined in (a) or (b);

(d) $Ar_1$—$X_1$— and $R^4$, together with the nitrogen atom to which $Ar_1$—$X_1$— is bonded and the carbon atom to which $R^4$ is bonded, form a 4- to 8-membered nitrogen-containing heterocyclic group that may be substituted with an aryl group or pyridinyl group, wherein one methylene group on the 4- to 8-membered nitrogen-containing heterocyclic group may be substituted with a methylene group substituted with 1 or 2 substituents selected from Substituent Group A1, a vinylene group that may be substituted with 1 to 3 substituents selected from Substituent Group A1, an oxygen atom, or an imino group that may be substituted with a substituent selected from Substituent Group A1, and the aryl group or pyridinyl group may be substituted with 1 to 3 substituents selected from Substituent Group A1; $X_b$ represents an oxygen atom; and $R^1$, $R^2$, $R^3$, and $X_a$ are as defined in (a) and (b);

(e) $R^1$ and $R^2$, together with the carbon atom to which they are bonded, form a C3-8 cycloalkyl group; and $R^3$, $R^4$, $X_1$, $X_a$, $X_b$, and $Ar_1$ are as defined in (a) and (b); or (f) $R^3$ and $R^4$, together with the carbon atom to which they are bonded, form a C3-8 cycloalkyl group; and $R^1$, $R^2$, $X_1$, $X_a$, $X_b$, and $Ar_1$ are as defined in (a) and (b), and particularly preferably, (a) $R^1$, $R^2$, $R^3$, and $R^4$ are the same or different and each represent a hydrogen atom or a C1-6 alkyl group;

$X_1$ represents a C1-6 alkylene group, wherein the C1-6 alkylene group may be substituted with 1 to 3 hydroxyl groups or C1-6 alkyl groups, wherein the C1-6 alkyl groups may be substituted with 1 to 3 hydroxyl $X_a$ represents a methoxy group or a fluorine atom;

$X_b$ represents an oxygen atom or a methylene group, provided that $X_b$ is only an oxygen atom when $X_a$ is a methoxy group; and $Ar_1$ represents an aryl group, pyridinyl group, aryloxy group, or pyridinyloxy group that may be substituted with 1 to 3 substituents selected from Substituent Group A1;

(b) $Ar_1$—$X_1$— represents a C3-8 cycloalkyl group condensed with a benzene ring, wherein one methylene group on the C3-8 cycloalkyl group may be substituted with an oxygen atom, the C3-8 cycloalkyl group may be substituted with 1 to 3 hydroxyl groups and/or C1-6 alkyl groups, and the benzene ring may be substituted with 1 to 3 substituents selected from Substituent Group A1; and $R^1$, $R^2$, $R^3$, $R^4$, $X_a$, and $X_b$ are as defined in (a); or (d) $Ar_1$—$X_1$— and $R^4$, together with the nitrogen atom to which $Ar_1$—$X_1$— is bonded and the carbon atom to which $R^4$ is bonded, form a 4- to 8-membered nitrogen-containing heterocyclic group that may be substituted with an aryl group or pyridinyl group, wherein one methylene group on the 4- to 8-membered nitrogen-containing heterocyclic group may be substituted with a methylene group substituted with 1 or 2 substituents selected from Substituent Group A1, a vinylene group that may be substituted with 1 to 3 substituents selected from Substituent Group A1, an oxygen atom, or an imino group that may be substituted with a substituent selected from Substituent Group A1, and the aryl group or pyridinyl group may be substituted with 1 to 3 substituents selected from Substituent Group A1; $X_b$ represents an oxygen atom; and $R^1$, $R^2$, $R^3$, and $X_a$ are as defined in (a) and (b).

In the compound of the formula (I) or pharmacologically acceptable salt thereof, $Ar_1$ is preferably an aryl group or pyridinyl group, or an aryl group or pyridinyl group substituted with 1 to 3 halogen atoms.

In the compound of the formula (I) or pharmacologically acceptable salt thereof, $Ar_1$ is more preferably a phenyl group or pyridinyl group, or a phenyl group or pyridinyl group substituted with 1 to 3 halogen atoms.

In the compound of the formula (I) or pharmacologically acceptable salt thereof, $X_a$ preferably represents a methoxy group or a fluorine atom.

In the compound of the formula (I) or pharmacologically acceptable salt thereof, $X_b$ preferably represents an oxygen atom or a methylene group, provided that $X_b$ is only an oxygen atom when $X_a$ is a methoxy group.

In the compound of the formula (I) or pharmacologically acceptable salt thereof, preferably, 1) $R^1$, $R^2$, $R^3$, and $R^4$ are the same or different and each represent a hydrogen atom or a C1-6 alkyl group; 2) one of $R^1$ and $R^2$ and one of $R^3$ and $R^4$ are the same or different and each represent a hydrogen atom or a C1-6 alkyl group; and the other of $R^1$ and $R^2$ and the other of $R^3$ and $R^4$, together with the carbon atoms to which they are respectively bonded, form a C3-8 cycloalkyl group, wherein the C3-8 cycloalkyl group may be substituted with 1 to 3 substituents selected from Substituent Group A1; 3) $R^1$ and $R^2$, together with the carbon atom to which they are bonded, form a C3-8 cycloalkyl group; and $R^3$ and $R^4$ are the same or different and each represent a hydrogen atom or a C1-6 alkyl group; or 4) $R^3$ and $R^4$, together with the carbon atom to which they are bonded, form a C3-8 cycloalkyl group; and $R^1$ and $R^2$ are the same or different and each represent a hydrogen atom or a C1-6 alkyl group.

In the compound of the formula (I) or pharmacologically acceptable salt thereof, $X_1$ preferably represents a C1-6 alkylene group, wherein the C1-6 alkylene group may be substituted with 1 to 3 hydroxyl groups or C1-6 alkyl groups, wherein the C1-6 alkyl groups may be substituted with 1 to 3 hydroxyl groups; $X_1$ more preferably represents —$CR^5R^6$—, wherein $R^5$ and $R^6$ are the same or different and each represent a hydrogen atom or a C1-6 alkyl group, wherein the C1-6 alkyl group may be substituted with 1 to 3 hydroxyl groups; and $X_1$ most preferably represents —CH—C(OH)$R^7$—, wherein $R^7$ represents a C1-6 alkyl group.

In the compound of the formula (I) or pharmacologically acceptable salt thereof, $Ar_1$ preferably represents an aryl group, pyridinyl group, aryloxy group, or pyridinyloxy group that may be substituted with 1 to 3 substituents selected from Substituent Group A1; and $Ar_1$ more preferably represents an aryl group or pyridinyl group that may be substituted with 1 to 3 substituents selected from Substituent Group A1.

In the compound of the formula (II) or pharmacologically acceptable salt thereof, $Ar_{1-a}$ preferably represents a phenyl group or pyridinyl group that may be substituted with 1 to 3 substituents selected from Substituent Group A1; and $Ar_{1-a}$ more preferably represents a phenyl group or pyridinyl group that may not be substituted or may be substituted with 1 to 3 halogen atoms.

In the compound of the formula (II) or pharmacologically acceptable salt thereof, preferably, $R^5$ and $R^6$ are the same or different and each represent a hydrogen atom or a C1-6 alkyl group, wherein the C1-6 alkyl group may be substituted with 1 to 3 hydroxyl groups.

In the compound of the formula (II) or pharmacologically acceptable salt thereof, $X_a$ preferably represents a methoxy group or a fluorine atom.

In the compound of the formula (II) or pharmacologically acceptable salt thereof, $X_b$ preferably represents an oxygen atom or a methylene group, provided that $X_b$ is only an oxygen atom when $X_a$ is a methoxy group.

In the compound of the formula (II) or pharmacologically acceptable salt thereof, preferably, 1) $R^1$, $R^2$, $R^3$, and $R^4$ are the same or different and each represent a hydrogen atom or a C1-6 alkyl group; 2) one of $R^1$ and $R^2$ and one of $R^3$ and $R^4$ are the same or different and each represent a hydrogen atom or a C1-6 alkyl group; and the other of $R^1$ and $R^2$ and the other of $R^3$ and $R^4$, together with the carbon atoms to which they are respectively bonded, form a C3-8 cycloalkyl group, wherein the C3-8 cycloalkyl group may be substituted with 1 to 3 substituents selected from Substituent Group A1; 3) $R^1$ and $R^2$, together with the carbon atom to which they are bonded, form a C3-8 cycloalkyl group; and $R^3$ and $R^4$ are the same or different and each represent a hydrogen atom or a C1-6 alkyl group; or 4) $R^3$ and $R^4$, together with the carbon atom to which they are bonded, form a C3-8 cycloalkyl group; and $R^1$ and $R^2$ are the same or different and each represent a hydrogen atom or a C1-6 alkyl group.

In the compound of the formula (I-a) or pharmacologically acceptable salt thereof, $X_1$ preferably represents a C1-6 alkylene group, wherein the C1-6 alkylene group may be substituted with 1 to 3 hydroxyl groups or C1-6 alkyl groups, wherein the C1-6 alkyl groups may be substituted with 1 to 3 hydroxyl groups; $X_1$ more preferably represents —$CR^5R^6$—, wherein $R^5$ and $R^6$ are the same or different and each represent a hydrogen atom or a C1-6 alkyl group, wherein the C1-6 alkyl group may be substituted with 1 to 3 hydroxyl groups; and $X_1$ most preferably represents —CH—C(OH)$R^7$—, wherein $R^7$ represents a C1-6 alkyl group.

In the compound of the formula (I-a) or pharmacologically acceptable salt thereof, $Ar_1$ preferably represents an aryl group; pyridinyl group, aryloxy group, or pyridinyloxy group that may be substituted with 1 to 3 substituents selected from Substituent Group A1;

and Ar$_1$ more preferably represents an aryl group or pyridinyl group that may be substituted with 1 to 3 substituents selected from Substituent Group A1.

In the compound of the formula (I-a) or pharmacologically acceptable salt thereof, preferably, 1) R$^1$, R$^2$, R$^3$, and R$^4$ are the same or different and each represent a hydrogen atom or a C1-6 alkyl group; 2) one of R$^1$ and R$^2$ and one of R$^3$ and R$^4$ are the same or different and each represent a hydrogen atom or a C1-6 alkyl group; and the other of R$^1$ and R$^2$ and the other of R$^3$ and R$^4$, together with the carbon atoms to which they are respectively bonded, form a C3-8 cycloalkyl group, wherein the C3-8 cycloalkyl group may be substituted with 1 to 3 substituents selected from Substituent Group A1; 3) R$^1$ and R$^2$, together with the carbon atom to which they are bonded, form a C3-8 cycloalkyl group; and R$^3$ and R$^4$ are the same or different and each represent a hydrogen atom or a C1-6 alkyl group; or 4) R$^3$ and R$^4$, together with the carbon atom to which they are bonded, form a C3-8 cycloalkyl group; and R$^1$ and R$^2$ are the same or different and each represent a hydrogen atom or a C1-6 alkyl group.

In the compound of the formula (I-b) or pharmacologically acceptable salt thereof, preferably, R$^{13}$ and R$^{14}$ are the same or different and represent a hydrogen atom or a substituent selected from Substituent Group A1; and more preferably, R$^{13}$ and R$^{14}$ are the same or different and each represent a hydrogen atom, a halogen atom, or a C1-6 alkoxy group.

In the compound of the formula (I-b) or pharmacologically acceptable salt thereof, Y preferably represents a methylene group or an oxygen atom.

In the compound of the formula (I-b) or pharmacologically acceptable salt thereof, preferably, 1) R$^1$, R$^2$, R$^3$, and R$^4$ are the same or different and each represent a hydrogen atom or a C1-6 alkyl group; 2) one of R$^1$ and R$^2$ and one of R$^3$ and R$^4$ are the same or different and each represent a hydrogen atom or a C1-6 alkyl group; and the other of R$^1$ and R$^2$ and the other of R$^3$ and R$^4$, together with the carbon atoms to which they are respectively bonded, form a C3-8 cycloalkyl group, wherein the C3-8 cycloalkyl group may be substituted with 1 to 3 substituents selected from Substituent Group A1; 3) R$^1$ and R$^2$, together with the carbon atom to which they are bonded, form a C3-8 cycloalkyl group; and R$^3$ and R$^4$ are the same or different and each represent a hydrogen atom or a C1-6 alkyl group; or 4) R$^3$ and R$^4$, together with the carbon atom to which they are bonded, form a C3-8 cycloalkyl group; and R$^1$ and R$^2$ are the same or different and each represent a hydrogen atom or a C1-6 alkyl group.

In the compound of the formula (I-c) or pharmacologically acceptable salt thereof, Ar$_{1-c}$ preferably represents a phenyl group or pyridinyl group that may be substituted with 1 to 3 substituents selected from Substituent Group A1; and Ar$_{1-c}$ more preferably represents a phenyl group or pyridinyl group that may not be substituted or may be substituted with 1 to 3 halogen atoms.

In the compound of the formula (I-c) or pharmacologically acceptable salt thereof, Z$_1$ preferably represents a methylene group or vinylene group that may be substituted with 1 or 2 substituents selected from Substituent Group A1, an oxygen atom, or an imino group that may be substituted with a substitutent selected from Substituent Group A1; Z$_1$ more preferably represents a methylene group that may be substituted with 1 or 2 substituents selected from Substituent Group A1, or an oxygen atom; and Z$_1$ most preferable represents a methylene group, wherein the methylene group may be substituted with 1 or 2 substituents which are the same or different and selected from the group consisting of a C1-6 alkyl group and a hydroxyl group, or an oxygen atom.

In the compound of the formula (I-c) or pharmacologically acceptable salt thereof, preferably, n and m are the same or different and each represent an integer of 0 to 2; and more preferably, n and m each represent 1.

In the compound of the formula (I-c) or pharmacologically acceptable salt thereof, preferably, 1) R$^1$ and R$^2$ are the same or different and each represent a hydrogen atom or a C1-6 alkyl group; or 2) R$^1$ and R$^2$, together with the carbon atom to which they are bonded, form a C3-8 cycloalkyl group.

In the compound of the formula (II-a), (II-b), or (II-d) or pharmacologically acceptable salt thereof, preferably, 1) R$^1$, R$^2$, R$^3$, and R$^4$ are the same or different and each represent a hydrogen atom or a C1-6 alkyl group; 2) one of R$^1$ and R$^2$ and one of R$^3$ and R$^4$ are the same or different and each represent a hydrogen atom or a C1-6 alkyl group; and the other of R$^1$ and R$^2$ and the other of R$^3$ and R$^4$, together with the carbon atoms to which they are respectively bonded, form a C3-8 cycloalkyl group, wherein the C3-8 cycloalkyl group may be substituted with 1 to 3 substituents selected from Substituent Group A1; 3) R$^1$ and R$^2$, together with the carbon atom to which they are bonded, form a C3-8 cycloalkyl group; and R$^3$ and R$^4$ are the same or different and each represent a hydrogen atom or a C1-6 alkyl group; or 4) R$^3$ and R$^4$, together with the carbon atom to which they are bonded, form a C3-8 cycloalkyl group; and R$^1$ and R$^2$ are the same or different and each represent a hydrogen atom or a C1-6 alkyl group.

In the compound of the formula (II-a), (II-b), or (II-d) or pharmacologically acceptable salt thereof, preferably, R$^5$ and R$^6$ are the same or different and each represent a hydrogen atom or a C1-6 alkyl group, wherein the C1-6 alkyl group may be substituted with 1 to 3 hydroxyl groups.

In the compound of the formula (II-a), (II-b), or (II-d) or pharmacologically acceptable salt thereof, Ar$_{1-a}$ preferably represents a phenyl group or pyridinyl group that may be substituted with 1 to 3 substituents selected from Substituent Group A1; and Ar$_{1-a}$ more preferably represents a phenyl group or pyridinyl group that may not be substituted or may be substituted with 1 to 3 halogen atoms In the compound of the formula (II-c) or (II-e) or pharmacologically acceptable salt thereof, preferably, 1) R$^1$, R$^2$, R$^3$, and R$^4$ are the same or different and each represent a hydrogen atom or a C1-6 alkyl group; 2) one of R$^1$ and R$^2$ and one of R$^3$ and R$^4$ are the same or different and each represent a hydrogen atom or a C1-6 alkyl group; and the other of R$^1$ and R$^2$ and the other of R$^3$ and R$^4$, together with the carbon atoms to which they are respectively bonded, form a C3-8 cycloalkyl group, wherein the C3-8 cycloalkyl group may be substituted with 1 to 3 substituents selected from Substituent Group A1; 3) R$^1$ and R$^2$, together with the carbon atom to which they are bonded, form a C3-8 cycloalkyl group; and R$^3$ and R$^4$ are the same or different and each represent a hydrogen atom or a C1-6 alkyl group; or 4) R$^3$ and R$^4$, together with the carbon atom to which they are bonded, form a C3-8 cycloalkyl group; and $R^1$ and $R^2$ are the same or different and each represent a hydrogen atom or a C1-6 alkyl group.

In the compound of the formula (II-c) or (II-e) or pharmacologically acceptable salt thereof,
$R^7$ preferably represents a hydrogen atom or a C1-6 alkyl group.

In the compound of the formula (II-c) or (II-e) or pharmacologically acceptable salt thereof,
$Ar_{1-a}$ preferably represents a phenyl group or pyridinyl group that may be substituted with 1 to 3 substituents selected from Substituent Group A1; and
$Ar_{1-a}$ more preferably represents a phenyl group or pyridinyl group that may not be substituted or may be substituted with 1 to 3 halogen atoms.

In particular, a compound selected from the following group or a pharmacologically acceptable salt thereof is particularly suitable, for example, and is useful as a therapeutic or prophylactic agent for a disease caused by amyloid-β such as Alzheimer's disease, senile dementia, Down's syndrome, or amyloidosis.

1) (Z)-2-[1-[3-methoxy-4-(4-methyl-1H-imidazol-1-yl)phenyl]methylidene]-4-(3,4,5-trifluorobenzyl)morpholin-3-one,
2) (Z)-2-[1-[3-methoxy-4-(4-methyl-1H-imidazol-1-yl)phenyl]methylidene]-4-(2,3,4-trifluorobenzyl)morpholin-3-one,
3) (Z)-(S)-2-[1-[3-methoxy-4-(4-methyl-1H-imidazol-1-yl)phenyl]methylidene]-6-methyl-4-(3,4,5-trifluorobenzyl)morpholin-3-one,
4) (Z)-(R)-2-[1-[3-methoxy-4-(4-methyl-1H-imidazol-1-yl)phenyl]methylidene]-6-methyl-4-(3,4,5-trifluorobenzyl)morpholin-3-one,
5) (Z)-(S)-2-[1-[3-methoxy-4-(4-methyl-1H-imidazol-1-yl)phenyl]methylidene]-6-methyl-4-(2,3,4-trifluorobenzyl)morpholin-3-one,
6) (Z)-(R)-2-[1-[3-methoxy-4-(4-methyl-1H-imidazol-1-yl)phenyl]methylidene]-6-methyl-4-(2,3,4-trifluorobenzyl)morpholin-3-one,
7) (Z)-4-[(S)-1-(4-fluorophenyl)ethyl]-2-[1-[3-methoxy-4-(4-methyl-1H-imidazol-1-yl)phenyl]methylidene]-6,6-dimethylmorpholin-3-one,
8) (Z)-(R)-4-[(S)-1-(4-fluorophenyl)ethyl]-2-[1-[3-methoxy-4-(4-methyl-1H-imidazol-1-yl)phenyl]methylidene]-6-methylmorpholin-3-one,
9) (Z)-(S)-4-[(S)-1-(4-fluorophenyl)ethyl]-2-[1-[3-methoxy-4-(4-methyl-1H-imidazol-1-yl)phenyl]methylidene]-6-methylmorpholin-3-one,
10) (Z)-2-[1-[3-methoxy-4-(4-methyl-1H-imidazol-1-yl)phenyl]methylidene]-4-[(S)-1-(3,4,5-trifluorophenyl)ethyl]morpholin-3-one,
11) (Z)-2-[1-[3-methoxy-4-(4-methyl-1H-imidazol-1-yl)phenyl]methylidene]-4-[(R)-1-(3,4,5-trifluorophenyl)ethyl]morpholin-3-one,
12) (Z)-4-[(S)-chroman-4-yl]-2-[1-[3-methoxy-4-(4-methyl-1H-imidazol-1-yl)phenyl]methylidene]-6,6-dimethylmorpholin-3-one,
13) (Z)-(S)-4-[(S)-chroman-4-yl]-2-[1-[3-methoxy-4-(4-methyl-1H-imidazol-1-yl)phenyl]methylidene]-6-methylmorpholin-3-one,
14) (Z)-(R)-4-[(S)-chroman-4-yl]-2-[1-[3-methoxy-4-(4-methyl-1H-imidazol-1-yl)phenyl]methylidene]-6-methylmorpholin-3-one,
15) (Z)-(6S,9aR)-6-(4-fluorophenyl)-3-{1-[3-methoxy-4-(4-methyl-1H-imidazol-1-yl)benzylidene]hexahydropyrido[2,1-c][1,4]oxazin-4-one,
16) (Z)-(6R,9aS)-6-(4-fluorophenyl)-3-{1-[3-methoxy-4-(4-methyl-1H-imidazol-1-yl)benzylidene]hexahydropyrido[2,1-c][1,4]oxazin-4-one,
17) (Z)-(S)-4-[(S)-1-(6-chloropyridin-3-yl)ethyl]-2-[1-[3-methoxy-4-(4-methyl-1H-imidazol-1-yl)phenyl]methylidene]-6-methylmorpholin-3-one,
18) (Z)-(S)-4-[(R)-1-(6-chloropyridin-3-yl)ethyl]-2-[1-[3-methoxy-4-(4-methyl-1H-imidazol-1-yl)phenyl]methylidene]-6-methylmorpholin-3-one,
19) (Z)-(S)-4-[(S)-1-(5-chloropyridin-2-yl)ethyl]-2-[1-[3-methoxy-4-(4-methyl-1H-imidazol-1-yl)phenyl]methylidene]-6-methylmorpholin-3-one,
20) (Z)-(S)-4-[(R)-1-(5-chloropyridin-2-yl)ethyl]-2-[1-[3-methoxy-4-(4-methyl-1H-imidazol-1-yl)phenyl]methylidene]-6-methylmorpholin-3-one,
21) (Z)-(S)-4-[(S)-1-(2,6-difluoropyridin-3-yl)ethyl]-2-[1-[3-methoxy-4-(4-methyl-1H-imidazol-1-yl)phenyl]methylidene]-6-methylmorpholin-3-one,
22) (Z)-(S)-4-[(R)-1-(2,6-difluoropyridin-3-yl)ethyl]-2-[1-[3-methoxy-4-(4-methyl-1H-imidazol-1-yl)phenyl]methylidene]-6-methylmorpholin-3-one,
23) (Z)-(S)-4-[(S)-1-(2,3-difluoropyridin-4-yl)ethyl]-2-[1-[3-methoxy-4-(4-methyl-1H-imidazol-1-yl)phenyl]methylidene]-6-methylmorpholin-3-one,
24) (Z)-(S)-4-[(R)-1-(2,3-difluoropyridin-4-yl)ethyl]-2-[1-[3-methoxy-4-(4-methyl-1H-imidazol-1-yl)phenyl]methylidene]-6-methylmorpholin-3-one,
25) (Z)-(S)-4-[(1R,2R)-2-hydroxy-1-(3,4,5-trifluorophenyl)propyl]-2-[1-[3-methoxy-4-(4-methyl-1H-imidazol-1-yl)phenyl]methylidene]-6-methylmorpholin-3-one,
26) (Z)-4-[(1R,2R)-2-hydroxy-1-(3,4,5-trifluorophenyl)propyl]-2-[1-[3-methoxy-4-(4-methyl-1H-imidazol-1-yl)phenyl]methylidene]-6,6-dimethylmorpholin-3-one,
27) (Z)-4-[(R)-1-(4-fluorophenyl)-2-hydroxyethyl]-2-[1-[3-methoxy-4-(4-methyl-1H-imidazol-1-yl)phenyl]methylidene]-6,6-dimethylmorpholin-3-one,
28) (Z)-(6R)-4-[(1R,2R)-2-hydroxy-1-(3,4,5-trifluorophenyl)propyl]-2-[1-[3-methoxy-4-(4-methyl-1H-imidazol-1-yl)phenyl]methylidene]-6-methylmorpholin-3-one,
29) (Z)-4-[(1R,2R)-2-hydroxy-1-(3,4,5-trifluorophenyl)propyl]-2-[1-[3-methoxy-4-(4-methyl-1H-imidazol-1-yl)phenyl]methylidene]morpholin-3-one,
30) (Z)-4-[(1R,2R)-1-(3,4-difluorophenyl)-2-hydroxypropyl]-2-[1-[3-methoxy-4-(4-methyl-1H-imidazol-1-yl)phenyl]methylidene]morpholin-3-one,
31) (Z)-(S)-4-[(1R,2R)-1-(4-fluorophenyl)-2-hydroxypropyl]-2-[1-[3-methoxy-4-(4-methyl-1H-imidazol-1-yl)phenyl]methylidene]-6-methylmorpholin-3-one,
32) (Z)-4-[(1R,2R)-1-(4-fluorophenyl)-2-hydroxypropyl]-2-[1-[3-methoxy-4-(4-methyl-1H-imidazol-1-yl)phenyl]methylidene]-6,6-dimethylmorpholin-3-one,
33) (Z)-(S)-4-[(1R,2R)-1-(3,4-difluorophenyl)-2-hydroxypropyl]-2-[1-[3-methoxy-4-(4-methyl-1H-imidazol-1-yl)phenyl]methylidene]-6-methylmorpholin-3-one,
34) (Z)-4-[(1R,2R)-1-(3,4-difluorophenyl)-2-hydroxypropyl]-2-[1-[3-methoxy-4-(methylimidazol-1-yl)phenyl]methylidene]-6,6-dimethylmorpholin-3-one,
35) (Z)-(S)-4-[(S)-2-hydroxy-1-methyl-1-(3,4,5-trifluorophenyl)ethyl]-2-[1-[3-methoxy-4-(4-methyl-1H-imidazol-1-yl)phenyl]methylidene]-6-methylmorpholin-3-one,
36) (Z)-(6S)-2-[1-[3-methoxy-4-(4-methyl-1H-imidazol-1-yl)phenyl]methylidene]-6-methyl-4-[(S)-1-(3,4,5-trifluorophenyl)ethyl]morpholin-3-one,
37) (Z)-(6S)-4-[1-(4-fluorophenyl)-1-methylethyl]-2-[1-[3-methoxy-4-(4-methyl-1H-imidazol-1-yl)phenyl]methylidene]-6-methylmorpholin-3-one,
38) (Z)-(6S)-4-[1-(4-fluorophenyl)cyclopropyl]-2-[1-[3-methoxy-4-(4-methyl-1H-imidazol-1-yl)phenyl]methylidene]-6-methylmorpholin-3-one,
39) (Z)-(6S,9aR)-3-{1-[3-methoxy-4-(4-methyl-1H-imidazol-1-yl)benzylidene]-6-(3,4,5-trifluorophenyl)hexahydropyrido[2,1-c][1,4]oxazin-4-one, 40) (Z)-(6S,9aR)-6-(3,4-difluorophenyl)-3-{1-[3-methoxy-4-(4-methyl-1H-imidazol-1-yl)benzylidene]hexahydropyrido[2,1-c][1,4]oxazin-4-one,
41) (Z)-(6S,9aR)-6-(2,6-difluoropyridin-3-yl)-3-{1-[3-methoxy-4-(4-methyl-1H-imidazol-1-yl)benzylidene]hexahydropyrido[2,1-c][1,4]oxazin-4-one,
42) (Z)-(S)-4-[(S)-1-(5-fluoropyridin-2-yl)ethyl]-2-[1-[3-methoxy-4-(4-methyl-1H-imidazol-1-yl)phenyl] methylidene]-6-methylmorpholin-3-one,
43) (Z)-(S)-4-[(S)-1-(2-chloropyridin-4-yl)ethyl]-2-[1-[3-methoxy-4-(4-methyl-1H-imidazol-1-yl)phenyl]methylidene]-6-methylmorpholin-3-one,
44) (Z)-(S)-4-[(S)-1-(2-chloro-3-fluoropyridin-4-yl)ethyl]-2-[1-[3-methoxy-4-(4-methyl-1H-imidazol-1-yl)phenyl]methylidene]-6-methylmorpholin-3-one,
45) (Z)-(S)-4-[(S)-1-(2,6-difluoropyridin-4-yl)ethyl]-2-[1-[3-methoxy-4-(4-methyl-1H-imidazol-1-yl)phenyl]methylidene]-6-methylmorpholin-3-one,
46) (Z)-4-[(S)-1-(2-chloropyridin-4-yl)ethyl]-2-[1-[3-methoxy-4-(4-methyl-1H-imidazol-1-yl)phenyl]methylidene]-6,6-dimethylmorpholin-3-one,
47) (Z)-4-[(S)-1-(2,6-difluoropyridin-3-yl)ethyl]-2-[1-[3-methoxy-4-(4-methyl-1H-imidazol-1-yl)phenyl]methylidene]-6,6-dimethylmorpholin-3-one,
48) (Z)-4-[(S)-1-(6-fluoropyridin-3-yl)ethyl]-2-[1-[3-methoxy-4-(4-methyl-1H-imidazol-1-yl)phenyl]methylidene]-6,6-dimethylmorpholin-3-one,
49) (Z)-4-[(S)-1-(6-chloropyridin-3-yl)ethyl]-2-[1-[3-methoxy-4-(4-methyl-1H-imidazol-1-yl)phenyl]methylidene]-6,6-dimethylmorpholin-3-one,
50) (Z)-4-[(S)-1-(2,3-difluoropyridin-4-yl)ethyl]-2-[1-[3-methoxy-4-(4-methyl-1H-imidazol-1-yl)phenyl]methylidene]-6,6-dimethylmorpholin-3-one,
51) (Z)-4-[(S)-1-(5-chloropyridin-2-yl)ethyl]-2-[1-[3-methoxy-4-(4-methyl-1H-imidazol-1-yl)phenyl]methylidene]-6,6-dimethylmorpholin-3-one,
52) (Z)-(R)-4-[(S)-1-(2,6-difluoropyridin-3-yl)ethyl]-2-[1-[3-methoxy-4-(4-methyl-1H-imidazol-1-yl)phenyl]methylidene]-6-methylmorpholin-3-one,
53) (Z)-(S)-4-(4-fluorobenzyl)-2-[1-[3-fluoro-4-(4-methyl-1H-imidazol-1-yl)phenyl]methylidene]-6-methylmorpholin-3-one,
54) (Z)-2-[1-[3-fluoro-4-(4-methyl-1H-imidazol-1-yl)phenyl]methylidene]-4-[(S)-1-(4-trifluorophenyl)ethyl]-6,6-dimethylmorpholin-3-one,
55) (Z)-4-[(S)-chroman-4-yl]-2-[1-[3-fluoro-4-(4-methyl-1H-imidazol-1-yl)phenyl]methylidene]-6,6-dimethylmorpholin-3-one,
56) (Z)-(S)-4-[(S)-chroman-4-yl]-2-[1-[3-fluoro-4-(4-methyl-1H-imidazol-1-yl)phenyl]methylidene]-6-methylmorpholin-3-one,
57) (Z)-(S)-2-[1-[3-fluoro-4-(4-methyl-1H-imidazol-1-yl)phenyl]methylidene]-4-[(1R,2R)-2-hydroxy-1-(3,4,5-trifluorophenyl)propyl]-6-methylmorpholin-3-one,
58) (Z)-(S)-4-[(1R,2R)-1-(3,4-difluorophenyl)-2-hydroxypropyl]-2-[1-[3-fluoro-4-(4-methyl-1H-imidazol-1-yl)phenyl]methylidene]-6-methylmorpholin-3-one,
59) (Z)-(S)-2-[1-[3-fluoro-4-(4-methyl-1H-imidazol-1-yl)phenyl]methylidene]-4-[(1R,2R)-1-(4-fluorophenyl)-2-hydroxypropyl]-6-methylmorpholin-3-one,
60) (Z)-2-[1-[3-fluoro-4-(4-methyl-1H-imidazol-1-yl)phenyl]methylidene]-4-[(1R,2R)-2-hydroxy-1-(3,4,5-trifluorophenyl)propyl]-6,6-dimethylmorpholin-3-one,
61) (Z)-4-[(1R,2R)-1-(3,4-difluorophenyl)-2-hydroxypropyl]-2-[1-[3-fluoro-4-(4-methyl-1H-imidazol-1-yl)phenyl]methylidene]-6,6-dimethylmorpholin-3-one,
62) 1-[1-(2,4-difluorophenyl)ethyl]-3-{1-[3-fluoro-4-(4-methyl-1H-imidazol-1-yl)phenyl]-(E)-methylidene}piperidin-2-one,
63) (E)-(S)-3-[(1-[3-fluoro-4-(4-methyl-1H-imidazol-1-yl)phenyl]methylidene}-1-[(1R,2R)-2-hydroxy-1-(3,4,5-trifluorophenyl)propyl]-5-methylpiperidin-2-one,
64) (E)-3-{1-[3-fluoro-4-(4-methyl-1H-imidazol-1-yl)phenyl]methylidene}-1-[(1R,2R)-2-hydroxy-1-(3,4,5-trifluorophenyl)propyl]piperidin-2-one,
65) (E)-3-{1-[3-fluoro-4-(4-methyl-1H-imidazol-1-yl)phenyl]methylidene}-1-[(2R,3R)-3-hydroxy-1,1-dimethylindane-2-yl]piperidin-2-one,
66) (E)-3-{1-[3-fluoro-4-(4-methyl-1H-imidazol-1-yl)phenyl]methylidene}-1-[(S)-2-hydroxy-1-methyl-1-(3,4,5-trifluorophenyl)ethyl]piperidin-2-one,
67) (E)-3-{1-[3-fluoro-4-(4-methyl-1H-imidazol-1-yl)phenyl]methylidene}-1-[1-(4-fluorophenyl)-1-methylethyl]piperidin-2-one,
68) (E)-(R)-3-{1-[3-fluoro-4-(4-methyl-1H-imidazol-1-yl)phenyl]methylidene}-1-[(1R,2R)-2-hydroxy-1-(3,4,5-trifluorophenyl)propyl]-5-methylpiperidin-2-one,
69) (E)-(S)-1-[(1R,2R)-1-(3,4-difluorophenyl)-2-hydroxypropyl]-3-{1-[3-fluoro-4-(4-methyl-1H-imidazol-1-yl)phenyl]methylidene}-5-methylpiperidin-2-one,
70) (Z)-(6S,8aR)-3-{1-[3-methoxy-4-(4-methyl-1H-imidazol-1-yl)benzylidene]-6-(3,4,5-trifluorophenyl)tetrahydropyrrolo[2,1-c][1,4]oxazin-4-one,
71) (6S,9aR)-6-(4-chlorophenyl)-3-{1-[3-methoxy-4-(4-methyl-1H-imidazol-1-yl)phenyl]-(Z)-methylidene}hexahydropyrido[2,1-c][1,4]oxazin-4-one,
72) (6R,9aR)-3-{1-[3-methoxy-4-(4-methyl-1H-imidazol-1-yl)phenyl]-(Z)-methylidene}-6-(3,4,5-trifluorophenyl)-tetrahydro[1,4]oxazino[3,4-c][1,4]oxazin-4-one,
73) (6R,9aR)-6-(3,4-difluorophenyl)-3-{1-[3-methoxy-4-(4-methyl-1H-imidazol-1-yl)phenyl]-(Z)-methylidene}-tetrahydro[1,4]oxazino[3,4-c][1,4]oxazin-4-one,
74) (6R,9aR)-6-(4-fluorophenyl)-3-{1-[3-methoxy-4-(4-methyl-1H-imidazol-1-yl)phenyl]-(Z)-methylidene}-tetrahydro[1,4]oxazino[3,4-c][1,4]oxazin-4-one and
75) (6R,9aR)-6-(4-chlorophenyl)-3-{1-[3-methoxy-4-(4-methyl-1H-imidazol-1-yl)phenyl]-(Z)-methylidene}-tetrahydro[1,4]oxazino[3,4-c]oxazin-4-one.

Preferable embodiments of the compound of the general formula (I) are as described above. The pharmaceutically active ingredient of the present invention is not limited to compounds specifically described in the present specification, and any embodiment may be arbitrarily selected within the definition of the compound of the general formula (I).

Methods for preparing the compound of the general formula (I) of the present invention will be described below.

The compound represented by the general formula (I):

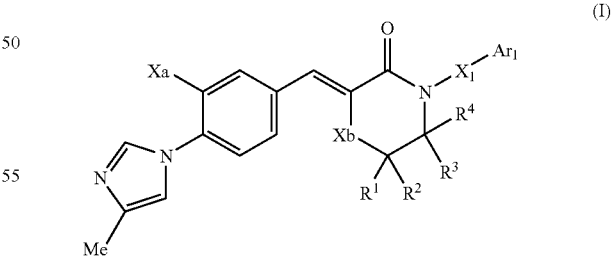

wherein $R^1$, $R^2$, $R^3$, $R^4$, $X_1$, $X_a$, $X_b$, and $Ar_1$ are as defined above, is synthesized according to a method such as the following General Preparation Method 1 or General Preparation Method 2, for example. It is obvious that, in order to prepare the compound of the present invention conveniently, the method comprises a protection reaction step and a deprotection reaction step appropriately, using a protecting group known to a person skilled in the art which is suitably selected for each step (see T. Greene et al., "Protective Groups in Organic Synthesis", John Wiley & Sons, Inc., New York, 1981, for example). It is also obvious that, in order to prepare the compound of the present invention conveniently, all isomers and isomer mixtures such as geometric isomers which can be generated from the structure of the compound, optical isomers based on asymmetric carbon, stereoisomers, and tautomers can be prepared as a single compound by a technique known to a person skilled in the art which is suitable for each step such as fractional crystallization or column chromatography.

General Preparation Method 1

Typically used General Preparation Method 1 for the compound of the general formula (I) of the present invention will be described below.

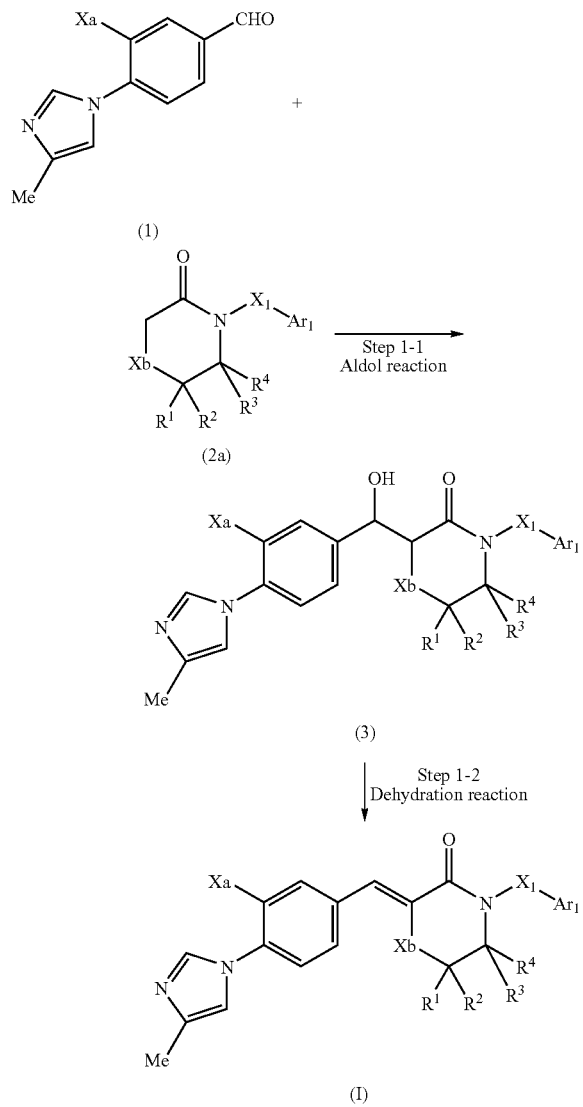

In the formula, $R^1$, $R^2$, $R^3$, $R^4$, $X_1$ (which may have a protecting group when $X_1$ contains a hydroxyl group), $X_a$, $X_b$, and $Ar_1$ are as defined above.

The above General Production Method 1 is an example of a method for preparing the compound of the general formula (I) comprising converting an aldehyde compound (1) and 0.3 to 3.0 equivalents of an amide compound (2a) with respect to the aldehyde compound (1) into an aldol adduct (3) by aldol reaction in Step 1-1 and then dehydrating the adduct.

Conversion of Aldol Adduct (3) into Compound (1)

The compound of the general formula (I) can be prepared by conversion of an aldol adduct (3) by dehydration reaction in Step 1-2. Specifically, the dehydration reaction in Step 1-2 varies according to the starting material and is not specifically limited insofar as the conditions are similar to those in this reaction. A known method described in many documents may be used for the reaction (see Jikken Kagaku Koza (Courses in Experimental Chemistry), vol. 19, Yuki Gosei (Organic Synthesis) [I], edited by The Chemical Society of Japan, Maruzen Co., Ltd., June 1992, p. 194-226, for example). Preferable examples of the method include i) a method of treating an aldol adduct (3) with an acid (see Jikken Kagaku Koza (Courses in Experimental Chemistry), vol. 19, Yuki Gosei (Organic Synthesis) [I], edited by The Chemical Society of Japan, Maruzen Co., Ltd., June 1992, p. 194-196, for example); and ii) a method of converting an alcohol group of an aldol adduct (3) into a leaving group such as a sulfonate group or halogen atom, and then treating the adduct with a base (see Jikken Kagaku Koza (Courses in Experimental Chemistry), vol. 19, Yuki Gosei (Organic Synthesis) [I], edited by The Chemical Society of Japan, Maruzen Co., Ltd., June 1992, p. 198-205, for example).

In the method i), the acid, solvent, and temperature conditions used vary according to the starting material and are not specifically limited. 0.1 to 10 equivalents of an acid such as hydrochloric acid, sulfuric acid, phosphoric acid, potassium hydrogen sulfide, oxalic acid, p-toluenesulfonic acid, a boron trifluoride-ether complex, thionyl chloride, or alumina oxide is used with respect to the aldol adduct (3). The method may be performed without a solvent, or with a solvent or a mixture thereof that does not inhibit the reaction and allows the starting material to be dissolved therein to a certain extent. Preferable examples of the solvent used include water, acetone, dimethyl sulfoxide, and hexamethylphosphoramide. In addition, a combination of 0.1 to 10 equivalents of an acid with respect to the aldol adduct (3) with an organic base such as pyridine may improve the reaction rate and reaction yield. The reaction temperature must be a temperature that can complete the reaction without promoting formation of an undesirable by-product, and is preferably room temperature to 200° C., for example. Under preferable reaction conditions, the reaction is preferably completed in 0.5 to 24 hours, for example, and the progress of the reaction can be monitored by a known chromatography technique. An undesirable by-product can be removed by a technique known to a person skilled in the art such as a conventional chromatography technique, extraction, or/and crystallization.

Preferable examples of the leaving group in the method ii) include an acetyl group, methanesulfonate group, p-toluenesulfonate group, chlorine atom, bromine atom and iodine atom. The method of conversion into such a leaving group varies according to the starting material and is not specifically limited. A method known to a person skilled in the art may be used as such a conversion method. Preferably 1.0 to 10 equivalents of an acetylating agent such as acetylchloride and acetic anhydride, or a sulfonating agent such as methanesulfonyl chloride and p-toluenesulfonyl chloride or 1.0 to 10 equivalents of a halogenating agent such as thionyl chloride with respect to the aldol adduct (3), for example, may be used preferably in a halogenated solvent such as methylene chloride and chloroform; a nonpolar solvent such as toluene and benzene; an ether solvent such as tetrahydrofuran or ethylene glycol dimethyl ether; or a mixed solvent thereof, for example. The reaction temperature must be a temperature that can complete the reaction without promoting formation of an undesirable by-product, and is preferably −78 to 100° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization. In the leaving reaction as the second step, preferably 0.1 to 10 equivalents of an organic base such as diazabicycloundecene, pyridine, 4-dimethylaminopyridine and triethylamine; a quaternary ammonium salt such as tetrabutylammonium hydroxide; an alkali metal salt of alcohol such as sodium methoxide or potassium tert-butoxide; an alkali metal hydroxide such as sodium hydroxide; an alkali metal carbonate such as lithium carbonate or potassium carbonate; or an organic metal reagent such as lithium diisopropylamide with respect to the aldol adduct (3), for example, is preferably used as a base preferably in a halogenated solvent such as methylene chloride; a nonpolar solvent such as toluene; a polar solvent such as acetonitrile, dimethylformamide, or dimethyl sulfoxide; an ether solvent such as tetrahydrofuran or ethylene glycol dimethyl ether; or a mixed solvent thereof, for example.

An organic base such as pyridine may also be used as a solvent. The reaction temperature must be a temperature that can complete the reaction without promoting formation of an undesirable by-product, and is preferably −78 to 100° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Preparation of Aldol Adduct (3)

The aldol adduct (3) can be prepared from an aldehyde compound (1) and an amide compound (2a) according to Step 1-1, for example. Specifically, the aldol reaction in Step 1-1 varies according to the starting material and is not specifically limited insofar as the conditions are similar to those in this reaction. A method known to a person skilled in the art may be used for the reaction (see Jikken Kagaku Koza (Courses in Experimental Chemistry), vol. 20, Yuki Gosei (Organic Synthesis) [II], edited by The Chemical Society of Japan, Maruzen Co., Ltd., July 1992, p. 94-100, for example). Preferable examples of the method include i) a method of converting an amide compound (2a) into an alkali metal enolate by preferably 1.0 to 5.0 equivalents of a base such as preferably lithium diisopropylamide, sodium hydride, or sodium methoxide, for example, and then reacting the enolate with an aldehyde compound (1) (see Jikken Kagaku Koza (Courses in Experimental Chemistry), vol. 20, Yuki Gosei (Organic Synthesis) [II], edited by The Chemical Society of Japan, Maruzen Co., Ltd., July 1992, p. 97-98, for example); and ii) a method of converting an amide compound (2a) into an alkali metal enolate by preferably 1.0 to 5.0 equivalents of a base such as preferably lithium diisopropylamide, sodium hydride, or sodium methoxide, for example, reacting the enolate with a silicon halide reagent such as preferably trimethylchlorosilane or tert-butyldimethylchlorosilane to once prepare silyl enol ether, and then reacting the ether with an aldehyde compound (1) in the presence of a Lewis acid such as preferably titanium tetrachloride or boron trifluoride (see Jikken Kagaku Koza (Courses in Experimental Chemistry), vol. 20, Yuki Gosei (Organic Synthesis) [II], edited by The Chemical Society of Japan, Maruzen Co., Ltd., July 1992, p. 96-97, for example).

The solvent and reaction temperature used vary according to the starting material and are not specifically limited. As a solvent that does not inhibit the reaction and allows the starting material to be dissolved therein to a certain extent, an ether solvent such as tetrahydrofuran, 1,4-dioxane, or diethyl ether; a halogenated solvent such as methylene chloride, 1,2-dichloroethane, or chloroform; a nonpolar solvent such as toluene or xylene; or a mixed solvent thereof may be preferably used, for example. The reaction temperature must be a temperature that can complete the reaction without promoting formation of an undesirable by-product, and is preferably −78° C. to room temperature, for example. Under preferable reaction conditions, the reaction is preferably completed in 0.5 to 24 hours, for example, and the progress of the reaction can be monitored by a known chromatography technique. An undesirable by-product can be removed by a technique known to a person skilled in the art such as a conventional chromatography technique, extraction, or/and crystallization.

Preparation of Aldehyde Compound (1)

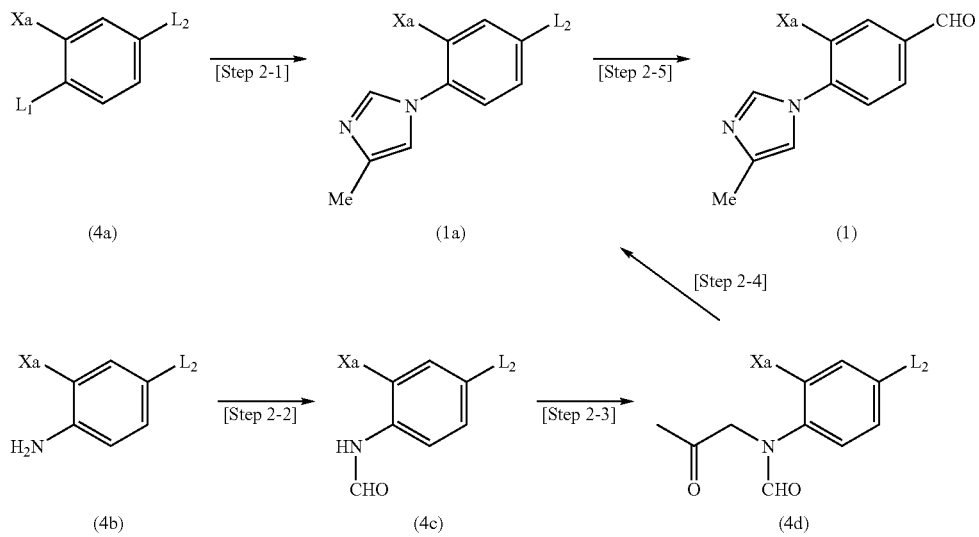

In the formula, $X_a$ is as defined above; $L_1$ represents a fluorine atom, a chlorine atom, a bromine atom, an iodine atom, a sulfonate group such as a triflate group, a trialkyltin group, a boronic acid group, or a boronate group; and $L_2$ represents a C1-C3 alkoxycarbonyl group such as a methyl ester group, an aldehyde group, or a cyano group.

Preparation of Aldehyde Compound (1)

The aldehyde compound (1) can be prepared from a compound (1a) as a starting material according to Step 2-5. Specifically, Step 2-5 varies according to the starting material and is not specifically limited insofar as the conditions are similar to those in this reaction. A method known to a person skilled in the art may be used for the reaction. For example, when $L_2$ is an alkoxycarbonyl group, a reduction reaction described in many known documents may be used (see Jikken Kagaku Koza (Courses in Experimental Chemistry), vol. 26, Yuki Gosei (Organic Synthesis) [VIII], edited by The Chemical Society of Japan, Maruzen Co., Ltd., April 1992, p. 159-266, for example). Preferably, the desired aldehyde compound can be obtained by a reduction method using a metal hydride such as diisobutylaluminum hydride, for example. More preferably, the desired aldehyde compound can be efficiently obtained by a reduction method using lithium aluminum hydride or an aluminum hydride complex in the presence of an amine, for example (see T. Abe et al., "Tetrahedron", 2001, vol. 57, p. 2701-2710, for example).

For example, when $L_2$ is a cyano group, a reduction reaction described in many known documents may be used (see Jikken Kagaku Koza (Courses in Experimental Chemistry), vol. 26, Yuki Gosei (Organic Synthesis) [VIII], edited by The Chemical Society of Japan, Maruzen Co., Ltd., April 1992, p. 159-266, for example). Preferably, the desired aldehyde compound can be obtained by a reduction method using a metal hydride such as sodium bis(2-methoxyethoxy)aluminum hydride or diisobutylaluminum hydride, for example (see Jikken Kagaku Koza (Courses in Experimental Chemistry), vol. 26, Yuki Gosei (Organic Synthesis) [VIII], edited by The Chemical Society of Japan, Maruzen Co., Ltd., April 1992, p. 231, for example).

Alternatively, the desired aldehyde compound can be synthesized by the steps of reducing a compound (1a) to an alcohol compound using a technique known to a person skilled in the art (see Jikken Kagaku Koza (Courses in Experimental Chemistry), vol. 26, Yuki Gosei (Organic Synthesis) [VIII], edited by The Chemical Society of Japan, Maruzen Co., Ltd., April 1992, p. 159-266, for example), and then oxidizing the alcohol compound to an aldehyde (see Jikken Kagaku Koza (Courses in Experimental Chemistry), vol. 23, Yuki Gosei (Organic Synthesis) [V], edited by The Chemical Society of Japan, Maruzen Co., Ltd., October 1991, p. 1-550, for example).

The base used in the reduction reaction varies according to the starting material and is not specifically limited. A secondary amine may be used as a base. Preferably, the desired aldehyde compound can be efficiently obtained when using 0.1 to 1.0 equivalents of a linear or cyclic secondary alkylamine such as diethylamine or pyrrolidine with respect to the compound (1a), for example. The solvent and reaction temperature used vary according to the starting material and are not specifically limited. As a solvent that does not inhibit the reaction and allows the starting material to be dissolved therein to a certain extent, an ether solvent such as tetrahydrofuran, 1,4-dioxane, or diethyl ether; a nonpolar solvent such as toluene or xylene; or a mixed solvent thereof may be preferably used, for example. The reaction temperature must be a temperature that can complete the reaction without promoting formation of an undesirable by-product, and is preferably −78° C. to room temperature, for example. Under preferable reaction conditions, the reaction is preferably completed in 0.5 to 24 hours, for example, and the progress of the reaction can be monitored by a known chromatography technique. An undesirable by-product can be removed by a technique known to a person skilled in the art such as a conventional chromatography technique, extraction, or/and crystallization.

The amount of the oxidizing agent used in the oxidation step varies according to the starting material and is not specifically limited. The amount is preferably 0.1 to 10 equivalents with respect to the compound (1a). The solvent and reaction temperature vary according to the starting material and are not specifically limited. As a solvent that does not inhibit the reaction and allows the starting material to be dissolved therein to a certain extent, an ether solvent such as tetrahydrofuran, 1,4-dioxane, or diethyl ether; a halogenated solvent such as methylene chloride, 1,2-dichloroethane, or chloroform; a nonpolar solvent such as toluene or xylene; or a mixed solvent thereof may be preferably used, for example. The reaction temperature must be a temperature that can complete the reaction without promoting formation of an undesirable by-product, and is preferably −78° C. to 100° C., for example. Under preferable reaction conditions, the reaction is preferably completed in 0.5 to 24 hours, for example, and the progress of the reaction can be monitored by a known chromatography technique. An undesirable by-product can be removed by a technique known to a person skilled in the art such as a conventional chromatography technique, extraction, or/and crystallization.

Preparation of Compound (1a)

The compound (1a) can be prepared from a compound (4a) as a starting material according to Step 2-1 or from a compound (4d) as a starting material according to Step 2-4, for example.

Step 2-1

Step 2-1 varies according to the starting material and is not specifically limited insofar as the conditions are similar to those in this reaction. A method known to a person skilled in the art may be used for the reaction. For example, the method in Step 2-1 may be substitution reaction from a compound (4a) as a starting material using 0.3 to 10 equivalent of methylimidazole with respect to the compound (4a). The solvent and reaction temperature used in this step vary according to the starting material and are not specifically limited. As a solvent that does not inhibit the reaction and allows the starting material to be dissolved therein to a certain extent, an ether solvent such as tetrahydrofuran, 1,4-dioxane, or diethyl ether; a halogenated solvent such as methylene chloride, 1,2-dichloroethane, or chloroform; a polar solvent such as dichlorobenzene, dimethylformamide, or N-methylpyrrolidone; a nonpolar solvent such as toluene, xylene, or mesitylene; an organic base solvent such as diazabicycloundecene, pyridine, or triethylamine; or a mixed solvent thereof may be preferably used, for example. The reaction temperature must be a temperature that can complete the reaction without promoting formation of an undesirable by-product, and is preferably 0° C. to 200° C., for example. In this step, 0.1 to 10 equivalents of an organic base such as diazabicycloundecene, pyridine, or triethylamine; an alkali metal salt of alcohol such as sodium methoxide or potassium tert-butoxide; an alkali metal hydroxide such as sodium hydroxide; or an alkali metal carbonate base such as cesium carbonate or potassium carbonate may be used with respect to the compound (4a), for example. Under preferable reaction conditions, the reaction is preferably completed in 0.5 to 24 hours, for example, and the progress of the reaction can be monitored by a known chromatography technique. An undesirable by-product can be removed by a technique known to a person skilled in the art such as a conventional chromatography technique, extraction, or/and crystallization.

Preparation of Compound (4a)

The compound (4a) is commercially available or can be prepared by a method known to a person skilled in the art. If not commercially available, the compound (4a) can be prepared by methylating a corresponding phenol compound by a method known to a person skilled in the art when $X_a$ is a methoxy group, for example.

Step 2-4

Step 2-4 varies according to the starting material and is not specifically limited insofar as the conditions are similar to those in this reaction. A method known to a person skilled in the art may be used for the reaction. The desired compound (1a) can be obtained by heating a compound (4d) and 1.0 to 20 equivalents of ammonia or an ammonium salt with respect to the compound (4d), for example. The solvent and reaction temperature used vary according to the starting material and are not specifically limited. As a solvent that does not inhibit the reaction and allows the starting material to be dissolved therein to a certain extent, an ether solvent such as tetrahydrofuran, 1,4-dioxane, or diethyl ether; a halogenated solvent such as methylene chloride, 1,2-dichloroethane, or chloroform; an alcohol solvent such as ethanol or isopropanol; a polar solvent such as dimethylformamide or N-methylpyrrolidone; a nonpolar solvent such as toluene or xylene; an organic acid such as acetic acid, propionic acid, or trifluoroacetic acid; or a mixed solvent thereof may be preferably used, for example. Preferably, the compound (1a) can be efficiently obtained by using 1.0 to 10 equivalents of ammonium acetate with respect to the compound (4d) in an acetic acid solvent, for example. The reaction temperature must be a temperature that can complete the reaction without promoting formation of an undesirable by-product, and is preferably room temperature to 200° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Preparation of Compound (4d)

The compound (4d) can be prepared from a compound (4c) as a starting material according to Step 2-3, for example. Specifically, Step 2-3 varies according to the starting material and is not specifically limited insofar as the conditions are similar to those in this reaction. A method known to a person skilled in the art may be used for the reaction. The compound (4d) can be obtained by stirring a compound (4c) and 2-halogenated acetone (0.5 to 5.0 equivalents of 2-chloroacetone, 2-bromoacetone, or 2-iodoacetone with respect to the compound (4c), for example) in the presence of a base, for example. 0.5 to 5.0 equivalents of the base is preferably used with respect to the compound (4c). Examples of the base used include alkali metal hydrides such as sodium hydride and lithium hydride; alkali metal salts such as potassium carbonate, sodium carbonate, and cesium carbonate; and metal alkoxides such as sodium methoxide and tert-butyl potassium. The solvent and reaction temperature used vary according to the starting material and are not specifically limited. As a solvent that does not inhibit the reaction and allows the starting material to be dissolved therein to a certain extent, an ether solvent such as tetrahydrofuran, 1,4-dioxane, or diethyl ether; a halogenated solvent such as methylene chloride, 1,2-dichloroethane, or chloroform; a polar solvent such as dimethylformamide or N-methylpyrrolidone; a nonpolar solvent such as toluene or xylene; or a mixed solvent thereof may be preferably used, for example. The reaction temperature must be a temperature that can complete the reaction without promoting formation of an undesirable by-product, and is preferably room temperature to 200° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Preparation of Compound (4c)

The desired compound (4c) can be obtained by a method of heating a compound (4b) under reflux in formic acid or a method of using formic acid and a dehydration condensation agent such as preferably an acid anhydride or dicyclohexylcarbodiimide, for example. The compound (4c) can be efficiently obtained by using preferably 1 to 20 equivalents of formic acid, for example, and preferably 1 to 3 equivalents of a dehydration condensation agent, for example. The solvent used varies according to the starting material and is not specifically limited. As a solvent that does not inhibit the reaction and allows the starting material to be dissolved therein to a certain extent, an ether solvent such as tetrahydrofuran, 1,4-dioxane, or diethyl ether; a halogenated solvent such as methylene chloride, 1,2-dichloroethane, or chloroform; a polar solvent such as dimethylformamide or N-methylpyrrolidone; a nonpolar solvent such as toluene or xylene; or a mixed solvent thereof may be preferably used, for example. The reaction temperature must be a temperature that can complete the reaction without promoting formation of an undesirable by-product, and is preferably room temperature to 100° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Preparation of Compound (4b)

The compound (4b) is commercially available or can be prepared by a method known to a person skilled in the art. If not commercially available, the compound (4b) can be prepared by methylating a corresponding nitrophenol compound by a method known to a person skilled in the art, and then reducing a nitro group, when $X_a$ is a methoxy group, for example.

Preparation of Amide Compound (2a)

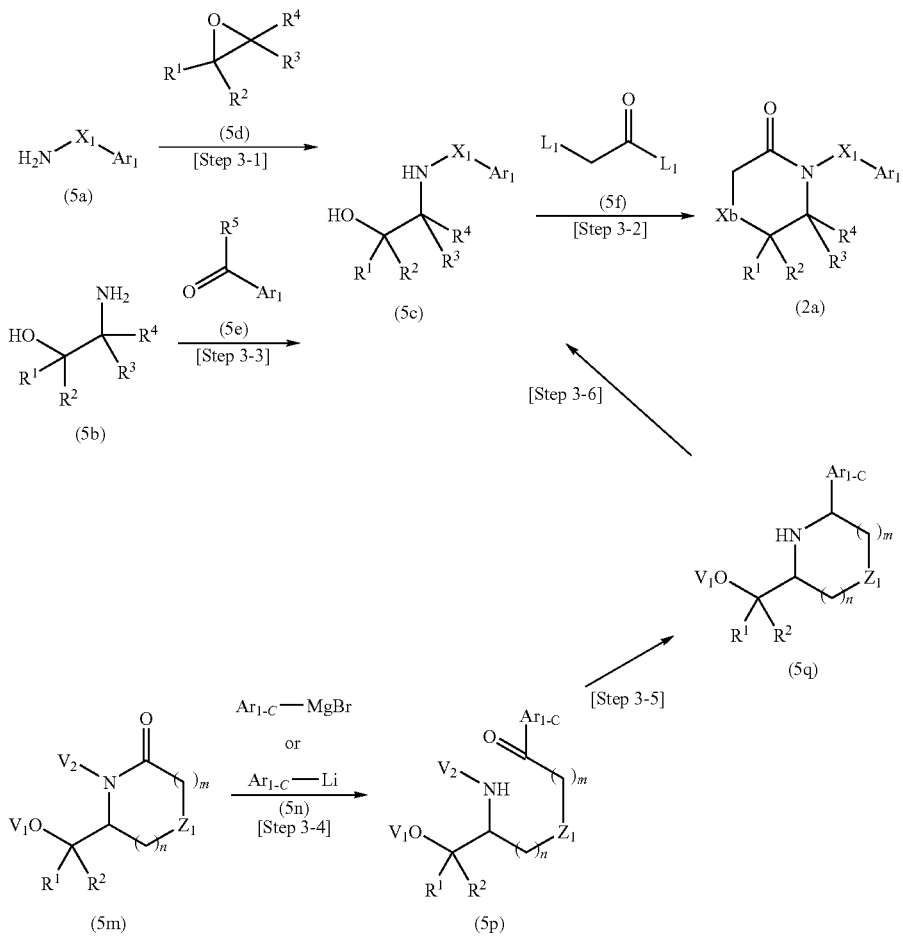

In the formula, L, $R^1$, $R^2$, $R^3$, $R^4$, $R^5$ (which may have a protecting group when $R^5$ contains a hydroxyl group); $X_1$ (which may have a protecting group when $X_1$ contains a hydroxyl group); $Ar_1$, $Ar_{1-c}$, $Z_1$, m, and n are as defined above; $X_b$ represents an oxygen atom; $V_1$ represents a protecting group for an oxygen atom such as a methyl group, ethyl group, benzyl group, allyl group, triphenylmethyl group, tert-butyl group, or tert-butyldimethylsilyl group; and $V_2$ represents a protecting group for a nitrogen atom such as a tert-butyloxycarbonyl group or benzyloxycarbonyl group.

The above reaction formula shows an example of a method for preparing the amide compound (2a). Specifically, the reaction formula shows (i) a method comprising converting an amine compound (5a) as a starting material that is commercially available or prepared using a method known to a person skilled in the art into a compound (5c) according to Step 3-1, and then forming an oxomorpholine ring in Step 3-2; (ii) a method comprising converting a compound (5b) as a starting material that is commercially available or prepared using a method known to a person skilled in the art into a compound (5c) according to Step 3-3, and then forming an oxomorpholine ring in Step 3-2, when the $X_1$ substituent contains at least one hydrogen atom; or (iii) a method comprising converting a compound (5m) as a starting material that is commercially available or prepared using a method known to a person skilled in the art into a compound (5p) by reaction with an organometallic reagent (5n) according to Step 3-4, converting the compound (5p) into a compound (5q) by nitrogen atom deprotection reaction and intramolecular reductive amination reaction in Step 3-5, converting the compound (5q) into a compound (5c) by oxygen atom deprotection reaction in Step 3-6, and then forming an oxomorpholine ring in Step 3-2.

Conversion of Compound (5c) into Amide Compound (2a)

Step 3-2 varies according to the starting material and is not specifically limited insofar as the conditions are similar to those in this reaction. The reaction may be performed by a method known to a person skilled in the art. Preferably, the reaction conveniently proceeds when vigorously stirring a compound (5c) and 1.0 to 10 equivalents of a compound (5f) with respect to the compound (5c) in a two-phase reaction solvent composed of an organic solvent and a basic solution, for example. The solvent and reaction temperature used vary according to the starting material and are not specifically limited. The solvent is preferably a solvent that does not inhibit the reaction and allows the starting material to be dissolved therein to a certain extent. Preferable examples of the solvent that can be used include ether solvents such as diethyl ether; halogenated solvents such as methylene chloride, 1,2-dichloroethane, and chloroform; and nonpolar solvents such as toluene and xylene. Preferable examples of the basic solution that can be used include solutions of alkali metal salts such as sodium hydroxide, potassium hydroxide, sodium carbonate, potassium carbonate, cesium carbonate, and sodium bicarbonate. The reaction temperature must be a temperature that can complete the reaction without promoting formation of an undesirable by-product, and is preferably −78° C. to room temperature, for example. Under preferable reaction conditions, the reaction is preferably completed in 0.5 to 24 hours, for example, and the progress of the reaction can be monitored by a known chromatography technique. An undesirable by-product can be removed by a technique known to a person skilled in the art such as a conventional chromatography technique, extraction, or/and crystallization.

Preferably, the reaction may also conveniently proceed when mixing a compound (5c) with 1.0 to 10 equivalents of a compound (5f) with respect to the compound (5c) under basic conditions, for example. The solvent and reaction temperature used vary according to the starting material and are not specifically limited. The solvent is preferably a solvent that does not inhibit the reaction and allows the starting material to be dissolved therein to a certain extent. Preferable examples of the solvent that can be used include ether solvents such as diethyl ether and tetrahydrofuran; halogenated solvents such as methylene chloride, 1,2-dichloroethane, and chloroform; and nonpolar solvents such as toluene and xylene. The base used varies according to the starting material and is not specifically limited. The amount of the base is preferably 1.0 to 10 equivalents with respect to the compound (5c). Examples of the base that can be used include alkali metal salts such as sodium hydroxide, potassium hydroxide, sodium carbonate, potassium carbonate, cesium carbonate, and sodium bicarbonate; and organic bases such as diazabicycloundecene, pyridine, 4-dimethylaminopyridine, and triethylamine. The reaction temperature must be a temperature that can complete the reaction without promoting formation of an undesirable by-product, and is preferably −78° C. to room temperature, for example. Under preferable reaction conditions, the reaction is preferably completed in 0.5 to 24 hours, for example, and the progress of the reaction can be monitored by a known chromatography technique. An undesirable by-product can be removed by a technique known to a person skilled in the art such as a conventional chromatography technique, extraction, or/and crystallization.

Preparation of Compound (5f)

The compound (5f) is commercially available or can be prepared by a method known to a person skilled in the art. The compound (5f) is preferably chloroacetyl chloride or bromoacetyl bromide, for example.

Preparation of Compound (5c)

The compound (5c) is commercially available or can be prepared by a method known to a person skilled in the art. Preferably, the compound (5c) can be prepared by (i) converting an amine compound (5a) as a starting material that is commercially available or prepared using a method known to a person skilled in the art into the compound (5c) according to Step 3-1; (ii) converting a compound (5b) as a starting material that is commercially available or prepared using a method known to a person skilled in the art into the compound (5c) according to Step 3-3; or (iii) converting a compound (5m) as a starting material that is commercially available or prepared using a method known to a person skilled in the art into a compound (5p) by reaction with an organometallic reagent (5n) according to Step 3-4, converting the compound (5p) into a compound (5q) by nitrogen atom deprotection reaction and intramolecular reductive amination reaction in Step 3-5, and converting the compound (5q) into the compound (5c) by oxygen atom deprotection reaction in Step 3-6, for example.

Conversion of Compound (5a) into Compound (5c)

Step 3-1 varies according to the starting material and is not specifically limited insofar as the conditions are similar to those in this reaction. A method known to a person skilled in the art may be used for the reaction. Preferable examples of the method include a ring opening reaction using a compound (5a) and 1.0 to 10 equivalents of an oxirane compound (5d) with respect to the compound (5a). The solvent and reaction temperature used vary according to the starting material and are not specifically limited. The solvent is preferably a solvent that does not inhibit the reaction and allows the starting material to be dissolved therein to a certain extent, or a mixed solvent thereof. Examples of the solvent that can be used include ether solvents such as diethyl ether; halogenated solvents such as methylene chloride, 1,2-dichloroethane, and chloroform; and nonpolar solvents such as toluene and xylene. A preferable result may be obtained without a solvent. The reaction temperature must be a temperature that can complete the reaction without promoting formation of an undesirable by-product, and is preferably room temperature to 300° C., for example. Under preferable reaction conditions, the reaction is preferably completed in 0.5 to 24 hours, for example, and the progress of the reaction can be monitored by a known chromatography technique. An undesirable by-product can be removed by a technique known to a person skilled in the art such as a conventional chromatography technique, extraction, or/and crystallization. The reaction may also preferably proceed by addition of a Lewis acid such as boron trifluoride, titanium tetraisopropoxide, or lithium perchlorate (see Synthesis, 2004, vol. 10, p. 15.63-1565, for example).

Preparation of Compound (5a)

The compound (5a) is commercially available or can be prepared by a method known to a person skilled in the art. If not commercially available, the compound (5a) can be prepared by a method described in a document and known to a person skilled in the art (see Shin Jikken Kagaku Koza (New Courses in Experimental Chemistry), vol. 14, Yuki Kagobutsu No Gosei To Hannou (Synthesis and Reaction of Organic Compounds) [III], edited by The Chemical Society of Japan, Maruzen Co., Ltd., February 1978, p. 1332-1399, for example). Preferable examples of the method include i) a method of converting a corresponding carbonyl derivative into the compound (5a) by reductive amination reaction; ii) a method of reducing a corresponding carbonyl derivative to an alcohol derivative, preparing an amine equivalent (preferably an azide group or imide group, for example) from the alcohol derivative by a substitution reaction known to a person skilled in the art, and then converting the amine equivalent into the compound (5a) by a conversion reaction known to a person skilled in the art; iii) a method of converting a corresponding carbonyl derivative into an oxime derivative, and then reducing the oxime derivative to the compound (5a) by a reduction reaction known to a person skilled in the art; iv) a method of converting a corresponding olefin compound into an alcohol derivative by oxidation reaction, preparing an amine equivalent (preferably an azide group or imide group, for example) from the alcohol derivative by a substitution reaction known to a person skilled in the art, and then converting the amine equivalent into the compound (5a) by a conversion reaction known to a person skilled in the art; and v) a method of converting a corresponding olefin compound into an aminoalcohol derivative by addition reaction, and converting the aminoalcohol derivative into the compound (5a) by a conversion reaction known to a person skilled in the art. The compound (5a) may be commercially available as an optically active compound or prepared by a method known to a person skilled in the art as an optically active compound (see Chem. Rev., 1994, vol. 94, p. 2483-2547; Tetrahedron Letters, 1996, vol. 37, p. 3219-3222; and Organic Letters, 2000, vol. 2, p. 2821-2824, for example). The compound of the present invention can be prepared as an optically active compound from this material as a starting material.

Preparation of Oxirane Compound (5d)

The oxirane compound (5d) is commercially available or can be prepared by a method known to a person skilled in the art. If not commercially available, the oxirane compound (5d) can be prepared by a method described in a document and known to a person skilled in the art (see Shin Jikken Kagaku Koza (New Courses in Experimental Chemistry), vol. 14, Yuki Kagobutsu No Gosei To Hannou (Synthesis and Reaction of Organic Compounds) [I], edited by The Chemical Society of Japan, Maruzen Co., Ltd., November 1977, p. 567-611, for example). The compound (5d) may be commercially available as an optically active compound or prepared by a method known to a person skilled in the art as an optically active compound (see K. B. Sharpless et al., "Comprehensive Organic Synthesis", B. M. Trost, Pergamon, 1991, vol. 7, ch. 3-2, for example). The compound of the present invention can be prepared as an optically active compound from this material as a starting material.

Conversion of Compound (5b) into Compound (5c)

Step 3-3 varies according to the starting material and is not specifically limited insofar as the conditions are similar to those in this reaction. A method known to a person skilled in the art may be used for the reaction. Preferably, the method may be reductive amination reaction of a compound (5b) with a carbonyl reaction (5e) (see Shin Jikken Kagaku Koza (New Courses in Experimental Chemistry), vol. 14, Yuki Kagobutsu No Gosei To Hannou (Synthesis and Reaction of Organic Compounds) [III], edited by The Chemical Society of Japan, Maruzen Co., Ltd., February 1978, p. 1380-1384, for example). For example, the method is preferably a method of heating under reflux a carbonyl compound (5e) and 0.5 to 5.0 equivalents of a compound (5b) in the presence of an acid catalyst such as more preferably a typical inorganic acid such as hydrochloric acid or sulfuric acid, an organic acid such as methanesulfonic acid, p-toluenesulfonic acid, or camphorsulfonic acid, or an organic acid salt such as pyridinium p-toluenesulfonate (preferably 0.01 to 0.5 equivalent, for example) to cause dehydration reaction, and reducing the resulting imine derivative to the desired amine derivative by preferably 1.0 to 10 equivalents of a metal hydride such as lithium aluminum hydride or sodium borohydride with respect to the imine derivative, for example. It is also possible to treat a carbonyl compound (5e) and 0.5 to 5.0 equivalents of a compound (5b) in an inert solvent such as tetrahydrofuran in the presence of a Lewis acid catalyst such as preferably titanium tetraisopropoxide (preferably 0.01 to 0.5 equivalent, for example), and then reduce the resultant by 1.0 to 10 equivalents of a metal hydride such as sodium borohydride. It is also preferable to employ a method of reducing a carbonyl derivative (5e) and preferably 0.5 to 5.0 equivalents of a compound (5b), for example, by preferably 1.0 to 10 equivalents of a metal hydride such as sodium triacetoxyborohydride or sodium cyanoborohydride, for example, in an inert solvent such as preferably dichloromethane, 1,2-dichloroethane, tetrahydrofuran, methanol, or ethanol to obtain the desired amine derivative. Preferably 1.0 to 10 equivalents of an acidic substance such as acetic acid or hydrochloric acid, for example, may be added in order to make the reaction conveniently proceed. The reaction temperature varies according to the starting material and is not specifically limited. However, the reaction temperature must be a temperature that can complete the reaction without promoting formation of an undesirable by-product, and is preferably room temperature to 100° C., for example. Under preferable reaction conditions, the reaction is preferably completed in 0.5 to 24 hours, for example, and the progress of the reaction can be monitored by a known chromatography technique. An undesirable by-product can be removed by a technique known to a person skilled in the art such as a conventional chromatography technique, extraction, or/and crystallization.

Preparation of Compound (5b)

The compound (5b) is commercially available or can be prepared by a method known to a person skilled in the art. If not commercially available, the compound (5b) can be prepared by a method described in a document and known to a person skilled in the art (see Shin Jikken Kagaku Koza (New Courses in Experimental Chemistry), vol. 14, Yuki Kagobutsu No Gosei To Hannou (Synthesis and Reaction of Organic Compounds) [III], edited by The Chemical Society of Japan, Maruzen Co., Ltd., February 1978, p. 1332-1399, for example). The compound (5b) may be commercially available as an optically active compound or prepared by a method known to a person skilled in the art as an optically active compound (see Tetrahedron Letters, 1996, vol. 37, p. 3219-3222, for example). The compound of the present invention can be prepared as an optically active compound from this material as a starting material.

Preparation of Carbonyl Compound (5e)

The carbonyl compound (5e) is commercially available or can be prepared by a method known to a person skilled in the art. If not commercially available, the carbonyl compound (5e) can be prepared by a method described in a document and known to a person skilled in the art (see Shin Jikken Kagaku Koza (New Courses in Experimental Chemistry), vol. 14, Yuki Kagobutsu No Gosei To Hannou (Synthesis and Reaction of Organic Compounds) [II], edited by The Chemical Society of Japan, Maruzen Co., Ltd., December 1977, p. 633-875, for example).

Conversion of Compound (5q) into Compound (5c)

Step 3-6 varies according to the starting material and is not specifically limited insofar as the conditions are similar to those in this reaction. A deprotection method known to a person skilled in the art may be used (see T. Greene et al., "Protective Groups in Organic Synthesis", John Wiley & Sons, Inc., New York, 1981, for example). Alternatively, Step 3-6 may preferably be performed by preparing a compound (5q) as an ester derivative, wherein $R^1$ and $R^2$ form a carbonyl group, and then reducing the ester derivative by a reduction reaction known to a person skilled in the art, when $R^1$ and $R^2$ are each a hydrogen atom, for example.

Preparation of Compound (5q)

The compound (5q) is commercially available or can be prepared by a method known to a person skilled in the art. If not commercially available, the compound (5q) can be preferably prepared from a compound (5p) as a starting material according to Step 3-5, for example. Specifically, the compound (5q) can be preferably prepared by the two steps of deprotecting the protecting group for the nitrogen atom of a compound (5p) by a deprotection method known to a person skilled in the art (see T. Greene et al., "Protective Groups in Organic Synthesis", John Wiley & Sons, Inc., New York, 1981, for example), and then subjecting the compound to intramolecular reductive amination reaction (see Shin Jikken Kagaku Koza (New Courses in Experimental Chemistry), vol. 14, Yuki Kagobutsu No Gosei To Hannou (Synthesis and Reaction of Organic Compounds) [III], edited by The Chemical Society of Japan, Maruzen Co., Ltd., February 1978, p. 1380-1384, for example). Alternatively, these steps may preferably be performed using a compound (5p), wherein $R^1$ and $R^2$ form a carbonyl group, as a starting material, for example.

Preparation of Compound (5p)

The compound (5p) is commercially available or can be prepared by a method known to a person skilled in the art. If not commercially available, the compound (5p) can be preferably prepared from a compound (5m) as a starting material according to Step 3-4, for example. For example, the compound (5p) can be conveniently prepared by reacting a compound (5m) with 0.5 to 5.0 equivalents of an organometallic reagent (5n) commercially available or prepared by a method known to a person skilled in the art by a nucleophilic reaction known to a person skilled in the art. The solvent used varies according to the starting material and is not specifically limited. The solvent is preferably a solvent that does not inhibit the reaction and allows the starting material to be dissolved therein to a certain extent, or a mixed solvent thereof. Examples of the solvent that can be used include ether solvents such as diethyl ether and tetrahydrofuran; halogenated solvents such as methylene chloride, 1,2-dichloroethane, and chloroform; and nonpolar solvents such as toluene and xylene. The reaction temperature varies according to the starting material and is not specifically limited. However, the reaction temperature must be a temperature that can complete the reaction without promoting formation of an undesirable by-product, and is preferably −78° C. to 50° C., for example. Under preferable reaction conditions, the reaction is preferably completed in 0.5 to 24 hours, for example, and the progress of the reaction can be monitored by a known chromatography technique. An undesirable by-product can be removed by a technique known to a person skilled in the art such as a conventional chromatography technique, extraction, or/and crystallization. Alternatively, it is preferable to use a compound (5m), wherein $R^1$ and $R^2$ form a carbonyl group, as a starting material, for example.

Preparation of Compound (5m)

The compound (5m) is commercially available or can be prepared by a method known to a person skilled in the art. If not commercially available, the compound (5m) can be preferably obtained by subjecting a corresponding starting material to a protection reaction known to a person skilled in the art, for example (see T. Greene et al., "Protective Groups in Organic Synthesis", John Wiley & Sons, Inc., New York, 1981; or T. Sakamoto et al., "J. Org. Chem.", 1996, vol. 61, p. 8496, for example). Alternatively, it is preferable to use a compound, wherein $R^1$ and $R^2$ form a carbonyl group, as a starting material, for example.

General Preparation Method 2

Typically used General Preparation Method 2 for the compound of the general formula (I) of the present invention will be described below.

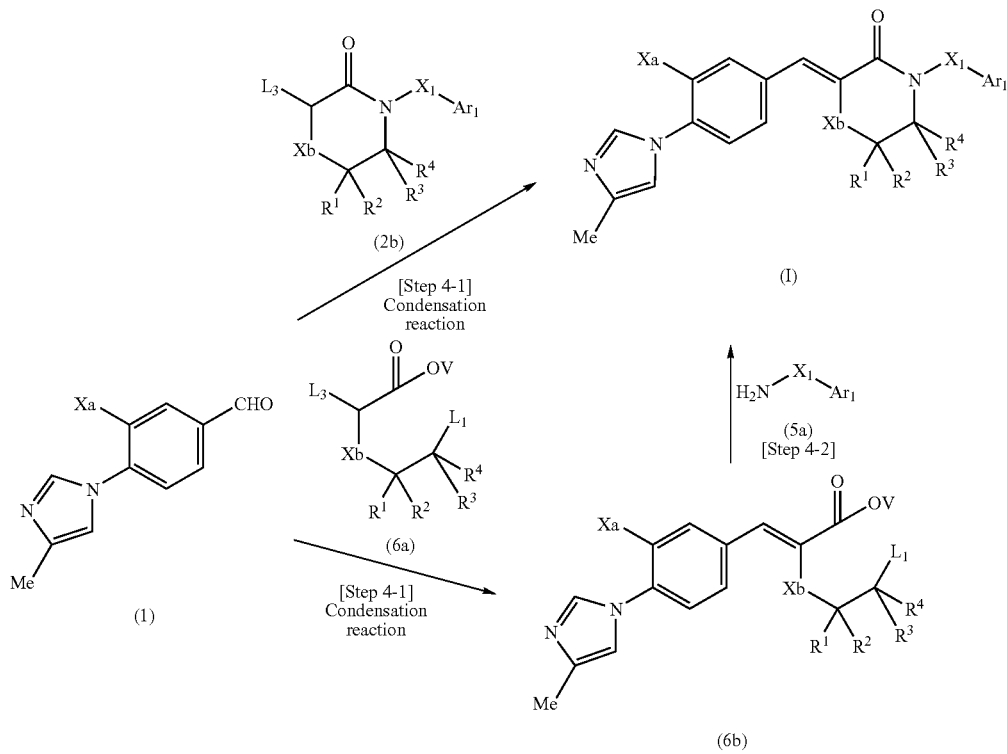

In the formula, $Ar_1$, $R^1$, $R^2$, $R^3$, $R^4$, $L_1$, $X_1$, $X_a$, and $X_b$ are as defined above; $L_3$ represents a triphenylphosphonium group, phosphite group, or silyl group; and V represents a protecting group for a carboxyl group such as a methyl group, ethyl group, benzyl group, allyl group, triphenylmethyl group, tert-butyl group, or tert-butyldimethylsilyl group.

The above General Preparation Method 2 is an example of a method for preparing the compound of the general formula (I) comprising condensing an aldehyde compound (1) with an amide compound (2b) in Step 4-1, or an example of a method for preparing the compound of the general formula (I) comprising condensing an aldehyde compound (1) with an ester compound (6a) in Step 4-1, and then reacting the resulting compound (6b) with an amine compound (5a) in Step 4-2.

Step 4-1

The condensation reaction of Step 4-1 varies according to the starting material and is not specifically limited insofar as the conditions are similar to those in this reaction. A known method described in many documents may be used for the reaction. Preferable examples of the method include Wittig reaction, Horner-Emmons reaction, and Peterson reaction (see Jikken Kagaku Koza (Courses in Experimental Chemistry), vol. 19, Yuki Gosei (Organic Synthesis) [I], edited by The Chemical Society of Japan, Maruzen Co., Ltd., June 1992, p. 57-85, for example).

The Wittig reaction is performed by using a compound (2b) or (6a), wherein $L_3$ is a triphenylphosphonium halide salt; preferably 0.8 to 1.5 equivalents of an aldehyde compound (1), for example; and preferably 1.0 to 5.0 equivalents of a base, for example. This reaction may be i) a method of first treating a compound (2b) or (6a) and a base to form a phosphorus ylide and then adding an aldehyde compound (1) to the ylide; or (ii) a method of adding a base in the presence of a compound (2b) or (6a) and an aldehyde compound (1). This reaction is preferably performed in the presence of a solvent from the viewpoint of operativity and stirring efficiency. The solvent used varies according to the starting material and the base used, and is not specifically limited insofar as the solvent does not inhibit the reaction and allows the starting material to be dissolved therein to a certain extent. Preferable examples of the solvent include polar solvents such as nitromethane, acetonitrile, 1-methyl-2-pyrrolidone, N,N-dimethylformamide, and dimethyl sulfoxide; ether solvents such as tetrahydrofuran, 1,4-dioxane, and 1,2-dimethoxyethane; nonpolar solvents such as benzene, toluene, and xylene; alcohol solvents such as ethanol and methanol; halogenated solvents such as chloroform and dichloromethane; water; and mixed solvents thereof. The base used varies according to the starting material and the solvent. Preferable examples of the base include alkali metal hydroxides such as sodium hydroxide, potassium hydroxide, and lithium hydroxide; alkali metal carbonates such as sodium carbonate, potassium carbonate, and sodium bicarbonate; alkali metal salts of alcohols such as sodium methoxide and potassium tert-butoxide; organic bases such as triethylamine, pyridine, and diazabicyclononene; organic metals such as butyl lithium and lithium diisobutylamide; and alkali metal hydrides such as sodium hydride. The reaction temperature must be a temperature that can complete the reaction without promoting formation of an undesirable by-product, and is preferably −78 to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction, or/and crystallization.

The Horner-Emmons reaction is performed by using a compound (2b) or (6a), wherein $L_3$ is a phosphite; preferably 0.8 to 1.5 equivalents of an aldehyde compound (1), for example; and preferably 1.0 to 5.0 equivalents of a base, for example. This reaction may be i) a method of first treating a compound (2b) or (6a) and a base to form a carbanion and then adding an aldehyde compound (1) to the carbanion; or (ii) a method of adding a base in the presence of a compound (2b) or (6a) and an aldehyde compound (1). This reaction is preferably performed in the presence of a solvent from the viewpoint of operativity and stirring efficiency. The solvent used varies according to the starting material and the base used, and is not specifically limited insofar as the solvent does not inhibit the reaction and allows the starting material to be dissolved therein to a certain extent. Preferable examples of the solvent include polar solvents such as 1-methyl-2-pyrrolidone, N,N-dimethylformamide, and dimethyl sulfoxide; ether solvents such as tetrahydrofuran, 1,4-dioxane, and 1,2-dimethoxyethane; nonpolar solvents such as benzene, toluene, and xylene; alcohol solvents such as ethanol and methanol; water; and mixed solvents thereof. The base used varies according to the starting material and the solvent. Preferable examples of the base include alkali metal hydroxides such as sodium hydroxide, potassium hydroxide, and lithium hydroxide; alkali metal carbonates such as sodium carbonate, potassium carbonate, and sodium bicarbonate; alkali metal salts of alcohols such as sodium methoxide and potassium tert-butoxide; organic bases such as triethylamine, pyridine, and diazabicyclononene; organic metals such as butyl lithium and lithium diisobutylamide; alkali metal hydrides such as sodium hydride; and alkali metal ammonium salts such as sodium amide. The reaction temperature must be a temperature that can complete the reaction without promoting formation of an undesirable by-product, and is preferably −78 to 150° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

The Peterson reaction is performed by using a compound (2b) or (6a), wherein $L_3$ is a silyl group; preferably 0.8 to 1.5 equivalents of an aldehyde compound (1), for example; and preferably 1.0 to 5.0 equivalents of a base, for example. This reaction may be i) a method of first treating a compound (2b) or (6a) and a base to form a carbanion and then adding an aldehyde compound (1) to the carbanion; or (ii) a method of adding a base in the presence of a compound (2b) or (6a) and an aldehyde compound (1). This reaction is preferably performed in the presence of a solvent from the viewpoint of operativity and stirring efficiency. The solvent used varies according to the starting material and the base used, and is not specifically limited insofar as the solvent does not inhibit the reaction and allows the starting material to be dissolved therein to a certain extent. Preferable examples of the solvent include polar solvents such as 1-methyl-2-pyrrolidone, N,N-dimethylformamide, and dimethyl sulfoxide; ether solvents such as tetrahydrofuran, 1,4-dioxane, and 1,2-dimethoxyethane; nonpolar solvents such as benzene, toluene, and xylene; alcohol solvents such as ethanol and methanol; water; and mixed solvents thereof. The base used varies according to the starting material and the solvent. Preferable examples of the base include alkali metal hydroxides such as sodium hydroxide, potassium hydroxide, and lithium hydroxide; alkali metal carbonates such as sodium carbonate, potassium carbonate, and sodium bicarbonate; alkali metal salts of alcohols such as sodium methoxide and potassium tert-butoxide; organic bases such as triethylamine, pyridine, and diazabicyclononene; organic metals such as butyl lithium and lithium diisobutylamide; alkali metal hydrides such as sodium hydride; and alkali metal ammonium salts such as sodium amide. The reaction temperature must be a temperature that can complete the reaction without promoting formation of an undesirable by-product, and is preferably −78 to 150° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

the resultant into the compound of the general formula (I) by the subsequent intramolecular amidation reaction. In this step, a compound (6b) and an amine compound (5a) can be converted into the compound of the general formula (I) in one reaction step by selecting appropriate conditions.

Preparation of Amide Compound (2b)

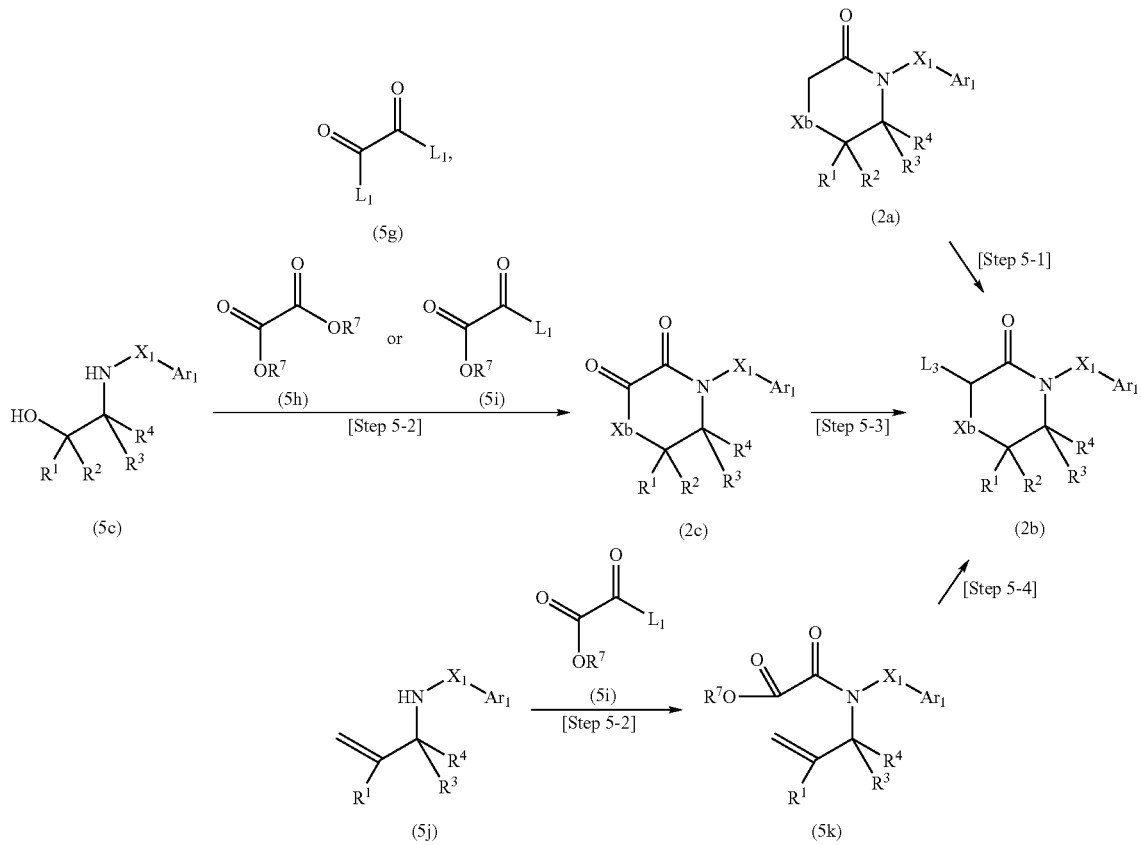

Step 4-2

Step 4-2 is an example of a method of reacting a compound (6b) with an amine compound (5a) and then converting the reaction product into the compound of the general formula (I). Examples of this step include i) a method of deprotecting the protecting group of a compound (6b) by a method known to a person skilled in the art (see T. Greene et al., "Protective Groups in Organic Synthesis" (John Wiley & Sons. Inc., New York, 1981, for example), performing dehydration condensation of the compound with an amine compound (5a) by a method known to a person skilled in the art (see Shin Jikken Kagaku Koza (New Courses in Experimental Chemistry), vol. 14, Yuki Kagobutsu No Gosei To Hannou (Synthesis and Reaction of Organic Compounds) [III], edited by The Chemical Society of Japan, Maruzen Co., Ltd., February 1978, p. 1136-1162; and "Yukikagaku Jikken No Tebiki (Introduction to Organic Chemistry Experiments) [4]", Kagaku-Dojin Publishing Company, Inc., September 1990, p. 27-52, for example), and converting the condensate into the compound of the general formula (I) by treatment under basic conditions; and ii) a method of coupling a compound (6b) with an amine compound (5a) by a method known to a person skilled in the art, deprotecting the protecting group, and converting In the formula, $Ar_1$, $L_1$, $L_3$, $R^1$, $R^2$, $R^3$, $R^4$, $X_1$, and $X_b$ are as defined above; and $R^7$ represents a lower alkyl group.

The above reaction formula shows an example of a method for preparing the amide compound (2b). Specifically, the amide compound (2b) can be prepared by a method known to a person skilled in the art, although the method varies according to the starting material. Preferable examples of the method include a method of preparing the amide compound (2b) from an amide compound (2a) as a starting material according to Step 5-1; a method of converting a compound (5c) as a starting material into a compound (2c) in Step 5-2, and then converting the compound (2c) into the amide compound (2b) in Step 5-3; and a method of converting a compound (5j) as a starting material into a compound (5k) in Step 5-2, and then converting the compound (5k) into the amide compound (2b) in Step 5-4.

Conversion of Amide Compound (2a) into Amide Compound (2b)

Step 5-1 varies according to the starting material and is not specifically limited insofar as the conditions are similar to those in this reaction. A method known to a person skilled in the art may be used for the reaction. Preferably, for example, Step 5-1 is i) Wittig reaction, wherein $L_3$ is a triphenylphosphonium group, and the reaction is a method of halogenating an amide compound (2a) by a method known to a person skilled in the art (see Jikken Kagaku Koza (Courses in Experimental Chemistry), vol. 19, Yuki Gosei (Organic Synthesis) [I], edited by The Chemical Society of Japan, Maruzen Co., Ltd., June 1992, p. 430-438, for example), and then reacting the compound with triphenylphosphine (see Organic Reaction, 1965, vol. 14, p. 270, for example). Alternatively, Step 5-1 is ii) Horner-Emmons reaction, wherein $L_3$ is a phosphite, and the reaction is a method of halogenating an amide compound (2a) by a method known to a person skilled in the art (see Jikken Kagaku Koza (Courses in Experimental Chemistry), vol. 19, Yuki Gosei (Organic Synthesis) [I], edited by The Chemical Society of Japan, Maruzen Co., Ltd., June 1992, p. 430-438, for example), and then reacting the compound with an alkyl phosphinite by Arbuzov reaction (see Chemical Review, 1981, vol. 81, p. 415, for example) or with a metal phosphonite by Becker reaction (see Journal of the American Chemical Society, 1945, vol. 67, p. 118.0, for example) to prepare the amide compound (2b) Alternatively, Step 5-1 may employ a method of preparing the amide compound (2b) from an amide compound (2a) and a chlorophosphate in the presence of a base (see The Journal of Organic Chemistry, 1989, vol. 54, p. 4750, for example). Alternatively, Step 5-1 is iii) Peterson reaction, wherein $L_3$ is a silyl group, and the reaction is a method of preparing the amide compound (2b) from an amide compound (2a) and a trialkylsilyl chloride in the presence of a base (see Journal of Organometallic Chemistry, 1983, vol. 248, p. 51, for example).

Conversion of Amide Compound (2c) into Amide Compound (2b)

Step 5-3 varies according to the starting material and is not specifically limited insofar as the conditions are similar to those in this reaction. A method known to a person skilled in the art may be used for the reaction. Preferably, for example, Step 5-3 may be a method of reducing an ester carbonyl moiety to an alcohol compound (see Jikken Kagaku Koza (Courses in Experimental Chemistry), vol. 26, Yuki Gosei (Organic Synthesis) [VIII], edited by The Chemical Society of Japan, Maruzen Co., Ltd., April 1992, p. 159-266, for example), converting the alcohol compound into a halogen compound (see Shin Jikken Kagaku Koza (New Courses in Experimental Chemistry), vol. 14, Yuki Kagobutsu No Gosei To Hannou (Synthesis and Reaction of Organic Compounds) [I], edited by The Chemical Society of Japan, Maruzen Co., Ltd., November 1977, p. 331-450, for example), and converting the halogen compound into a Wittig reagent (2b) (see Organic Reaction, 1965, vol. 14, p. 270, for example) or into a Horner-Emmons reagent (2b) by Arbuzov reaction (see Chemical Review, 1981, vol. 81, p. 415, for example). Alternatively, the alcohol compound can be converted into a Wittig reagent (2b) by reaction with triallylphosphorus hydrobromide (see Synth. Commun., 1996, vol. 26, p. 3091-3095; and Tetrahedron Lett., 2001, vol. 42, p. 1309-1331, for example).

Preparation of Amide Compound (2c)

The amide compound (2c) can be prepared by a method known to a person skilled in the art, although the method varies according to the starting material. Preferably, the amide compound (2c) can be prepared from a compound (5c) as a starting material through Step 5-2, for example. Preferably, in this step, the reaction conveniently proceeds when vigorously stirring a compound (5c) and 1.0 to 10 equivalents of a compound (5g) with respect to the compound (5c) in a two-phase reaction solvent composed of an organic solvent and a basic solution, for example. The solvent and reaction temperature used vary according to the starting material and are not specifically limited. The solvent is preferably a solvent that does not inhibit the reaction and allows the starting material to be dissolved therein to a certain extent, or a mixed solvent thereof. Preferable examples of the organic solvent that can be used include ether solvents such as diethyl ether; halogenated solvents such as methylene chloride, 1,2-dichloroethane, and chloroform; and nonpolar solvents such as toluene and xylene. 1.0 or more equivalents of the basic solution is preferably used. Preferable examples of the basic solution that can be used include solutions of alkali metal salts such as sodium hydroxide, potassium hydroxide, sodium carbonate, potassium carbonate, cesium carbonate, and sodium bicarbonate. The reaction temperature must be a temperature that can complete the reaction without promoting formation of an undesirable by-product, and is preferably −78° C. to room temperature, for example. Under preferable reaction conditions, the reaction is preferably completed in 0.5 to 24 hours, for example, and the progress of the reaction can be monitored by a known chromatography technique. An undesirable by-product can be removed by a technique known to a person skilled in the art such as a conventional chromatography technique, extraction, or/and crystallization.

It is also possible to use for Step 5-2 a method of reacting a compound (5c) with preferably 1.0 to 5.0 equivalents of a compound (5g), for example, in the presence of a base such as preferably an organic amine including triethylamine, isopropylethylamine, or pyridine (preferably 1.0 to 5.0 equivalents, for example). The solvent and reaction temperature used vary according to the starting material and are not specifically limited. The solvent is preferably a solvent that does not inhibit the reaction and allows the starting material to be dissolved therein to a certain extent. Preferable examples of the organic solvent that can be used include ether solvents such as diethyl ether; halogenated solvents such as methylene chloride, 1,2-dichloroethane, and chloroform; and nonpolar solvents such as toluene and xylene. The reaction temperature must be a temperature that can complete the reaction without promoting formation of an undesirable by-product, and is preferably −78° C. to 100° C., for example. Under preferable reaction conditions, the reaction is preferably completed in 0.5 to 24 hours, for example, and the progress of the reaction can be monitored by a known chromatography technique. An undesirable by-product can be removed by a technique known to a person skilled in the art such as a conventional chromatography technique, extraction, or/and crystallization.

In Step 5-2, the reaction may also conveniently proceed when heating a compound (5c) and 1.0 to 20 equivalents of a compound (5h), wherein $R^7$ is lower alkyl, with respect to the compound (5c). The solvent and reaction temperature used vary according to the starting material and are not specifically limited. The solvent is preferably a solvent that does not inhibit the reaction and allows the starting material to be dissolved therein to a certain extent, or a mixed solvent thereof. Preferable examples of the organic solvent that can be used include ether solvents such as diethyl ether; halogenated solvents such as methylene chloride, 1,2-dichloroethane, and 1,2-dichlorobenzene; nonpolar solvents such as toluene and xylene; polar solvents such as dimethylformamide and N-methylpyrrolidone; and alcohol solvents such as methanol, ethanol, 2-propanol, and tert-butanol. The reaction may also conveniently proceed without a solvent. The reaction temperature must be a temperature that can complete the reaction without promoting formation of an undesirable by-product, and is preferably 50° C. to 200° C., for example. Under preferable reaction conditions, the reaction is preferably completed in 0.5 to 24 hours, for example, and the progress of the reaction can be monitored by a known chromatography technique. An undesirable by-product can be removed by a technique known to a person skilled in the art such as a conventional chromatography technique, extraction, or/and crystallization.

In Step 5-2, the reaction may also conveniently proceed when using a compound (5c) and 1.0 to 5.0 equivalents of a compound (5l) under the above-described reaction conditions or a combination thereof. The reaction may also conveniently proceed by addition of a phase transfer catalyst that is a quaternary ammonium salt such as tetrabutylammonium chloride or benzyltriethylammonium chloride, or an acidic compound such as p-toluenesulfonic acid or camphorsulfonic acid.

Preparation of Compounds (5g), (5h), and (5i)

The compounds (5g), (5h), and (5i) are commercially available or can be prepared by a method known to a person skilled in the art. If not commercially available, the compounds may be prepared by esterification or halogenation of a corresponding oxalic acid derivative by a method known to a person skilled in the art.

Conversion of Compound (5k) into Oxomorpholine Compound (2b)

Step 5-4 varies according to the starting material and is not specifically limited insofar as the conditions are similar to those in this reaction. A method known to a person skilled in the art may be used for the reaction. Preferably, for example, Step 5-4 may be a method of converting an olefin moiety of a compound (5k) into a hemiacetal derivative by oxidative cleavage reaction and intramolecular cyclization reaction (see Shin Jikken Kagaku Koza (New Courses in Experimental Chemistry), vol. 14, Yuki Kagobutsu No Gosei To Hannou (Synthesis and Reaction of Organic Compounds) [I], edited by The Chemical Society of Japan, Maruzen Co., Ltd., November 1977, p. 331-450, for example), and converting the hemiacetal derivative into a Wittig reagent (2b) (see Organic Reaction, 1965, vol. 14, p. 270, for example) or into a Horner-Emmons reagent (2b) by Arbuzov reaction (see Chemical Review, 1981, vol. 81, p. 415, for example). The hemiacetal derivative can also be converted into a Wittig reagent (2b) by reaction with triallylphosphorus hydrobromide (see Synth. Commun., 1996, vol. 26, p. 3091-3095; and Tetrahedron Lett., 2001, vol. 42, p. 1309-1331, for example). The oxidative cleavage reaction of an olefin moiety varies according to the starting material and is not specifically limited insofar as the conditions are similar to those in this reaction. Ozone oxidation is preferable, for example (see Shin Jikken Kagaku Koza (New Courses in Experimental Chemistry), vol. 15, Sanka To Kangen (Oxidation and Reduction) [I-2], edited by The Chemical Society of Japan, Maruzen Co., Ltd., September 1976, p. 563-603, for example). The oxidative cleavage reaction and the intramolecular cyclization reaction may continuously proceed under suitable reaction conditions, and this is convenient for preparing a compound (2b).

Preparation of Compound (5k)

The compound (5k) can be prepared from a compound (5j) and preferably 1.0 to 5.0 equivalents of a compound (5l) with respect to the compound (5j), for example, according to Step 5-2.

Preparation of Compound (5j)

The compound (5j) is commercially available or can be prepared by a method known to a person skilled in the art. If not commercially available, the compound (5j) is preferably prepared by intramolecular hydroamination reaction of an amine compound or sulfonylamide compound having an allenyl group using a metal catalyst, when $R^4$ and $X_1$ are bonded to each other to form a nitrogen-containing heterocycle, for example (see Journal of The American Chemical Society, 2003, vol. 125, p. 11956; and Tetrahedron Lett., 1998, vol. 39, p. 5421-5424, for example). This reaction varies according to the starting material and is not specifically limited insofar as the conditions are similar to those in this reaction. The metal catalyst is preferably 0.001 to 0.1 equivalent of a palladium complex such as palladium (II) acetate, dichlorobis(triphenylphosphine)palladium (II), tetrakis(triphenylphosphine) palladium (0), or an allylpalladium chloride dimer, for example. The reaction may also conveniently proceed by addition of preferably 0.001 to 0.1 equivalent, for example, of a phosphorus ligand such as preferably 2,2'-bis(diphenylphosphino)-1,1'-binaphthyl or 1,1'-bis(diphenylphosphino)ferrocene. The reaction may also conveniently proceed by addition of preferably 0.001 to 10 equivalents of acetic acid or hydrochloric acid, for example. The solvent and reaction temperature used vary according to the starting material and are not specifically limited. The solvent is preferably a solvent that does not inhibit the reaction and allows the starting material to be dissolved therein to a certain extent, or a mixed solvent thereof. Preferable examples of the organic solvent that can be used include ether solvents such as diethyl ether and tetrahydrofuran; halogenated solvents such as methylene chloride and 1,2-dichloroethane; nonpolar solvents such as toluene and xylene; polar solvents such as dimethylformamide and N-methylpyrrolidone; and alcohol solvents such as methanol, ethanol, 2-propanol, and tert-butanol. The reaction temperature must be a temperature that can complete the reaction without promoting formation of an undesirable by-product, and is preferably 50° C. to 200° C., for example. Under preferable reaction conditions, the reaction is preferably completed in 0.5 to 24 hours, for example, and the progress of the reaction can be monitored by a known chromatography technique. An undesirable by-product can be removed by a technique known to a person skilled in the art such as a conventional chromatography technique, extraction, or/and crystallization.

Preparation of Compound (6a)

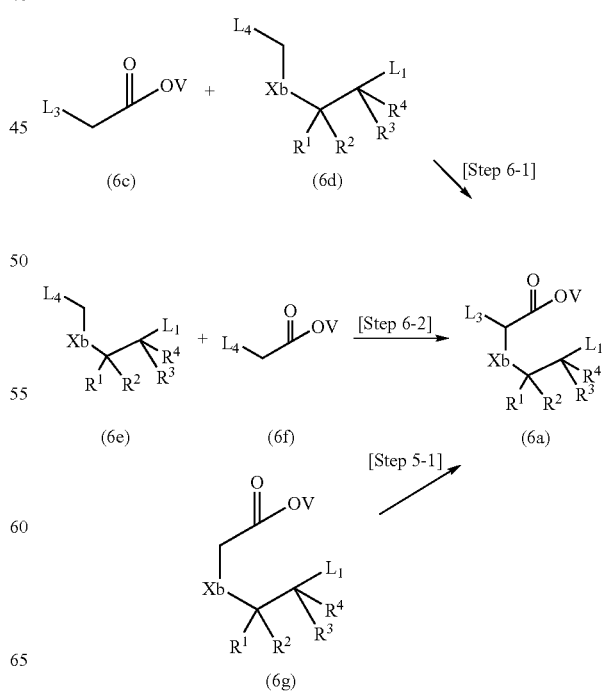

In the formula, $R^1$, $R^2$, $R^3$, $R^4$, V, $L_1$, $L_3$, and $X_b$ are as defined above; and $L_4$ is as defined for $L_1$.

The above reaction formula shows an example of preparation of the compound (6a). Specifically, the compound (6a) is commercially available or can be obtained by a technique represented by the above reaction formula and known to a person skilled in the art (see C. Patois et al., "Synth. Commun.", 1991, vol. 22, p. 2391; and J. A. Jackson et al., "J. Org. Chem.", 1989, vol. 20, p. 5556, for example). Step 6-1 is a step of obtaining the desired compound (6a) by treating a phosphonate compound (6c) with 1.0 to 2.0 equivalents of a compound (6d) with respect to the phosphonate compound (6c) under basic conditions, for example. Alternatively, Step 6-2 is a step of obtaining the desired compound (6a) by treating a compound (6e) with 1.0 to 2.0 equivalents of an ester compound (6f) under basic conditions, for example. The desired compound (6a) can also be obtained from a compound (6g) according to the above-described Step 5-1, for example.

The base used in this step varies according to the starting material and is not limited. 1.0 to 1.5 equivalents of a base such as sodium hydride, n-butyl lithium, lithium diisopropylamide, lithium bis(trimethylsilyl)amide, or sodium bis(trimethylsilyl)amide is preferably used, for example. The solvent used in the this step varies according to the starting material, and is not specifically limited insofar as the solvent does not inhibit the reaction and allows the starting material to be dissolved therein to a certain extent. Preferable examples of the solvent include hexane, toluene, diethyl ether, tetrahydrofuran, N,N-dimethylformamide, hexamethylphosphoric triamide, and a mixed solvent as described above. The reaction temperature must be a temperature that can complete the reaction without promoting formation of an undesirable by-product, and is preferably −78° C. to 150° C. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique or/and crystallization.

The phosphonate compound (6c), compound (6d), compound (6e), ester compound (6f), and compound (6g) used in this step are commercially available or can be obtained by a technique known to a person skilled in the art.

The compound of the general formula (I) or pharmacologically acceptable salt thereof according to the present invention has an effect of reducing Aβ40 or Aβ42 production, and thus is effective as a prophylactic or therapeutic agent for a disease caused by amyloid-β and is particularly effective as a prophylactic or therapeutic agent for a neurodegenerative disease caused by Aβ such as Alzheimer's disease or Down's syndrome.

Compounds included in the present invention exhibit excellent pharmaceutical utility, for example, in vitro activity, in vivo activity, solubility, stability, pharmacokinetics, and reduction in toxicity.

The prophylactic or therapeutic agent for a disease caused by Aβ according to the present invention can be prepared by a conventional method. Preferable examples of the dosage form include tablets, powders, fine granules, granules, coated tablets, capsules, syrups, troches, inhalants, suppositories, injections, ointments, ophthalmic solutions, ophthalmic ointments, nasal drops, ear drops, cataplasms, and lotions. The therapeutic or prophylactic agent can be prepared by using ingredients typically used such as an expicient, a binder, a lubricant, a colorant, and a corrective, and ingredients used where necessary such as a stabilizer, an emulsifier, an absorbefacient, a surfactant, a pH adjuster, a preservative, and an antioxidant, and can be prepared by blending ingredients generally used as materials for a pharmaceutical preparation. Examples of such ingredients include animal and vegetable oils such as soybean oil, beef tallow, and synthetic glyceride; hydrocarbons such as liquid paraffin, squalane, and solid paraffin; ester oils such as octyldodecyl myristate and isopropyl myristate; higher alcohols such as cetostearyl alcohol and behenyl alcohol; a silicone resin; silicone oil; surfactants such as polyoxyethylene fatty acid ester, sorbitan fatty acid ester, glycerin fatty acid ester, polyoxyethylene sorbitan fatty acid ester, polyoxyethylene hydrogenated castor oil, and a polyoxyethylene-polyoxypropylene block copolymer; water-soluble polymers such as hydroxyethylcellulose, polyacrytic acid, a carboxyvinyl polymer, polyethylene glycol, polyvinylpyrrolidone, and methylcellulose; lower alcohols such as ethanol and isopropanol; polyhydric alcohols such as glycerin, propylene glycol, dipropylene glycol, and sorbitol; sugars such as glucose and sucrose; inorganic powders such as silicic anhydride, magnesium aluminum silicate, and aluminum silicate; and purified water. Examples of the expicient used include lactose, corn starch, saccharose, glucose, mannitol, sorbitol, crystalline cellulose, and silicon dioxide. Examples of the binder used include polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, a polypropylene glycol-polyoxyethylene block copolymer, and meglumine. Examples of the disintegrator used include starch, agar, gelatin powder, crystalline cellulose, calcium carbonate, sodium bicarbonate, calcium citrate, dextrin, pectin, and carboxymethylcellulose calcium. Examples of the lubricant used include magnesium stearate, talc, polyethylene glycol, silica, and hydrogenated vegetable oil. Examples of the colorant used include those that are permitted to be added to pharmaceuticals. Examples of the corrective used include cocoa powder, menthol, empasm, mentha oil, borneol, and cinnamon powder.

For example, an oral preparation is prepared by adding an active ingredient compound or a salt thereof or a hydrate of the compound or salt, an excipient, and, where necessary, a binder, a disintegrator, a lubricant, a colorant, and a corrective, for example, and then forming the mixture into powder, fine granules, granules, tablets, coated tablets, or capsules, for example, by a conventional method. It is obvious that tablets or granules may be appropriately coated, for example, sugar coated, where necessary. A syrup or an injection preparation is prepared by adding a pH adjuster, a solubilizer, and an isotonizing agent, for example, and a solubilizing aid, a stabilizer, and the like where necessary by a conventional method. An external preparation may be prepared by any conventional method without specific limitations. As a base material, any of various materials usually used for a pharmaceutical, a quasi drug, a cosmetic, or the like may be used. Examples of the base material include materials such as animal and vegetable oils, mineral oils, ester oils, waxes, higher alcohols, fatty acids, silicone oils, surfactants, phospholipids, alcohols, polyhydric alcohols, water-soluble polymers, clay minerals, and purified water. A pH adjuster, an antioxidant, a chelator, a preservative and fungicide, a colorant, a flavor, or the like may be added where necessary. Further, an ingredient having a differentiation inducing effect such as a blood flow enhancer, a bactericide, an antiphlogistic, a cell activator, vitamin, amino acid, a humectant, or a keratolytic agent may be blended where necessary. The dose of the therapeutic or prophylactic agent of the present invention varies according to the degree of symptoms, age, sex, body weight, mode of administration, type of salt, and specific type of disease, for example. Typically, the compound of the formula (I) or pharmacologically acceptable salt thereof according to the present invention is orally administered to an adult at about 30 μg to 10 g, preferably 100 μg to 5 g, and more preferably 100 μg to 100 mg per day, or is administered to an adult by injection at about 30 μg to 1 g, preferably 100 μg to 500 mg, and more preferably 100 μg to 30 mg per day, in a single dose or multiple doses, respectively.

The present invention will now be described in detail with reference to examples and test examples. However, the examples and test examples are provided only for illustration purposes. The prophylactic or therapeutic agent for a disease caused by Aβ according to the present invention is not limited to the following specific examples in any case. A person skilled in the art can fully implement the present invention by making various modifications to not only the following examples and test examples but also the claims of the present specification, and such modifications are within the scope of the claims of the present specification.

The following abbreviations are used in the following examples.
DMF: Dimethylformamide
THF: Tetrahydrofuran
LAH: Lithium aluminum hydride
WSC: 1-Ethyl-3-(3-dimethylaminopropyl)carbodiimide hydrochloride
HOBT: 1-Hydroxybenzotriazole
DIEA: Diisopropylethylamine
TEA: Triethylamine
TBAF: Tetrabutylammonium fluoride
DBU: 1,8-Diazabicyclo[5.4.0]undec-7-ene
t: Tertiary
LDA: Lithium diisopropylamine

EXAMPLE 1

Synthesis of (Z)-2-[1-[3-methoxy-4-(4-methyl-1H-imidazol-1-yl)phenyl]methylidene]-4-(3,4,5-trifluorobenzyl)morpholin-3-one

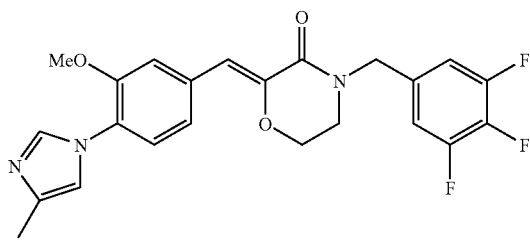

Synthesis of 3-methoxy-4-(4-methyl-1H-imidazol-1-yl)benzaldehyde

Synthesis of methyl 3-methoxy-4-nitrobenzoate

Methyl iodide (463 g) was added dropwise to a mixture of 3-hydroxy-4-nitrobenzoic acid (199 g) with potassium carbonate (450 g) in DMF (1 L) at room temperature. The reaction solution was stirred at room temperature overnight, and then methyl iodide (230 g) was added to the reaction solution. The reaction solution was further stirred at room temperature for six hours. The reaction solution was added to ice water, and the precipitated solid was collected by filtration. The resulting solid was dried at 50° C. overnight to obtain 178 g of the title compound. The property values corresponded to the reported values (CAS #5081-37-8).

Synthesis of methyl 4-amino-3-methoxybenzoate

10% palladium-carbon (containing 50% water, 15 g) was added to a solution of methyl 3-methoxy-4-nitrobenzoate (150 g) in methanol (600 mL) and THF (300 mL), and the reaction solution was stirred at a hydrogen pressure of 0.9 MPa at 50° C. to 64° C. for 6.5 hours. The reaction solution was left to cool to room temperature and then filtered through celite. The resulting filtrate was concentrated under reduced pressure to obtain 134 g of the title compound. The property values corresponded to the reported values (CAS #41608-64-4).

Synthesis of methyl 4-formylamino-3-methoxybenzoate

Acetic anhydride (268 mL) was added dropwise to formic acid (401 mL) at room temperature, and the reaction solution was stirred at room temperature for 40 minutes. A solution of methyl 4-amino-3-methoxybenzoate (134 g) in THF (600 mL) was added dropwise to the reaction solution at room temperature, and the reaction solution was stirred for one hour. 3.8 L of ice water was added to the reaction solution, and the precipitated solid was filtered and further washed with water (2 L). The resulting solid was dried at 50° C. overnight to obtain 111 g of the title compound. The property values corresponded to the reported values (CAS #700834-18-0).

Synthesis of methyl 4-[formyl-(2-oxopropyl)amino]-3-methoxybenzoate

Chloroacetone (84.5 mL) was added dropwise to a mixture of methyl 4-formylamino-3-methoxybenzoate (111 g), cesium carbonate (346 g), and potassium iodide (8.78 g) in DMF (497 mL) at room temperature, and the reaction solution was stirred for three hours. Cesium carbonate (173 g) and chloroacetone (42.0 mL) were added to the reaction solution, which was then stirred at room temperature for two hours. Ice water and ethyl acetate were added to the reaction solution, and the organic layer was separated. Ethyl acetate was added to the aqueous layer, and the organic layer was separated. The organic layers were combined and washed with water and brine in this order. The resulting organic layers were dried over anhydrous magnesium sulfate and then concentrated under reduced pressure. The residue was diluted with toluene, and the solution was concentrated under reduced pressure. tert-Butyl methyl ether and heptane were added to the resulting residue, and the precipitated solid was collected by filtration and washed with a solution of 50% tert-butyl methyl ether in heptane. The resulting solid was air-dried overnight to obtain 118 g of the title compound.
$^1$H-NMR (CDCl$_3$)δ(ppm):
2.19(s, 3H), 3.91(s, 3H), 3.94(s, 3H), 4.49(s, 2H), 7.31(d, J=8.0 Hz, 1H), 7.63(d, J=2.0 Hz, 1H), 7.69(dd, J=8.0, 2.0 Hz, 1H), 8.33 (s, 1H).

Synthesis of methyl 3-methoxy-4-(4-methyl-1H-imidazol-1-yl)benzoate

A solution of methyl 4-[formyl-(2-oxopropyl)amino]-3-methoxybenzoate (118 g) and ammonium acetate (172 g) in acetic acid (255 mL) was heated and stirred at 140° C. for one hour. After the reaction was completed, the reaction solution was neutralized with aqueous ammonia under ice-cooling. Ethyl acetate was added to the reaction solution, and the organic layer was separated. The resulting organic layer was dried over anhydrous magnesium sulfate and then filtered on a silica gel pad, and the filtrate was concentrated under reduced pressure. tert-Butyl methyl ether and heptane were added to the residue, and the precipitated solid was collected by filtration and washed with a solution of 50% tert-butyl methyl ether in heptane. The resulting solid was air-dried overnight to obtain 68.4 g of the title compound. Further, the crystallization mother liquor was concentrated under reduced pressure, and the residue was purified by silica gel column chromatography (elution solvent: heptane-ethyl acetate system) to obtain 22.3 g of the title compound.

$^1$H-NMR (CDCl$_3$)δ(ppm):
2.30(s, 3H), 3.94(s, 3H), 3.96(s, 3H), 6.98(brs, 1H), 7.32(d, J=8.4 Hz, 1H), 7.71-7.73(m, 2H), 7.79(brs, 1H).

Synthesis of 3-methoxy-4-(4-methyl-1H-imidazol-1-yl)benzaldehyde

A solution of pyrrolidine (18 mL) in THF (45 mL) was added dropwise to a solution of sodium bis(2-methoxyethoxy)aluminum hydride (65% solution in toluene, 56 mL) in THF (60 mL) at −5° C. or less over 15 minutes. The reaction solution was stirred at room temperature for one hour. Then, a suspension of tert-butoxide (2.10 g) in THF (15 mL) was added dropwise to the reaction solution at room temperature, and the reaction solution was stirred for 15 minutes. The above reaction solution was added dropwise to a solution of methyl 3-methoxy-4-(4-methyl-1H-imidazol-1-yl)benzoate (20 g) in THF (50 mL) under ice-cooling over 30 minutes. The reaction solution was stirred at room temperature for two hours, and then a 5 N sodium hydroxide solution (150 mL) was added dropwise to the reaction solution. Ethyl acetate was added to the reaction solution, and the organic layer was separated. The organic layer was washed with a saturated ammonium chloride solution and brine in this order. The organic layer was dried over anhydrous magnesium sulfate and filtered on a silica gel pad, and then the filtrate was concentrated under reduced pressure. The residue was diluted with ethyl acetate, and the precipitated solid was collected by filtration. The resulting solid was air-dried overnight to obtain 7.10 g of the title compound. Further, the crystallization mother liquor was concentrated under reduced pressure, and the residue was purified by silica gel column chromatography (elution solvent: heptane-ethyl acetate-2-propanol system) to obtain 2.65 g of the title compound.

$^1$H-NMR (CDCl$_3$)δ(ppm):
2.31(s, 3H), 3.97(s, 3H), 7.02(brs, 1H), 7.44(d, J=8.0 Hz, 1H), 7.55(dd, J=1.6, 8.0 Hz, 1H), 7.58(d, J=1.6 Hz, 1H), 7.84(brs, 1H), 10.00(s, 1H).

Synthesis of 2-[(3,4,5-trifluorobenzyl)amino]ethanol

Sodium triacetoxyborohydride (14.1 g) was added to a solution of 3,4,5-trifluorobenzaldehyde (5.0 mL), ethanolamine (3.52 g), and acetic acid (10.1 mL) in THF (100 mL) under ice-cooling, and the reaction solution was stirred at room temperature for four hours and 30 minutes. Ice water was added to the reaction solution. The reaction solution was adjusted to pH 7 to 8 by a 5 N sodium hydroxide solution and saturated sodium bicarbonate, followed by extraction with chloroform. The organic layer was dried over anhydrous magnesium sulfate and then filtered, and the mother liquor was concentrated under reduced pressure. The residue was purified by column chromatography using a silica gel (chloroform:methanol=1:100 to 1:5) to obtain 6.91 g of the title compound.

$^1$H-NMR (CDCl$_3$)δ(ppm):
2.80(t, J=4.8 Hz, 2H), 3.69(t, J=4.8 Hz, 2H), 3.78(s, 2H), 6.96-7.00(m, 2H).

Synthesis of 4-(3,4,5-trifluorobenzyl)morpholine-2,3-dione

A mixture of 2-[(3,4,5-trifluorobenzyl)amino]ethanol (6.91 g) and diethyl oxalate (20 mL) was stirred at 170° C. for one hour. The reaction solution was concentrated under reduced pressure, and then a diethyl ether was added to the residue. The precipitated crystals were collected by filtration and then air-dried to obtain 7.38 g of the title compound.

$^1$H-NMR(CDCl$_3$)δ(ppm):
3.61(t, J=4.8 Hz, 2H), 4.49(t, J=4.8 Hz, 2H), 4.63(s, 2H), 6.95-6.99(m, 2H).

Synthesis of 2-hydroxy-4-(3,4,5-trifluorobenzyl)morpholin-3-one

A 1 M solution of lithium tri-sec-butylborohydride in THF (31.4 mL) was added dropwise to a solution of 4-(3,4,5-trifluorobenzyl)morpholine-2,3-dione (7.38 g) in THF at −15° C., and the reaction solution was stirred for two hours. A 5 N sodium hydroxide solution (2.85 mL) and 30% aqueous hydrogen peroxide (968 μL) were added dropwise to the reaction solution at 20° C. or less, which was then stirred at 10° C. for one hour. Sodium bisulfite (888 mg) was added to the reaction solution, which was then stirred for 30 minutes. Brine and chloroform were added to the reaction solution, and the organic layer was separated. The organic layer was dried over anhydrous magnesium sulfate and then concentrated under reduced pressure. The residue was purified by column chromatography using a silica gel (heptane:ethyl acetate=1:1 to 0:100) to obtain 3.94 g of the title compound.

$^1$H-NMR (CDCl$_3$)δ(ppm):
3.11-3.16(m, 1H), 3.47-3.54(m, 1H), 3.80-3.86(m, 1H), 4.28-4.35(m, 1H), 4.40(d, J=14.8 Hz, 1H), 4.67(d, J=14.8 Hz, 1H), 5.37 (s, 1H), 6.90-6.94(m, 2H).

Synthesis of (Z)-2-[1-[3-methoxy-4-(4-methyl-1H-imidazol-1-yl)phenyl]methylidene]-4-(3,4,5-trifluorobenzyl)morpholin-3-one Thionyl chloride (16.1 mL) was added to a solution of 2-hydroxy-4-(3,4,5-trifluorobenzyl)morpholin-3-one (3.94 g) in methylene chloride, and the reaction solution was stirred at 50° C. for one hour. The reaction solution was concentrated under reduced pressure, and the residue was diluted with methylene chloride. Then, triphenylphosphine (5.2 g) was added under ice-cooling, and the reaction solution was stirred at room temperature for 4.5 hours. The reaction solution was concentrated under reduced pressure. Ethanol (64.6 mL), TEA (4.2 mL), and 3-methoxy-4-(4-methyl-1H-imidazol-1-yl)benzaldehyde (2.72 g) were added to the residue, and the reaction solution was heated under reflux for two hours. The reaction solution was concentrated under reduced pressure, and the residue was diluted with 2 N aqueous hydrochloric acid and ethyl acetate. Then, the aqueous layer was separated. The organic layer was washed with 2 N aqueous hydrochloric acid. Then, the total aqueous layers were combined and made alkaline with a concentrated sodium hydroxide solution. The organic layer was separated by extraction from the alkaline solution with chloroform, and then dried over anhydrous magnesium sulfate and concentrated under reduced pressure. The residue was purified by column chromatography using NH silica gel (heptane:ethyl acetate=1:1 to 0:100) to obtain 1.92 g of the title compound.

$^1$H-NMR (CDCl$_3$)δ(ppm):
2.34(s, 3H), 3.56(t, J=4.8 Hz, 2H), 3.87(s, 3H), 4.28(t, J=4.8 Hz, 2H), 4.66(s, 2H), 6.93(s, 1H), 6.95-6.99(m, 3H), 7.23(d, J=8.0 Hz, 1H), 7.40(dd, J=8.0, 1.2 Hz, 1H), 7.42(d, J=1.2 Hz, 1H), 7.85(s, 1H).
ESI-MS; m/z444[M$^+$+H].

EXAMPLE 2

Synthesis of (Z)-2-[1-[3-methoxy-4-(4-methyl-1H-imidazol-1-yl)phenyl]methylidene]-4-(2,3,4-trifluorobenzyl)morpholin-3-one

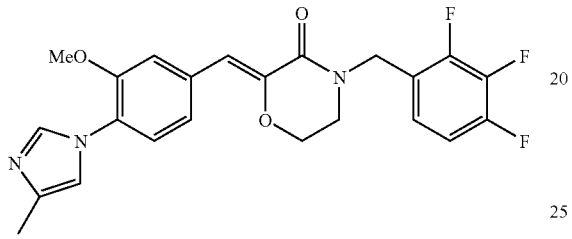

Synthesis of 2-[(2,3,4-trifluorobenzyl)amino]ethanol 891 mg of the title compound was obtained from 2,3,4-trifluorobenzaldehyde (1.0 g), ethanolamine (573 mg), acetic acid (1.79 mL), and sodium triacetoxyborohydride (2.65 g) in the same manner as in Example 1.

$^1$H-NMR (CDCl$_3$)δ(ppm):
2.80(t, J=5.2 Hz, 2H), 3.69(t, J=5.2 Hz, 2H), 3.88(s, 2H), 6.94-6.96(m, 1H), 7.07-7.09(m, 1H).

Synthesis of 4-(2,3,4-trifluorobenzyl)morpholine-2,3-dione 903 mg of the title compound was obtained from 2-[(2,3,4-trifluorobenzyl)amino]ethanol (891 mg) and diethyl oxalate (8.0 mL) in the same manner as in Example 1.

$^1$H-NMR (CDCl$_3$)δ(ppm):
3.70(t, J=5.2 Hz, 2H), 4.50(t, J=5.2 Hz, 2H), 4.73(s, 2H), 6.97-7.04(m, 1H), 7.18-7.25(m, 1H).

Synthesis of 2-hydroxy-4-(2,3,4-trifluorobenzyl)morpholin-3-one 126 mg of the title compound was obtained from 4-(2,3,4-trifluorobenzyl)morpholine-2,3-dione (350 mg) and a 1 M solution of lithium tri-sec-butylborohydride in THF (1.49 mL) in the same manner as in Example 1.

$^1$H-NMR (CDCl$_3$)δ(ppm):
3.20-3.25(m, 1H), 3.53-3.59(m, 1H), 3.81-3.86(m, 1H), 4.26-4.33(m, 1H), 4.60(d, J=15.2 Hz, 1H), 4.67(d, J=15.2 Hz, 1H), 5.31 (s, 1H), 6.96-7.01(m, 1H), 7.13-7.15(m, 1H).

Synthesis of (Z)-2-[1-[3-methoxy-4-(4-methyl-1H-imidazol-1-yl)phenyl]methylidene]-4-(2,3,4-trifluorobenzyl)morpholin-3-one 95.8 mg of the title compound was obtained from 2-hydroxy-4-(2,3,4-trifluorobenzyl)morpholin-3-one (126 mg), thionyl chloride (516 μL), triphenylphosphine (166 mg), and 3-methoxy-4-(4-methyl-1H-imidazol-1-yl)benzaldehyde (93.9 mg) in the same manner as in Example 1.

$^1$H-NMR (CDCl$_3$)δ(ppm):
2.35(s, 3H), 3.64(t, J=4.8 Hz, 2H), 3.86(s, 3H), 4.28(t, J=4.8 Hz, 2H), 4.75(s, 2H), 6.89(s, 1H), 6.95(s, 1H), 6.97-7.02(m, 1H), 7.17-7.24(m, 2H), 7.38(dd, J=8.4, 1.2 Hz, 1H), 7.41(d, J=1.2 Hz, 1H), 7.88(s, 1H).
ESI-MS; m/z444[M$^+$+H].

EXAMPLE 3

Synthesis of (Z)-(S)-2-[1-[3-methoxy-4-(4-methyl-1H-imidazol-1-yl)phenyl]methylidene]-6-methyl-4-(3,4,5-trifluorobenzyl)morpholin-3-one

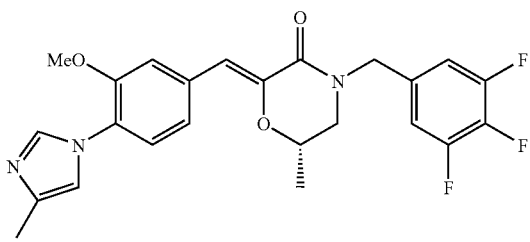

Synthesis of (S)-1-(3,4,5-trifluorobenzylamino)propan-2-ol 410 mg of the title compound was obtained from 3,4,5-trifluorobenzaldehyde (370 mg), (S)-1-amino-2-propanol (260 mg), acetic acid (0.662 mL), and sodium triacetoxyborohydride (981 mg) in the same manner as in Example 1.

$^1$H-NMR (CDCl$_3$)δ(ppm):
1.17(d, J=6.4 Hz, 3H), 2.45(dd, J=12.0, 9.2 Hz, 1H), 2.72 (dd, J=12.0, 2.8 Hz, 1H), 3.75(d, J=13.2 Hz, 1H), 3.80(d, J=13.2 Hz, 1H), 3.82-3.85(m, 1H), 6.96-7.00(m, 2H).

Synthesis of (S)-6-methyl-4-(3,4,5-trifluorobenzyl)morpholine-2,3-dione 439 mg of the title compound was obtained from (S)-1-(3,4,5-trifluorobenzylamino)propan-2-ol (410 mg) and diethyl oxalate (2.0 mL) in the same manner as in Example 1.

$^1$H-NMR (CDCl$_3$)67(ppm):
1.44(d, J=6.4 Hz, 3H), 3.35(dd, J=13.6, 3.2 Hz, 1H), 3.55 (dd, J=13.6, 9.6 Hz, 1H), 4.55(d, J=15.2 Hz, 1H), 4.67(d, J=15.2 Hz, 1H), 4.73-4.78(m, 1H), 6.94-6.98(m, 2H).

Synthesis of (S)-2-hydroxy-6-methyl-4-(3,4,5-trifluorobenzyl)morpholin-3-one 308 mg of the title compound was obtained from (S)-6-methyl-4-(3,4,5-trifluorobenzyl)morpholine-2,3-dione (400 mg) and a 1 M solution of lithium tri-sec-butylborohydride in THF (1.70 mL) in the same manner as in Example 1.

$^1$H-NMR (CDCl$_3$)δ(ppm):
1.26(d, J=6.0 Hz, 3H), 3.06(dd, J=12.0, 3.2 Hz, 1H), 3.22 (dd, J=12.0, 12.0 Hz, 1H), 4.36(d, J=14.8 Hz, 1H), 4.46-4.52 (m, 1H), 4.66(d, J=14.8 Hz, 1H), 5.37(s, 1H), 6.90-6.94(m, 2H).

Synthesis of (Z)-(S)-2-[1-[3-methoxy-4-(4-methyl-1H-imidazol-1-yl)phenyl]methylidene]-6-methyl-4-(3,4,5-trifluorobenzyl)morpholin-3-one 339 mg of the title compound was obtained from (S)-2-hydroxy-6-methyl-4-(3,4,5-trifluorobenzyl)morpholin-3-one (308 mg), thionyl chloride (817 μL), triphenylphosphine (353 mg), and 3-methoxy-4-(4-methyl-1H-imidazol-1-yl)benzaldehyde (218 mg) in the same manner as in Example 1.

$^1$H-NMR (CDCl$_3$)δ(ppm):

1.46(d, J=6.4 Hz, 3H), 2.34(s, 3H), 3.28(dd, J=12.8, 2.8 Hz, 1H), 3.50(dd, J=12.8, 9.6 Hz, 1H), 3.87(s, 3H), 4.36-4.40 (m, 1H), 4.58(d, J=14.8 Hz, 1H), 4.69(d, J=14.8 Hz, 1H), 6.90(s, 1H), 6.94-6.98(m, 3H), 7.23(d, J=8.4 Hz, 1H), 7.37 (dd, J=8.4, 2.0 Hz, 1H), 7.54(d, J=2.0 Hz, 1H), 7.85(s, 1H).

ESI-MS; m/z458[M$^+$+H].

EXAMPLE 4

Synthesis of (Z)-(R)-2-[1-[3-methoxy-4-(4-methyl-1H-imidazol-1-yl)phenyl]methylidene]-6-methyl-4-(3,4,5-trifluorobenzyl)morpholin-3-one

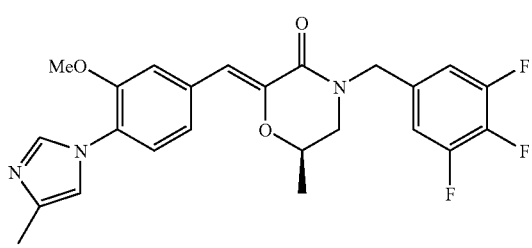

Synthesis of (R)-1-(3,4,5-trifluorobenzylamino)propan-2-ol 1.1 g of the title compound was obtained from 3,4,5-trifluorobenzaldehyde (1.0 g), (R)-1-amino-2-propanol (704 mg), acetic acid (1.79 mL), and sodium triacetoxyborohydride (2.65 g) in the same manner as in Example 1. The NMR values of the compound corresponded to those of the S-isomer.

Synthesis of (R)-6-methyl-4-(3,4,5-trifluorobenzyl)morpholine-2,3-dione 1.15 g of the title compound was obtained from (R)-1-(3,4,5-trifluorobenzylamino)propan-2-ol (1.1 g) and diethyl oxalate (4.0 mL) in the same manner as in Example 1. The NMR values of the compound corresponded to those of the S-isomer.

Synthesis of (R)-2-hydroxy-6-methyl-4-(3,4,5-trifluorobenzyl)morpholin-3-one 323 mg of the title compound was obtained from (R)-6-methyl-4-(3,4,5-trifluorobenzyl)morpholine-2,3-dione (400 mg) and a 1 M solution of lithium tri-sec-butylborohydride in THF (1.70 mL) in the same manner as in Example 1. The NMR values of the compound corresponded to those of the S-isomer.

Synthesis of (Z)-(R)-2-[1-[3-methoxy-4-(4-methyl-1H-imidazol-1-yl)phenyl]methylidene]-6-methyl-4-(3,4,5-trifluorobenzyl)morpholin-3-one 346 mg of the title compound was obtained from (R)-2-hydroxy-6-methyl-4-(3,4,5-trifluorobenzyl)morpholin-3-one (323 mg), thionyl chloride (853 μL), triphenylphosphine (368 mg), and 3-methoxy-4-(4-methyl-1H-imidazol-1-yl)benzaldehyde (228 mg) in the same manner as in Example 1. The NMR values of the compound corresponded to those of the S-isomer.

EXAMPLE 5

Synthesis of (Z)-(S)-2-[1-[3-methoxy-4-(4-methyl-1H-imidazol-1-yl)phenyl]methylidene]-6-methyl-4-(2,3,4-trifluorobenzyl)morpholin-3-one

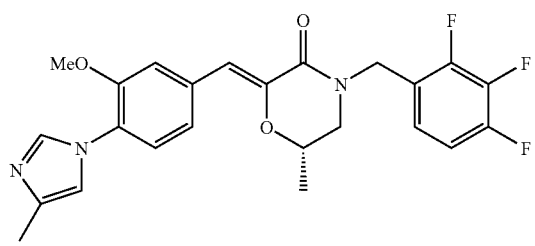

Synthesis of (S)-1-(2,3,4-trifluorobenzylamino)propan-2-ol 968 mg of the title compound was obtained from 2,3,4-trifluorobenzaldehyde (1.0 g), (S)-1-amino-2-propanol (704 mg), acetic acid (1.79 mL), and sodium triacetoxyborohydride (2.65 g) in the same manner as in Example 1.

$^1$H-NMR (CDCl$_3$)δ(ppm):

1.16(d, J=6.0 Hz, 3H), 2.47(dd, J=11.6, 9.2 Hz, 1H), 2.72 (dd, J=11.6, 2.8 Hz, 1H), 3.83-3.88(m, 1H), 3.89(s, 2H), 6.92-6.99(m, 1H), 7.06-7.10(m, 1H).

Synthesis of (S)-6-methyl-4-(2,3,4-trifluorobenzyl)morpholine-2,3-dione 917 mg of the title compound was obtained from (S)-1-(2,3,4-trifluorobenzylamino)propan-2-ol (968 mg) and diethyl oxalate (8.0 mL) in the same manner as in Example 1.

$^1$H-NMR(CDCl$_3$)δ(ppm):

1.45(d, J=6.4 Hz, 3H), 3.48(dd, J=13.6, 3.2 Hz, 1H), 3.62 (dd, J=13.6, 10.0 Hz, 1H), 4.66(d, J=15.2 Hz, 1H), 4.74-4.80 (m, 1H), 4.75(d, J=15.2 Hz, 1H), 7.00-7.03(m, 1H), 7.21-7.27 (m, 1H).

Synthesis of (S)-2-hydroxy-6-methyl-4-(2,3,4-trifluorobenzyl)morpholin-3-one 196 mg of the title compound was obtained from (S)-6-methyl-4-(2,3,4-trifluorobenzyl)morpholine-2,3-dione (350 mg) and a 1 M solution of lithium tri-sec-butylborohydride in THF (1.49 mL) in the same manner as in Example 1.

$^1$H-NMR (CDCl$_3$)δ(ppm):

1.25(d, J=7.2 Hz, 3H), 3.13(dd, J=12.0, 3.2 Hz, 1H), 3.26 (dd, J=12.0, 12.0 Hz, 1H), 4.47-4.51(m, 1H), 4.58(d, J=15.6 Hz, 1H), 4.64(d, J=15.6 Hz, 1H), 5.33(s, 1H), 6.95-7.00(m, 1H), 7.12-7.15(m, 1H).

Synthesis of (Z)-(S)-2-[1-[3-methoxy-4-(4-methyl-1H-imidazol-1-yl)phenyl]methylidene]-6-methyl-4-(2,3,4-trifluorobenzyl)morpholin-3-one 197 mg of the title compound was obtained from (S)-2-hydroxy-6-methyl-4-(2,3,4-trifluorobenzyl)morpholin-3-one (196 mg), thionyl chloride (500 μL), triphenylphosphine (243 mg), and 3-methoxy-4-(4-methyl-1H-imidazol-1-yl)benzaldehyde (139 mg) in the same manner as in Example 1.

$^1$H-NMR (CDCl$_3$)δ(ppm):
1.46(d, J=6.4 Hz, 3H), 2.31(s, 3H), 3.39(dd, J=12.8, 2.8 Hz, 1H), 3.55(dd, J=12.8, 9.6 Hz, 1H), 3.85(s, 3H), 4.37-4.40 (m, 1H), 4.68(d, J=15.2 Hz, 1H), 4.77(d, J=15.2 Hz, 1H), 6.86(s, 1H), 6.93 (s, 1H), 6.94-7.03(m, 1H), 7.16-7.24(m, 1H), 7.21(d, J=8.4 Hz, 1H), 7.33(dd, J=8.4, 2.0 Hz, 1H), 7.52(d, J=2.0 Hz, 1H), 7.75(s, 1H).
ESI-MS; m/z458[M$^+$+H].

EXAMPLE 6

Synthesis of (Z)-(R)-2-[1-[3-methoxy-4-(4-methyl-1H-imidazol-1-yl)phenyl]methylidene]-6-methyl-4-(2,3,4-trifluorobenzyl)morpholin-3-one

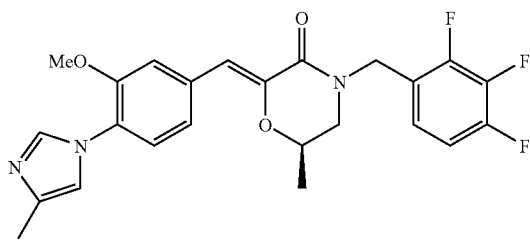

Synthesis of (R)-1-(2,3,4-trifluorobenzylamino)propan-2-ol 1.09 g of the title compound was obtained from 2,3,4-trifluorobenzaldehyde (1.0 g), (R)-1-amino-2-propanol (704 mg), acetic acid (1.79 mL), and sodium triacetoxyborohydride (2.65 g) in the same manner as in Example 1. The NMR values of the compound corresponded to those of the S-isomer.

Synthesis of (R)-6-methyl-4-(2,3,4-trifluorobenzyl)morpholine-2,3-dione 874 mg of the title compound was obtained from (R)-1-(2,3,4-trifluorobenzylamino)propan-2-ol (1.09 g) and diethyl oxalate (8.0 mL) in the same manner as in Example 1. The NMR values of the compound corresponded to those of the S-isomer.

Synthesis of (R)-2-hydroxy-6-methyl-4-(2,3,4-trifluorobenzyl)morpholin-3-one 213 mg of the title compound was obtained from (R)-6-methyl-4-(2,3,4-trifluorobenzyl)morpholine-2,3-dione (350 mg) and a 1 M solution of lithium tri-sec-butylborohydride in THF (1.49 mL) in the same manner as in Example 1. The NMR values of the compound corresponded to those of the S-isomer.

Synthesis of (Z)-(R)-2-[1-[3-methoxy-4-(4-methyl-1H-imidazol-1-yl)phenyl]methylidene]-6-methyl-4-(2,3,4-trifluorobenzyl)morpholin-3-one 187 mg of the title compound was obtained from (R)-2-hydroxy-6-methyl-4-(2,3,4-trifluorobenzyl)morpholin-3-one (213 mg), thionyl chloride (500 μL), triphenylphosphine (264 mg), and 3-methoxy-4-(4-methyl-1H-imidazol-1-yl)benzaldehyde (151 mg) in the same manner as in Example 1. The NMR values of the compound corresponded to those of the S-isomer.

EXAMPLE 7

Synthesis of (Z)-4-[(S)-1-(4-fluorophenyl)ethyl]-2-[1-[3-methoxy-4-(4-methyl-1H-imidazol-1-yl)phenyl]methylidene]-6,6-dimethylmorpholin-3-one

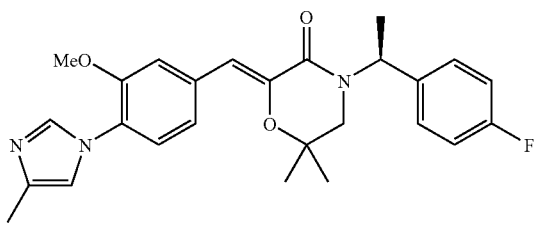

Synthesis of 1-[(S)-1-(4-fluorophenyl)ethylamino]-2-methylpropan-2-ol

Isobutylene oxide (1.0 g) and (S)-1-(4-fluorophenyl)ethylamine (2.25 mL) were added to a solution of lithium perchlorate (14.8 g) in an ether (27.8 mL) at room temperature, and the reaction solution was stirred at room temperature for 1.5 hours. Isobutylene oxide (0.5 mL) was added to the reaction solution, which was then stirred overnight. Ice water and chloroform were added to the reaction solution, and the organic layer was separated. Thereafter, the organic layer was dried over anhydrous magnesium sulfate and then concentrated under reduced pressure. The residue was purified by column chromatography using a silica gel (chloroform:2-propanol=100:1 to 1:1) to obtain 2.13 g of the title compound.

$^1$H-NMR (CDCl$_3$)δ(ppm):
1.13(s, 3H), 1.16(s, 3H), 1.35(d, J=6.8 Hz, 3H), 2.32(d, J=11.6 Hz, 1H), 2.44(d, J=11.6 Hz, 1H), 3.75(q, J=6.8 Hz, 1H), 6.99-7.10(m, 2H), 7.23-7.30(m, 2H).

Synthesis of 4-[(S)-1-(4-fluorophenyl)ethyl]-6,6-dimethylmorpholine-2,3-dione 1.44 g of the title compound was obtained from 1-[(S)-1-(4-fluorophenyl)ethylamino]-2-methylpropan-2-ol (2.13 g) and diethyl oxalate (7.0 mL) in the same manner as in Example 1.

$^1$H-NMR (CDCl$_3$)δ(ppm):
1.19(s, 3H), 1.44(s, 3H), 1.56(d, J=6.8 Hz, 3H), 3.00(d, J=13.6 Hz, 1H), 3.31(d, J=13.6 Hz, 1H), 6.02(q, J=6.8 Hz, 1H), 7.06-7.10(m, 2H), 7.30-7.36(m, 2H).

Synthesis of 4-[(S)-1-(4-fluorophenyl)ethyl]-2-hydroxy-6,6-dimethylmorpholin-3-one 1.22 g of the title compound was obtained from 4-[(S)-1-(4-fluorophenyl)ethyl]-6,6-dimethylmorpholine-2,3-dione (1.20 g) and a 1 M solution of lithium tri-sec-butylborohydride in THF (4.97 mL) in the same manner as in Example 1.
$^1$H-NMR (CDCl$_3$)δ(ppm):
0.97(s, 1.5H), 1.08(s, 1.5H), 1.24(s, 1.5H), 1.31(s, 1.5H), 1.52(d, J=6.8 Hz, 1.5H), 1.53(d, J=6.8 Hz, 1.5H), 2.05(s, 3H), 2.79(d, J=12.8 Hz, 0.5H), 2.87(d, J=12.8 Hz, 0.5H), 3.08(d, J=12.8 Hz, 0.5H), 3.13(d, J=12.8 Hz, 0.5H), 3.77(brs, 1H), 5.26(d, J=4.0 Hz, 0.5H), 5.29(d, J=4.0 Hz, 0.5H), 5.93(q, J=6.8 Hz, 0.5H), 5.99(q, J=6.8 Hz, 0.5H), 7.03-7.07(m, 2H), 7.26-7.35(m, 2H).

Synthesis of (Z)-4-[(S)-1-(4-fluorophenyl)ethyl]-2-[1-[3-methoxy-4-(4-methyl-1H-imidazol-1-yl)phenyl]methylidene]-6,6-dimethylmorpholin-3-one 500 mg of the title compound was obtained from 4-[(S)-1-(4-fluorophenyl)ethyl]-2-hydroxy-6,6-dimethylmorpholin-3-one (1.21 g), thionyl chloride (3.3 mL), triphenylphosphine (1.42 g), and 3-methoxy-4-(4-methyl-1H-imidazol-1-yl)benzaldehyde (880 mg) in the same manner as in Example 1.
$^1$H-NMR (CDCl$_3$)δ(ppm):
1.35(d, J=6.8 Hz, 3H), 1.57(d, J=7.2 Hz, 3H), 2.30(s, 3H), 2.89 (dd, J=12.8, 9.2 Hz, 1H), 3.18(dd, J=12.8, 2.8 Hz, 1H), 3.85(s, 3H), 4.31-4.36(m, 1H), 6.11(q, J=7.2 Hz, 1H), 6.88(s, 1H), 6.93(s, 1H), 7.03-7.08(m, 2H), 7.20(d, J=8.0 Hz, 1H), 7.29-7.35(m, 3H), 7-52(d, J=2.0 Hz, 1H), 7.75(s, 1H).
ESI-MS; m/z450[M$^+$+H].

EXAMPLES 8 AND 9

Synthesis of (Z)-(R)-4-[(S)-1-(4-fluorophenyl)ethyl]-2-[1-[3-methoxy-4-(4-methyl-1H-imidazol-1-yl)phenyl]methylidene]-6-methylmorpholin-3-one and (Z)-(S)-4-[(S)-1-(4-fluorophenyl)ethyl]-2-[1-[3-methoxy-4-(4-methyl-1H-imidazol-1-yl)phenyl]methylidene]-6-methylmorpholin-3-one

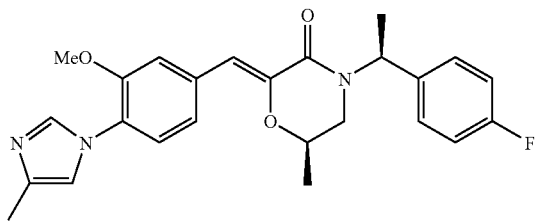

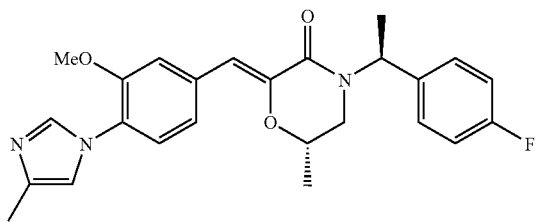

Synthesis of 1-[(S)-1-(4-fluorophenyl)ethylamino]propan-2-one

A mixture of (S)-1-(4-fluorophenyl)ethylamine (5.0 g), chloroacetone (4.78 mL), cesium carbonate (13.9 g), and DMF (50 mL) was stirred at room temperature overnight. The reaction solution was diluted with water and ethyl acetate, and then the organic layer was separated. The organic layer was dried over anhydrous magnesium sulfate and then concentrated under reduced pressure. The residue was purified by column chromatography using a silica gel (hexane:ethyl acetate=5:1 to 0:100) to obtain 5.1 g of the title compound.
$^1$H-NMR (CDCl$_3$)δ(ppm):
1.37(d, J=6.8 Hz, 3H), 2.07(s, 3H), 3.37(s, 2H), 3.74(q, J=6.8 Hz, 1H), 6.97-7.03(m, 2H), 7.24-7.29(m, 2H).
ESI-MS; m/z196[M$^+$+H].

Synthesis of 1-[(S)-1-(4-fluorophenyl)ethylamino]propan-2-ol

Sodium borohydride (2.39 g) was added to a solution of 1-[(S)-1-(4-fluorophenyl)ethylamino]propan-2-one (2.5 g) in ethanol (25 mL) under ice-cooling, and then the reaction solution was stirred at room temperature for one hour. The reaction solution was diluted with ice water and ethyl acetate, and then the organic layer was separated. The organic layer was dried over anhydrous magnesium sulfate and then concentrated under reduced pressure. The residue was purified by column chromatography using a silica gel (chloroform:2-propanol=100:1 to 0:100) to obtain 1.18 g of the title compound as a diastereomer mixture.
$^1$H-NMR (CDCl$_3$)δ(ppm):
1.09(d, J=6.4 Hz, 0.9H), 1.10(d, J=6.0 Hz, 2.1H), 1.35(d, J=7.2 Hz, 0.9H), 1.36(d, J=6.4 Hz, 2.1H), 2.22(dd, J=12.0, 9.6 Hz, 0.3H), 2.33(dd, J=12.0, 9.2 Hz, 0.7H), 2.52(dd, J=12.4, 3.6 Hz, 0.7H), 2.59(dd, J=11.6, 2.8 Hz, 0.3H), 3.61-3.66(m, 0.3H), 3.74-3.80(m, 0.7H), 6.99-7.03(m, 2H), 7.24-7.29(m, 2H).

Synthesis of 4-[(S)-1-(4-fluorophenyl)ethyl]-6-methylmorpholine-2,3-dione 1.20 g of the title compound was obtained as a diastereomer mixture from 1-[(S)-1-(4-fluorophenyl)ethylamino]propan-2-ol (1.18 g) and diethyl oxalate (4.06 mL) in the same manner as in Example 1.
$^1$H-NMR (CDCl$_3$)δ(ppm):
1.31(d, J=6.8 Hz, 1.8H), 1.37(d, J=6.8 Hz, 1.2H), 1.55(d, J=6.8 Hz, 1.2H), 1.56(d, J=6.8 Hz, 1.8H), 2.96(dd, J=12.0, 9.6 Hz, 0.6H), 3.04(dd, J=12.0, 3.6 Hz, 0.4H), 3.26(dd, J=12.0, 3.6 Hz, 0.6H), 3.38(dd, J=12.0, 9.6 Hz, 0.4H), 4.42-4.52(m, 0.4H), 4.64-4.74(m, 0.6H), 5.93-6.02(m, 1H), 7.09-7.12(m, 2H), 7.29-7.39(m, 2H).

Synthesis of 4-[(S)-1-(4-fluorophenyl)ethyl]-2-hydroxy-6-methylmorpholin-3-one 382 mg of the title compound was obtained as a diastereomer mixture from 4-[(S)-1-(4-fluorophenyl)ethyl]-6-methylmorpholine-2,3-dione (500 mg) and a 1 M solution of lithium tri-sec-butylborohydride in THF (2.19 mL) in the same manner as in Example 1.
$^1$H-NMR (CDCl$_3$)δ(ppm):
1.19(d, J=6.8 Hz, 1.5H), 1.20(d, J=6.8 Hz, 1.5H), 1.53(d, J=6.8 Hz, 3H), 2.61(dd, J=12.4, 10.8 Hz, 0.5H), 2.74(dd, J=12.0, 2.8 Hz, 0.5H), 2.94(dd, J=12.4, 2.8 Hz, 0.5H), 3.12(dd, J=12.0, 11.2 Hz, 0.5H), 4.11-4.26(m, 0.5H), 4.37-4.42

(m, 0.5H), 5.35(s, 0.5H), 5.37(s, 0.5H), 5.95(q, J=6.8 Hz, 0.5H), 5.99(q, J=6.8 Hz, 0.5H), 7.02-7.07(m, 2H), 7.25-7.32 (m, 2H).

Synthesis of (Z)-(R)-4-[(S)-1-(4-fluorophenyl)ethyl]-2-[1-[3-methoxy-4-(4-methyl-1H-imidazol-1-yl) phenyl]methylidene]-6-methylmorpholin-3-one and (Z)-(S)-4-[(S)-1-(4-fluorophenyl)ethyl]-2-[1-[3-methoxy-4-(4-methyl-1H-imidazol-1-yl)phenyl]methylidene]-6-methylmorpholin-3-one 628 mg of the title compound was obtained as a diastereomer-mixture from 4-[(S)-1-(4-fluorophenyl)ethyl]-2-hydroxy-6-methylmorpholin-3-one (382 mg), thionyl chloride (330 μL), triphenylphosphine (504 mg), and 3-methoxy-4-(4-methyl-1H-imidazol-1-yl)benzaldehyde (294 mg) in the same manner as in Example 1. A part of the diastereomer mixture was separated by CHIRALCEL™ OJ-H manufactured by Daicel Chemical Industries, Ltd. (2 cm×25 cm; mobile phase: hexane:ethanol=80:20) to obtain the title optically active compound with a retention time of 25 minutes (>95% de) and the title optically active compound with a retention time of 29 minutes (>95% de).

The property values of the title optically active compound with a retention time of 25 minutes (Example 8) are as follows.

$^1$H-NMR (CDCl$_3$)δ(ppm):
1.38(d, J=6.4 Hz, 3H), 1.55(d, J=7.2 Hz, 3H), 2.30(s, 3H), 2.97(dd, J=12.8, 2.4 Hz, 1H), 3.33(dd, J=12.8, 9.6 Hz, 1H), 3.85(s, 3H), 4.09-4.12(m, 1H), 6.13(q, J=7.2 Hz, 1H), 6.89(s, 1H), 6.94(s, 1H), 7.03-7.09(m, 2H), 7.21(d, J=8.4 Hz, 1H), 7.32-7.36(m, 3H), 7.53(d, J=2.8 Hz, 1H), 7.74(s, 1H).

ESI-MS; m/z436[M$^+$+H].

The property values of the title optically active compound with a retention time of 29 minutes (Example 9) are as follows.

$^1$H-NMR (CDCl$_3$)δ(ppm):
1.35(d, J=6.8 Hz, 3H), 1.57(d, J=7.2 Hz, 3H), 2.30(s, 3H), 2.89(dd, J=12.8, 9.2 Hz, 1H), 3.18(dd, J=12.8, 2.8 Hz, 1H), 3.85(s, 3H), 4.31-4.36(m, 1H), 6.11(q, J=7.2 Hz, 1H), 6.88(s, 1H), 6.93(s, 1H), 7.03-7.08(m, 2H), 7.20(d, J=8.0 Hz, 1H), 7.29-7.35(m, 3H), 7.52(d, J=2.0 Hz, 1H), 7.75(s, 1H).

ESI-MS; m/z436[M$^+$+H].

EXAMPLES 10 AND 11

Synthesis of (Z)-2-[1-[3-methoxy-4-(4-methyl-1H-imidazol-1-yl)phenyl]methylidene]-4-[(S)-1-(3,4,5-trifluorophenyl)ethyl]morpholin-3-one and (Z)-2-[1-[3-methoxy-4-(4-methyl-1H-imidazol-1-yl)phenyl]methylidene]-4-[(R)-1-(3,4,5-trifluorophenyl)ethyl]morpholin-3-one

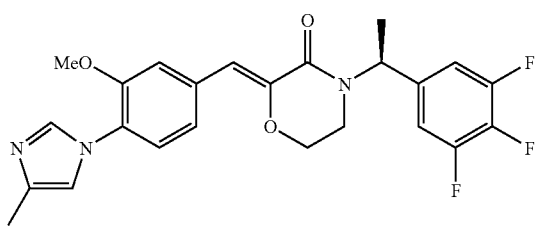

-continued

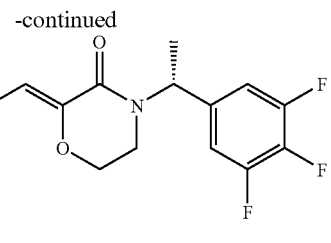

Synthesis of 2-[1-(3,4,5-trifluorophenyl)ethylamino]ethanol

A mixture of 3,4,5-trifluoroacetophenone (2.0 g), ethanolamine (2.0 g), and toluene (20 mL) was heated under reflux in a Dean-Stark apparatus for 2.5 hours. The reaction solution was concentrated under reduced pressure, and then the residue was diluted with ethanol (30 mL) and sodium borohydride (1.0 g) was added under ice-cooling. The mixture was stirred at room temperature for three hours and then diluted with a 2 N sodium hydroxide solution and chloroform. Thereafter, the organic layer was separated. The organic layer was dried over anhydrous magnesium sulfate and then concentrated under reduced pressure. The residue was purified by column chromatography using a silica gel (chloroform: methanol=50:1 to 5:1) to obtain 860 mg of the title compound.

$^1$H-NMR (CDCl$_3$)δ(ppm):
1.36(d, J=6.8 Hz, 3H), 2.56-2.68(m, 1H), 2.68-2.73(m, 1H), 3.62-3.80(m, 3H), 6.92-7.00(m, 2H).

Synthesis of 4-[1-(3,4,5-trifluorophenyl)ethyl]morpholine-2,3-dione 340 mg of the title compound was obtained from 2-[1-(3,4,5-trifluorophenyl)ethylamino]ethanol (860 mg) and diethyl oxalate (5.0 mL) in the same manner as in Example 1.

$^1$H-NMR (CDCl$_3$)δ(ppm):
1.55(d, J=6.4 Hz, 3H), 3.15-3.21(m, 1H), 3.52-3.59(m, 1H), 4.31-4.37(m, 1H), 4.41-4.46(m, 1H), 5.90(q, J=6.4 Hz, 1H), 6.97-7.01(m, 2H).

Synthesis of 2-hydroxy-4-[1-(3,4,5-trifluorophenyl) ethyl]morpholin-3-one 273 mg of the title compound was obtained as a diastereomer mixture from 4-[1-(3,4,5-trifluorophenyl)ethyl]morpholine-2,3-dione (340 mg) and a 1 M solution of lithium tri-sec-butylborohydride in THF (1.45 mL) in the same manner as in Example 1.

$^1$H-NMR (CDCl$_3$)δ(ppm):
1.52(d, J=7.2 Hz, 3H), 2.78-2.83(m, 0.5H), 2.95-3.03(m, 0.5H), 3.10-3.15(m, 0.5H), 3.43-3.50(m, 0.5H), 3.78-3.84(m, 0.5H), 4.12-4.18(m, 0.5H), 4.22-4.28(m, 0.5H), 4.24(brs, 1H), 5.34(s, 0.5H), 5.36(s, 0.5H), 5.88-5.98(m, 1H), 6.92-6.99(m, 1H).

Synthesis of (Z)-2-[1-[3-methoxy-4-(4-methyl-1H-imidazol-1-yl)phenyl]methylidene]-4-[(S)-1-(3,4,5-trifluorophenyl)ethyl]morpholin-3-one and (Z)-2-[1-[3-methoxy-4-(4-methyl-1H-imidazol-1-yl)phenyl]methylidene]-4-[(R)-1-(3,4,5-trifluorophenyl)ethyl]morpholin-3-one 145 mg of the title compound was obtained as a racemate from 2-hydroxy-4-[1-(3,4,5-trifluorophenyl)ethyl]morpholin-3-one (273 mg), thionyl chloride (1.12 mL), triphenylphosphine (360 mg), and 3-methoxy-4-(4-methyl-1H-imidazol-1-yl)benzaldehyde (204 mg) in the same manner as in Example 1.

$^1$H-NMR (CDCl$_3$)δ(ppm):
1.55(d, J=6.8 Hz, 3H), 2.29(s, 3H), 3.08-3.13(m, 1H), 3.48-3.55(m, 1H), 3.85(s, 3H), 4.08-4.14(m, 1H), 4.23-4.27 (m, 1H), 6.06(q, J=6.8 Hz, 1H), 6.90(s, 1H), 6.92(s, 1H), 6.96-7.02(m, 2H), 7.20(d, J=8.0 Hz, 1H), 7.37(dd, J=8.0, 1.6 Hz, 1H), 7.38(d, J=1.6 Hz, 1H), 7.71(s, 1H).

ESI-MS; m/z458[M$^+$+H].

A part of the racemate was separated by CHIRALPAK™ IA manufactured by Daicel Chemical Industries, Ltd. (2 cm×25 cm; mobile phase: hexane:ethanol=80:20) to obtain the title optically active compound with a retention time of 21 minutes (>99% ee: Example 11) and the title optically active compound with a retention time of 24 minutes (95% ee: Example 10). The NMR values of the optically active compounds corresponded to those of the racemate.

EXAMPLE 12

Synthesis of (Z)-4-[(S)-chroman-4-yl]-2-[1-[3-methoxy-4-(4-methyl-1H-imidazol-1-yl)phenyl]methylidene]-6,6-dimethylmorpholin-3-one

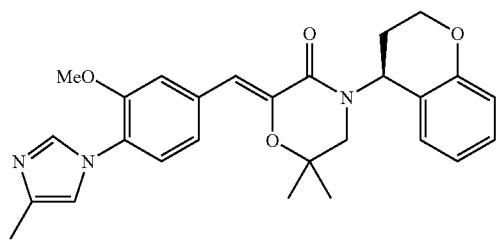

Synthesis of 1-[[(S)-chroman-4-yl]amino]-2-methylpropan-2-ol 5.62 g of the title compound was obtained from lithium perchlorate (29.6 g), an ether (55.6 mL), (S)-4-aminochroman (4.13 g) obtained by a method described in a document (see T. Mukaiyama et al., "A European Journal of Chemistry", 2003, vol. 9, p. 4485-4509, for example), and isobutylene oxide (3.46 mL) in the same manner as in Example 7.

$^1$H-NMR (CDCl$_3$)δ(ppm):
1.20(s, 6H), 1.93-1.98(m, 1H), 2.04-2.09(m, 1H), 2.69(s, 2H), 3.80-3.85(m, 1H), 4.19-4.32(m, 2H), 6.83(d, J=8.4 Hz, 1H), 6.91(t, J=8.4 Hz, 1H), 7.17(t, J=8.4 Hz, 1H), 7.33(d, J=8.4 Hz, 1H).

Synthesis of 4-[(S)-chroman-4-yl]-6,6-dimethylmorpholine-2,3-dione 1.53 g of the title compound was obtained from 1-[[(S)-chroman-4-yl]amino]-2-methylpropan-2-ol (5.62 g) and diethyl oxalate (20 mL) in the same manner as in Example 7.

$^1$H-NMR (CDCl$_3$)δ(ppm):
1.45(s, 3H), 1.48(s, 3H), 2.10-2.17(m, 1H), 2.23-2.27(m, 1H), 3.23(s, 2H), 4.18-4.30(m, 2H), 5.96(dd, J=8.4, 7.2 Hz, 1H), 6.90(d, J=8.4 Hz, 1H), 6.95(t, J=8.4 Hz, 1H), 7.05(d, J=8.4 Hz, 1H), 7.23(t, J=8.4 Hz, 1H).

Synthesis of 4-[(S)-chroman-4-yl]-2-hydroxy-6,6-dimethylmorpholin-3-one 1.11 g of the title compound was obtained from 4-[(S)-chroman-4-yl]-6,6-dimethylmorpholine-2,3-dione (1.50 g) and a 1 M solution of lithium tri-sec-butylborohydride in THF (6.0 mL) in the same manner as in Example 7.

$^1$H-NMR (CDCl$_3$)δ(ppm):
1.26(s, 3H), 1.31(s, 1.5H), 1.32(s, 1.5H), 2.10-2.25(m, 2H), 2.99(d, J=13.2 Hz, 0.5H), 3.05(d, J=13.2 Hz, 1H), 3.12 (d, J=13.2 Hz, 0.5H), 4.17-4.25(m, 1H), 4.26-4.35(m, 1H), 5.36(s, 0.5H), 5.37(s, 0.5H), 5.89-5.99(m, 1H), 6.84-6.87(m, 1H), 6.90-6.94(m, 1H), 7.01-7.04(m, 0.5H), 7.08-7.11(m, 0.5H), 7.16-7.21(m, 1H).

Synthesis of (Z)-4-[(S)-chroman-4-yl]-2-[1-[3-methoxy-4-(4-methyl-1H-imidazol-1-yl)phenyl]methylidene]-6,6-dimethylmorpholin-3-one Triphenylphosphonium bromide (292 mg) was added to a solution of 4-[(S)-chroman-4-yl]-2-hydroxy-6,6-dimethylmorpholin-3-one (196 mg) in acetonitrile (10 mL), and the reaction solution was heated under reflux for two hours. The reaction solution was concentrated under reduced pressure. Ethanol (15 mL), TEA (221 μL), and 3-methoxy-4-(4-methyl-1H-imidazol-1-yl)benzaldehyde (138 mg) were added to the residue, and the reaction solution was heated under reflux for 2.5 hours. The reaction solution was concentrated under reduced pressure and diluted with a saturated sodium bicarbonate solution and ethyl acetate, and then the organic layer was separated. The organic layer was dried over anhydrous magnesium sulfate and concentrated under reduced pressure. The residue was purified by column chromatography using NH silica gel (heptane:ethyl acetate=1:1 to 0:100) and further purified by column chromatography using a silica gel (heptane:ethyl acetate=1:1 to 0:100) to obtain 167 mg of the title compound.

$^1$H-NMR (CDCl$_3$)δ(ppm):
1.42(s, 3H), 1.44(s, 3H), 2.14-2.22(m, 2H), 2.33(s, 3H), 3.12(d, J=12.8 Hz, 1H), 3.19(d, J=12.8 Hz, 1H), 3.87(s, 3H), 4.22-4.34(m, 2H), 6.13(dd, J=8.8, 6.8 Hz, 1H), 6.86-6.95(m, 4H), 7.10(d, J=7.2 Hz, 1H), 7.19(d, J=7.2 Hz, 1H), 7.22(d, J=8.4 Hz, 1H), 7.37(dd, J=8.4, 1.6 Hz, 1H), 7.57(d, J=1.6 Hz, 1H), 7.80(s, 1H).

ESI-MS; m/z460[M$^+$+H].

EXAMPLES 13 AND 14

Synthesis of (Z)-(S)-4-[(S)-chroman-4-yl]-2-[1-[3-methoxy-4-(4-methyl-1H-imidazol-1-yl)phenyl]methylidene]-6-methylmorpholin-3-one and (Z)-(R)-4-[(S)-chroman-4-yl]-2-[1-[3-methoxy-4-(4-methyl-1H-imidazol-1-yl)phenyl]methylidene]-6-methylmorpholin-3-one

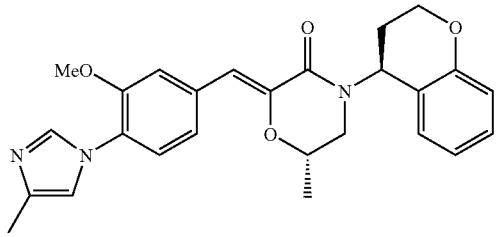

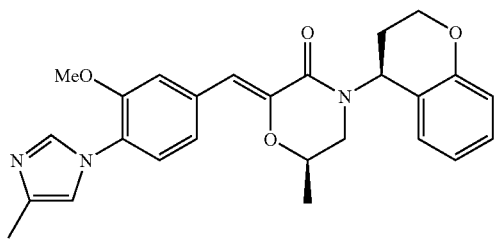

70.3 mg of the title compound was obtained as a diastereomer mixture from lithium perchlorate (3.56 g), an ether (6.7 mL), (S)-4-aminochroman (1.0 g), and propylene oxide (609 μL) as starting materials in the same manner as Example 7. The mixture was separated by CHIRALPAK™ AD-H manufactured by Daicel Chemical Industries, Ltd. (2 cm×25 cm; mobile phase: ethanol 100%) to obtain the title optically active compound with a retention time of 18 minutes (>99% de) and the title optically active compound with a retention time of 20 minutes (95% de).

The property values of the title optically active compound with a retention time of 18 minutes (Example 13) are as follows.

$^1$H-NMR (CDCl$_3$)δ(ppm):
1.41(d, J=6.0 Hz, 3H), 2.28-2.10(m, 2H), 2.33(s, 3H), 3.09 (dd, J=13.2, 3.2 Hz, 1H), 3.17(dd, J=13.2, 8.8 Hz, 1H), 3.87(s, 3H), 4.20-4.40(m, 3H), 6.07(dd, J=9.2, 6.8 Hz, 1H), 6.86-6.95(m, 4H), 7.06(d, J=7.6 Hz, 1H), 7.18(d, J=8.4 Hz, 1H), 7.23(d, J=8.0 Hz, 1H), 7.38(d, J=8.4 Hz, 1H), 7.55(s, 1H), 7.81(s, 1H).
ESI-MS; m/z446[M$^+$+H].

The property values of the title optically active compound with a retention time of 20 minutes (Example 14) are as follows.

$^1$H-NMR (CDCl$_3$)δ(ppm):
1.41(d, J=6.4 Hz, 3H), 2.10-2.21(m, 2H), 2.36(s, 3H), 3.09 (dd, J=12.8, 2.8 Hz, 1H), 3.33(dd, J=12.8, 10.0 Hz, 1H), 3.87(s, 3H), 4.21-4.38(m, 3H), 6.14(dd, J=9.2, 7.2 Hz, 1H), 6.86-6.96(m, 4H), 7.06(d, J=7.6 Hz, 1H), 7.18-7.26(m, 2H), 7.38(d, J=8.4 Hz, 1H), 7.57(s, 1H), 7.89(s, 1H).
ESI-MS; m/z446[M$^+$+H].

EXAMPLE 15

Synthesis of (Z)-(S)-4-(6-chloropyridin-2-ylmethyl)-2-[1-[3-methoxy-4-(4-methyl-1H-imidazol-1-yl)phenyl]methylidene]-6-methylmorpholin-3-one

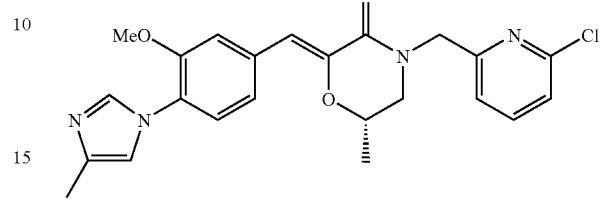

Synthesis of (S)-1-[(6-chloropyridin-2-ylmethyl)amino]propan-2-ol 394 mg of the title compound was obtained from 2-chloro-6-formylpyridine (500 mg), (S)-1-amino-2-propanol (318 mg), acetic acid (0.808 mL), and sodium triacetoxyborohydride (1.12 g) in the same manner as in Example 1.
$^1$H-NMR (CDCl$_3$)δ(ppm):
1.16(d, J=6.0 Hz, 3H), 2.49(dd, J=12.0, 9.2 Hz, 1H), 2.78 (dd, J=12.0, 2.8 Hz, 1H), 3.83-3.87(m, 1H), 3.93(s, 2H), 7.23(d, J=8.0 Hz, 1H), 7.24(d, J=8.0 Hz, 1H), 7.64(t, J=8.0 Hz, 1H).

Synthesis of (S)-4-(6-chloropyridin-2-ylmethyl)-6-methylmorpholine-2,3-dione 411 mg of the title compound was obtained from (S)-1-[(6-chloropyridin-2-ylmethyl)amino]propan-2-ol (394 mg) and diethyl oxalate (3.0 mL) in the same manner as in Example 1.
$^1$H-NMR(CDCl$_3$)δ(ppm):
1.46(d, J=6.8 Hz, 3H), 3.71(dd, J=13.6, 3.2 Hz, 1H), 3.79 (dd, J=13.6, 9.6 Hz, 1H), 4.69(d, J=15.2 Hz, 1H), 4.77(d, J=15.2 Hz, 1H), 4.84-4.90(m, 1H), 7.30(d, J=8.0 Hz, 1H), 7.32(d, J=8.0 Hz, 1H), 7.68(t, J=8.0 Hz, 1H).

Synthesis of (S)-4-(6-chloropyridin-2-ylmethyl)-2-hydroxy-6-methylmorpholin-3-one 273 mg of the title compound was obtained from (S)-4-(6-chloropyridin-2-ylmethyl)-6-methylmorpholine-2,3-dione (411 mg) and a 1 M solution of lithium tri-sec-butylborohydride in THF (1.64 mL) in the same manner as in Example 1.
$^1$H-NMR (CDCl$_3$)δ(ppm):
1.27(d, J=6.0 Hz, 3H), 3.30(dd, J=12.0, 3.2 Hz, 1H), 3.39 (dd, J=12.0, 10.8 Hz, 1H), 4.48-4.52(m, 1H), 4.49(d, J=15.2 Hz, 1H), 4.81(d, J=15.2 Hz, 1H), 5.35(s, 1H), 7.27(d, J=7.6 Hz, 1H), 7.28(d, J=7.6 Hz, 1H), 7.66(t, J=7.6 Hz, 1H).

Synthesis of (Z)-(S)-4-(6-chloropyridin-2-ylmethyl)-2-[1-[3-methoxy-4-(4-methyl-1H-imidazol-1-yl)phenyl]methylidene]-6-methylmorpholin-3-one 27.9 mg of the title compound was obtained from (S)-4-(6-chloropyridin-2-ylmethyl)-2-hydroxy-6-methylmorpholin-3-one (237 mg), thionyl chloride (1.01 mL), triphenylphosphine (315 mg), and 3-methoxy-4-(4-methyl-1H-imidazol-1-yl)benzaldehyde (21.6 mg) in the same manner as in Example 1.

¹H-NMR (CDCl₃)δ(ppm):
1.47(d, J=6.4 Hz, 3H), 2.34(s, 3H), 3.57(dd, J=12.8, 2.8 Hz, 1H), 3.68(dd, J=12.0, 10.0 Hz, 1H), 3.86(s, 3H), 4.43-4.46(m, 1H), 4.76(s, 2H), 6.85(s, 1H), 6.95(s, 1H), 7.22(d, J=8.0 Hz, 1H), 7.31(d, J=7.6 Hz, 1H), 7.33(d, J=8.0 Hz, 1H), 7.35(dd, J=7.6, 1.6 Hz, 1H), 7.55(d, J=1.6 Hz, 1H), 7.66(t, J=8.0 Hz, 1H), 7.84(s, 1H).

EXAMPLES 16 AND 17

Synthesis of (Z)-(6S,9aR)-6-(4-fluorophenyl)-3-{1-[3-methoxy-4-(4-methyl-1H-imidazol-1-yl)benzylidene]hexahydropyrido[2,1-c][1,4]oxazin-4-one and (Z)-(6R,9aS)-6-(4-fluorophenyl)-3-{1-[3-methoxy-4-(4-methyl-1H-imidazol-1-yl)benzylidene]hexahydropyrido[2,1-c][1,4]oxazin-4-one

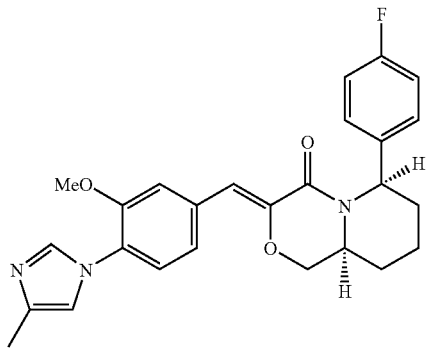

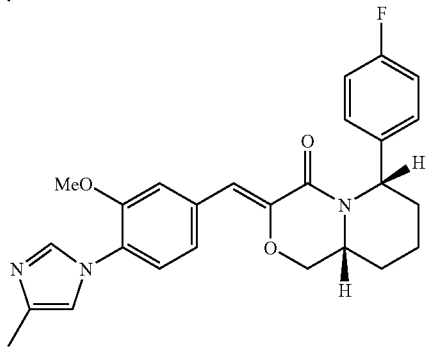

Synthesis of 1-(4-fluorophenyl)hepta-5,6-dienyl-1-amine 2.65 g of the title compound was obtained from (4-fluorobenzyl)-(4-fluorobenzylidene)amine (3 g) and 6-iodohexa-1,2-diene (2.97 g) according to the method described in Journal of the American Chemical Society, 2003, vol. 125, p. 11956. The property values of the compound are as follows.
¹H-NMR (CDCl₃)δ(ppm):
1.25-1.37(m, 1H), 1.39-1.50(m, 1H), 1.63-1.75(m, 2H), 1.95-2.04(m, 2H), 3.88(d, J=6.8 Hz, 1H), 4.63(dt, J=6.8, 2.8 Hz, 2H), 5.04(quintet, J=6.8 Hz, 1H), 6.99(t, J=8.8 Hz, 2H), 7.26(dd, J=8.8, 5.6 Hz, 2H).

Synthesis of (2R*,6S*)-2-(4-fluorophenyl)-6-vinylpiperidine

Acetic acid (0.74 mL) was added to a solution of an allylpalladium chloride dimer (472 mg) and 1,1'-bis(diphenylphosphino)ferrocene (1.43 g) in THF (200 mL), and the reaction solution was stirred at room temperature for 10 minutes. A solution of 1-(4-fluorophenyl)hepta-5,6-dienyl-1-amine (2.65 g) in THF (50 mL) was added to the reaction solution, which was then stirred at 70° C. for 1.5 hours. The reaction solution was left to cool to room temperature. Then, diethyl ether and 1 N aqueous hydrochloric acid were added to the reaction solution, and the aqueous layer was separated. The resulting aqueous layer was washed with diethyl ether, and then a 5 N sodium hydroxide solution was added to the aqueous layer until the pH was adjusted to 11 or less. Chloroform was added to the aqueous layer, and the organic layer was separated. The resulting organic layer was dried over magnesium sulfate and concentrated under reduced pressure to obtain 2.4 g of the title compound. The property values of the compound are as follows.
¹H-NMR (CDCl₃)δ(ppm):
1.24-1.60(m, 3H), 1.67-1.77(m, 2H), 1.88-1.95(m, 1H), 3.24-3.30(m, 1H), 3.67(dd, J=11.2, 2.8 Hz, 1H), 5.01(brd, J=10.4 Hz, 1H), 5.17(brd, J=16.8 Hz, 1H), 5.88(ddd, J=16.8, 10.4, 6.4 Hz, 1H), 6.98(t, J=8.8 Hz, 2H), 7.35(dd, J=8.8, 5.6 Hz, 2H).
ESI-MS; m/z 206[M⁺+H].

Synthesis of ethyl [(2R*,6S*)-2-(4-fluorophenyl)-6-vinylpiperidin-1-yl]oxoacetate Ethyl oxalate chloride (0.5 mL) was added to a solution of (2R*,6S*)-2-(4-fluorophenyl)-6-vinylpiperidine (520 mg) and DIEA (0.66 mL) in methylene chloride (10 mL), and the reaction solution was stirred at room temperature for one hour. Chloroform and 1 N aqueous hydrochloric acid were added to the reaction solution, and the organic layer was separated. The resulting organic layer was washed with saturated sodium bicarbonate water, dried over magnesium sulfate, and then concentrated under reduced pressure. The residue was purified by silica gel column chromatography (elution solvent: heptane->heptane:ethyl acetate=1:1) to obtain 426 mg of the title compound. The property value of the compound is as follows.
ESI-MS; m/z 306[M⁺+H].

Synthesis of (6R*,9aS*)-6-(4-fluorophenyl)-3-hydroxyhexahydropyrido[2,1-c][1,4]oxazin-4-one A solution of ethyl [(2R*,6S*)-2-(4-fluorophenyl)-6-vinylpiperidin-1-yl]oxoacetate (220 mg) in methanol (5 mL) was cooled to −78° C., and ozone gas was bubbled through the reaction solution for 20 minutes. Sodium borohydride (164 mg) was added to the reaction solution while stirring at −78° C., and the reaction solution was stirred at that temperature for 30 minutes. Ethyl acetate and a saturated ammonium chloride solution were added to the reaction solution, and the organic layer was separated. The resulting organic layer was dried over magnesium sulfate and then concentrated under reduced pressure. The residue was purified by silica gel column chromatography (elution solvent: heptane:ethyl acetate=1:1->ethyl acetate) to obtain 26 mg of the title compound. The property values of the compound are as follows.
¹H-NMR (CDCl₃)δ(ppm):
1.35-1.50(m, 2H), 1.57-1.67(m, 2H), 2.05-2.26(m, 2H), 3.57(brs, 1H), 3.80(dd, J=11.6, 3.6 Hz, 1H), 3.88-3.98(m, 1H), 4.11(t, J=11.6 Hz, 1H), 5.22(t, J=4.0 Hz, 1H), 5.28(s, 1H), 7.01(t, J=8.8 Hz, 2H), 7.19(dd, J=8.8, 5.6 Hz, 2H).
ESI-MS; m/z 220 [M⁺+H].

Synthesis of [(6R*,9aS*)-6-(4-fluorophenyl)-4-oxooctahydropyrido[2,1-c][1,4]oxazin-3-yl]triphenylphosphonium bromide A solution of (6R*,9aS*)-6-(4-fluorophenyl)-3-hydroxyhexahydropyrido[2,1-c][1,4]oxazin-4-one (26 mg) and triphenylphosphonium bromide (40 mg) in acetonitrile (3 mL) was heated under reflux for one hour and 30 minutes. The reaction solution was left to cool to room temperature, and then the solvent was evaporated under reduced pressure to obtain 57 mg of the title compound. The property value of the compound is as follows.

ESI-MS; m/z 510[M+].

Synthesis of (Z)-(6S*,9aR*)-6-(4-fluorophenyl)-3-[1-[3-methoxy-4-(4-methyl-1H-imidazol-1-yl)benzylidene]hexahydropyrido[2,1-c][1,4]oxazin-4-one Triethylamine (0.03 mL) was added to a solution of [(6R*,9aS*)-6-(4-fluorophenyl)-4-oxooctahydropyrido[2,1-c][1,4]oxazin-3-yl]triphenylphosphonium bromide (57 mg) and 3-methoxy-4-(4-methyl-1H-imidazol-1-yl)benzaldehyde (21 mg) in ethanol (5 mL), and the reaction solution was stirred at room temperature for two hours. The reaction solution was concentrated under reduced pressure. Then, the residue was purified by silica gel column chromatography (carrier: Chromatorex NH; elution solvent: heptane:ethyl acetate=1:1->ethyl acetate) to obtain 27 mg of the title compound. The property values of the compound are as follows.

¹H-NMR (CDCl₃)δ(ppm):
1.40-1.58(m, 2H), 1.65-1.76(m, 2H), 2.18-2.25(m, 2H), 2.31(s, 3H), 3.85(s, 3H), 4.07(q, J=10.8 Hz, 1H), 4.07-4.15 (m, 1H), 4.34(dd, J=10.8, 2.4 Hz, 1H), 5.38(t, J=4.0 Hz, 1H), 6.82(s, 1H), 6.92(brs, 1H), 7.02(t, J=8.4 Hz, 2H), 7.20(d, J=8.0 Hz, 1H), 7.22(dd, J=8.0,3.6 Hz, 2H), 7.37(dd, J=8.0, 1.2 Hz, 1H), 7.39(d, J=1.2 Hz, 1H), 7.74(d, J=1.2 Hz, 1H).
ESI-MS; m/z 448[M+H].

Synthesis of (Z)-(6S,9aR)-6-(4-fluorophenyl)-3-{1-[3-methoxy-4-(4-methyl-1H-imidazol-1-yl)benzylidene]hexahydropyrido[2,1-c][1,4]oxazin-4-one and (Z)-(6R,9aS)-6-(4-fluorophenyl)-3-{1-[3-methoxy-4-(4-methyl-1H-imidazol-1-yl)benzylidene]hexahydropyrido[2,1-c][1,4]oxazin-4-one The racemate (Z)-(6S*,9aR*)-6-(4-fluorophenyl)-3-{1-[3-methoxy-4-(4-methyl-1H-imidazol-1-yl)benzylidene]hexahydropyrido[2,1-c][1,4]oxazin-4-one obtained above (27 mg) was separated by CHIRALCEL™ OJ-H manufactured by Daicel Chemical Industries, Ltd. (2 cm×25 cm; mobile phase: hexane:ethanol=1:1) to obtain the title optically active compound with a retention time of 24 minutes (6.7 mg; >99% ee) and the title optically active compound with a retention time of 31 minutes (4.9 mg; >99% ee). The property values of the title optically active compound with a retention time of 24 minutes (Example 16) are as follows.

¹H-NMR (CDCl₃)δ(ppm):
1.40-1.58(m, 2H), 1.65-1.76(m, 2H), 2.18-2.25(m, 2H), 2.31(s, 3H), 3.85(s, 3H), 4.07(q, J=10.8 Hz, 1H), 4.07-4.15 (m, 1H), 4.34(dd, J=10.8,2.4 Hz, 1H), 5.38(t, J=4.0 Hz, 1H), 6.82(s, 1H), 6.92(brs, 1H), 7.02(t, J=8.4 Hz, 2H), 7.20(d, J=8.0 Hz, 1H), 7.22(dd, J=8.0,3.6 Hz, 2H), 7.37(dd, J=8.0, 1.2 Hz, 1H), 7.39(d, J=1.2 Hz, 1H), 7.74(d, J=1.2 Hz, 1H).
ESI-MS; m/z 448[M+H].

The property values of the title optically active compound with a retention time of 31 minutes (Example 17) are as follows.

¹H-NMR (CDCl₃)δ(ppm):
1.40-1.58(m, 2H), 1.65-1.76(m, 2H), 2.18-2.25(m, 2H), 2.31(s, 3H), 3.85(s, 3H), 4.07(q, J=10.8 Hz, 1H), 4.07-4.15 (m, 1H), 4.34(dd, J=10.8, 2.4 Hz, 1H), 5.38(t, J=4.0 Hz, 1H), 6.82(s, 1H), 6.92(brs, 1H), 7.02(t, J=8.4 Hz, 2H), 7.20(d, J=8.0 Hz, 1H), 7.22 (dd, J=8.0,3.6 Hz, 2H), 7.37(dd, J=8.0, 1.2 Hz, 1H), 7.39(d, J=1.2 Hz, 1H), 7.74(d, J=1.2 Hz, 1H).
ESI-MS; m/z 448 [M+H].

EXAMPLES 18 AND 19

Synthesis of (Z)-(S)-4-[(S)-1-(6-chloropyridin-3-yl)ethyl]-2-[1-[3-methoxy-4-(4-methyl-1H-imidazol-1-yl)phenyl]methylidene]-6-methylmorpholin-3-one and (Z)-(S)-4-[(R)-1-(6-chloropyridin-3-yl)ethyl]-2-[1-[3-methoxy-4-(4-methyl-1H-imidazol-1-yl)phenyl]methylidene]-6-methylmorpholin-3-one

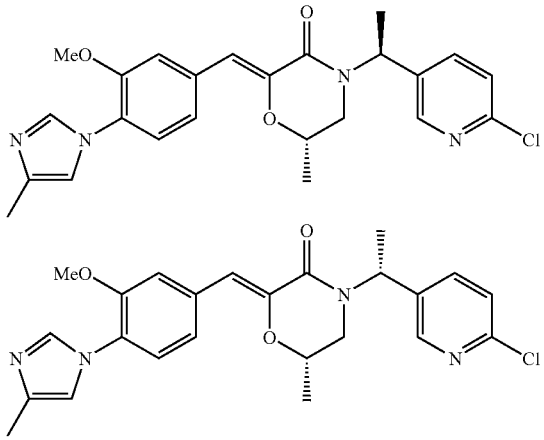

Synthesis of (S)-1-[1-(6-chloropyridin-3-yl)ethylamino]propan-2-ol 44.9 mg of the title compound was obtained from lithium perchlorate (340 mg), an ether (0.64 mL), 1-(6-chloropyridin-3-yl)ethylamine (100 mg: CAS #132219-51-3), and (S)-propylene oxide (61 μL) in the same manner as in Example 7.

¹H-NMR (CDCl₃)δ(ppm):
1.11(d, J=6.4 Hz, 1.5H), 1.12(d, J=6.4 Hz, 1.5H), 1.39(d, J=6.8 Hz, 1.5H), 1.40(d, J=6.8 Hz, 1.5H), 2.21(dd, J=12.0, 9.2 Hz, 0.5H), 2.38(dd, J=12.0, 8.8 Hz, 0.5H), 2.49(dd, J=12.0, 2.4 Hz, 0.5H), 2.63(dd, J=12.0, 2.8 Hz, 0.5H), 3.68-3.87(m, 2H), 7.31(d, J=8.0 Hz, 0.5H), 7.32(d, J=8.0 Hz, 0.5H), 7.67(dd, J=8.0, 2.0 Hz, 0.5H), 7.68(dd, J=8.0, 2.0 Hz, 0.5H), 8.30(d, J=2.0 Hz, 0.5H), 8.31(d, J=2.0 Hz, 0.5H).

Synthesis of (S)-4-[1-(6-chloropyridin-3-yl)ethyl]-6-methylmorpholine-2,3-dione 37.4 mg of the crude title compound was obtained from (S)-1-[1-(6-chloropyridin-3-yl)ethylamino]propan-2-ol (44.8 mg) and diethyl oxalate (1.0 mL) in the same manner as in Example 7.

¹H-NMR (CDCl₃)δ(ppm):

1.36(d, J=6.0 Hz, 1.5H), 1.41(d, J=6.0 Hz, 1.5H), 1.62(d, J=7.2 Hz, 1.5H), 1.65(d, J=7.2 Hz, 1.5H), 3.03-3.11(m, 1H), 3.34(dd, J=14.0, 3.2 Hz, 0.5H), 3.47(dd, J=13.6, 10.4 Hz, 0.5H), 4.52-4.55(m, 0.5H), 4.71-4.76(m, 0.5H), 5.94-5.99(m, 1H), 7.37(d, J=8.4 Hz, 1H), 7.64(dd, J=8.4, 2.4 Hz, 0.5H), 7.68(dd, J=8.4, 2.4 Hz, 0.5H), 8.37(d, J=2.4 Hz, 0.5H), 8.39 (d, J=2.4 Hz, 0.5H).

Synthesis of (S)-4-[1-(6-chloropyridin-3-yl)ethyl]-2-hydroxy-6-methylmorpholin-3-one 3.9 mg of the title compound was obtained from (S)-4-[1-(6-chloropyridin-3-yl)ethyl]-6-methylmorpholine-2,3-dione (37.4 mg) and a 1 M solution of lithium tri-sec-butylborohydride in THF (153 μL) in the same manner as in Example 7.

¹H-NMR (CDCl₃)δ(ppm):
1.22(d, J=7.2 Hz, 1.5H), 1.23(d, J=7.2 Hz, 1.5H), 1.57(d, J=8.4 Hz, 3H), 2.68(dd, J=12.0, 10.8 Hz, 0.5H), 2.75(dd, J=12.0, 2.8 Hz, 0.5H), 3.02(dd, J=12.0, 2.8 Hz, 0.5H), 3.18 (dd, J=12.0, 10.8 Hz, 0.5H), 4.26-4.30(m, 0.5H), 4.43-4.47 (m, 0.5H), 5.34(s, 0.5H), 5.36(s, 0.5H), 5.96(q, J=7.2 Hz, 0.5H), 5.99(q, J=7.2 Hz, 0.5H), 7.33(d, J=8.4 Hz, 0.5H), 7.34(d, J=8.4 Hz, 0.5H), 7.59(dd, J=8.4, 2.4 Hz, 0.5H), 7.63 (dd, J=8.4, 2.4 Hz, 0.5H), 8.34(d, J=2.4 Hz, 0.5H), 8.35(d, J=2.4 Hz, 0.5H).

Synthesis of (Z)-(S)-4-[(S)-1-(6-chloropyridin-3-yl) ethyl]-2-[1-[3-methoxy-4-(4-methyl-1H-imidazol-1-yl)phenyl]methylidene]-6-methylmorpholin-3-one and (Z)-(S)-4-[(R)-1-(6-chloropyridin-3-yl)ethyl]-2-[1-[3-methoxy-4-(4-methyl-1H-imidazol-1-yl)phenyl]methylidene]-6-methylmorpholin-3-one The title compound was obtained as a diastereomer mixture from (S)-4-[1-(6-chloropyridin-3-yl)ethyl]-2-hydroxy-6-methylmorpholin-3-one (3.9 mg), triphenylphosphonium bromide (5.81 mg), and 3-methoxy-4-(4-methyl-1H-imidazol-1-yl)benzaldehyde (3.43 mg) in the same manner as in Examples 16 and 17. The diastereomer mixture was separated by CHIRALPAKT™ AD-H manufactured by Daicel Chemical Industries, Ltd. (2 cm×25 cm; mobile phase: ethanol 100%) to obtain the title optically active compound with a retention time of 19 minutes (1.25 mg; >80% de) and the title optically active compound with a retention time of 25 minutes (0.85 mg; >84% de).

The property values of the title optically active compound with a retention time of 19 minutes (Example 19) are as follows.

¹H-NMR (CDCl₃)δ(ppm):
1.39(d, J=6.8 Hz, 3H), 1.62(d, J=6.8 Hz, 3H), 2.36(s, 3H), 2.96(dd, J=13.2, 4.8 Hz, 1H), 3.26(dd, J=13.2, 2.4 Hz, 1H), 3.86(s, 3H), 4.31-4.40(m, 1H), 6.13(q, J=6.8 Hz, 1H), 6.88(s, 1H), 6.96(s, 1H), 7.22(d, J=8.4 Hz, 1H), 7.34(d, J=8.0 Hz, 1H), 7.36(d, J=8.0 Hz, 1H), 7.52(s, 1H), 7.64(dd, J=8.4, 2.8 Hz, 1H), 7.93(s, 1H), 8.38(d, J=2.8 Hz, 1H).

ESI-MS; m/z 453 [M⁺+H].

The property values of the title optically active compound with a retention time of 25 minutes (Example 18) are as follows.

¹H-NMR (CDCl₃)δ(ppm):
1.42(d, J=6.0 Hz, 3H), 1.61(d, J=7.2 Hz, 3H), 2.39(s, 3H), 2.99(d d, J=12.8, 2.4 Hz, 1H), 3.41(dd, J=12.8, 10.4 Hz, 1H), 3.87(s, 3H), 4.10-4.20(m, 1H), 6.15(q, J=7.2 Hz, 1H), 6.89(s, 1H), 6.97(s, 1H), 7.23(d, J=8.4 Hz, 1H), 7.35(d, J=7.6 Hz, 1H), 7.37(d, J=7.6 Hz, 1H), 7.55(s, 1H), 7.67(dd, J=8.4, 2.4 Hz, 1H), 7.99(s, 1H), 8.39(d, J=2.4 Hz, 1H).

ESI-MS; m/z 453[M⁺+H].

EXAMPLES 20 AND 21

Synthesis of (Z)-(S)-4-[(S)-1-(5-chloropyridin-2-yl) ethyl]-2-[1-[3-methoxy-4-(4-methyl-1H-imidazol-1-yl)phenyl]methylidene]-6-methylmorpholin-3-one and (Z)-(S)-4-[(R)-1-(5-chloropyridin-2-yl)ethyl]-2-[1-[3-methoxy-4-(4-methyl-1H-imidazol-1-yl)phenyl]methylidene]-6-methylmorpholin-3-one

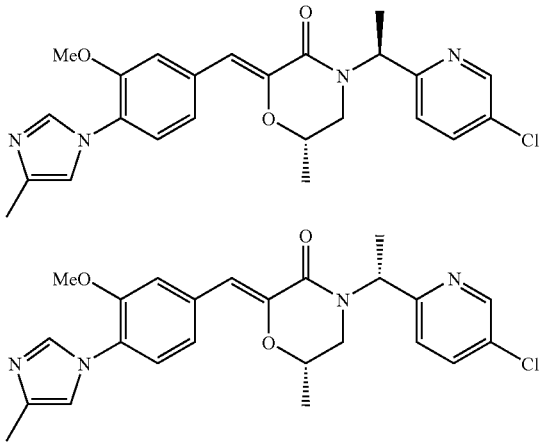

Synthesis of 1-(5-chloropyridin-2-yl)ethanol

Copper iodide (148 mg), 1-ethoxyvinyltri-n-butyltin (2.97 mL), and bis(triphenylphosphine)palladium (II) chloride (183 mg) were added to a solution of 2-bromo-5-chloropyridine (1 g) in acetonitrile (30 mL), and the reaction solution was stirred in a nitrogen atmosphere at 100° C. for three hours. The reaction solution was returned to room temperature. 10 mL of 5 N hydrochloric acid was added, and the reaction solution was heated under reflux for 30 minutes. The reaction solution was returned to room temperature and neutralized with a 5 N sodium hydroxide solution. Diethyl ether was added to the reaction solution, and the organic layer was separated. The organic layer was dried over anhydrous magnesium sulfate, and then the solvent was evaporated under reduced pressure. The residue was dissolved in tetrahydrofuran (30 mL) and methanol (10 mL). Sodium borohydride (492 mg) was added, and the reaction solution was stirred at room temperature for one hour. Water and diethyl ether were added to the reaction solution, and the organic layer was separated. The organic layer was washed with brine and dried over anhydrous magnesium sulfate. The solvent was evaporated under reduced pressure, and the residue was purified by silica gel column chromatography (elution solvent: hexane-diethyl ether) to obtain 503 mg of the title compound.

¹H-NMR (CDCl₃)δ(ppm):

1.50(d, J=6.8 Hz, 3H), 4.90(q, J=6.8 Hz, 1H), 7.28(dd, J=0.8, 0.8 Hz, 1H), 7.67(dd, J=8.4, 2.8 Hz, 1H), 8.50(dd, J=2.8, 0.8 Hz, 1H).

Synthesis of 2-(1-azidoethyl)-5-chloropyridine

Diphenylphosphoryl azide (1.0 mL) was added to a solution of 1-(5-chloropyridin-2-yl)ethanol (503 mg) in toluene (8 mL) in a nitrogen atmosphere. The reaction solution was ice-cooled, and 1,8-diazabicyclo[5,4,0]undec-7-ene (0.69 mL) was added dropwise to the solution. The reaction solution was stirred for three hours. Then, the solution was returned to room temperature and stirred overnight. Water and diethyl ether were added to the reaction solution, and the organic layer was separated. The organic layer was dried over magnesium sulfate, and then the solvent was evaporated under reduced pressure. The residue was purified by silica gel column chromatography (elution solvent: hexane-diethyl ether) to obtain 337 mg of the title compound.
$^1$H-NMR (CDCl$_3$)δ(ppm):
1.60(d, J=6.8 Hz, 3H), 4.66(q, J=6.8 Hz, 1H), 7.32(d, J=8.4 Hz, 1H), 7.69(dd, J=8.4, 2.8 Hz, 1H), 8.54(d, J=2.8 Hz, 1H).

Synthesis of 1-(5-chloropyridin-2-yl)ethylamine

Water (3 mL) and triphenylphosphine (702 mg) were added to a solution of 2-(1-azidoethyl)-5-chloropyridine (333 mg) in tetrahydrofuran (10 mL), and the reaction solution was stirred at 60° C. for two hours. The reaction solution was returned to room temperature. Dichloromethane and 5 N hydrochloric acid were added to the reaction solution, and the aqueous layer was separated. The aqueous layer was made basic (pH 14) with a 5 N sodium hydroxide solution. Then, dichloromethane was added to the reaction solution, and the organic layer was separated. The organic layer was dried over anhydrous magnesium sulfate, and the solvent was evaporated under reduced pressure to obtain 260 mg of the title compound.
$^1$H-NMR (CDCl$_3$)δ(ppm):
1.42(d, J=6.4 Hz, 3H), 4.18(q, J=6.4 Hz, 1H), 7.28(d, J=8.4 Hz, 1H), 7.63(dd, J=8.4, 2.4 Hz, 1H), 8.50(d, J=2.4 Hz, 1H).

Synthesis of (Z)-(S)-4-[(S)-1-(5-chloropyridin-2-yl)ethyl]-2-[1-[3-methoxy-4-(4-methyl-1H-imidazol-1-yl)phenyl]methylidene]-6-methylmorpholin-3-one and (Z)-(S)-4-[(R)-1-(5-chloropyridin-2-yl)ethyl]-2-[1-[3-methoxy-4-(4-methyl-1H-imidazol-1-yl)phenyl]methylidene]-6-methylmorpholin-3-one 115 mg of the title compound was obtained as a diastereomer mixture from 1-(5-chloropyridin-2-yl)ethylamine (200 mg) as a starting material in the same manner as in Examples 18 and 19. A part of the diastereomer mixture was separated by CHIRALPAK™ IA manufactured by Daicel Chemical Industries, Ltd. (2 cm×25 cm; mobile phase: ethanol 100%) to obtain the title optically active compound with a retention time of 17 minutes (12.3 mg; >99% de) and the title optically active compound with a retention time of 20 minutes (21.4 mg; 94% de).
The property values of the title optically active compound with a retention time of 17 minutes (Example 20) are as follows.
$^1$H-NMR (CDCl$_3$)δ(ppm):
1.38(d, J=6.4 Hz, 3H), 1.61(d, J=7.2 Hz, 3H), 2.31(s, 3H), 3.19(dd, J=13.2, 9.6 Hz, 1H), 3.52(dd, J=13.2, 2.4 Hz, 1H), 3.85(s, 3H), 4.33-4.42(m, 1H), 6.04(q, J=7.2 Hz, 1H), 6.83(s, 1H), 6.93(s, 1H), 7.20(d, J=8.0 Hz, 1H), 7.32(dd, J=8.0,1.6 Hz, 1H), 7.33(d, J=8.4 Hz, 1H), 7.51(d, J=1.6 Hz, 1H), 7.65 (dd, J=8.4, 2.4 Hz, 1H), 7.77(s, 1H), 8.52(d, J=2.4 Hz, 1H).
ESI-MS; m/z 453[M$^+$+H].
The property values of the title optically active compound with a retention time of 20 minutes (Example 21) are as follows.
$^1$H-NMR(CDCl$_3$)δ(ppm):
1.45(d, J=6.4 Hz, 3H), 1.60(d, J=7.2 Hz, 3H), 2.55(s, 3H), 3.48(dd, J=12.8, 10.0 Hz, 1H), 3.60(dd, J=12.8, 2.4 Hz, 1H), 3.89(s, 3H), 4.20-4.27(m, 1H), 5.97(q, J=7.2 Hz, 1H), 6.81(s, 1H), 7.02(s, 1H), 7.22(d, J=7.6 Hz, 1H), 7.37(d, J=8.4 Hz, 1H), 7.38(dd, J=7.6,1.2 Hz, 1H), 7.60(d, J=1.2 Hz, 1H), 7.66 (dd, J=8.4, 2.4 Hz, 1H), 8.48(s, 1H), 8.51(d, J=2.4 Hz, 1H).
ESI-MS; m/z 453[M$^+$+H].

EXAMPLES 22 AND 23

Synthesis of (Z)-(S)-4-[(S)-1-(2,6-difluoropyridin-3-yl)ethyl]-2-[1-[3-methoxy-4-(4-methyl-1H-imidazol-1-yl)phenyl]methylidene]-6-methylmorpholin-3-one and (Z)-(S)-4-[(R)-1-(2,6-difluoropyridin-3-yl)ethyl]-2-[1-[3-methoxy-4-(4-methyl-1H-imidazol-1-yl)phenyl]methylidene]-6-methylmorpholin-3-one

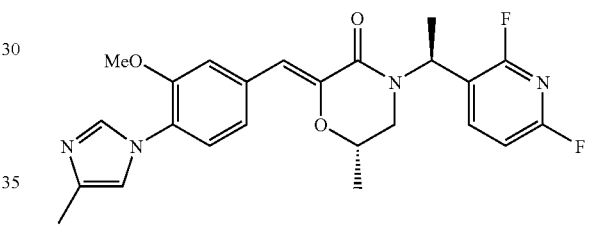

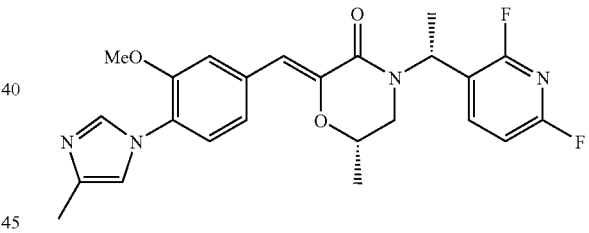

Synthesis of 2,6-difluoronicotinic acid

A solution of n-butyl lithium in THF (2.62 M, 29.1 mL) was added dropwise to a solution of diisopropylamine (11.7 mL) in tetrahydrofuran (310 mL) under ice-cooling in a nitrogen atmosphere. The reaction solution was stirred under ice-cooling for one hour and then cooled to −78° C. A solution of 2,6-difluoropyridine (8 g) in tetrahydrofuran (10 mL) was added dropwise to the reaction solution. The reaction solution was stirred at −0.78° C. for three hours. Then, an excess amount of crushed dry ice was added in a nitrogen stream, and the reaction solution was stirred at −78° C. for 20 minutes and at room temperature for three hours. Water and diethyl ether were added to the reaction solution, and the aqueous layer was separated. The aqueous layer was adjusted to pH 1 by concentrated hydrochloric acid. Ethyl acetate was added to the aqueous layer, and the organic layer was separated. The organic layer was dried over anhydrous magnesium sulfate, and the solvent was evaporated under reduced pressure to obtain 10.4 g of the title compound.

¹H-NMR (CD₃OD)δ(ppm):
7.08(dd, J=8.4, 2.8 Hz, 1H), 8.58(dd, J=17.2, 8.4 Hz, 1H).

Synthesis of
2,6-difluoro-N-methoxy-N-methylnicotinamide

N,O-dimethylhydroxylamine hydrochloride (14.7 g), WSC (28.9 g), and HOBt (20.4 g) were added to a solution of 2,6-difluoronicotinic acid (6 g) and diisopropylethylamine (10 mL) in DMF (100 mL), and the reaction solution was stirred at room temperature for two days. Water and ethyl acetate were added to the reaction solution, and the organic layer was separated. The organic layer was dried over anhydrous magnesium sulfate, and the solvent was evaporated under reduced pressure. The resulting residue was purified by silica gel column chromatography (carrier: Chromatorex NH; elution solvent: ethyl acetate) to obtain 7.01 g of the title compound.
¹H-NMR (CDCl₃)δ(ppm):
3.37(s, 3H), 3.58(brs, 3H), 6.90(dd, J=8.0, 2.8 Hz, 1H), 8.02(dd, J=16.0, 8.0 Hz, 1H).

1-(2,6-difluoropyridin-3-yl)ethanone

A solution of methylmagnesium bromide in THF (0.96 M, 88.1 mL) was added to a solution of 2,6-difluoro-N-methoxy-N-methylnicotinamide (7.01 g) in tetrahydrofuran (180 mL) under ice-cooling, and the reaction solution was stirred under ice-cooling for two hours. A saturated ammonium chloride solution and ethyl acetate were added to the reaction solution under ice-cooling, and the organic layer was separated. The organic layer was washed with brine and dried over anhydrous magnesium sulfate. The solvent was evaporated under reduced pressure, and the residue was purified by silica gel column chromatography (elution solvent: hexane-ethyl acetate) to obtain 4.74 g of the title compound.
¹H-NMR (CDCl₃)δ(ppm):
2.05(s, 3H), 6.93-6.97(m, 1H), 8.46-8.52(m, 1H).

1-(2,6-difluoropyridin-3-yl)ethanone oxime

Hydroxylamine sulfate (13.1 g) and sodium acetate (10.9 g) were added to a solution of 1-(2,6-difluoropyridin-3-yl) ethanone (4.18 g) in aqueous THF (50%, 200 mL), and the reaction solution was stirred at room temperature overnight. Water and ethyl acetate were added to the reaction solution, and the organic layer was separated. The organic layer was dried over anhydrous magnesium sulfate, and the solvent was evaporated under reduced pressure. The resulting residue was purified by silica gel column chromatography (carrier: Chromatorex NH; elution solvent: ethyl acetate) to obtain 2.44 g of the title compound.
¹H-NMR (CDCl₃)δ(ppm):
2.05(s, 3H), 6.93-6.97(m, 1H), 8.46-8.52(m, 1H).

1-(2,6-difluoropyridin-3-yl)ethylamine

Zinc (9.29 g) was added in three portions to a solution of 1-(2,6-difluoropyridin-3-yl)ethanone oxime (2.44 g) in trifluoroacetic acid (100 mL), and the reaction solution was stirred at room temperature for two hours. The reaction solution was made basic (pH 14) with 5 N sodium hydroxide and filtered through celite, and the celite was washed with chloroform. The organic layer was separated and dried over anhydrous magnesium sulfate, and the solvent was evaporated under reduced pressure to obtain 1.61 g of the title compound.

¹H-NMR (CDCl₃)δ(ppm):
1.42(d, J=6.8 Hz, 1H), 4.39(q, J=6.8 Hz, 1H), 6.82(dd, J=8.0, 2.8 Hz, 1H), 8.02(dd, J=1.7.2, 8.0 Hz, 1H).

Synthesis of (Z)-(S)-4-[(S)-1-(2,6-difluoropyridin-3-yl)ethyl]-2-[1-[3-methoxy-4-(4-methyl-1H-imidazol-1-yl)phenyl]methylidene]-6-methylmorpholin-3-one and (Z)-(S)-4-[(R)-1-(2,6-difluoropyridin-3-yl) ethyl]-2-[1-[3-methoxy-4-(4-methyl-1H-imidazol-1-yl)phenyl]methylidene]-6-methylmorpholin-3-one The title compound (170 mg) was obtained as a diastereomer mixture from 1-(2,6-difluoropyridin-3-yl)ethylamine (330 mg) as a starting material in the same manner as in Examples 18 and 19. The resulting diastereomer mixture (10 mg) was separated by CHIRALPAK™ IA manufactured by Daicel Chemical Industries, Ltd. (2 cm×25 cm; mobile phase: hexane:ethanol=7:3) to obtain the title optically active compound with a retention time of 33 minutes (4.7 mg) and the title optically active compound with a retention time of 39 minutes (3.8 mg).
The property value of the title compound diastereomer mixture is as follows.
ESI-MS; m/z 455[M⁺+H]
The property values of the title optically active compound with a retention time of 33 minutes (Example 22) are as follows.
¹H-NMR (CDCl₃)δ(ppm):
1.44(d, J=6.4 Hz, 3H), 1.67(d, J=7.2 Hz, 3H), 2.31(s, 3H), 3.23(d d, J=12.8, 10.0 Hz, 1H), 3.42(dd, J=12.8, 2.8 Hz, 1H), 3.84(s, 3H), 4.37(m, 1H), 5.74(q, J=7.2 Hz, 1H), 6.81(s, 1H), 6.87(dd, J=8.0, 2.8 Hz, 1H), 6.93(dd, J=1.2,1.2 Hz, 1H), 7.20(d, J=8.0 Hz, 1H), 7.31(dd, J=8.4, 1.6 Hz, 1H), 7.50(d, J=1.6 Hz, 1H), 7.77(s, 1H), 8.00(m, 1H).
The property values of the title optically active compound with a retention time of 39 minutes (Example 23) are as follows.
¹H-NMR (CDCl₃)δ(ppm):
1.46(d, J=6.4 Hz, 3H), 1.65(d, J=7.2 Hz, 3H), 2.32(s, 3H), 3.32(d d, J=12.8, 2.8 Hz, 1H), 3.50(dd, J=12.8, 9.6 Hz, 1H), 3.85(s, 3H), 4.29(m, 1H), 5.80(q, J=7.2 Hz, 1H), 6.82(s, 1H), 6.87(dd, J=8.0, 2.8 Hz, 1H), 6.93(dd, J=1.2, 1.2 Hz, 1H), 7.20(d, J=8.0 Hz, 1H), 7.31(dd, J=8.0, 1.6 Hz, 1H), 7.51(d, J=1.6 Hz, 1H), 7.79(s, 1H), 7.99(m, 1H).
Another synthesis in Example 22

Synthesis of (Z)-(S)-4-[(S)-1-(2,6-difluoropyridin-3-yl)ethyl]-2-[1-[3-methoxy-4-(4-methyl-1H-imidazol-1-yl)phenyl]methylidene]-6-methylmorpholin-3-one

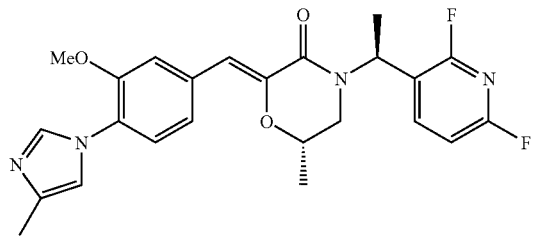

Synthesis of 1-(2,6-difluoropyridin-3-yl)ethanol

Diisopropylamine (134 mL) was added dropwise to a mixed solution composed of a solution of n-butyl lithium in hexane (2.62 M, 368 mL) and tetrahydrofuran (800 mL) in a nitrogen atmosphere at −60° C. or less. The reaction solution was stirred for 30 minutes, and then a solution of 2,6-difluoropyridine (100 g) in tetrahydrofuran (100 mL) was added dropwise to the reaction solution at −60° C. or less. The reaction solution was stirred for one hour, and then acetaldehyde (97.6 mL) was added dropwise to the reaction solution. Then, 2 N aqueous hydrochloric acid (1,000 ml) was added dropwise to the reaction solution. Thereafter, ethyl acetate (1,000 mL) and toluene (1,000 mL) were added to the reaction solution, and the organic layer was separated. The organic layer was concentrated under reduced pressure to obtain 129 g of the title compound.

$^1$H-NMR (CDCl$_3$)δ(ppm):

1.51(d, J=5.6 Hz, 3H), 2.00(s, 1H), 5.13-5.16(m, 1H), 6.84 (dd, J=8.0, 2.1 Hz, 1H), 8.05(dd, J=16.0, 8.0 Hz, 1H).

Synthesis of (S)-1-[(S)-1-(2,6-difluoropyridin-3-yl)ethylamino]propan-2-ol (+)-di-p-toluoyl-D-tartrate A solution of 1-(2,6-difluoropyridin-3-yl)ethanol (216 g) in toluene (300 mL) was added to a solution of thionyl bromide (337 g) in toluene (1,500 mL) under ice-cooling, and the reaction solution was stirred at room temperature for three hours. Ice water and toluene were added to the reaction solution, and the organic layer was separated. The organic layer was washed with water (1,000 mL) three times. The organic layer was dried over anhydrous magnesium sulfate and then filtered through a silica gel pad. (S)-1-amino-2-propanol (157 g), cesium carbonate (1.28 kg), and DMF (2,500 mL) were added to the filtrate, and the reaction solution was stirred at room temperature overnight. The reaction solution was filtered, and then the mother liquor was concentrated under reduced pressure. The residue was diluted with ethanol (1,000 mL). Then, a solution of (+)-di-p-toluoyl-D-tartaric acid (152 g) in ethanol (500 mL) was added, and the reaction solution was stirred at room temperature for one hour. The precipitated crystals were collected by filtration and washed with ethanol. The crystals were dried at 80° C. for two hours and suspended in an ethanol (2,000 mL)-heptane (1,000 mL) mixed solvent. Then, the reaction solution was heated and stirred at 80° C. One hour later, the reaction solution was returned to room temperature, and the crystals were collected by filtration. The crystals were washed with ethanol and dried at 80° C. overnight to obtain 155 g of the title compound.

$^1$H-NMR (DMSO-d$_6$)δ(ppm):

1.02(d, J=6.0 Hz, 6H), 1.37(d, J=6.8 Hz, 6H), 2.36(s, 6H), 2.37-2.51(m, 4H), 3.67-3.71(m, 2H), 4.14-4.16(m, 2H), 5.65 (s, 2H), 7.21(dd, J=8.0, 2.0 Hz, 2H), 7.31(d, J=8.4 Hz, 4H), 7.82(d, J=8.4 Hz, 4H), 8.27(dd, J=17.6, 8.0 Hz, 2H).

Synthesis of (S)-4-[(S)-1-(2,6-difluoropyridin-3-yl)ethyl]-6-methylmorpholine-2,3-dione (S)-1-[(S)-1-(2,6-difluoropyridin-3-yl)ethylamino]propan-2-ol (+)-di-p-toluoyl-D-tartrate (199 g) was dissolved in 5 N aqueous sodium hydroxide (450 mL), water (1,000 mL), and 50% toluene-THF (2,000 mL), and the organic layer was separated. The aqueous layer was washed with 50% toluene-THF (800 mL) three times. The organic layers were combined and concentrated under reduced pressure. Then, diethyl oxalate (200 mL) was added to the residue, and the reaction solution was heated and stirred at 140 to 150° C. Three hours later, the reaction solution was diluted with toluene (500 mL) and then ice-cooled while stirring. The precipitated crystals were collected by filtration, washed with toluene and diethyl ether, and then air-dried to obtain 103 g of the title compound.

$^1$H-NMR (CDCl$_3$)δ(ppm):

1.43(d, J=6.8 Hz, 3H), 1.70(d, J=6.8 Hz, 3H), 3.36(dd, J=13.2, 8.8 Hz, 1H), 3.52(dd, J=13.2, 2.1 Hz, 1H), 4.72-4.78 (m, 1H), 5.59(q, J=6.8 Hz, 1H), 6.88(dd, J=8.0, 2.8 Hz, 1H), 8.01(dd, J=16.8, 8.0 Hz, 1H).

Synthesis of (S)-4-[(S)-1-(2,6-difluoropyridin-3-yl)ethyl]-2-hydroxy-6-methylmorpholin-3-one A 1 M solution of lithium tri-sec-butylborohydride in THF (20 mL) was added dropwise to a solution of (S)-4-[(S)-1-(2,6-difluoropyridin-3-yl)ethyl]-6-methylmorpholine-2,3-dione (4.5 g) in THF at −50° C. or less, and the reaction solution was stirred for two hours. A 5 N sodium hydroxide solution (1.66 mL) and 30% aqueous hydrogen peroxide (6.78 mL) were added dropwise to the reaction solution at −10° C. or less, and the reaction solution was stirred for one hour. Sodium bisulfite (520 mg) was added to the reaction solution, which was then stirred for 30 minutes. Brine and 50% toluene-THF were added to the reaction solution, and the organic layer was separated. The aqueous layer was washed with 50% toluene-THF. The organic layers were combined and concentrated under reduced pressure. The residue was purified by column chromatography using a silica gel (heptane:ethyl acetate=1:1 to 0:100) to obtain 4.52 g of the title compound.

$^1$H-NMR (CDCl$_3$)δ(ppm):

1.25(d, J=6.8 Hz, 2.58H), 1.30(d, J=6.8 Hz, 0.42H), 1.60 (d, J=6.8 Hz, 2.58H), 1.62(d, J=6.8 Hz, 0.42H), 2.90(dd, J=12.8, 8.8 Hz, 0.86H), 3.09(dd, J=12.8, 8.8 Hz, 0.14H), 3.11(dd, J=12.8, 2.1 Hz, 0.86H), 3.31(dd, J=12.8, 2.1 Hz, 0.14H), 4.39-4.49(m, 1H), 5.14(s, 0.14H), 5.30(s, 0.86H), 5.50(q, J=6.8 Hz, 0.14H), 5.71(q, J=6.8 Hz, 0.86H), 6.87(dd, J=8.0, 2.8 Hz, 1H), 7.96(dd, J=16.8, 8.0 Hz, 1H).

Synthesis of (Z)-(S)-4-[(S)-1-(2,6-difluoropyridin-3-yl)ethyl]-2-[1-[3-methoxy-4-(4-methyl-1H-imidazol-1-yl)phenyl]methylidene]-6-methylmorpholin-3-one Triphenylphosphonium bromide (6.52 g) was added to a solution of (S)-4-[(S)-1-(2,6-difluoropyridin-3-yl)ethyl]-2-hydroxy-6-methylmorpholin-3-one (4.3 g) in acetonitrile, and the reaction solution was heated under reflux for one hour. Triethylamine (5.28 mL) and 3-methoxy-4-(4-methyl-1H-imidazol-1-yl)benzaldehyde (3.42 g) were added to the reaction solution, which was then heated under reflux for 1.5 hours. The reaction solution was concentrated under reduced pressure, and the residue was diluted with 2 N aqueous hydrochloric acid and ethyl acetate. Then, the aqueous layer was separated. The organic layer was washed with 2 N aqueous hydrochloric acid. Then, the total aqueous layers were combined and made alkaline with a concentrated sodium hydroxide solution. The organic layer was separated by extraction from the alkaline solution with ethyl acetate, and then washed with saturated sodium bicarbonate. The organic layer was dried over anhydrous magnesium sulfate and concentrated under reduced pressure. The residue was purified by column chromatography using NH silica gel (heptane:ethyl acetate=1:1 to 0:100) to obtain 4.06 g of the title compound. The property values corresponded to those in Example 22.

EXAMPLES 24 AND 25

Synthesis of (Z)-(S)-4-[(S)-1-(2,3-difluoropyridin-4-yl)ethyl]-2-[1-[3-methoxy-4-(4-methyl-1H-imidazol-1-yl)phenyl]methylidene]-6-methylmorpholin-3-one and (Z)-(S)-4-[(R)-1-(2,3-difluoropyridin-4-yl)ethyl]-2-[1-[3-methoxy-4-(4-methyl-1H-imidazol-1-yl)phenyl]methylidene]-6-methylmorpholin-3-one

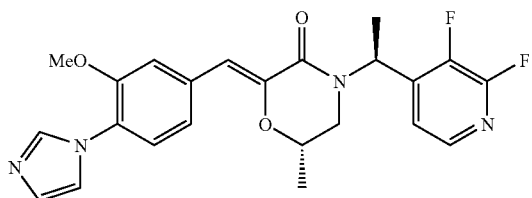

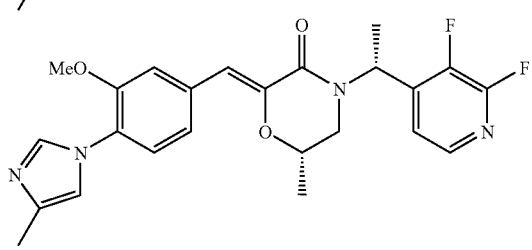

1-(2,6-difluoropyridin-3-yl)ethylamine 1.13 g of the title compound was obtained from 2,3-difluoroisonicotinic acid (2.49 g) that is a known compound (see Journal of Organic Chemistry, 2005, vol. 70, p. 3039-3045) in the same manner as in Examples 22 and 23.

¹H-NMR (CDCl₃)δ(ppm):
1.44(d, J=6.8 Hz, 3H), 4.50(q, J=6.8 Hz, 1H), 7.33(dd, J=4.8, 4.8 Hz, 1H), 7.94(d, J=4.8 Hz, 1H).

Synthesis of (Z)-(S)-4-[(S)-1-(2,3-difluoropyridin-4-yl)ethyl]-2-[1-[3-methoxy-4-(4-methyl-1H-imidazol-1-yl)phenyl]methylidene]-6-methylmorpholin-3-one and (Z)-(S)-4-[(R)-1-(2,3-difluoropyridin-4-yl)ethyl]-2-[1-[3-methoxy-4-(4-methyl-1H-imidazol-1-yl)phenyl]methylidene]-6-methylmorpholin-3-one The title compound (500 mg) was obtained as a diastereomer mixture from 1-(2,6-difluoropyridin-3-yl)ethylamine (500 mg) as a starting material in the same manner as in Examples 18 and 19. The resulting diastereomer mixture (10 mg) was separated by CHIRALPAK™ IA manufactured by Daicel Chemical Industries, Ltd. (2 cm×25 cm; mobile phase: hexane:ethanol=7:3) to obtain the title optically active compound with a retention time of 39 minutes (2.6 mg) and the title optically active compound with a retention time of 43 minutes (3.0 mg).

The property value of the title compound diastereomer mixture is as follows.
ESI-MS; m/z 455[M⁺+H].

The property values of the title optically active compound with a retention time of 39 minutes (Example 24) are as follows.

¹H-NMR (CDCl₃)δ(ppm):
1.46(d, J=6.8 Hz, 3H), 1.67(d, J=7.2 Hz, 3H), 2.31(s, 3H), 3.24(d d, J=13.2, 9.6 Hz, 1H), 3.43(dd, J=13.2, 2.8 Hz, 1H), 3.85(s, 3H), 4.39(m, 1H), 5.93(q, J=7.2 Hz, 1H), 6.83(s, 1H), 6.94(dd, J=0.8, 0.8 Hz, 1H), 7.19-7.27(m, 2H), 7.32(dd, J=8.4, 1.6 Hz, 1H), 7.51(d, J=1.6 Hz, 1H), 7.79(d, J=1.2 Hz, 1H), 7.99(dd, J=5.2, 0.8 Hz, 1H).

The property values of the title optically active compound with a retention time of 43 minutes (Example 25) are as follows.

¹H-NMR (CDCl₃)δ(ppm):
1.49(d, J=6.4 Hz, 3H), 1.66(d, J=7.2 Hz, 3H), 2.32(s, 3H), 3.29(d d, J=12.8, 2.8 Hz, 1H), 3.54(dd, J=12.8, 9.6 Hz, 1H), 3.85(s, 3H), 4.34(m, 1H), 5.97(q, J=7.2 Hz, 1H), 6.84(s, 1H), 6.94(s, 1H), 7.18-7.23(m, 2H), 7.33(dd, J=8.4, 1.6 Hz, 1H), 7.51(d, J=1.6 Hz, 1H), 7.80(d, J=1.2 Hz, 1H), 7.99(dd, J=5.2, 0.8 Hz, 1H).

EXAMPLE 26

Synthesis of (Z)-(S)-4-[(1R,2R)-2-hydroxy-1-(3,4,5-trifluorophenyl)propyl]-2-[1-[3-methoxy-4-(4-methyl-1H-imidazol-1-yl)phenyl]methylidene]-6-methylmorpholin-3-one

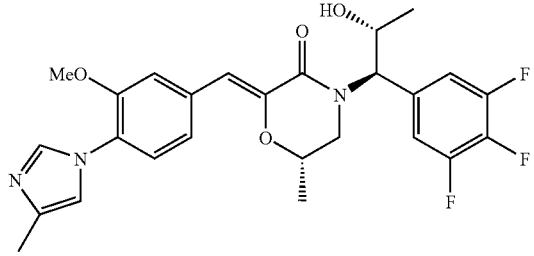

Synthesis of 1,2,3-trifluoro-5-[(E)-propenyl]benzene

Tetrakistriphenylphosphine palladium (0) (4.66 g) and cesium fluoride (21.4 g) were added to a solution of 1-bromo-3,4,5-trifluorobenzene (8.5 g) and trans-1-propen-1-ylboronic acid (4.1 g) in dioxane (95 ml) and water (5 ml) in a nitrogen atmosphere, and the reaction solution was stirred at 80° C. for five hours. The reaction solution was returned to room temperature. Then, hexane and water were added to the reaction solution, and the insoluble matter was removed by filtration. The organic layer was separated and then washed with water, and the insoluble matter was removed by filtration again. The organic layer was separated and then sequentially washed with water and brine. The organic layer was dried over anhydrous magnesium sulfate, and then the solvent was evaporated under reduced pressure. The resulting crude product was purified by silica gel column chromatography (hexane) to obtain 5.83 g of the title compound.

¹H-NMR (CDCl₃)δ(ppm):
1.88(d, J=6.0 Hz, 3H), 6.18(qd, J=6.0, 16.0 Hz, 1H), 6.24 (d, J=16.0 Hz, 1H), 6.85-6.96(m, 2H).

Synthesis of (1S,2S)-1-(3,4,5-trifluorophenyl)propane-1,2-diol 1,2,3-Trifluoro-5-[(E)-propenyl]-benzene (5.83 g) was added to an ice-cooled mixed solution of AD-Mix-α (47.5 g) and methanesulfonamide (3.22 g) in tert-butanol (170 ml) and water (170 ml), and the reaction solution was stirred at 5° C. overnight. Then, sodium sulfite (51 g) was added to the reaction solution, which was then stirred for one hour. The reaction solution was subjected to extraction with methylene chloride three times. The combined organic layers were washed with a 2 N sodium hydroxide solution, and then the sodium hydroxide layer was subjected to extraction with methylene chloride again. The organic layers were combined and dried over anhydrous magnesium sulfate, and then the solvent was evaporated under reduced pressure. The resulting crude product was purified by silica gel column chromatography (hexane:ethyl acetate=9:1 to 1:1) to obtain 5.54 g of the title compound.

$^1$H-NMR (CDCl$_3$)δ(ppm):
1.12(d, J=6.4 Hz, 3H), 2.20(brs, 1H), 2.79(brs, 1H), 3.78 (qd, J=6.4, 6.4 Hz, 1H), 4.34(d, J=6.4 Hz, 1H), 6.96-7.05(m, 2H).

Synthesis of (1R,2S)-1-azido-1-(3,4,5-trifluorophenyl)propan-2-ol

A sodium hydroxide pellet (110 mg) was added to a solution of (1S,2S)-1-(3,4,5-trifluorophenyl)propane-1,2-diol (5.54 g) in dimethyl carbonate (15 ml) in a nitrogen atmosphere, and the reaction solution was stirred at 70° C. for 45 minutes. Then, the external temperature was raised to 100° C., and dimethyl carbonate was removed by spraying nitrogen. Further, dimethyl carbonate (5 ml) was added to the residue, and dimethyl carbonate was removed by spraying nitrogen. THF was added to the residue, and the insoluble matter was removed by filtration through celite. Then, the solvent was evaporated under reduced pressure to obtain 6.13 g of a carbonate compound.

Water (0.5 ml) and sodium azide (1.92 g) were added to a solution of the carbonate compound in DMF (20 ml) in a nitrogen atmosphere, and the reaction solution was stirred at 110° C. overnight. Diethyl ether was added to the reaction solution returned to room temperature, and the reaction solution was sequentially washed with water (three times) and brine. The organic layer was dried over anhydrous magnesium sulfate, and then the solvent was evaporated under reduced pressure. The resulting residue was purified by silica gel column chromatography (hexane:ethyl acetate=19:1 to 9:1) to obtain 5.16 g of the title compound.

$^1$H-NMR (CDCl$_3$)δ(ppm):
1.14(d, J=6.4 Hz, 3H), 1.79(brs, 1H), 3.97(qd, J=6.4, 4.8 Hz, 1H), 4.42(d, J=4.8 Hz, 1H), 6.96-7.05(m, 2H).

Synthesis of tert-butyl [(1R,2S)-2-hydroxy-1-(3,4,5-trifluorophenyl)propyl]carbamate Triphenylphosphine (5.85 g) was added to a solution of (1R,2S)-1-azido-1-(3,4,5-trifluorophenyl)propan-2-ol (5.16 g) in THF (75 ml) in a nitrogen atmosphere, and the reaction solution was stirred at room temperature for 10 minutes. Thereafter, water (5 ml) was added to the reaction solution, which was then stirred at 60° C. for 3.5 hours. The reaction solution was returned to room temperature, and di-tert-butyl dicarbonate (5.35 g) was added to the reaction solution, which was then stirred at room temperature for 45 minutes. The solvent was evaporated under reduced pressure, and then the resulting residue was purified by silica gel column chromatography (toluene:ethyl acetate=9:1) to obtain 5.88 g of the title compound.

$^1$H-NMR (CDCl$_3$)δ(ppm):
1.07 (d, J=6.4 Hz, 3H), 1.41 (s, 9H), 4.10 (brs, 1H), 4.47 (brs, 1H), 5.44 (brs, 1H), 6.92-7.01 (m, 2H).

Synthesis of (1R,2R)-2-tert-butoxycarbonylamino-1-methyl-2-(3,4,5-trifluorophenyl)ethyl 4-nitrobenzoate Diisopropyl azodicarboxylate (6 ml) was added dropwise to a solution of tert-butyl [(1R,2S)-2-hydroxy-1-(3,4,5-trifluorophenyl)propyl]carbamate (5.88 g), 4-nitrobenzoic acid (4.84 g), and triphenylphosphine (7.59 g) in THF (100 ml) under ice-cooling in a nitrogen atmosphere, and the reaction solution was stirred at room temperature for two hours. The solvent was evaporated under reduced pressure, and the resulting residue was purified by silica gel column chromatography (toluene:ethyl acetate=97:3). Then, the resulting powder was triturated with toluene-hexane to obtain 6.69 g of the title compound.

$^1$H-NMR (CDCl$_3$)δ(ppm):
1.37 (s, 9H), 1.38 (d, J=6.4 Hz, 3H), 4.85 (brs, 1H), 5.16 (d, J=9.2 Hz, 1H), 5.41 (qd, J=6.4, 6.0 Hz, 1H), 6.92-7.01 (m, 2H), 8.16 (d, J=8.8 Hz, 2H), 8.29 (d, J=8.8 Hz, 2H).

Synthesis of tert-butyl [(1R,2R)-2-hydroxy-1-(3,4,5-trifluorophenyl)propyl]carbamate Potassium carbonate powder (6.43 g) was added to a mixed solution of (1R,2R)-2-tert-butoxycarbonylamino-1-methyl-2-(3,4,5-trifluorophenyl)ethyl 4-nitrobenzoate (7.03 g) in methanol (90 ml)-THF (10 ml), and the reaction solution was stirred at room temperature for one hour. Ethyl acetate was added to the reaction solution, which was then sequentially washed with water and brine (twice). The organic layer was dried over anhydrous magnesium sulfate, and the solvent was evaporated under reduced pressure. Diethyl ether was added to the resulting residue, and the insoluble matter was removed by filtration. The filtrate was concentrated, and the resulting residue was purified by silica gel column chromatography (toluene:ethyl acetate=6:1) to obtain 4.49 g of the title compound.

$^1$H-NMR (CDCl$_3$)δ(ppm):
1.28 (d, J=6.4 Hz, 3H), 1.44 (s, 9H), 4.01 (brs, 1H), 4.48 (brs, 1H), 5.35 (brs, 1H), 6.90-7.00 (m, 2H).

Synthesis of tert-butyl [(1R,2R)-2-tert-butyldiphenylsilanyloxy-1-(3,4,5-trifluorophenyl)propyl]carbamate Tert-Butylchlorodiphenylsilane (2.0 ml) was added in four portions to a solution of tert-butyl [(1R,2R)-2-hydroxy-1-(3,4,5-trifluorophenyl)propyl]carbamate (610 mg) and imidazole (817 mg) in DMF (3 ml) in a nitrogen atmosphere, and the reaction solution was stirred at room temperature for three hours. Ethyl acetate was added to the reaction solution, which was then sequentially washed with water, 1 N hydrochloric acid, water, a saturated sodium bicarbonate solution, and brine. The organic layer was dried over anhydrous magnesium sulfate, and then the solvent was evaporated under reduced pressure. The resulting residue was purified by silica gel column chromatography (hexane:diethyl ether 49:1 to 19:1) to obtain 684 mg of the title compound.

$^1$H-NMR (CDCl$_3$)δ(ppm):
0.95 (s, 9H)1.13 (d, J=6.4 Hz, 3H), 1.47 (s, 9H), 4.02 (brs, 1H), 4.46 (brs, 1H), 5.34 (brs, 1H), 6.69-6.80 (m, 2H), 7.28-7.46 (m, 8H), 7.55 (d, J=8.4 Hz, 2H).

Synthesis of (1R,2R)-2-tert-butyldiphenylsilanyloxy-1-(3,4,5-trifluorophenyl)propylamine Trifluoroacetic acid (0.5 ml) was added to a solution of tert-butyl [(1R,2R)-2-tert-butyldiphenylsilanyloxy-1-(3,4,5-trifluorophenyl)propyl]carbamate (370 mg) in methylene chloride (2 ml), and the reaction solution was stirred at room temperature for 11 hours. A saturated sodium bicarbonate solution was added to the reaction solution, followed by extraction with ethyl acetate. The organic layer was washed with a saturated sodium bicarbonate solution and brine, and then the solvent was evaporated under reduced pressure to obtain 275 mg of the title compound.

$^1$H-NMR (CDCl$_3$)δ(ppm):
0.93 (d, J=6.4 Hz, 3H), 1.02 (s, 9H), 3.81 (d, J=4.8 Hz, 1H), 3.91 (d q, J=4.8, 6.0 Hz, 1H), 6.88-6.97 (m, 2H), 7.32-7.46 (m, 6H), 7.57 (d, J=8.0 Hz, 2H), 7.55 (d, J=8.0 Hz, 2H).

Synthesis of (S)-1-[(1R,2R)-2-tert-butyldiphenylsilanyloxy-1-(3,4,5-trifluorophenyl)propylamino]propan-2-ol A solution of (S)-(−)-propylene oxide (0.1 ml) and (1R,2R)-2-tert-butyldiphenylsilanyloxy-1-(3,4,5-trifluorophenyl)propylamine (212 mg) in diethyl ether (1 ml) was added to a suspension of lithium perchlorate (750 mg) in diethyl ether (1 ml), and the reaction solution was stirred in a nitrogen atmosphere at room temperature overnight. Methylene chloride and ice water were added to the reaction solution. After stirring the reaction solution, the organic layer was separated. The aqueous layer was subjected to extraction with methylene chloride again. The organic layers were combined and dried over anhydrous magnesium sulfate, and then the solvent was concentrated under reduced pressure. The resulting residue was purified by silica gel column chromatography (ethyl acetate:heptane=9:1 to 4:1) to obtain 172 mg of the title compound.

$^1$H-NMR (CDCl$_3$)δ(ppm):
0.83 (d, J=6.0 Hz, 3H), 1.06 (s, 9H), 1.08 (m, 3H), 2.20-2.50 (m, 3H), 3.47 (brs, 1H), 3.59 (brs, 1H), 3.86 (brs, 1H), 6.78-6.95 (m, 2H), 7.36-7.48 (m, 6H), 7.67 (d, J=6.8 Hz, 4H).

Synthesis of (S)-4-[(1R,2R)-2-tert-butyldiphenylsilanyloxy-1-(3,4,5-trifluorophenyl)propyl]-6-methyl-morpholine-2,3-dione Oxalyl chloride (45 μl) was added dropwise to a solution of (S)-1-[(1R,2R)-2-tert-butyldiphenylsilanyloxy-1-(3,4,5-trifluorophenyl)propylamino]propan-2-ol (171 mg), TEA (0.17 ml), and 4-(N,N-dimethylamino)pyridine (8 mg) in methylene chloride (2 ml) under ice-cooling in a nitrogen atmosphere, and the reaction solution was stirred at the same temperature for two hours. Ice water was added to the reaction solution, followed by extraction with ethyl acetate. Then, the organic layer was sequentially washed with water, 1 N hydrochloric acid, water, a saturated sodium bicarbonate solution, and brine. The organic layer was dried over anhydrous magnesium sulfate, and the solvent was evaporated under reduced pressure. The resulting residue was purified by silica gel column chromatography (heptane:ethyl acetate=9:1 to 3:1) to obtain 96 mg of the title compound.

$^1$H-NMR (CDCl$_3$)δ(ppm):
1.02 (s, 9H), 1.19 (d, J=6.0 Hz, 3H), 1.28 (d, J=6.4 Hz, 3H), 3.20 (dd, J=5.6, 13.2 Hz, 1H), 3.68 (dd, J=2.4, 13.2 Hz, 1H), 4.42 (dq, J=5.6, .0 Hz, 1H), 4.62 (ddq, J=2.4, 5.6, 6.4 Hz, 1H), 5.51 (d, J=5.6 Hz, 1H), 6.82-6.94 (m, 2H), 7.40-7.54 (m, 6H), 7.62 (d, J=8.0 Hz, 2H), 7.67 (d, J=8.0 Hz, 2H).

Synthesis of (S)-4-[(1R,2R)-2-tert-butyldiphenylsilanyloxy-1-(3,4,5-trifluorophenyl)propyl]-2-hydroxy-6-methylmorpholin-3-one A solution of lithium tri-sec-butylborohydride (1.06 mol) in THF (0.25 ml) was added dropwise to a solution of (S)-4-[(1R,2R)-2-tert-butyldiphenylsilanyloxy-1-(3,4,5-trifluorophenyl)propyl]-6-methylmorpholine-2,3-dione (95 mg) in THF (3 ml) in a nitrogen atmosphere at −20° C., and the reaction solution was stirred at the same temperature for 30 minutes. A 5 N sodium hydroxide solution (0.03 ml) and 30% aqueous hydrogen peroxide (0.07 ml) were added to the reaction solution, which was then stirred under ice-cooling for one hour. Thereafter, Sodium bisulfite powder (20 mg) was added, and the reaction solution was stirred at room temperature for 30 minutes. Brine was added to the reaction solution, followed by extraction with ethyl acetate. The organic layer was washed with brine and dried over anhydrous magnesium sulfate, and then the solvent was evaporated under reduced pressure. The resulting residue was purified by silica gel column chromatography (heptane:ethyl acetate=1:1) to obtain 93 mg of the title compound.

$^1$H-NMR (CDCl$_3$)δ(ppm):
1.01 (s, 9H), 1.11 (d, J=6.0 Hz, 3H), 1.19 (d, J=6.4 Hz, 3H), 2.88 and 2.99 (dd, J=12.0, 12.0 Hz, 1H), 3.12 and 3.48 (dd, J=2.4, 12.0 Hz, 1H), 3.16 and 3.91 (d, J=2.8 Hz, 1H), 4.35-4.55 (m, 2H), 5.11 and 5.30 (d, J=3.6 Hz, 1H), 5.40 and 5.49 (d, J=6.8 Hz, 1H), 6.79-6.94 (m, 2H), 7.38-7.54 (m, 6H), 7.65 (d, J=8.0 Hz, 2H), 7.69 (d, J=8.0 Hz, 2H).

Synthesis of (Z)-(S)-4-[(1R,2R)-2-hydroxy-1-(3,4,5-trifluorophenyl)propyl]-2-[1-[3-methoxy-4-(4-methyl-1H-imidazol-1-yl)phenyl]methylidene]-6-methylmorpholin-3-one A solution of (S)-4-[(1R,2R)-2-tert-butyldiphenylsilanyloxy-1-(3,4,5-trifluorophenyl)propyl]-2-hydroxy-6-methylmorpholin-3-one (92 mg) and triphenylphosphine hydrobromide (68 mg) in acetonitrile (4 ml) was heated under reflux in a nitrogen atmosphere for one hour. The solvent was evaporated under reduced pressure, and the resulting residue was dissolved in ethanol (4 ml). To this reaction solution, 3-methoxy-4-(4-methyl-1H-imidazol-1-yl)benzaldehyde obtained in Example 1 (40 mg) and TEA (0.12 ml) were added, and the reaction solution was stirred in a nitrogen atmosphere at room temperature overnight. The solvent was evaporated under reduced pressure. The resulting residue was dissolved in trifluoroacetic acid (1 ml), and the reaction solution was stirred at room temperature for two hours. The reaction solution is poured into a saturated sodium bicarbonate solution, followed by extraction with ethyl acetate. The organic layer was washed with a saturated sodium bicarbonate solution and brine, and then the solvent was evaporated under reduced pressure. The resulting residue was purified by column chromatography using NH silica gel (heptane:ethyl acetate=1:1 to 0:1) to obtain 61.9 mg of the title compound.

$^1$H-NMR (CDCl$_3$)δ(ppm):
1.33 (d, J=6.0 Hz, 3H), 1.42 (d, J=6.0 Hz, 3H), 2.34 (s, 3H), 3.20 (dd, J=9.6, 12.8 Hz, 1H), 3.61 (dd, J=2.4, 12.8 Hz, 1H), 3.85 (s, 3H), 4.42-4.52 (m, 2H), 5.35 (d, J=6.8 Hz, 1H), 6.85 (s, 1H), 6.95 (s, 1H), 7.06-7.15 (m, 2H), 7.22 (d, J=8.0 Hz, 1H), 7.33 (dd, J=1.6, 8.0 Hz, 1H), 7.53 (d, J=1.6 Hz, 1H), 7.86 (s, 1H).
ESI-MS; m/z 502 [M$^+$+H].

EXAMPLE 27

Synthesis of (Z)-4-[(1R,2R)-2-hydroxy-1-(3,4,5-trifluorophenyl)propyl]-2-[1-[3-methoxy-4-(4-methyl-1H-imidazol-1-yl)phenyl]methylidene]-6,6-dimethylmorpholin-3-one

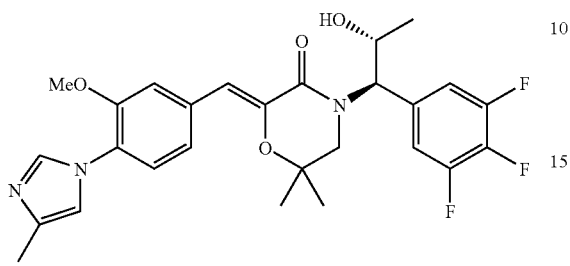

3.15 mg of the title compound was obtained from (1R,2R)-2-tert-butyldiphenylsilanyloxy-1-(3,4,5-trifluorophenyl)propylamine obtained in Example 26 (280 mg) and isobutylene oxide (63 μl) as starting materials in the same manner as in Example 26.

$^1$H-NMR (CDCl$_3$)δ(ppm):

1.28 (s, 3H), 1.34 (d, J=6.0 Hz, 3H), 1.47 (s, 3H), 2.31 (s, 3H)3.19 (d, J=12.8 Hz, 1H), 3.61 (d, J=12.8 Hz, 1H), 3.85 (s, 3H), 4, 46 (dq, J=6.8, 6.0 Hz, 1H), 5.40 (d, J=6.8 Hz, 1H), 6.91 (s, 1H), 6.93 (s, 1H), 7.09-7.17 (m, 2H), 7.21 (d, J=8.4 Hz, 1H), 7.32 (dd, J=1.6, 8.4 Hz, 1H), 7.53 (d, J=1.6 Hz, 1H), 7.77 (s, 1H).

ESI-MS; m/z 516[M$^+$+H].

EXAMPLE 28

Synthesis of (Z)-4-[(R)-1-(4-fluorophenyl)-2-hydroxyethyl]-2-[1-[3-methoxy-4-(4-methyl-1H-imidazol-1-yl)phenyl]methylidene]-6,6-dimethylmorpholin-3-one

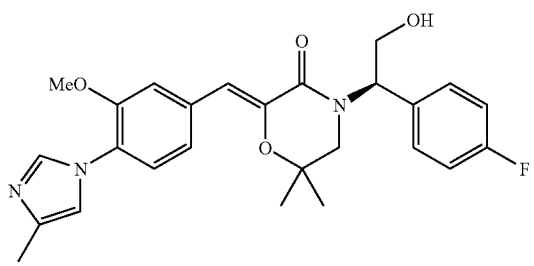

3.48 mg of the title compound was obtained from (R)-2-tert-butyldiphenylsilanyloxy-1-(4-fluorophenyl)ethylamine (300 mg) and isobutylene oxide (101 μL) as starting materials in the same manner as in Example 26.

$^1$H-NMR (CDCl$_3$)δ(ppm):

1.25 (s, 3H), 1.43 (s, 3H), 2.34 (s, 3H), 3.06 (d, J=12.8 Hz, 1H), 3.39 (d, J=12.8 Hz, 1H), 3.84 (s, 3H), 4.12-4.23 (m, 2H), 5.87 (dd, J=6.0, 2.4 Hz, 1H), 6.88 (s, 1H), 6.94 (s, 1H), 7.04-7.09 (m, 2H), 7.19 (dd, J=8.4, 4.8 Hz, 1H), 7.29-7.34 (m, 3H), 7.52 (d, J=4.8 Hz, 1H), 7.92 (s, 1H).

ESI-MS; m/z 466[M$^+$+H].

EXAMPLE 29

Synthesis of (Z)-(6R)-4-[(1R,2R)-2-hydroxy-1-(3,4,5-trifluorophenyl)propyl]-2-[1-[3-methoxy-4-(4-methyl-1H-imidazol-1-yl)phenyl]methylidene]-6-methylmorpholin-3-one

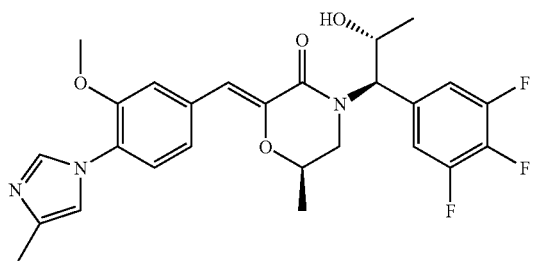

144 mg of the title compound was obtained from (1R,2R)-2-tert-butyldiphenylsilanyloxy-1-(3,4,5-trifluorophenyl)propylamine obtained in Example 26 (500 mg) and (R)-(+)-propylene oxide (0.12 ml) as starting materials in the same manner as in Example 26.

$^1$H-NMR (CDCl$_3$)δ(ppm):

1.33 (d, J=6.4 Hz, 3H), 1.42 (d, J=6.4 Hz, 3H), 2.30 (s, 3H), 3.25 (dd, J=12.8, 2.4 Hz, 1H), 3.62 (dd, J=12.8, 10.0 Hz, 1H), 3.84 (s, 3H), 4.19 (ddd, J=10.0, 6.4, 2.4 Hz, 1H), 4.50 (td, J=6.4, .0 Hz, 1H), 5.41 (d, J=6.0 Hz, 1H), 6.86 (s, 1H), 6.93 (s, 1H), 7.05-7.16 (m, 2H), 7.20 (d, J=8.0 Hz, 1H), 7.32 (dd, J=8.0, 1.6 Hz, 1H), 7.51 (d, J=1.6 Hz, 1H), 7.74 (s, 1H).

EXAMPLE 30

Synthesis of (Z)-4-[(1R,2R)-2-hydroxy-1-(3,4,5-trifluorophenyl)propyl]-2-[1-[3-methoxy-4-(4-methyl-1H-imidazol-1-yl)phenyl]methylidene]morpholin-3-one

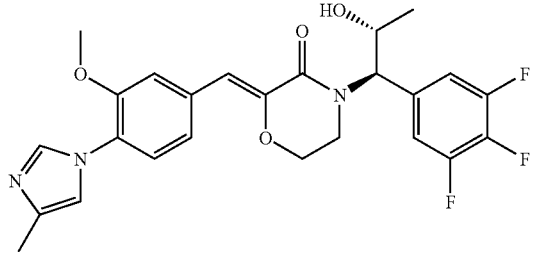

Synthesis of ethyl [(1R,2R)-2-tert-butyldiphenylsilanyloxy-1-(3,4,5-trifluorophenyl)propylamino]acetate Cesium carbonate (242 mg) and ethyl bromoacetate (103 μl) are added to a solution of (1R,2R)-2-tert-butyldiphenylsilanyloxy-1-(3,4,5-trifluorophenyl)propylamine obtained in Example 26 (274 mg) in DMF (5 ml), and the reaction solution was stirred at room temperature for 11 hours. Ice water and ethyl acetate were added to the reaction solution, and the organic layer was separated. The organic layer was sequentially washed with half-saturated brine and brine and dried over anhydrous magnesium sulfate, and then the solvent was evaporated under reduced pressure. The resulting residue was purified by silica gel column chromatography (hexane:diethyl ether=19:1) to obtain 190 mg of the title compound.

$^1$H-NMR (CDCl$_3$)δ(ppm):

0.75 (d, J=6.4 Hz, 3H), 1.09 (s, 9H), 1.26 (t, J=7.2 Hz, 3H), 3.03 (d, J=16.8 Hz, 1H), 3.24 (d, J=16.8 Hz, 1H), 3.57 (d, J=6.8 Hz, 1H), 3.80-3.92 (m, 1H), 4.19 (q, J=7.2 Hz, 2H), 6.88-6.98 (m, 2H), 7.36-7.48 (m, 6H), 7.67-7.77 (m, 4H).

Synthesis of 2-[(1R,2R)-2-tert-butyldiphenylsilanyloxy-1-(3,4,5-trifluorophenyl)propylamino]ethanol Lithium borohydride (20 mg) was added to a solution of ethyl [(1R,2R)-2-tert-butyldiphenylsilanyloxy-1-(3,4,5-trifluorophenyl)propylamino]acetate (158 mg) in THF (3 ml) in a nitrogen atmosphere, and the reaction solution was stirred at room temperature for one day. A saturated sodium sulfate solution was added to the reaction solution, and then the precipitated insoluble matter was removed by filtration through celite. Methanol was added to the filtrate, and then the solvent was evaporated under reduced pressure. The resulting residue was purified by silica gel column chromatography (heptane:ethyl acetate=4:1) to obtain 103 mg of the title compound.

ESI-MS; M/Z 488[MH$^+$]

Synthesis of 4-[(1R,2R)-2-tert-butyldiphenylsilanyloxy-1-(3,4,5-trifluorophenyl)propyl]morpholine-2,3-dione A solution of 2-[(1R,2R)-2-tert-butyldiphenylsilanyloxy-1-(3,4,5-trifluorophenyl)propylamino]ethanol (102 mg) in diethyl oxalate (2 ml) was stirred at 170° C. for one hour and 30 minutes. Diethyl oxalate was evaporated under reduced pressure, and the resulting residue was purified by silica gel column chromatography (heptane:ethyl acetate 9:1 to 6:1) to obtain 48 mg of the title compound.

$^1$H-NMR (CDCl$_3$)δ(ppm):

0.99 (s, 9H), 1.18 (d, J=6.0 Hz, 3H), 3.47 (ddd, J=14.0, 5.6, 3.2 Hz, 1H), 3.83 (ddd, J=14.0, 8.0, .6 Hz, 1H), 4.27-4.43 (m, 3H), 5.54 (d, J=5.2 Hz, 1H), 6.80-6.90 (m, 2H), 7.36-7.54 (m, 6H), 7.62 (d, J=8.0 Hz, 2H), 7.67 (d, J=8.0 Hz, 2H).

Synthesis of (Z)-4-[(1R,2R)-2-hydroxy-1-(3,4,5-trifluorophenyl)propyl]-2-[1-[3-methoxy-4-(4-methyl-1H-imidazol-1-yl)phenyl]methylidene]morpholin-3-one 18 mg of the title compound was obtained from 4-[(1R, 2R)-2-tert-butyldiphenylsilanyloxy-1-(3,4,5-trifluorophenyl)propyl]morpholine-2,3-dione (47 mg) in the same manner as in Example 26.

$^1$H-NMR (CDCl$_3$)δ(ppm):

1.33 (d, J=6.0 Hz, 3H), 2.40 (s, 3H), 3.41 (ddd, J=13.2, 6.4, 3.2 Hz, 1H), 3.81 (ddd, J=13.2, 7.2, 3.2 Hz, 1H), 3.87 (s, 3H), 4.17 (ddd, J=11.2, 7.2, 3.2 Hz, 1H), 4.30 (ddd, J=11.2, 6.4, 3.2 Hz, 1H), 4.51 (dt, J=6.4, 6.0 Hz, 1H), 5.42 (d, J=6.4 Hz, 1H), 6.88 (s, 1H), 6.98 (s, 1H), 7.08-7.17 (m, 2H), 7.23 (d, J=8.0 Hz, 1H), 7.40 (dd, J=8.0, 1.6 Hz, 1H), 7.43 (d, J=1.6 Hz, 1H), 8.04 (s, 1H).

EXAMPLE 31

Synthesis of (Z)-4-[(1R,2R)-1-(3,4-difluorophenyl)-2-hydroxypropyl]-2-[1-[3-methoxy-4-(4-methyl-1H-imidazol-1-yl)phenyl]methylidene]morpholin-3-one

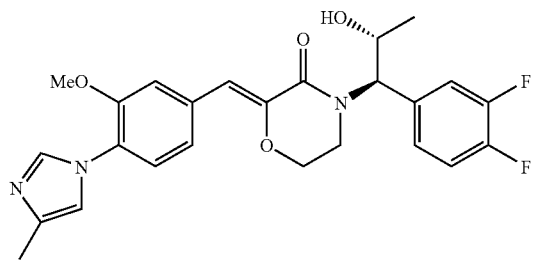

Synthesis of (1R,2R)-2-tert-butyldiphenylsilanyloxy-1-(3,4-difluorophenyl)propylamine 5.37 g of the title compound was obtained from 1-bromo-3,4-difluorobenzene (19 g) in the same manner as in Example 26. The property values of the compound are as follows.

$^1$H-NMR (CDCl$_3$)δ(ppm):

0.86 (d, J=6.4 Hz, 3H), 1.03 (s, 9H), 3.82 (d, J=6.0 Hz 1H), 3.89 (dq, J=6.4, 6.0 Hz, 1H), 6.95-7.13 (m, 3H), 7.32-7.44 (m, 6H), 7.59 (dd, J=7.2, 2.8 Hz, 2H), 7.65 (dd, J=7.2, 2.8 Hz, 2H).

Synthesis of (Z)-4-[(1R,2R)-1-(3,4-difluorophenyl)-2-hydroxypropyl]-2-[1-[3-methoxy-4-(4-methyl-1H-imidazol-1-yl)phenyl]methylidene]morpholin-3-one 7.3 mg of the title compound was obtained from (1R,2R)-2-tert-butyldiphenylsilanyloxy-1-(3,4-difluorophenyl)propylamine (825 mg) in the same manner as in Example 26. The property values of the compound are as follows.

$^1$H-NMR (CDCl$_3$)δ(ppm):

1.33 (d, J=6.4 Hz, 3H), 2.29 (s, 3H), 3.38 (m, 1H), 3.76 (m, 1H), 3.84 (s, 3H), 4.13 (m, 1H), 4.27 (m, 1H), 4.51 (dq, J=7.6, 6.4 Hz, 1H), 5.44 (d, J=7.6 Hz, 1H), 6.87 (s, 1H), 6.92 (s, 1H), 7.14-7.20 (m, 3H), 7.27-7.39 (m, 3H), 7.70 (s, 1H).

EXAMPLE 32

Synthesis of (Z)-(S)-4-[(1R,2R)-1-(4-fluorophenyl)-2-hydroxypropyl]-2-[1-[3-methoxy-4-(4-methyl-1H-imidazol-1-yl)phenyl]methylidene]-6-methylmorpholin-3-one

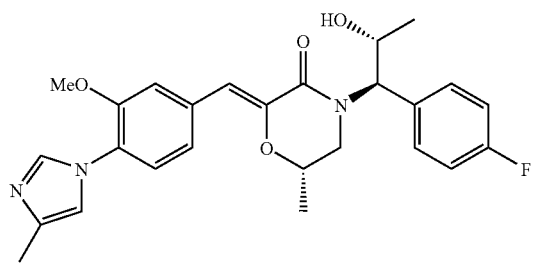

Synthesis of (1R,2R)-2-tert-butyldiphenylsilanyloxy-1-(4-fluorophenyl)propylamine 113 mg of the title compound was obtained from 1-bromo-4-fluorobenzene in the same manner as in Example 26. The property values of the compound are as follows.

$^1$H-NMR (CDCl$_3$)δ(ppm):

0.83 (d, J=6.4 Hz, 3H), 1.03 (s, 9H), 3.85 (d, J=6.0 Hz, 1H), 3.92 (dq, J=6.4, 6.0 Hz, 1H), 6.92-6.97 (m, 2H), 7.21-7.25 (m, 2H), 7.31-7.43 (m, 6H), 7.59 (dd, J=7.2, 2.8 Hz, 2H), 7.66 (dd, J=7.2, 2.8 Hz, 2H).

Synthesis of (Z)-(S)-4-[(1R,2R)-1-(4-fluorophenyl)-2-hydroxypropyl]-2-[1-[3-methoxy-4-(4-methyl-1H-imidazol-1-yl)phenyl]methylidene]-6-methylmorpholin-3-one The title compound was obtained from (1R,2R)-2-tert-butyldiphenylsilanyloxy-1-(4-fluorophenyl)propylamine in the same manner as in Example 26. The property values of the compound are as follows.

$^1$H-NMR (CDCl$_3$)δ(ppm):

1.30 (d, J=6.0 Hz, 3H), 1.38 (d, J=6.4 Hz, 3H), 2.29 (s, 3H), 3.12 (dd, J=12.8, 10.0 Hz, 1H), 3.51 (dd, J=12.8, 2.8 Hz, 1H), 3.83 (s, 3H), 4.39-4.50 (m, 2H), 5.41 (d, J=7.6 Hz, 1H), 6.84 (s, 1H), 6.92 (s, 1H), 7.04-7.08 (m, 2H), 7.19 (d, J=8.0 Hz, 1H), 7.30-7.38 (m, 3H), 7.50 (s, 1H), 7.70 (s, 1H).

EXAMPLE 33

Synthesis of (Z)-4-[(1R,2R)-1-(4-fluorophenyl)-2-hydroxypropyl]-2-[1-[3-methoxy-4-(4-methyl-1H-imidazol-1-yl)phenyl]methylidene]-6,6-dimethylmorpholin-3-one

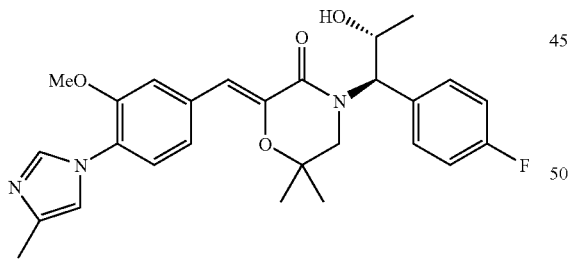

259 mg of the title compound was obtained from (1R,2R)-2-tert-butyldiphenylsilanyloxy-1-(4-fluorophenyl)propylamine in the same manner as in Example 27. The property values of the compound are as follows.

$^1$H-NMR (CDCl$_3$)δ(ppm):

1.20 (s, 3H), 1.31 (d, J=6.0 Hz, 3H), 1.43 (s, 3H), 2.29 (s, 3H), 3.15 (d, J=12.8 Hz, 1H), 3.52 (d, J=12.8 Hz, 1H), 3.83 (s, 3H), 4.45 (dq, J=8.8, 6.0 Hz, 1H), 5.47 (d, J=8.8 Hz, 1H), 6.89 (s, 1H), 6.91 (s, 1H), 7.03-7.08 (m, 2H), 7.18 (d, J=8.0 Hz, 1H), 7.30 (dd, J=8.0, 1.6 Hz, 1H), 7.36-7.40 (m, 2H), 7.52 (d, J=1.6 Hz, 1H), 7.70 (s, 1H).

EXAMPLE 34

Synthesis of (Z)-(S)-4-[(1R,2R)-1-(3,4-difluorophenyl)-2-hydroxypropyl]-2-[1-[3-methoxy-4-(4-methyl-1H-imidazol-1-yl)phenyl]methylidene]-6-methylmorpholin-3-one

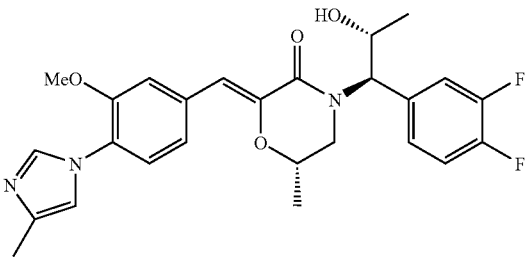

198 mg of the title compound was obtained from (1R,2R)-2-tert-butyldiphenylsilanyloxy-1-(3,4-difluorophenyl)propylamine in the same manner as in Example 26. The property values of the compound are as follows.

$^1$H-NMR (CDCl$_3$)δ(ppm):

1.32 (d, J=6.4 Hz, 3H), 1.40 (d, J=6.0 Hz, 3H), 2.29 (s, 3H), 3.16 (dd, J=12.8, 10.0 Hz, 1H), 3.56 (dd, J=12.8, 2.8 Hz, 1H), 3.83 (s, 3H), 4.41-4.48 (m, 2H), 5.38 (d, J=7.6 Hz, 1H), 6.84 (s, 1H), 6.92 (s, 1H), 7.11-7.20 (m, 3H), 7.26-7.32 (m, 2H), 7.50 (s, 1H), 7.70 (s, 1H).

EXAMPLE 35

Synthesis of (Z)-4-[(1R,2R)-1-(3,4-difluorophenyl)-2-hydroxypropyl]-2-[1-[3-methoxy-4-(methylimidazol-1-yl)phenyl]methylidene]-6,6-dimethylmorpholin-3-one

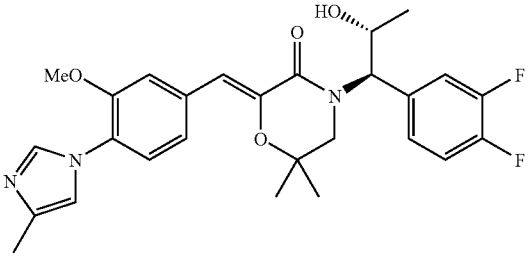

172 mg of the title compound was obtained from (1R,2R)-2-tert-butyldiphenylsilanyloxy-1-(3,4-difluorophenyl)propylamine in the same manner as in Example 27. The property values of the compound are as follows.

$^1$H-NMR (CDCl$_3$)δ(ppm):

1.24 (s, 3H), 1.33 (d, J=6.4 Hz, 3H), 1.45 (s, 3H), 2.29 (s, 3H), 3.17 (d, J=12.8 Hz, 1H), 3.56 (d, J=12.8 Hz, 1H), 3.84 (s, 3H), 4.45 (dq, J=7.6, 6.4 Hz, 1H), 5.42 (d, J=7.6 Hz, 1H), 6.89 (s, 1H), 6.91 (s, 1H), 7.14-7.20 (m, 3H), 7.27-7.32 (m, 2H), 7.52 (s, 1H), 7.70 (s, 1H).

EXAMPLE 36

Synthesis of (Z)-(S)-4-[(S)-2-hydroxy-1-methyl-1-(3,4,5-trifluorophenyl)ethyl]-2-[1-[3-methoxy-4-(4-methyl-1H-imidazol-1-yl)phenyl]methylidene]-6-methylmorpholin-3-one

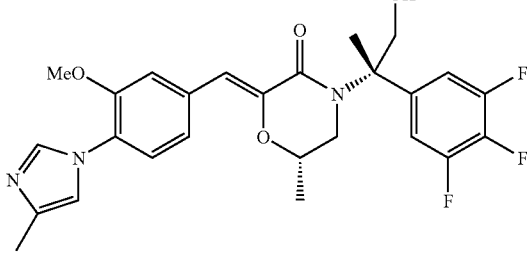

2.2 mg of the title compound was obtained from (S)-4-[(S)-2-tert-butyldiphenylsilanyloxy-1-methyl-1-(3,4,5-trifluorophenyl)ethyl]morpholine-2,3-dione in the same manner as in Example 26, using (R)-2-tert-butyldiphenylsilanyloxy-1-methyl-1-(3,4,5-trifluorophenyl)ethylamine prepared according to a document (J. Org. Chem. 2001, 66, p. 8778, for example) as a starting material. The property values of the compound are as follows.

$^1$H-NMR (CDCl$_3$)$\delta$(ppm):
1.43 (d, J=6.4 Hz, 3H), 1.70 (s, 3H), 2.32 (s, 3H), 3.14 (m, 1H), 3.20 (m, 1H), 3.72 (d, J=12.8 Hz, 1H), 3.86 (s, 3H), 4.14 (d, J=12.8 Hz, 1H), 4.33 (m, 1H), 6.79 (s, 1H), 6.95 (s, 1H), 6.95-7.01 (m, 2H), 7.22 (d, J=8.0 Hz, 1H), 7.34 (d, J=8.0 Hz, 1H), 7.50 (s, 1H), 7.85 (s, 1H).

EXAMPLE 37

Synthesis of (Z)-(6S)-2-[1-[3-methoxy-4-(4-methyl-1H-imidazol-1-yl)phenyl]methylidene]-6-methyl-4-[(S)-1-(3,4,5-trifluorophenyl)ethyl]morpholin-3-one

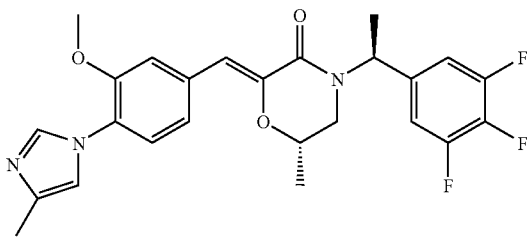

Synthesis of (R)-1-(3,4,5-trifluorophenyl)ethanol

To a solution of (+)-DIP-chloride (11.8 g) in THF (200 ml) cooled to −30° C., 3,4,5-trifluoroacetophenone (5.0 g) [CAS 220141-73-1] was added dropwise in a nitrogen atmosphere. The reaction solution was stirred at the same temperature for five hours and at room temperature at one hour, and then THF was evaporated under reduced pressure. 6.5 ml of diethanolamine was added dropwise to a solution of the resulting residue in diethyl ether (150 ml), and the reaction solution was stirred at room temperature overnight. The insoluble matter was removed by filtration, and then the solvent was evaporated. Hexane was added to the resulting residue, and the insoluble matter was removed by filtration again. The filtrate was purified by silica gel column chromatography (heptane:ethyl acetate=19:1 to 4:1) to obtain 3.69 g of the title compound.

$^1$H-NMR (CDCl$_3$)$\delta$(ppm):
1.46 (d, J=6.8 Hz, 3H), 4.85 (q, J=6.8, 1H), 6.98-7.05 (m, 2H).

Synthesis of 5-((S)-1-azidoethyl)-1,2,3-trifluorobenzene

To a solution of (R)-1-(3,4,5-trifluorophenyl)ethanol (3.6 g) and diphenylphosphoric azide (6.0 ml) in toluene (70 ml), 1,8-diazabicyclo[5,4,0]undec-7-ene (4.1 ml) was added dropwise under ice-cooling. The reaction solution was stirred at the same temperature for one hour and at room temperature overnight. Water was added to the reaction solution, and the organic layer was separated. Then, the aqueous layer was subjected to extraction with toluene again. The organic layers were combined and sequentially washed with 1 N hydrochloric acid, water, a saturated sodium bicarbonate solution, and brine. The organic layers were dried over anhydrous magnesium sulfate, and then the solvent was evaporated under reduced pressure. The resulting residue was purified by silica gel column chromatography (heptane:ethyl acetate=49:1) to obtain 858 mg of the title compound.

$^1$H-NMR (CDCl$_3$)$\delta$(ppm):
1.50 (d, J=6.8 Hz, 3H), 4.56 (q, J=6.8, 1H), 6.92-7.01 (m, 2H).

Synthesis of (S)-1-(3,4,5-trifluorophenyl)ethylamine

Triphenylphosphine (1.23 g) was added to a solution of 5-((S)-1-azidoethyl)-1,2,3-trifluorobenzene (858 mg) in THF (20 ml) in a nitrogen atmosphere, and the reaction solution was stirred at room temperature for five minutes. Thereafter, water (2.5 ml) was added to the reaction solution, which was then stirred at 60° C. for 2.5 hours. The reaction solution was returned to room temperature, followed by extraction with 2 N hydrochloric acid (twice). The hydrochloric acid extraction layer was washed with ethyl acetate and then made basic with a 5 N sodium hydroxide solution, followed by extraction with methylene chloride (twice). The methylene chloride layer was dried over anhydrous magnesium sulfate, and the solvent was evaporated under reduced pressure to obtain 348 mg of the title compound. Further, the following operation was performed in order to collect the title compound remaining in the ethyl acetate dilution of the reaction solution. Diethyl ether was added to the dilution, followed by extraction with water. The water extraction layer was washed with diethyl ether and then made basic with a 5 N sodium hydroxide solution, followed by extraction with methylene chloride (twice). The methylene chloride layer was dried over anhydrous magnesium sulfate, and the solvent was evaporated under reduced pressure to obtain 413 mg of the title compound.

$^1$H-NMR (CDCl$_3$)$\delta$(ppm):
1.33 (d, J=6.4 Hz, 3H), 4.08 (q, J=6.4, 1H), 6.95-7.04 (m, 2H).

Synthesis of (Z)-(6S)-2-[1-[3-methoxy-4-(4-methyl-1H-imidazol-1-yl)phenyl]methylidene]-6-methyl-4-[(S)-1-(3,4,5-trifluorophenyl)ethyl]morpholin-3-one 882 mg of the title compound was obtained from (S)-1-(3,4,5-trifluorophenyl)ethylamine (1.15 g) and (S)-(−)-propylene oxide (0.46 ml) as starting materials in the same manner as in Examples 18 and 19.

¹H-NMR (CDCl₃)δ(ppm):
1.40 (d, J=6.4 Hz, 3H), 1.54 (d, J=7.2 Hz, 3H), 2.29 (s, 3H), 2.96 (dd, J=12.8, 5.6 Hz, 1H), 3.20 (dd, J=12.8, 3.2 Hz, 1H), 3.85 (s, 3H), 4.30-4.40 (m, 1H), 6.04 (q, J=7.2 Hz, 1H), 6.88 (s, 1H), 6.92 (d, J=1.2 Hz, 1H), 6.92-7.00 (m, 2H), 7.20 (d, J=8.0 Hz, 1H), 7.33 (dd, J=8.0, 1.6 Hz, 1H), 7.50 (d, J=1.6 Hz, 1H), 7.86 (d, J=1.2 Hz, 1H).

EXAMPLE 38

Synthesis of (Z)-(6S)-4-[1-(4-fluorophenyl)-1-methylethyl]-2-[1-[3-methoxy-4-(4-methyl-1H-imidazol-1-yl)phenyl]methylidene]-6-methylmorpholin-3-one

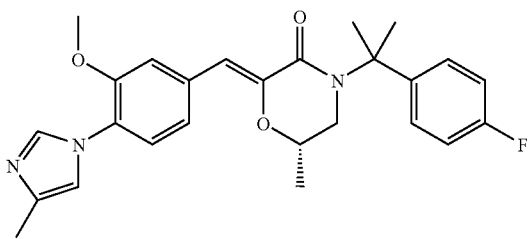

97.8 mg of the title compound was obtained from 1-(4-fluorophenyl)-1-methylethylamine (500 mg) [CAS #17797-10-3] and (S)-(−)-propylene oxide (0.23 ml) as starting materials in the same manner as in Example 26.

¹H-NMR (CDCl₃)δ(ppm):
1.50 (d, J=6.0 Hz, 3H), 1.76 (s, 3H), 1.77 (s, 3H), 2.28 (s, 3H), 3.49 (dd, J=13.2, 9.6 Hz, 1H), 3.56 (dd, J=13.2, 2.8 Hz, 1H), 3.82 (s, 3H), 4.38 (dtd, J=9.6, 6.0, 2.8 Hz, 1H), 6.66 (s, 1H), 6.91 (s, 1H), 7.00 (dd, J=8.8, 8.8 Hz, 2H), 7.16 (d, J=8.0 Hz, 1H), 7.24-7.33 (m, 3H), 7.45 (d, J=1.2 Hz, 1H), 7.68 (d, J=1.6 Hz, 1H).

EXAMPLE 39

Synthesis of (Z)-(6S)-4-[1-(4-fluorophenyl)cyclopropyl]-2-[1-[3-methoxy-4-(4-methyl-1H-imidazol-1-yl)phenyl]methylidene]-6-methylmorpholin-3-one

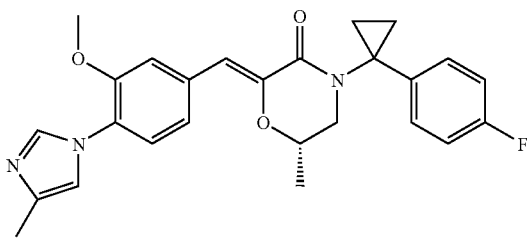

213 mg of the title compound was obtained from 1-(4-fluorophenyl)cyclopropylamine (726 mg) [CAS #474709-83-6] and (S)-(−)-propylene oxide (0.4 ml) as starting materials in the same manner as in Example 26.

¹H-NMR (CDCl₃)δ(ppm):
1.30-1.42 (m, 4H), 1.44 (d, J=6.0 Hz, 3H), 2.29 (s, 3H), 3.47 (dd, J=12.8, 3.2 Hz, 1H), 3.53 (dd, J=12.8, 9.6 Hz, 1H), 3.84 (s, 3H), 4.33 (dtd, J=9.6, 6.0, 3.2 Hz, 1H), 6.82 (s, 1H), 6.92 (d, J=1.2 Hz, 1H), 6.99 (dd, J=8.8, 8.8 Hz, 2H), 7.18 (d, J=8.0 Hz, 1H), 7.30 (dd, J=8.0, 2.0 Hz, 1H), 7.35 (dd, J=8.8, 5.2 Hz, 2H), 7.49 (d, J=2.0 Hz, 1H), 7.68 (d, J=1.2 Hz, 1H).

EXAMPLE 40

Synthesis of (Z)-(6S,9aR)-3-{1-[3-methoxy-4-(4-methyl-1H-imidazol-1-yl)benzylidene]-6-(3,4,5-trifluorophenyl)hexahydropyrido[2,1-c][1,4]oxazin-4-one

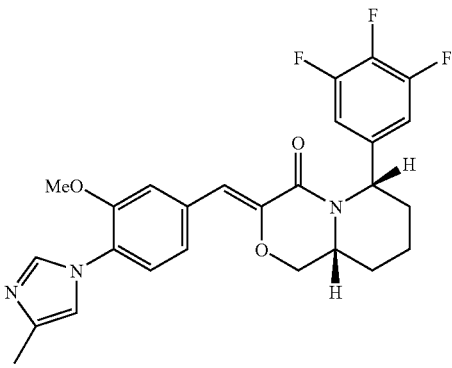

Synthesis of methyl(R)-2-tert-butoxycarbonylamino-6-oxo-6-(3,4,5-trifluorophenyl)hexanoate To a solution of (R)-6-oxopiperidine-1,2-dicarboxylic acid 1-tert-butyl ester 2-methyl ester (CAS No. 183890-36-0, 7.5 g) in THF (200 mL), 3,4,5-trifluorophenylmagnesium bromide (0.35 M solution in diethyl ether, 100 mL) was added dropwise at −40° C., and the reaction solution was stirred at room temperature for six hours. A saturated ammonium chloride solution and ethyl acetate were added to the reaction solution, and the organic layer was separated. The resulting organic layer was dried over magnesium sulfate and then concentrated under reduced pressure. The residue was purified by silica gel column chromatography (elution solvent: heptane->heptane:ethyl acetate=1:1) to obtain 4.0 g of the title compound. The property value of the compound is as follows.

ESI-MS; m/z 412[M⁺+Na].

Synthesis of methyl(2R,6S)-6-(3,4,5-trifluorophenyl)piperidine-2-carboxylate

A solution of 4 N hydrochloric acid in ethyl acetate (20 mL) was added to a solution of methyl(R)-2-tert-butoxycarbonylamino-6-oxo-6-(3,4,5-trifluorophenyl)hexanoate (4.0 g) in ethyl acetate (20 mL), and the reaction solution was stirred at room temperature for 14 hours. The reaction solution was concentrated under reduced pressure. Then, ethyl acetate and saturated sodium bicarbonate water were added to the residue, and the organic layer was separated. The resulting organic layer was dried over magnesium sulfate and then concentrated under reduced pressure. 10% palladium-carbon (100 mg) was added to a solution of the resulting residue in ethyl acetate (50 mL), and the reaction solution was stirred in a hydrogen stream at room temperature for six hours. The reaction solution was filtered through celite, and the filtrate was concentrated under reduced pressure to obtain 2.7 g of the title compound. The property value of the compound is as follows.

ESI-MS; m/z 274[M⁺+H].

Synthesis of [(2R,6S)-6-(3,4,5-trifluorophenyl)piperidin-2-yl]methanol

LAH (75 mg) was added in three portions to a solution of methyl(2R,6S)-6-(3,4,5-trifluorophenyl)piperidine-2-carboxylate (270 mg) in THF (5 mL) at −20° C. over 15 minutes. The reaction solution was stirred at −20° C. for one hour, and water (0.1 mL), a 5 N sodium hydroxide solution (0.1 mL), and water (0.3 mL) were sequentially added to the reaction solution. The mixture was heated to room temperature and filtered through celite. The filtrate was concentrated under reduced pressure to obtain 242 mg of the title compound. The property value of the compound is as follows.

ESI-MS; m/z 246[M$^+$+H].

Synthesis of (4R,6S)-6-(3,4,5-trifluorophenyl)hexahydropyrido[2,1-c][1,4]oxazine-3,4-dione A mixture of [(2R,6S)-6-(3,4,5-trifluorophenyl)piperidin-2-yl]methanol (242 mg) with diethyl oxalate (1.3 mL) was heated and stirred at 120° C. for one hour. The reaction solution was left to cool to room temperature, and the precipitated solid was collected by filtration. The resulting solid was washed with an ether and air-dried to obtain 228 mg of the title compound. The property values of the compound are as follows.

$^1$H-NMR (CDCl$_3$)δ(ppm):
1.36-1.48 (m, 1H), 1.58-1.67 (m, 1H), 1.70-1.87 (m, 2H), 2.10-2.24 (m, 2H), 4.09-4.18 (m, 1H), 4.37 (t, J=11.6 Hz, 1H), 4.43 (dd, J=11.6, 3.6 Hz, 1H), 5.19 (t, J=4.0 Hz, 1H), 6.82-6.90 (m, 2H).

Synthesis of (4R,6S)-3-hydroxy-6-(3,4,5-trifluorophenyl)hydroxyhexahydropyrido[2,1-c][1,4]oxazin-4-one A 1 M solution of lithium tri-sec-butylborohydride in THF (0.79 mL) was added dropwise to a solution of (4R,6S)-6-(3,4,5-trifluorophenyl)hexahydropyrido[2,1-c][1,4]oxazine-3,4-dione (228 mg) in THF (10 mL) at −15° C., and the reaction solution was stirred at −15° C. for three hours. A 5 N sodium hydroxide solution (0.25 mL) and 20% aqueous hydrogen peroxide (0.05 mL) were sequentially added to the reaction solution at −15° C. The reaction solution was left to cool to room temperature and stirred for one hour. Ethyl acetate and a sodium sulfite solution were added to the reaction solution, and the organic layer was separated. The resulting organic layer was washed with brine, dried over magnesium sulfate, and then concentrated under reduced pressure. The residue was purified by silica gel column chromatography (elution solvent: heptane:ethyl acetate=1:1->ethyl acetate) to obtain 240 mg of the title compound. The property value of the compound is as follows.

ESI-MS; m/z 302 [M$^+$+H].

Synthesis of (Z)-(6S,9aR)-3-{1-[3-methoxy-4-(4-methyl-1H-imidazol-1-yl)benzylidene]-6-(3,4,5-trifluorophenyl)hexahydropyrido[2,1-c][1,4]oxazin-4-one A solution of (4R,6S)-3-hydroxy-6-(3,4,5-trifluorophenyl)hydroxyhexahydropyrido[2,1-c][1,4]oxazin-4-one (240 mg) and triphenylphosphonium bromide (328 mg) in acetonitrile (10 mL) was heated under reflux for one hour and then left to cool to room temperature. To the reaction solution, 3-methoxy-4-(4-methyl-1H-imidazol-1-yl)benzaldehyde (172 mg) and triethylamine (0.33 mL) were added, and the reaction solution was stirred at room temperature for 13 hours. Ethyl acetate and saturated sodium bicarbonate water were added to the reaction solution, and the organic layer was separated. The resulting organic layer was washed with brine, dried over magnesium sulfate, and then concentrated under reduced pressure. The residue was purified by silica gel column chromatography (carrier: Chromatorex NH; elution solvent: heptane:ethyl acetate=1:1->ethyl acetate->ethyl acetate:methanol=9:1) to obtain 1,300 mg of the title compound. The property values of the compound are as follows.

$^1$H-NMR (CDCl$_3$)δ(ppm):
1.38-1.58 (m, 2H), 1.66-1.84 (m, 2H), 2.06-2.14 (m, 1H), 2.17-2.28 (m, 1H), 2.30 (s, 3H), 3.86 (s, 3H), 4.04 (t, J=10.0 Hz, 1H), 4.06-4.14 (m, 1H), 4.36 (brd, J=8.4 Hz, 1H), 5.26 (t, J=4.0 Hz, 1H), 6.83 (s, 1H), 6.86-6.93 (m, 2H), 6.94 (brs, 1H), 7.21 (d, J=8.0 Hz, 1H), 7.38 (dd, J=8.0, 1.6 Hz, 1H), 7.39 (d, J=1.6 Hz, 1H), 7.73 (brs, 1H).

EXAMPLE 41

Synthesis of (Z)-(6S,9aR)-6-(3,4-difluorophenyl)-3-{1-[3-methoxy-4-(4-methyl-1H-imidazol-1-yl)benzylidene]hexahydropyrido[2,1-c][1,4]oxazin-4-one

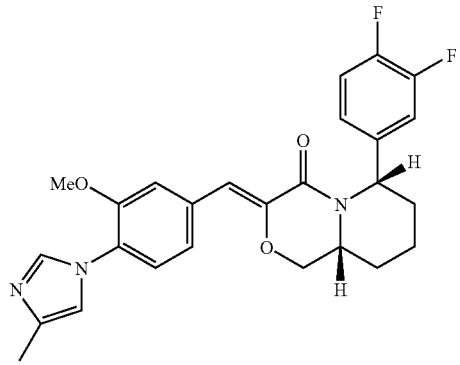

Synthesis of methyl(R)-2-tert-butoxycarbonylamino-6-(3,4-difluorophenyl)-6-oxohexanoate To a solution of (R)-6-oxopiperidine-1,2-dicarboxylic acid 1-tert-butyl ester 2-methyl ester (CAS No. 183890-36-0, 5.8 g) in THF (200 mL), 3,4-difluorophenylmagnesium bromide (0.5 M solution in THF, 50 mL) was added dropwise at −40° C., and the reaction solution was stirred at −40° C. for seven hours. A saturated ammonium chloride solution and ethyl acetate were added to the reaction solution, and the mixture was heated to room temperature. Thereafter, the organic layer was separated, and the resulting organic layer was dried over magnesium sulfate and then concentrated under reduced pressure. The residue was purified by silica gel column chromatography (elution solvent: heptane->heptane:ethyl acetate=1:1) to obtain 3.8 g of the title compound. The property value of the compound is as follows.

ESI-MS; m/z 394[M$^+$+Na].

Synthesis of methyl(2R,6S)-6-(3,4-difluorophenyl)piperidine-2-carboxylate

A solution of 4 N hydrochloric acid in ethyl acetate (20 mL) was added to a solution of methyl(R)-2-tert-butoxycarbonylamino-6-(3,4-difluorophenyl)-6-oxohexanoate (3.8 g) in ethyl acetate (20 mL), and the reaction solution was stirred at room temperature for 5.5 hours. The reaction solution was concentrated under reduced pressure. Then, ethyl acetate and saturated sodium bicarbonate water were added to the residue, and the organic layer was separated. The resulting organic layer was dried over magnesium sulfate and then concentrated under reduced pressure. 10% palladium-carbon (50 mg) was added to a solution of the resulting residue in methanol (20 mL), and the reaction solution was stirred in a hydrogen stream at room temperature for two hours. The reaction solution was filtered through celite, and the filtrate was concentrated under reduced pressure to obtain 2.1 g of the title compound. The property value of the compound is as follows.

ESI-MS; m/z 256[M$^+$+H].

Synthesis of [(2R,6S)-6-(3,4-difluorophenyl)piperidin-2-yl]methanol

LAH (90 mg) was added in three portions to a solution of methyl(2R,6S)-6-(3,4-difluorophenyl)piperidine-2-carboxylate (300 mg) in THF (5 mL) at −15° C. over 15 minutes. The reaction solution was stirred at −15° C. for one hour, and water (0.1 mL), a 5 N sodium hydroxide solution (0.1 mL), and water (0.3 mL) were sequentially added to the reaction solution. The mixture was heated to room temperature and filtered through celite. The filtrate was concentrated under reduced pressure to obtain 267 mg of the title compound. The property value of the compound is as follows.

ESI-MS; m/z 228 [M$^+$+H].

Synthesis of (4R,6S)-6-(3,4-difluorophenyl)hexahydropyrido[2,1-c][1,4]oxazine-3,4-dione A mixture of [(2R,6S)-6-(3,4-difluorophenyl)piperidin-2-yl]methanol (267 mg) with diethyl oxalate (1.6 mL) was heated and stirred at 120° C. for one hour. The reaction solution was left to cool to room temperature, and the precipitated solid was collected by filtration. The resulting solid was washed with an ether and air-dried to obtain 19.2 mg of the title compound. The property values of the compound are as follows.

$^1$H-NMR (CDCl$_3$)δ(ppm):
1.38-1.48 (m, 1H), 1.55-1.66 (m, 1H), 1.68-1.83 (m, 2H), 2.12-2.25 (m, 2H), 3.99-4.18 (m, 1H), 4.35 (t, J=11.6 Hz, 1H), 4.42 (dd, J=11.6, 3.2 Hz, 1H), 5.27 (t, J=4.0 Hz, 1H), 6.94-6.99 (m, 1H), 7.01-7.07 (m, 1H), 7.10-7.17 (m, 1H).

Synthesis of (4R,6S)-6-(3,4-difluorophenyl)-3-hydroxyhexahydropyrido[2,1-c][1,4]oxazin-4-one A 1 M solution of lithium tri-sec-butylborohydride in THF (0.71 mL) was added dropwise to a solution of (4R,6S)-6-(3,4-difluorophenyl)hexahydropyrido[2,1-c][1,4]oxazine-3,4-dione (192 mg) in THF (10 mL) at −15° C., and the reaction solution was stirred at −15° C. for three hours. A 5 N sodium hydroxide solution (0.25 mL) and 20% aqueous hydrogen peroxide (0.05 mL) were sequentially added to the reaction solution at −15° C. The reaction solution was left to cool to room temperature and stirred for one hour. Ethyl acetate and a sodium sulfite solution were added to the reaction solution, and the organic layer was separated. The resulting organic layer was washed with brine, dried over magnesium sulfate, and then concentrated under reduced pressure. The residue was purified by silica gel column chromatography (elution solvent: heptane:ethyl acetate=1:1->ethyl acetate) to obtain 151 mg of the title compound. The property value of the compound is as follows.

ESI-MS; m/z 284[M$^+$+H].

Synthesis of (Z)-(6S,9aR)-6-(3,4-difluorophenyl)-3-{1-[3-methoxy-4-(4-methyl-1H-imidazol-1-yl)benzylidene]hexahydropyrido[2,1-c][1,4]oxazin-4-one A solution of (4R,6S)-6-(3,4-difluorophenyl)-3-hydroxyhexahydropyrido[2,1-c][1,4]oxazin-4-one (151 mg) and triphenylphosphonium bromide (220 mg) in acetonitrile (7 mL) was heated under reflux for one hour and then left to cool to room temperature. To the reaction solution, 3-methoxy-4-(4-methyl-1H-imidazol-1-yl)benzaldehyde (115 mg) and triethylamine (0.22 mL) were added, and the reaction solution was stirred at room temperature for 12 hours. Ethyl acetate and saturated sodium bicarbonate water were added to the reaction solution, and the organic layer was separated. The resulting organic layer was washed with brine, dried over magnesium sulfate, and then concentrated under reduced pressure. The residue was purified by silica gel column chromatography (carrier: Chromatorex NH; elution solvent: heptane:ethyl acetate=1:1->ethyl acetate) to obtain 150 mg of the title compound. The property values of the compound are as follows.

ESI-MS; m/z 466[M$^+$+H].
$^1$H-NMR (CDCl$_3$)δ(ppm):
1.38-1.58 (m, 2H), 1.66-1.80 (m, 2H), 2.10-2.28 (m, 2H), 2.30 (s, 3H), 3.85 (s, 3H), 4.03 (t, J=10.4 Hz, 1H), 4.05-4.16 (m, 1H), 4.35 (dd, J=10.4, 2.0 Hz, 1H), 5.33 (t, J=4.0 Hz, 1H), 6.82 (s, 1H), 6.92 (brs, 1H), 6.98-7.02 (m, 1H), 7.04-7.16 (m, 2H), 7.20 (d, J=8.0 Hz, 1H), 7.35 (d, J=2.0 Hz, 1H), 7.36 (dd, J=8.0, 2.0 Hz, 1H), 7.71 (d, J=1.2 Hz, 1H).

EXAMPLE 42

Synthesis of (Z)-(6S,9aR)-6-(2,6-difluoropyridin-3-yl)-3-{1-[3-methoxy-4-(4-methyl-1H-imidazol-1-yl)benzylidene]hexahydropyrido[2,1-c][1,4]oxazin-4-one

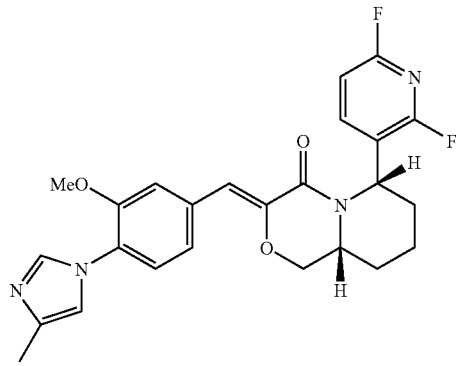

Synthesis of methyl(R)-2-tert-butoxycarbonylamino-6-(2,6-difluoropyridin-3-yl)-6-oxohexanoate LDA (1.5 M solution in THF, 3.2 mL) was added to a solution of 2,6-difluoropyridine (492 mg) in THF (25 mL) at −78° C., and the reaction solution was stirred at −78° C. for 2.5 hours. A solution of (R)-6-oxopiperidine-1,2-dicarboxylic acid 1-tert-butyl ester 2-methyl ester (CAS No. 183890-36-0, 1.0 g) in THF (5 mL) was added to the reaction solution at −78° C. The reaction solution was stirred at −78° C. for one hour and at 0° C. for 2.5 hours. A saturated ammonium chloride solution and ethyl acetate were added to the reaction solution, and the mixture was heated to room temperature. Thereafter, the organic layer was separated, and the resulting organic layer was dried over magnesium sulfate and then concentrated under reduced pressure. The residue was purified by silica gel column chromatography (elution solvent: heptane:ethyl acetate=1:1->ethyl acetate) to obtain 148 mg of the title compound. The property value of the compound is as follows.

ESI-MS; m/z 395[M$^+$+Na].

Synthesis of (Z)-(6S,9aR)-6-(2,6-difluoropyridin-3-yl)-3-{1-[3-methoxy-4-(4-methyl-1H-imidazol-1-yl)benzylidene]hexahydropyrido[2,1-c][1,4]oxazin-4-one 18 mg of the title compound was obtained from methyl(R)-2-tert-butoxycarbonylamino-6-(2,6-difluoropyridin-3-yl)-6-oxohexanoate (148 mg) in the same manner as in Example 41. The property values of the compound are as follows.

$^1$H-NMR (CDCl$_3$)δ(ppm):
1.44-1.63 (m, 2H), 1.68-1.81 (m, 1H), 1.85-1.94 (m, 1H), 2.09-2.27 (m, 2H), 2.29 (s, 3H), 3.84 (s, 3H), 4.05 (t, J=10.0 Hz, 1H), 4.07-4.15 (m, 1H), 4.39 (brd, J=8.4 Hz, 1H), 5.25 (t, J=5.2 Hz, 1H), 6.76 (s, 1H), 6.79 (dd, J=8.0, 3.2 Hz, 1H), 6.92 (brs, 1H), 7.19 (d, J=7.6 Hz, 1H), 7.35 (dd, J=7.6, 1.6 Hz, 1H), 7.36 (d, J=1.6 Hz, 1H), 7.70 (brs, 1H), 7.73 (dd, J=17.2, 8.0 Hz, 1H).

EXAMPLES 43 AND 44

Synthesis of (Z)-4-[(R)-1-(2,6-difluoropyridin-3-yl)ethyl]-2-[1-[3-methoxy-4-(4-methyl-1H-imidazol-1-yl)phenyl]methylidene]-morpholin-3-one and (Z)-4-[(S)-1-(2,6-difluoropyridin-3-yl)ethyl]-2-[1-[3-methoxy-4-(4-methyl-1H-imidazol-1-yl)phenyl]methylidene]-morpholin-3-on

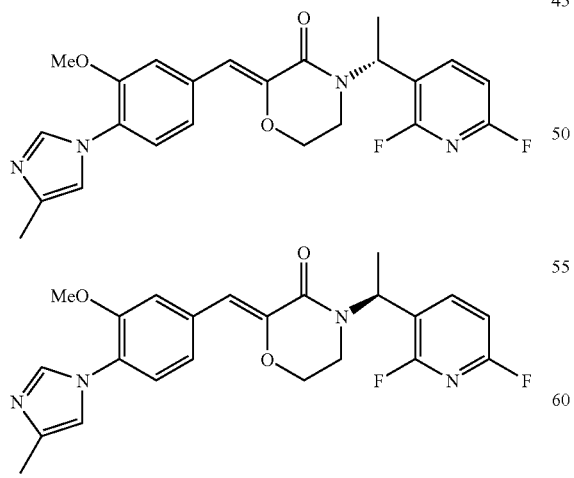

The title compound racemate was obtained from 2,6-difluoropyridine, aminoethanol, and 3-methoxy-4-(4-methyl-1H-imidazol-1-yl)benzaldehyde as starting materials in the same manner as in the other synthesis in Example 22. The resulting racemate was separated by CHIRALPAK™ IA manufactured by Daicel Chemical Industries, Ltd. (2 cm×25 cm; mobile phase: hexane:ethanol=6:4) to obtain the title optically active compound with a retention time of 18 minutes (38.7 mg) and the title optically active compound with a retention time of 22 minutes (37.9 mg).

The property values of the title optically active compound with a retention time of 18 minutes (Example 43) are as follows.

$^1$H-NMR (CDCl$_3$)δ(ppm):
1.68 (d, J=6.8 Hz, 3H), 2.29 (s, 3H), 3.41-3.47 (m, 1H), 3.63-3.68 (m, 1H), 3.85 (s, 3H), 4.22-4.28 (m, 2H), 5.77 (q, J=6.8 Hz, 1H), 6.83 (s, 1H), 6.87 (dd, J=8.4, 2.8 Hz, 1H), 6.92 (s, 1H), 7.20 (d, J=8.4 Hz, 1H), 7.35 (d, J=8.4 Hz, 1H), 7.38 (s, 1H), 7.71 (s, 1H), 8.00 (dd, J=16.8, 8.4 Hz, 1H).

The property values of the title optically active compound with a retention time of 22 minutes (Example 44) are as follows.

$^1$H-NMR (CDCl$_3$)δ(ppm):
1.68 (d, J=6.8 Hz, 3H), 2.29 (s, 3H), 3.41-3.47 (m, 1H), 3.63-3.68 (m, 1H), 3.85 (s, 3H), 4.22-4.28 (m, 2H), 5.77 (q, J=6.8 Hz, 1H), 6.83 (s, 1H), 6.87 (dd, J=8.4, 2.8 Hz, 1H), 6.92 (s, 1H), 7.20 (d, J=8.4 Hz, 1H), 7.35 (d, J=8.4 Hz, 1H), 7.38 (s, 1H), 7.71 (s, 1H), 8.00 (dd, J=16.8, 8.4 Hz, 1H).

EXAMPLES 45 AND 46

Synthesis of (Z)-(S)-4-[(S)-1-(2-fluoropyridin-5-yl)ethyl]-2-[1-[3-methoxy-4-(4-methyl-1H-imidazol-1-yl)phenyl]methylidene]-6-methylmorpholin-3-one and (Z)-(S)-4-[(R)-1-(2-fluoropyridin-5-yl)ethyl]-2-[1-[3-methoxy-4-(4-methyl-1H-imidazol-1-yl)phenyl]methylidene]-6-methylmorpholin-3-one

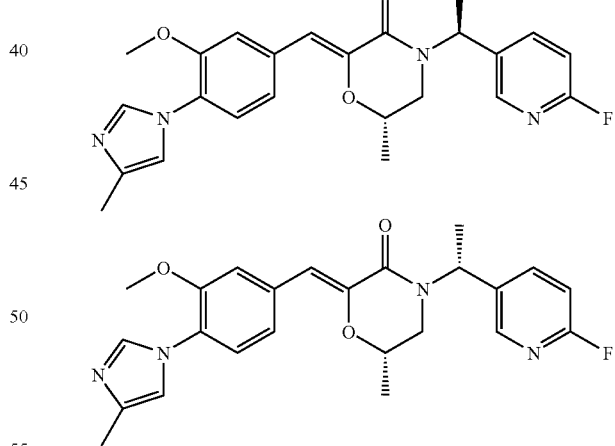

Synthesis of 1-(6-fluoropyridin-3-yl)ethylamine 1-(6-Fluoropyridin-3-yl)ethanone (7.8 g) was synthesized from 6-fluoronicotinic acid (10 g) in the same manner as in Example 22. The title compound (457 mg) was obtained from 1-(6-fluoropyridin-3-yl)ethanone (1.09 g). The property values of the compound are as follows.

$^1$H-NMR (CDCl$_3$)δ(ppm):
1.40 (d, J=6.4 Hz, 3H), 4.21 (q, J=6.4 Hz, 1H), 6.90 (dd, J=3.2, 8.4 Hz, 1H), 7.84 (m, 1H), 8.17 (d, J=0.8 Hz, 1H).

Synthesis of (Z)-(S)-4-[(S)-1-(6-fluoropyridin-3-yl)ethyl]-2-[1-[3-methoxy-4-(4-methyl-1H-imidazol-1-yl)phenyl]methylidene]-6-methylmorpholin-3-one and (Z)-(S)-4-[(R)-1-(6-fluoropyridin-3-yl)ethyl]-2-[1-[3-methoxy-4-(4-methyl-1H-imidazol-1-yl)phenyl]methylidene]-6-methylmorpholin-3-one The title compound diastereomer mixture (48 mg) was obtained as a crude product from 1-(6-fluoropyridin-3-yl)-ethylamine (457 mg) in the same manner as in Example 22. The resulting diastereomer mixture (45 mg) was separated by CHIRALPAK™ IA manufactured by Daicel Chemical Industries, Ltd. (2 cm×25 cm; mobile phase: hexane:ethanol=8:2) to obtain the title optically active compound with a retention time of 57 minutes (20 mg) and the title optically active compound with a retention time of 63 minutes (6.8 mg).

The property value of the title compound diastereomer mixture is as follows.

ESI-MS; m/z 437[M$^+$+H].

The property values of the title optically active compound with a retention time of 57 minutes are as follows.

$^1$H-NMR (CDCl$_3$)δ(ppm):
1.39 (d, J=6.4 Hz, 3H), 1.62 (d, J=7.6 Hz, 3H), 2.30 (d, J=0.8 Hz, 3H), 2.95 (dd, J=9.6, 12.8 Hz, 1H), 3.26 (dd, J=2.8, 13.2 Hz, 1H), 3.85 (s, 3H), 4.37 (m, 1H), 6.15 (q, J=7.2 Hz, 1H), 6.89 (s, 1H), 6.93 (s, 1H), 6.96 (dd, J=2.8, 8.4 Hz, 1H), 7.21 (d, J=8.0 Hz, 1H), 7.34 (m, 1H), 7.51 (d, J=1.6 Hz, 1H), 7.12 (d, J=1.2 Hz, 1H), 7.77 (m, 1H), 8.21 (dd, J=1.2, 1.2 Hz, 1H).

The property values of the title optically active compound with a retention time of 63 minutes are as follows.

$^1$H-NMR (CDCl$_3$)δ(ppm):
1.42 (d, J=6.4 Hz, 3H), 1.61 (d, J=7.2 Hz, 3H), 2.30 (s, 3H), 2.99 (dd, J=2.8, 12.4 Hz, 1H), 3.40 (dd, J=10.0, 12.4 Hz, 1H), 3.86 (s, 3H), 4.13 (m, 1H), 6.17 (q, J=6.8 Hz, 1H), 6.89 (s, 1H), 6.94 (s, 1H), 6.96 (dd, J=2.8, 8.8 Hz, 1H), 7.21 (d, J=8.4 Hz, 1H), 7.34 (dd, J=1.6, 8.4 Hz, 1H), 7.53 (d, J=1.6 Hz, 1H), 7.73 (d, J=1.2 Hz, 1H), 7.81 (m, 1H), 8.22 (d, J=1.6 Hz, 1H).

EXAMPLES 47 AND 48

Synthesis of (Z)-(S)-4-[(S)-1-(2-fluoropyridin-4-yl)ethyl]-2-{1-[3-methoxy-4-(4-methyl-1H-imidazol-1-yl)phenyl]methylidene}-6-methylmorpholin-3-one and (Z)-(S)-4-[(R)-1-(2-fluoropyridin-4-yl)ethyl]-2-{1-[3-methoxy-4-(4-methyl-1H-imidazol-1-yl)phenyl]methylidene}-6-methylmorpholin-3-one

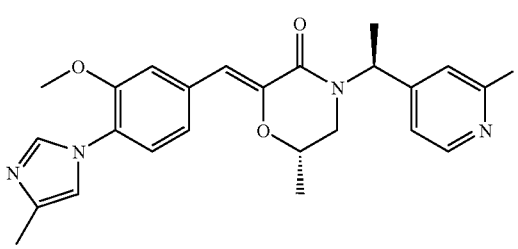

-continued

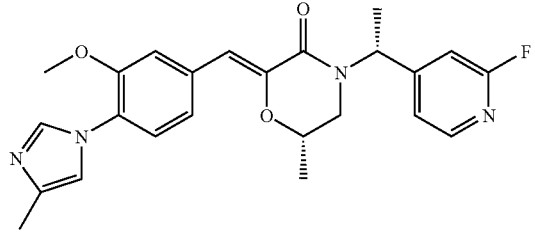

The title compound was obtained as a diastereomer mixture in the same manner as in Example 22 from 1-(2-fluoropyridin-4-yl)-ethylamine prepared in the same manner as in Example 22. The compound was separated by CHIRALCEL OD-H manufactured by Daicel Chemical Industries, Ltd. (2 cm×25 cm; mobile phase: ethanol-hexane system) to obtain the title compound with a retention time of 23 minutes (Example 47) and the title compound with a retention time of 26 minutes (Example 48). The property values of the title compound of Example 47 are as follows.

$^1$H-NMR (CDCl$_3$) δ (ppm):
1.42 (d, J=6.0 Hz, 3H), 1.60 (d, J=7.2 Hz, 3H), 2.30 (s, 3H), 3.03 (dd, J=12.4, 9.2 Hz, 1H), 3.24 (dd, J=13.2, 2.8 Hz, 1H), 3.86 (s, 3H), 4.34-4.42 (m, 1H), 6.11 (t, J=7.2 Hz, 1H), 6.89 (brs, 1H), 6.90 (s, 1H), 6.94 (brs, 1H), 7.14 (brd, J=5.2 Hz, 1H), 7.22 (d, J=8.0 Hz, 1H), 7.35 (dd, J=8.0, 1.6 Hz, 1H), 7.52 (d, J=1.6 Hz, 1H), 7.73 (d, J=1.2 Hz, 1H), 8.23 (d, J=5.2 Hz, 1H).

EXAMPLES 49 AND 50

Synthesis of (Z)-(S)-4-[(S)-1-(5-fluoropyridin-2-yl)ethyl]-2-[1-[3-methoxy-4-(4-methyl-1H-imidazol-1-yl)phenyl]methylidene]-6-methylmorpholin-3-one and (Z)-(S)-4-[(R)-1-(5-fluoropyridin-2-yl)ethyl]-2-[1-[3-methoxy-4-(4-methyl-1H-imidazol-1-yl)phenyl]methylidene]-6-methylmorpholin-3-one

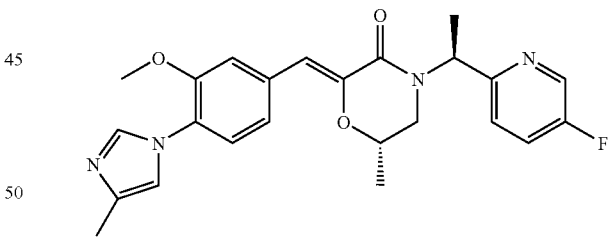

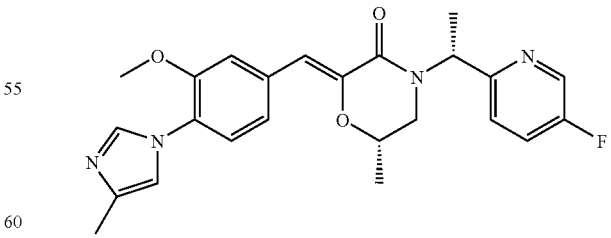

Synthesis of 1-(5-fluoropyridin-2-yl)ethanone

Copper iodide (811 mg), 1-ethoxyvinyltri-n-butyltin (19.2 mL), and bis(triphenylphosphine)palladium (II) chloride (1 g) were added to a solution of 2-bromo-5-fluoropyridine (5 g)

in acetonitrile (250 mL), and the reaction solution was heated and stirred in a nitrogen atmosphere at 100° C. for two hours. The reaction solution was returned to room temperature, and the solvent was evaporated under reduced pressure. The residue was diluted with ethyl acetate and washed with brine. The organic layer was dried over magnesium sulfate, and the solvent was evaporated under reduced pressure. The residue was diluted with acetone (120 mL), and (1S)-(+)-10-camphorsulfonic acid (9.9 g) was added to the reaction solution. After confirming production of the target product by thin-layer chromatography, the solvent was evaporated under reduced pressure. The residue was diluted with an ether and neutralized with sodium carbonate. Water was added to the reaction solution, and the organic solution was separated. The organic layer was dried over magnesium sulfate, and the residue was purified by silica gel column chromatography (carrier: Chromatorex; elution solvent: hexane-ethyl acetate) to obtain 3.55 g of the title compound. The property values of the compound are as follows.

$^1$H-NMR (CDCl$_3$)δ(ppm):

2.71 (s, 3H), 7.51 (m, 1H), 8.11 (ddd, J=0.4, 4.8, 8.8 Hz, 1H), 8.51 (d, J=2.8 Hz, 1H).

Synthesis of 1-(5-fluoropyridin-2-yl)ethylamine

The title compound (483 mg) was obtained from 1-(5-fluoropyridin-2-yl)ethanone (525 mg) in the same manner as in Example 22. The property values of the compound are as follows.

$^1$H-NMR (CDCl$_3$)δ(ppm):

1.42 (d, J=6.4 Hz, 3H), 4.18 (q, J=6.4 Hz, 1H), 7.30-7.37 (m, 2H), 8.41 (d, J=2.4 Hz, 1H).

Synthesis of (Z)-(S)-4-[(S)-1-(5-fluoropyridin-2-yl) ethyl]-2-[1-[3-methoxy-4-(4-methyl-1H-imidazol-1-yl)phenyl]methylidene]-6-methylmorpholin-3-one and (Z)-(S)-4-[(R)-1-(5-fluoropyridin-2-yl)ethyl]-2-[1-[3-methoxy-4-(4-methyl-1H-imidazol-1-yl)phenyl]methylidene]-6-methylmorpholin-3-one The title compound diastereomer mixture (248 mg) was obtained as a crude product from 1-(5-fluoropyridin-2-yl)-ethylamine (483 mg) in the same manner as in Example 22. The resulting diastereomer mixture (30 mg) was separated by CHIRALPAK™ OD-H manufactured by Daicel Chemical Industries, Ltd. (2 cm×25 cm; mobile phase: hexane:etha-nol=8:2) and CHIRALPAK™ AD-H manufactured by Daicel Chemical Industries, Ltd. (2 cm×25 cm; mobile phase: ethanol) to obtain the title optically active compound with a retention time of 23 minutes (1.7 mg) and the title optically active compound with a retention time of 27 minutes (3.9 mg).

The property value of the title compound diastereomer mixture is as follows.

ESI-MS; m/z 437[M$^+$+H].

The property values of the title optically active compound with a retention time of 23 minutes are as follows.

$^1$H-NMR (CDCl$_3$)δ(ppm):

1.37 (d, J=6.4 Hz, 3H), 1.61 (d, J=7.2 Hz, 3H), 2.29 (s, 3H), 3.17 (d d, J=1.2, 13.2 Hz, 1H), 3.52 (dd, J=2.8, 13.2 Hz, 1H), 3.84 (s, 3H), 4.37 (m, 1H), 6.06 (q, J=6.4 Hz, 1H), 6.84 (s 1H), 6.92 (s, 1H), 7.20 (d, J=8.4 Hz, 1H), 7.32 (m, 1H), 7.37-7.40 (m, 2H), 7.51 (d, J=1.2 Hz, 1H), 7.71 (d, J=1.2 Hz, 1H), 8.42 (dd, J=1.2, 1.2 Hz, 1H).

The property values of the title optically active compound with a retention time of 27 minutes are as follows.

$^1$H-NMR (CDCl$_3$)δ(ppm):

1.43 (d, J=6.8 Hz, 3H), 1.60 (d, J=7.2 Hz, 3H), 2.29 (s, 3H), 3.43-3.56 (m, 2H), 3.85 (s, 3H), 4.17 (m, 1H), 6.02 (q, J=6.8 Hz, 1H), 6.83 (s>1H), 6.93 (s, 1H), 7.20 (d, J=8.0 Hz, 1H), 7.32 (d,1H), 7.36-7.43 (m, 2H), 7.53 (d, J=1.6 Hz, 1H), 7.71 (d, J=1.2 Hz, 1H), 8.41 (d, J=1.6 Hz, 1H).

EXAMPLE 51

Synthesis of (Z)-(S)-4-[(S)-1-(2-chloropyridin-4-yl) ethyl]-2-[1-[3-methoxy-4-(4-methyl-1H-imidazol-1-yl)phenyl]methylidene]-6-methylmorpholin-3-one

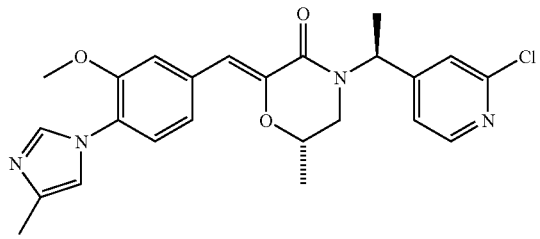

Synthesis of 1-(2-chloropyridin-4-yl)ethanone

The title compound (7.18 g) was obtained from 2-chloroi-sonicotinic acid (8.5 g) in the same manner as in Example 22. The property values of the compound are as follows.

$^1$H-NMR (CDCl$_3$)δ(ppm):

2.63 (s, 3H), 7.66 (m, 1H), 7.77 (m, 1H), 8.59 (m, 1H).

Synthesis of (R)-1-(2-chloropyridin-4-yl)ethanol

A solution of 1-(2-chloropyridin-4-yl)ethanone (7.18 g) in tetrahydrofuran (10 mL) was added dropwise to a solution of (+)-DIP-chloride (19.2 g) in tetrahydrofuran (340 mL) at −20° C., and the reaction solution was stirred at the same temperature overnight. The reaction solution was returned to room temperature, and the solvent was evaporated under reduced pressure. The residue was diluted with an ether, diethanolamine (12.1 g) was added to the diluent, and the reaction solution was stirred at room temperature for four hours. The insoluble matter was separated by filtration through celite, and the mother liquor was concentrated under reduced pressure. The residue was purified by silica gel column chromatography (carrier: Chromatorex, elution solvent: heptane-ethyl acetate) to obtain the title compound (3.84 g). The property values of the compound are as follows.

$^1$H-NMR (CDCl$_3$)δ(ppm):

1.50 (d, J=6.8 Hz, 3H), 4.90 (m, 1H), 7.21 (m, 1H), 7.36 (m, 1H), 8.34 (dd, J=0.4, 5.2 Hz, 1H).

Synthesis of 4-((S)-1-azidoethyl)-2-chloropyridine

Diphenylphosphoryl azide (6.57 mL) was added to a solution of (R)-1-(2-chloropyridin-4-yl)ethanol in toluene (50 mL) in a nitrogen atmosphere, and the reaction solution was cooled to 0° C. DBU (4.52 mL) was added to the reaction solution, which was then heated to room temperature and stirred overnight. Water and an ether were added to the reaction solution, and the organic layer was separated. The organic layer was dried over magnesium sulfate, and the residue was purified by silica gel chromatography (carrier:

Chromatorex; elution solvent: hexane-ethyl acetate) to obtain the title compound (4.44 g) The property values of the compound are as follows.

$^1$H-NMR (CDCl$_3$)δ(ppm):

1.55 (d, J=6.8 Hz, 3H), 4.62 (d, J=6.8 Hz, 1H), 7.18 (m, 1H), 7.30 (m, 1H), 8.39 (dd, J=0.4, 5.2 Hz, 1H).

Synthesis of (S)-1-(2-chloropyridin-4-yl)ethylamine

Triphenylphosphine (9.56 g) was added to a solution of 4-((S)-1-azidoethyl)-2-chloropyridine (4.44 g) in tetrahydrofuran-water (4:1, 50 mL), and the reaction solution was heated and stirred at 60° C. for two hours. The reaction solution was returned to room temperature, and the solvent was evaporated under reduced pressure. Chloroform and 5 N hydrochloric acid were added to the residue, and the aqueous layer was separated. The aqueous layer was made basic with 5 N sodium hydroxide. Chloroform was added to the reaction solution, and the organic layer was separated. The organic layer was dried over magnesium sulfate, and the solvent was evaporated under reduced pressure to obtain the title compound (2.24 g). The property values of the compound are as follows.

$^1$H-NMR (CDCl$_3$)δ(ppm):

1.38 (d, J=6.8 Hz, 3H), 4.12 (d, J=6.8 Hz, 1H), 7.36 (m, 1H), 7.30 (m, 1H), 8.31 (d, J=5.2 Hz, 1H).

Synthesis of (Z)-(S)-4-[(S)-1-(2-chloropyridin-4-yl)ethyl]-2-[1-[3-methoxy-4-(4-methyl-1H-imidazol-1-yl)phenyl]methylidene]-6-methylmorpholin-3-one The title compound containing a geometric isomer (518 mg) was obtained from (S)-1-(2-chloropyridin-4-yl)ethylamine (1.25 g) in the same manner as in Examples 18 and 19. The resulting mixture (54 mg) was separated by CHIRAL-PAK™ IA manufactured by Daicel Chemical Industries, Ltd. (2 cm×25 cm; mobile phase: hexane:ethanol=7:3) to obtain the title compound with a retention time of 38 minutes (6.5 mg).

The property values of the compound are as follows. The property values of the title optically active compound with a retention time of 38 minutes are as follows.
ESI-MS; m/z 453[M$^+$+H].

$^1$H-NMR (CDCl$_3$)δ(ppm):

1.42 (d, J=6.8 Hz, 3H), 1.59 (d, J=7.2 Hz, 3H), 2.30 (d, J=0.8 Hz, 3H), 3.02 (dd, J=9.6, 12.8 Hz, 1H), 3.23 (dd, J=2.4, 13.2 Hz, 1H), 3.85 (s, 3H), 4.36 (m, 1H), 6.07 (q, J=7.2 Hz, 1H), 6.90 (s, 1H), 6.94 (dd, J=1.2, 1.2 Hz, 1H), 7.17 (m, 1H), 7.22 (d, J=8.0 Hz, 1H), 7.28 (m, 1H), 7.36 (m, 1H), 7.52 (d, J=1.2 Hz, 1H), 7.73 (d, J=1.2 Hz, 1H), 8.39 (dd, J=0.8, 5.2 Hz, 1H).

EXAMPLE 52

Synthesis of (Z)-(S)-4-[(S)-1-(2-chloro-3-fluoropyridin-4-yl)ethyl]-2-[1-[3-methoxy-4-(4-methyl-1H-imidazol-1-yl)phenyl]methylidene]-6-methylmorpholin-3-one

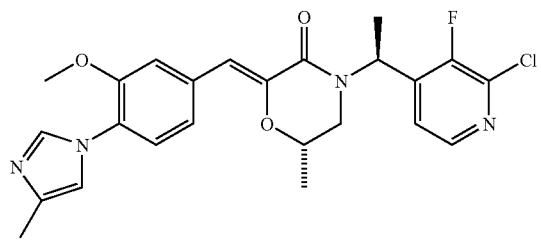

Synthesis of 2-chloro-3-fluoroisonicotinic acid

The title compound (6.34 g) was obtained from 2-chloro-3-fluoropyridine (5 g) in the same manner as in Example 22. The property values of the compound are as follows.

$^1$H-NMR (DMSO-d$_6$)δ(ppm):

7.78 (dd, J=4.8, 4.8 Hz, 1H), 8.27 (d, J=4.8 Hz, 1H).

Synthesis of (S)-1-(2-chloro-3-fluoropyridin-4-yl)ethylamine

The title compound (3.13 g) was obtained from 2-chloro-3-fluoroisonicotinic acid (6.34 g) in the same manner as in Example 51. The property values of the compound are as follows.

$^1$H-NMR (CDCl$_3$)δ(ppm):

1.42 (d, J=6.8 Hz, 3H), 4.45 (q, J=6.8 Hz, 1H), 7.40 (ddd, J=0.4, 4.8, 4.8 Hz, 1H), 8.18 (d, J=4.8 Hz, 1H).

Synthesis of (Z)-(S)-4-[(S)-1-(2-chloro-3-fluoropyridin-4-yl)ethyl]-2-[1-[3-methoxy-4-(4-methyl-1H-imidazol-1-yl)phenyl]methylidene]-6-methylmorpholin-3-one The title compound containing a geometric isomer (623 mg) was obtained from (S)-1-(2-chloro-3-fluoropyridin-4-yl)ethylamine (1.2 g) in the same manner as in Examples 18 and 19. The resulting mixture (14 mg) was separated by CHIRALPAK™ IA manufactured by Daicel Chemical Industries, Ltd. (2 cm×25 cm; mobile phase: hexane:ethanol=1:1) to obtain the title compound with a retention time of 24 minutes (9.5 mg). The property values of the compound are as follows.

ESI-MS; m/z 471[M$^+$+H].

$^1$H-NMR (CDCl$_3$)δ(ppm):

1.46 (d, J=6.4 Hz, 3H), 1.67 (d, J=7.2 Hz, 3H), 2.29 (s, 3H), 3.23 (d d, J=9.6, 12.4 Hz, 1H), 3.41 (dd, J=2.4, 12.8 Hz, 1H), 3.85 (s, 3H), 4.38 (m, 1H), 5.87 (q, J=7.2 Hz, 1H), 6.83 (s, 1H), 6.93 (s, 1H), 7.20 (d, J=8.4 Hz, 1H), 7.30-7.33 (m, 2H), 7.50 (d, J=1.2 Hz, 1H), 7.72 (s, 1H), 8.23 (d, J=5.2 Hz, 1H).

EXAMPLE 53

Synthesis of (Z)-(S)-4-[(S)-1-(2,6-difluoropyridin-4-yl)ethyl]-2-[1-[3-methoxy-4-(4-methyl-1H-imidazol-1-yl)phenyl]methylidene]-6-methylmorpholin-3-one

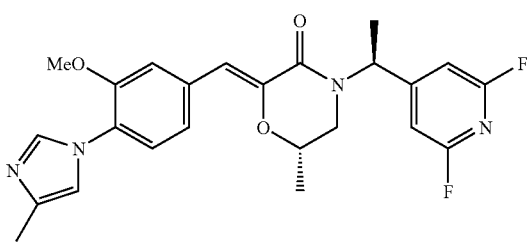

The title compound was obtained in the same manner as in Examples 18 and 19 from (S)-1-(2,6-difluoropyridin-4-yl)ethylamine obtained in the same manner as in Example 51.

ESI-MS; m/z 455[M$^+$+H].

$^1$H-NMR (CDCl$_3$)δ(ppm):

1.44 (d, J=6.4 Hz, 3H), 1.61 (d, J=7.2 Hz, 3H), 2.30 (s, 3H), 3.09 (dd, J=9.2, 12.8 Hz, 1H), 3.27 (dd, J=2.4, 12.8 Hz, 1H), 3.86 (s, 3H), 4.34-4.44 (m, 1H), 6.09 (q, J=7.2 Hz, 1H), 6.78 (s, 2H), 6.90 (s, 1H), 6.94 (s, 1H), 7.22 (d, J=8.0 Hz, 1H), 7.35 (d, J=8.0 Hz, 1H), 7.52 (s, 1H), 7.72 (s, 1H).

EXAMPLE 54

Synthesis of (Z)-4-[(S)-1-(2-chloropyridin-4-yl)ethyl]-2-[1-[3-methoxy-4-(4-methyl-1H-imidazol-1-yl)phenyl]methylidene]-6,6-dimethylmorpholin-3-one

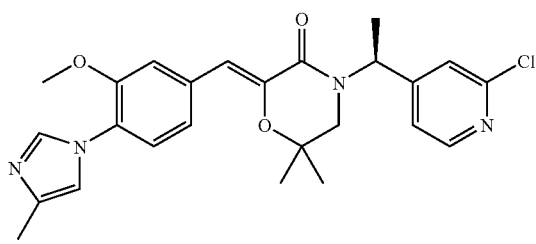

Synthesis of 4-[(S)-1-(2-chloropyridin-4-yl)ethyl]-6,6-dimethylmorpholine-2,3-dione Lithium perchlorate (10.2 g) was added to a solution of (S)-1-(2-chloropyridin-4-yl)ethylamine obtained in Example 51 (1 g) in an ether (18.5 mL), and the reaction solution was stirred for five minutes. Isobutylene oxide (1.7 mL) was added to the reaction solution, which was then stirred overnight. A 5 N sodium hydroxide solution was added to the reaction solution at 0° C., followed by extraction with chloroform. The organic layer was dried over magnesium sulfate, and the solvent was evaporated under reduced pressure. Dichloromethane (20 mL) and pyridine (20 mL) were added to the residue, and the reaction solution was cooled to 0° C. Oxalyl chloride (669 μL) was added to the reaction solution, which was then stirred at 0° C. for one hour and at room temperature for one hour. Oxalyl chloride (0.4 mL) was added to the reaction solution, which was further stirred for one hour. The solvent was evaporated under reduced pressure. Water and ethyl acetate were added to the residue, and the organic layer was separated. The organic layer was dried over magnesium sulfate, and the residue was purified by silica gel column chromatography (Chromatorex; elution solvent: heptane-ethyl acetate) to obtain the title compound (1.07 g). The property values of the compound are as follows.

$^1$H-NMR (CDCl$_3$)δ(ppm):

1.31 (s, 3H), 1.49 (s, 3H), 1.59 (d, J=7.2 Hz, 3H), 3.05 (d, J=13.6, 1H), 3.35 (d, J=14.0 Hz, 1H), 5.97 (q, J=7.2 Hz, 1H), 7.21 (ddd, J=0.8, 1.2, 5.2 Hz, 1H), 7.30 (dd, J=0.8, 0.8 Hz, 1H), 8.42 (d, J=5.2 Hz, 1H).

Synthesis of (Z)-4-[(S)-1-(2-chloropyridin-4-yl)ethyl]-2-[1-[3-methoxy-4-(4-methyl-1H-imidazol-1-yl)phenyl]methylidene]-6,6-dimethylmorpholin-3-one The title compound containing a geometric isomer (1.33 g) was obtained from 4-[(S)-1-(2-chloropyridin-4-yl)ethyl]-6,6-dimethylmorpholine-2,3-dione (1.07 g) in the same manner as in Examples 18 and 19. The resulting mixture (56 mg) was separated by CHIRALPAK™ IA manufactured by Daicel Chemical Industries, Ltd. (2 cm×25 cm; mobile phase: hexane:ethanol=7:3) to obtain the title compound with a retention time of 36 minutes (13 mg). The property values of the compound are as follows.

ESI-MS; m/z 467[M$^+$+H].

$^1$H-NMR (CDCl$_3$)δ(ppm):

1.31 (s, 3H), 1.46 (s, 3H), 1.57 (d, J=7.2 Hz, 3H), 2.30 (s, 3H), 2.95 (d, J=12.8 Hz, 1H), 3.29 (d, J=12.8 Hz, 1H), 3.86 (s, 3H), 6.13 (q, J=7.2 Hz, 1H), 6.93 (dd, J=1.2, 1.2 Hz, 1H), 6.94 (s, 1H), 7.20-7.23 (m, 2H), 7.31 (dd, J=0.8, 0.8 Hz, 1H), 7.35 (dd, J=1.6, 8.0 Hz, 1H), 7.53 (d, J=1.6 Hz, 1H), 7.72 (d, J=1.2 Hz, 1H), 8.40 (d, J=4.8 Hz, 1H).

EXAMPLE 55

Synthesis of (Z)-4-[(S)-1-(2,6-difluoropyridin-3-yl)ethyl]-2-[1-[3-methoxy-4-(4-methyl-1H-imidazol-1-yl)phenyl]methylidene]-6,6-dimethylmorpholin-3-one

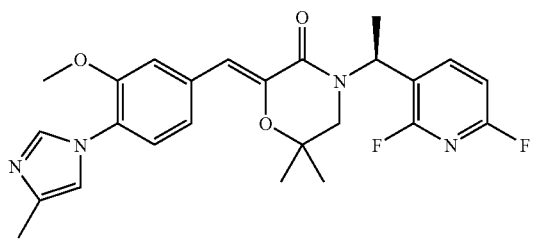

Synthesis of (S)-1-(2,6-difluoropyridin-3-yl)ethylamine

The title compound (9.36 g) was obtained from 2,6-difluoropyridine (15 g) in the same manner as in Example 52. The property values of the compound are as follows.

$^1$H-NMR (CDCl$_3$)δ(ppm):

1.40 (d, J=6.8 Hz, 3H), 4.37 (q, J=6.8 Hz, 1H), 6.81 (dd, J=2.8, 8.0 Hz, 1H), 8.02 (dd, J=8.0, 8.0 Hz, 1H).

Synthesis of (Z)-4-[(S)-1-(2,6-difluoropyridin-3-yl)ethyl]-2-[1-[3-methoxy-4-(4-methyl-1H-imidazol-1-yl)phenyl]methylidene]-6,6-dimethylmorpholin-3-one The title compound containing a geometric isomer (422 mg) was obtained from (S)-1-(2,6-difluoropyridin-3-yl)ethylamine (500 mg) in the same manner as in Examples 18 and 19. The resulting mixture (10 mg) was separated by CHIRALPAK™ IA manufactured by Daicel Chemical Industries, Ltd. (2 cm×25 cm; mobile phase: hexane:ethanol=7:3) to obtain the title compound with a retention time of 28 minutes (6.8 mg). The property values of the compound are as follows.

ESI-MS; m/z 469[M$^+$+H].
$^1$H-NMR (CDCl$_3$)δ(ppm):
1.35 (s, 3H), 1.46 (s, 3H), 1.65 (d, J=7.2 Hz, 3H), 2.30 (d, J=0.8 Hz, 3H), 3.20 (d, J=12.8 Hz, 1H), 3.43 (d, J=12.4 Hz, 1H), 3.84 (s, 3H), 5.86 (q, J=7.2 Hz, 1H), 6.86 (s, 1H), 6.88 (dd, J=2.8, 8.4 Hz, 1H), 6.92 (m, 1H), 7.19 (d, J=8.4 Hz, 1H), 7.31 (dd, J=2.0, 8.4 Hz, 1H), 7.51 (d, J=1.6 Hz, 1H), 7.71 (d, J=1.6 Hz, 1H), 8.01 (dd, J=8.0, 9.2 Hz, 1H).

EXAMPLE 56

Synthesis of (Z)-4-[(S)-1-(6-fluoropyridin-3-yl)ethyl]-2-[1-[3-methoxy-4-(4-methyl-1H-imidazol-1-yl)phenyl]methylidene]-6,6-dimethylmorpholin-3-one

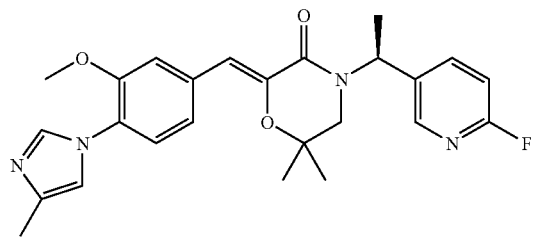

Synthesis of (S)-1-(6-fluoropyridin-3-yl)ethylamine

The title compound (3.95 g) was obtained from 6-fluoronicotinic acid (10 g) in the same manner as in Example 52. The property values of the compound are as follows.
$^1$H-NMR (CDCl$_3$)δ(ppm):
1.40 (d, J=6.4 Hz, 3H), 4.21 (q, J=6.4 Hz, 1H), 6.90 (dd, J=3.2, 8.4 Hz, 1H), 7.84 (m, 1H), 8.17 (d, J=0.8 Hz, 1H).

Synthesis of (Z)-4-[(S)-1-(6-fluoropyridin-3-yl)ethyl]-2-[1-[3-methoxy-4-(4-methyl-1H-imidazol-1-yl)phenyl]methylidene]-6,6-dimethylmorpholin-3-one The title compound containing a geometric isomer (1.02 g) was obtained from (S)-1-(6-fluoropyridin-3-yl)ethylamine (500 mg) in the same manner as in Examples 18 and 19. The resulting mixture (1.01 g) was recrystallized from ethyl acetate/ether to obtain the title optically active compound (120 mg). The property values of the compound are as follows.
$^1$H-NMR (CDCl$_3$)δ(ppm):
1.23 (s, 3H), 1.45 (s, 3H), 1.61 (d, J=7.2 Hz, 1H), 2.30 (s, 3H), 2.92 (d, J=12.8 Hz, 1H), 3.32 (d, J=12.4 Hz, 1H), 3.85 (s, 3H), 6.21 (q, J=7.2 Hz, 1H), 6.92-6.97 (m, 3H), 7.21 (d, J=8.0 Hz, 1H), 7.33 (dd, J=0.8, 8.0 Hz, 1H), 7.52 (d, J=1.2 Hz, 1H), 7.71 (d, J=0.8 Hz, 1H), 7.81 (m, 1H), 8.22 (s, 1H).

EXAMPLE 57

Synthesis of (Z)-4-[(S)-1-(6-chloropyridin-3-yl)ethyl]-2-[1-[3-methoxy-4-(4-methyl-1H-imidazol-1-yl)phenyl]methylidene]-6,6-dimethylmorpholin-3-one

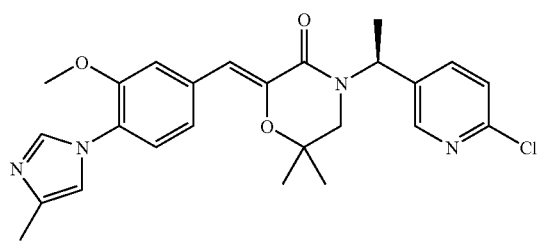

Synthesis of (S)-1-(6-chloropyridin-3-yl)ethylamine

The title compound (7.04 g) was obtained from 6-chloronicotinic acid (13 g) in the same manner as in Example 52. The property values of the compound are as follows.
$^1$H-NMR (CDCl$_3$)δ(ppm):
1.39 (d, J=6.4 Hz, 3H), 4.19 (q, J=6.4 Hz, 1H), 7.29 (d, J=8.0 Hz, 1H), 7.70 (dd, J=2.4, 8.0 Hz, 1H), 8.36 (d, J=2.4 Hz, 1H).

Synthesis of (Z)-4-[(S)-1-(6-chloropyridin-3-yl)ethyl]-2-[1-[3-methoxy-4-(4-methyl-1H-imidazol-1-yl)phenyl]methylidene]-6,6-dimethylmorpholin-3-one The title compound containing a geometric isomer was obtained from (S)-1-(6-chloropyridin-3-yl)ethylamine (600 mg) in the same manner as in Examples 18 and 19, and stirred in a solution of trifluoroacetic acid/chloroform/4 N hydrochloric acid (5/5/2) in ethyl acetate for four hours to isomerize the E-isomer to the Z-isomer. The reaction solution was neutralized with a 5 N NaOH solution, followed by extraction with ethyl acetate. The organic layer was dried over magnesium sulfate, and the solvent was evaporated under reduced pressure. The residue was purified by silica gel column chromatography (Chromatorex NH; heptane/ethyl acetate->ethyl acetate/methanol) to obtain the title compound (251 mg).
$^1$H-NMR (CDCl$_3$)δ(ppm):
1.24 (s, 3H), 1.45 (s, 3H), 1.60 (d, J=7.2 Hz, 1H), 2.30 (s, 3H), 2.92 (d, J=12.4 Hz, 1H), 3.30 (d, J=12.4 Hz, 1H), 3.85 (s, 3H), 6.19 (q, J=7.2 Hz, 1H), 6.92 (s<1H), 6.93 (d, J=3.2 Hz, 1H), 7.20 (d, J=8.4 Hz, 1H), 7.32-7.36 (m, 2H), 7.52 (s, 1H), 7.68 (dd, J=2.4, 8.4 Hz, 1H), 7.71 (d, J=0.8 Hz, 1H), 8.40 (d, J=2.4 Hz, 1H).

EXAMPLE 58

Synthesis of (Z)-4-[(S)-1-(2,3-difluoropyridin-4-yl)ethyl]-2-[1-[3-methoxy-4-(4-methyl-1H-imidazol-1-yl)phenyl]methylidene]-6,6-dimethylmorpholin-3-one

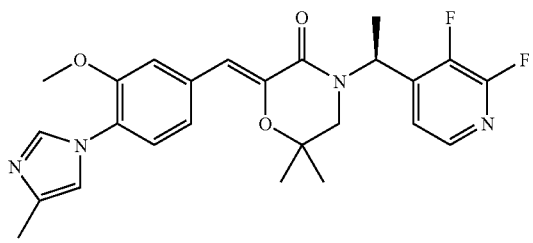

Synthesis of (S)-1-(2,3-difluoropyridin-4-yl)ethylamine

The title compound (7.09 g) was obtained from 2,3-difluoroisonicotinic acid (16.6 g) that is a known compound (see The Journal of Organic Chemistry, 2005, vol. 70, p. 3039-3045) in the same manner as in Example 52. The property values of the compound are as follows.

¹H-NMR (CDCl₃)δ(ppm):
1.42 (d, J=6.4 Hz, 3H), 4.49 (q, J=6.4 Hz, 1H), 7.32 (dd, J=4.8, 4.8 Hz, 1H), 7.93 (d, J=4.8 Hz, 1H).

Synthesis of (Z)-4-[(S)-1-(2,3-difluoropyridin-4-yl)ethyl]-2-[1-[3-methoxy-4-(4-methyl-1H-imidazol-1-yl)phenyl]methylidene]-6,6-dimethylmorpholin-3-one The title compound containing a geometric isomer was obtained from (S)-1-(2,3-difluoropyridin-4-yl)ethylamine (1 g) in the same manner as in Examples 18 and 19, and isomerized in the same manner as in Example 57 to obtain the title compound (830 mg). The property values of the compound are as follows.

ESI-MS; m/z 469[M⁺+H].
¹H-NMR (CDCl₃)δ(ppm):
1.37 (s, 3H), 1.47 (s, 3H), 1.65 (d, J=7.2 Hz, 1H), 2.30 (s, 3H), 3.18 (d, J=12.4 Hz, 1H), 3.42 (d, J=12.4 Hz, 1H), 3.85 (s, 3H), 6.04 (q, J=7.2 Hz, 1H), 6.88 (s 1H), 6.93 (s, 1H), 7.20 (d, J=8.4 Hz, 1H), 7.23-7.33 (m, 2H), 7.51 (s, 1H), 7.71 (s, 1H), 8.00 (d, J=3.2 Hz, 1H).

EXAMPLE 59

Synthesis of (Z)-4-[(S)-1-(5-fluoropyridin-2-yl)ethyl]-2-[1-[3-methoxy-4-(4-methyl-1H-imidazol-1-yl)phenyl]methylidene]-6,6-dimethylmorpholin-3-one

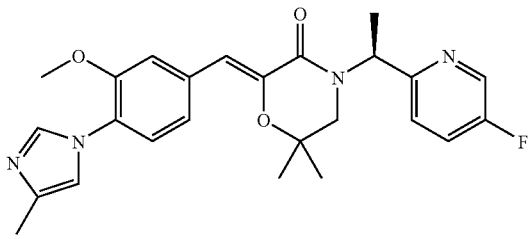

Synthesis of (S)-1-(5-fluoropyridin-2-yl)ethylamine

The title compound (1.23 g) was obtained from 1-(5-fluoropyridin-2-yl)ethanone described in Example 49 (3.05 g) in the same manner as in Example 52. The property values of the compound are as follows.

¹H-NMR (CDCl₃)δ(ppm):
1.42 (d, J=6.4 Hz, 3H), 4.17 (q, J=6.4 Hz, 1H), 7.30-7.39 (m, 1H), 8.40 (d, J=2.4 Hz, 1H).

Synthesis of (Z)-4-[(S)-1-(5-fluoropyridin-2-yl)ethyl]-2-[1-[3-methoxy-4-(4-methyl-1H-imidazol-1-yl)phenyl]methylidene]-6,6-dimethylmorpholin-3-one The title compound containing a geometric isomer was obtained from (S)-1-(5-fluoropyridin-2-yl)ethylamine (700 mg) in the same manner as in Examples 18 and 19, and isomerized in the same manner as in Example 57 to obtain the title compound (640 mg). The property values of the compound are as follows.

ESI-MS; m/z 451[M⁺H].
¹H-NMR (CDCl₃)δ(ppm):
1.16 (s, 3H), 1.46 (s, 3H), 1.59 (d, J=6.8 Hz, 1H), 2.29 (s, 3H), 3.34 (d, J=12.8 Hz, 1H), 3.47 (d, J=12.8 Hz, 1H), 3.84 (s, 3H), 6.10 (q, J=7.2 Hz, 1H), 6.86 (s 1H), 6.92 (dd, J=1.2, 1.2 Hz, 1H), 7.19 (d, J=8.4 Hz, 1H), 7.31 (dd, J=2.0, 8.4 Hz, 1H), 7.36-7.46 (m, 2H), 7.53 (d, J=2.8 Hz, 1H), 7.70 (m, 1H), 8.41 (d, J=2.8 Hz 1H).

EXAMPLE 60

Synthesis of (Z)-4-[(S)-1-(5-chloropyridin-2-yl)ethyl]-2-[1-[3-methoxy-4-(4-methyl-1H-imidazol-1-yl)phenyl]methylidene]-6,6-dimethylmorpholin-3-one

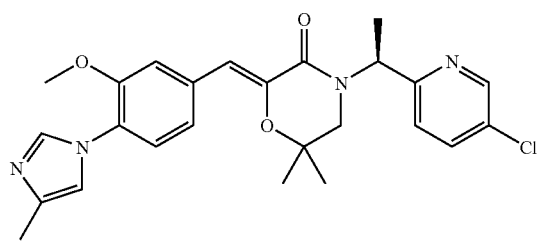

Synthesis of (S)-1-(5-chloropyridin-2-yl)ethylamine

The title compound (2.72 g) was obtained from 1-(5-chloropyridin-2-yl)ethanone described in Example 20 (4.29 g) in the same manner as in Example 52. The property values of the compound are as follows.

$^1$H-NMR (CDCl$_3$)δ(ppm):

1.42 (d, J=6.4 Hz, 3H), 4.17 (q, J=6.4 Hz, 1H), 7.30-7.39 (m, 1H), 8.40 (d, J=2.4 Hz, 1H).

Synthesis of (Z)-4-[(S)-1-(5-chloropyridin-2-yl)ethyl]-2-[1-[3-methoxy-4-(4-methyl-1H-imidazol-1-yl)phenyl]methylidene]-6,6-dimethylmorpholin-3-one The title compound containing a geometric isomer was obtained from (S)-1-(5-chloropyridin-2-yl)ethylamine (1 g) in the same manner as in Examples 18 and 19, and isomerized in the same manner as in Example 57 to obtain the title compound (310 mg). The property values of the compound are as follows.

ESI-MS; m/z 467[M$^+$+H].

$^1$H-NMR (CDCl$_3$)δ(ppm):

1.19 (s, 3H), 1.46 (s, 3H), 1.59 (d, J=6.8 Hz, 1H), 2.29 (s, 3H), 3.35 (d, J=12.8 Hz, 1H), 3.48 (d, J=12.8 Hz, 1H), 3.84 (s, 3H), 6.08 (q, J=6.8 Hz, 1H), 6.86 (s 1H), 6.92 (s, 1H), 7.19 (d, J=8.0 Hz, 1H), 7.31 (d, J=8.4 Hz, 1H), 7.38 (d, J=8.0 Hz, 1H), 7.53 (s, 1H), 7.66 (d d, J=1.6, 8.4, 1H), 7.70 (s, 1H), 8.51 (d, J=2.0 Hz, 1H).

The compounds in Tables 1-1 and 1-2 were obtained in the same manner.

TABLE 1-1

| Example | E$_1$ | DATA: MS m/z | Note |
|---|---|---|---|
| 61 | (3-fluoro-4-pyridinyl)ethyl* | M$^+$ + H: 437 (ESI) | Optically active compound |
| 62 | (3-pyridinyl)ethyl* | M$^+$ + H: 419 (ESI) | Optically active compound |

TABLE 1-2

| Example | E$_1$ | DATA: MS m/z | Note |
|---|---|---|---|
| 63 | (2,6-difluoro-3-pyridinyl)ethyl* | M$^+$ + H: 455 (ESI) | Optically active compound |
| 64 | (2,6-difluoro-3-pyridinyl)ethyl* | M$^+$ + H: 455 (ESI) | Optically active compound |

EXAMPLE 65

Synthesis of (Z)-(S)-4-(4-fluorobenzyl)-2-[1-[3-fluoro-4-(4-methyl-1H-imidazol-1-yl)phenyl]methylidene]-6-methylmorpholin-3-one 9.06 mg of the title compound was obtained from (S)-4-(4-fluorobenzyl)-2-hydroxy-6-methylmorpholin-3-one, thionyl chloride, triphenylphosphine, and 3-fluoro-4-(4-methyl-1H-imidazol-1-yl)benzaldehyde in the same manner as in Example 5.

$^1$H-NMR (CDCl$_3$)δ(ppm):

1.44 (d, J=6.8 Hz, 3H), 2.38 (s, 3H), 3.26 (dd, J=12.8, 3.2 Hz, 1H), 3.43 (dd, J=12.8, 9.6 Hz, 1H), 4.32-4.40 (m, 1H), 4.62 (d, J=14.4 Hz, 1H), 4.73 (d, J=14.4 Hz, 1H), 6.87 (s, 1H), 7.01-7.09 (m, 3H), 7.27-7.35 (m, 3H), 7.50 (d, J=8.4 Hz, 1H), 7.77 (d, J=12.8 Hz, 1H), 7.96 (s, 1H).

EXAMPLE 66

Synthesis of (Z)-2-[1-[3-fluoro-4-(4-methyl-1H-imidazol-1-yl)phenyl]methylidene]-4-[(S)-1-(4-trifluorophenyl)ethyl]-6,6-dimethylmorpholin-3-one

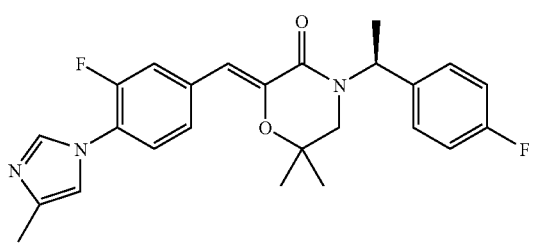

31.55 mg of the title compound was obtained from 4-[(S)-1-(4-fluorophenyl)ethyl]-2-hydroxy-6,6-dimethylmorpholin-3-one, thionyl chloride, triphenylphosphine, and 3-fluoro-4-(4-methyl-1H-imidazol-1-yl)benzaldehyde in the same manner as in Example 7.

$^1$H-NMR (CDCl$_3$)δ(ppm):
1.20 (s, 3H), 1.43 (s, 3H), 1.55 (d, J=6.8 Hz, 3H), 2.34 (s, 3H), 2.90 (d, J=12.8 Hz, 1H), 3.24 (d, J=12.8 Hz, 1H), 6.16 (q, J=6.8 Hz, 1H), 6.87 (s, 1H), 7.00 (s, 1H), 7.04-7.08 (m, 2H), 7.28-7.36 (m, 3H), 7.47 (dd, J=8.4, 1.6 Hz, 1H), 7.74 (dd, J=12.8, 1.6 Hz, 1H), 7.85 (s 1H).

EXAMPLE 67

Synthesis of (Z)-4-(4-fluorobenzyl)-2-[1-[3-fluoro-4-(4-methyl-1H-imidazol-1-yl)phenyl]methylidene]-6,6-dimethyl morpholin-3-one

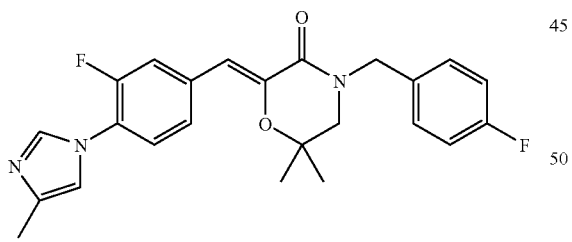

44.7 mg of the title compound was obtained from 4-(4-fluorobenzyl)-2-hydroxy-6,6-dimethylmorpholin-3-one, thionyl chloride, triphenylphosphine, and 3-fluoro-4-(4-methyl-1H-imidazol-1-yl)benzaldehyde in the same manner as in Example 7.

$^1$H-NMR (CDCl$_3$)δ(ppm):
1.39 (s, 6H), 2.57 (s, 3H), 3.35 (s, 2H), 4.67 (s, 2H), 6.89 (s, 1H), 7.03-7.08 (m, 2H), 7.13 (s, 1H), 7.29-7.33 (m, 2H), 7.41 (dd, J=8.0, 8.0 Hz, 1H), 7.57 (d, J=8.0 Hz, 1H), 7.82 (d, J=12.8 Hz, 1H), 8.70 (s, 1H).

EXAMPLE 68

Synthesis of (Z)-4-[(S)-chroman-4-yl]-2-[1-[3-fluoro-4-(4-methyl-1H-imidazol-1-yl)phenyl]methylidene]-6,6-dimethylmorpholin-3-one

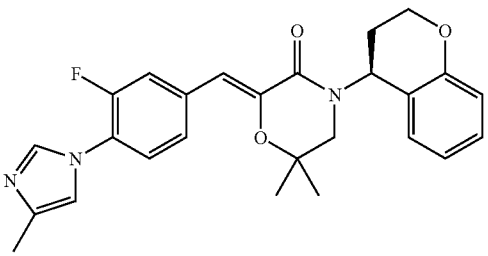

25.4 mg of the title compound was obtained from 4-[(S)-chroman-4-yl]-2-hydroxy-6,6-dimethylmorpholin-3-one, triphenylphosphonium bromide, and 3-fluoro-4-(4-methyl-1H-imidazol-1-yl)benzaldehyde in the same manner as in Example 12.

$^1$H-NMR (CDCl$_3$)δ(ppm):
1.43 (s, 3H), 1.45 (s, 3H), 2.14-2.21 (m, 2H), 2.34 (s, 3H), 3.12 (d, J=13.2 Hz, 1H), 3.19 (d, J=13.2 Hz, 1H), 4.23-4.33 (m, 2H), 6.11 (t, J=7.2 Hz, 1H), 6.86-6.95 (m, 3H), 7.01 (s, 1H), 7.09 (d, J=8.0 Hz, 1H), 7.20 (t, J=8.0 Hz, 1H), 7.32 (t, J=8.0 Hz, 1H), 7.49 (d, J=8.0 Hz, 1H), 7.76 (dd, J=12.8, 1.2 Hz, 1H), 7.82 (s, 1H).

EXAMPLES 69 AND 70

Synthesis of (Z)-(S)-4-[(S)-chroman-4-yl]-2-[1-[3-fluoro-4-(4-methyl-1H-imidazol-1-yl)phenyl]methylidene]-6-methylmorpholin-3-one and (Z)-(R)-4-[(S)-chroman-4-yl]-2-[1-[3-fluoro-4-(4-methyl-1H-imidazol-1-yl)phenyl]methylidene]-6-methylmorpholin-3-one

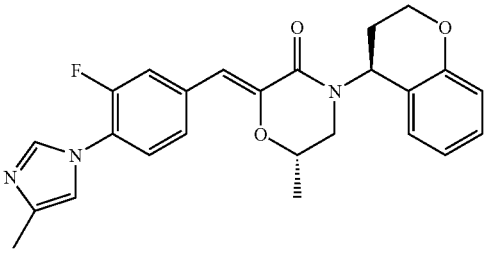

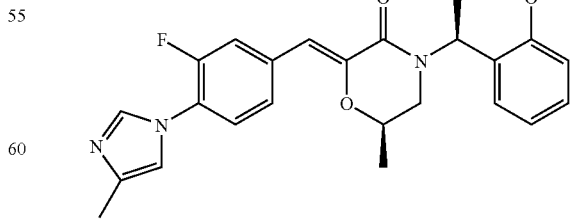

66.4 mg of the title compound was obtained as a diastereomer mixture from 4-[(S)-chroman-4-yl]-2-hydroxy-6-methylmorpholin-3-one, triphenylphosphonium bromide, and 3-fluoro-4-(4-methyl-1H-imidazol-1-yl)benzaldehyde as starting materials in the same manner as in Examples 12, 13, and 14. The mixture was separated by CHIRALPAK™ AD-H manufactured by Daicel Chemical Industries, Ltd. (2 cm×25 cm; mobile phase: ethanol 100%) to obtain the title optically active compound with a retention time of 20 minutes (>99% de) and the title optically active compound with a retention time of 24 minutes (>99% de).

The property values of the title optically active compound with a retention time of 20 minutes (Example 69) are as follows.

$^1$H-NMR (CDCl$_3$)δ(ppm):

1.43 (d, J=6.0 Hz, 3H), 2.14-2.24 (m, 2H), 2.35 (s, 3H), 3.12-3.15 (m, 2H), 4.24-4.38 (m, 3H), 6.05 (dd, J=8.8, 6.4 Hz, 1H), 6.86-6.89 (m, 2H), 6.93 (t, J=7.2 Hz, 1H), 7.01-7.07 (m, 2H), 7.20 (t, J=8.0 Hz, 1H), 7.33 (t, J=8.0 Hz, 1H), 7.51 (d, J=8.0 Hz, 1H), 7.78 (d, J=12.8 Hz, 1H), 7.87 (s, 1H).

The property values of the title optically active compound with a retention time of 24 minutes (Example 70) are as follows.

$^1$H-NMR (CDCl$_3$)δ(ppm):

1.42 (d, J=6.0 Hz, 3H), 2.14-2.20 (m, 2H), 2.36 (s, 3H), 3.10 (dd, J=12.8, 2.4 Hz, 1H), 3.32 (dd, J=12.8, 10.0 Hz, 1H), 4.24-4.37 (m, 3H), 6.13 (t, J=8.4 Hz, 1H), 6.86-6.94 (m, 3H), 7.02-7.07 (m, 2H), 7.20 (t, J=8.4 Hz, 1H), 7.33 (t, J=8.4 Hz, 1H), 7.51 (d, J=8.4 Hz, 1H), 7.78 (dd, J=8.4, 1.2 Hz, 1H), 7.89 (s, 1H).

EXAMPLE 71

Synthesis of (Z)-(S)-4-(6-chloropyridin-2-ylmethyl)-2-[1-[3-fluoro-4-(4-methyl-1H-imidazol-1-yl)phenyl]methylidene]-6-methylmorpholin-3-one

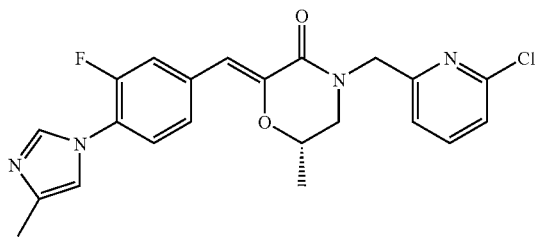

24.3 mg of the title compound was obtained from (S)-4-(6-chloropyridin-2-ylmethyl)-2-hydroxy-6-methylmorpholin-3-one, thionyl chloride, triphenylphosphine, and 3-fluoro-4-(4-methyl-1H-imidazol-1-yl)benzaldehyde in the same manner as in Example 15.

$^1$H-NMR (CDCl$_3$)δ(ppm):

1.48 (d, J=6.0 Hz, 3H), 2.33 (s, 3H), 3.59 (dd, J=12.8, 2.8 Hz, 1H), 3.68 (dd, J=12.8, 9.6 Hz, 1H), 4.43-4.47 (m, 1H), 4.73 (d, J=14.8 Hz, 1H), 4.78 (d, J=14.8 Hz, 1H), 6.82 (s, 1H), 7.00 (s, 1H), 7.26-7.33 (m, 3H), 7.47 (dd, J=8.4, 1.6 Hz, 1H), 7.66 (dd, J=8.0, 8.0 Hz, 1H), 7.75 (dd, J=12.8, 1.6 Hz, 1H), 7.80 (s, 1H).

EXAMPLE 72

Synthesis of (Z)-(S)-4-[(S)-1-(6-chloropyridin-3-yl)ethyl]-2-[1-[3-fluoro-4-(4-methyl-1H-imidazol-1-yl)phenyl]methylidene]-6-methylmorpholin-3-one

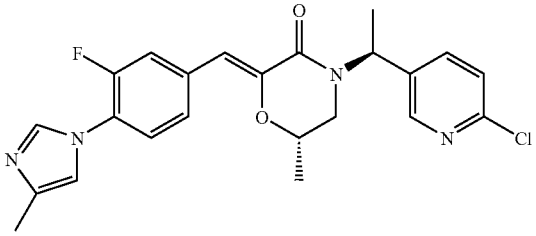

The title compound (11.6 mg) was obtained from 3-fluoro-4-(4-methyl-1H-imidazol-1-yl)benzaldehyde as a starting material in the same manner as in Examples 18 and 19.

$^1$H-NMR (CDCl$_3$)δ(ppm):

1.40 (d, J=6.4 Hz, 3H), 1.62 (d, J=7.2 Hz, 3H), 2.31 (s, 3H), 2.95 (dd, J=12.8, 9.2 Hz, 1H), 3.28 (dd, J=12.8, 2.8 Hz, 1H), 4.35-4.41 (m, 1H), 6.12 (q, J=7.2 Hz, 1H), 6.85 (s, 1H), 6.99 (s, 1H), 7.31 (t, J=8.4 Hz, 1H), 7.34 (d, J=8.4 Hz, 1H), 7.46 (dd, J=8.4, 2.0 Hz, 1H), 7.63 (dd, J=8.4, 2.4 Hz, 1H), 7.72 (dd, J=13.2, 2.0 Hz, 1H), 7.74 (s, 1H), 8.38 (d, J=2.4 Hz, 1H).

EXAMPLE 73

Synthesis of (Z)-(S)-4-[(S)-1-(2,6-difluoropyridin-3-yl)ethyl]-2-[1-[3-fluoro-4-(4-methyl-1H-imidazol-1-yl)phenyl]methylidene]-6-methylmorpholin-3-one

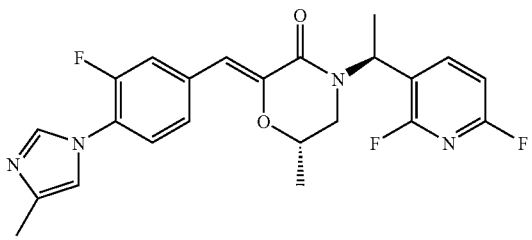

The title compound (11.2 mg) was obtained from 3-fluoro-4-(4-methyl-1H-imidazol-1-yl)benzaldehyde as a starting material in the same manner as in the other synthesis in Example 22.

$^1$H-NMR (CDCl$_3$)δ(ppm):

1.45 (d, J=6.4 Hz, 3H), 1.67 (d, J=6.8 Hz, 3H), 2.30 (s, 3H), 3.22 (dd, J=12.8, 5.2 Hz, 1H), 3.44 (dd, J=12.8, 3.2 Hz, 1H), 4.34-4.42 (m, 1H), 5.73 (q, J=6.8 Hz, 1H), 6.76 (s, 1H), 6.87 (dd, J=8.0, 3.2 Hz, 1H), 6.97 (s, 1H), 7.29 (d, J=8.0 Hz, 1H), 7.42 (d, J=8.0 Hz, 1H), 7.70 (d, J=11.2 Hz, 1H), 7.75 (s, 1H), 7.99 (dd, J=16.0, 8.0 Hz, 1H).

EXAMPLE 74

Synthesis of (Z)-(S)-2-[1-[3-fluoro-4-(4-methyl-1H-imidazol-1-yl)phenyl]methylidene]-4-[(1R,2R)-2-hydroxy-1-(3,4,5-trifluorophenyl)propyl]-6-methyl-morpholin-3-one

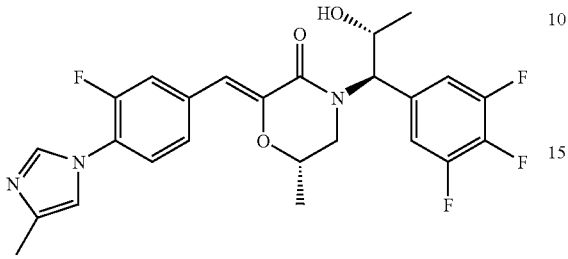

Synthesis of 3-fluoro-4-(4-methyl-1H-imidazol-1-yl)benzaldehyde

To a solution of 3,4-difluorobenzaldehyde (40.0 g) in DMF (533 mL), 4-methylimidazole (46.4 g) and potassium carbonate (78.0 g) were added at room temperature, and the reaction solution was stirred at 90° C. for six hours. The reaction solution was left to cool to room temperature. Ethyl acetate was added to the reaction solution, which was then sequentially washed with water and brine. The resulting organic layer was dried over magnesium sulfate and then concentrated under reduced pressure. The residue was purified by silica gel column chromatography (elution solvent: heptane-ethyl acetate system) and solidified with tert-butyl methyl ether to obtain 10.1 g of the title compound. The property values of the compound are as follows.

$^1$H-NMR (CDCl$_3$)δ(ppm):
2.33 (d, J=0.8 Hz, 3H), 7.07 (brs, 1H), 7.57 (dd, J=7.2, 7.2 Hz, 1H), 7.76-7.82 (m, 2H), 7.87 (brs, 1H), 10.01 (d, J=1.6 Hz, 1H).

Synthesis of (Z)-(S)-2-[1-[3-fluoro-4-(4-methyl-1H-imidazol-1-yl)phenyl]methylidene]-4-[(1R,2R)-2-hydroxy-1-(3,4,5-trifluorophenyl)propyl]-6-methyl-morpholin-3-one A solution of (S)-4-[(1R,2R)-2-tert-butyldiphenylsilanyloxy-1-(3,4,5-trifluorophenyl)propyl]-2-hydroxy-6-methyl-morpholin-3-one (2.16 g) and triphenylphosphine hydrobromide (1.61 g) in acetonitrile (70 ml) was heated under reflux in a nitrogen atmosphere for one hour. The solvent was evaporated under reduced pressure, and the resulting residue was dissolved in ethanol (80 ml). To this reaction solution, 3-fluoro-4-(4-methyl-1H-imidazol-1-yl)benzaldehyde (869 mg) and TEA (2.68 ml) were added, and the reaction solution was stirred in a nitrogen atmosphere at room temperature for 1 hours. The solvent was evaporated under reduced pressure. The resulting residue was dissolved in a mixed solvent of trifluoroacetic acid (30 ml) and methylene chloride (30 ml), and the reaction solution was stirred at room temperature for 13 hours. The reaction solution is poured into a saturated sodium bicarbonate solution, followed by extraction with ethyl acetate. The organic layer was washed with a saturated sodium bicarbonate solution and brine, and then the solvent was evaporated under reduced pressure. The resulting residue was purified by column chromatography using NH silica gel (heptane:ethyl acetate=1:1 to 0:1) and solidified with heptane-ethyl acetate to obtain 1.32 g of the title compound.

$^1$H-NMR (CDCl$_3$)δ(ppm):
1.33 (d, J=6.4 Hz, 3H), 1.42 (d, J=6.0 Hz, 3H), 2.30 (s, 3H), 3.19 (dd, J=12.4, 9.2 Hz, 1H), 3.63 (dd, J=12.4, 2.0 Hz, 1H), 4.44-4.49 (m, 2H), 5.36 (d, J=6.8 Hz, 1H), 6.80 (s, 1H), 6.97 (s, 1H), 7.09 (dd, J=8.4, 6.4 Hz, 2H), 7.29 (t, J=8.4 Hz, 1H), 7.44 (dd, J=8.4, 2.0 Hz, 1H), 7.71 (dd, J=12.8, 1.2 Hz, 1H), 7.74 (s, 1H).

EXAMPLE 75

Synthesis of (Z)-(S)-4-[(1R,2R)-1-(3,4-difluorophenyl)-2-hydroxypropyl]-2-[1-[3-fluoro-4-(4-methyl-1H-imidazol-1-yl)phenyl]methylidene]-6-methyl-morpholin-3-one

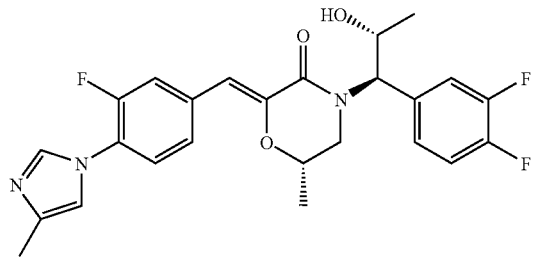

1.15 g of the title compound was obtained in the same manner as in Example 26 from (S)-4-[(1R,2R)-2-tert-butyl-diphenylsilanyloxy-1-(3,4-difluorophenyl)propyl]-2-hydroxy-6-methylmorpholin-3-one prepared from 1-bromo-4,5-difluorobenzene as a starting material and 3-fluoro-4-(4-methyl-1H-imidazol-1-yl)benzaldehyde.

$^1$H-NMR (CDCl$_3$)δ(ppm):
1.31 (d, J=6.4 Hz, 3H), 1.41 (d, J=6.8 Hz, 3H), 2.20 (d, J=6.4 Hz, 1H), 2.30 (s, 3H), 3.15 (dd, J=12.8, 9.6 Hz, 1H), 3.57 (dd, J=12.8, 2.4 Hz, 1H), 4.42-4.48 (m, 2H), 5.38 (d, J=7.6 Hz, 1H), 6.80 (s, 1H), 6.97 (s, 1H), 7.12-7.18 (m, 2H), 7.26-7.31 (m, 2H), 7.44 (dd, J=8.4, 2.0 Hz, 1H), 7.71 (dd, J=12.8, 1.6 Hz, 1H), 7.73 (s

EXAMPLE 76

Synthesis of (Z)-(S)-2-[1-[3-fluoro-4-(4-methyl-1H-imidazol-1-yl)phenyl]methylidene]-4-[(1R,2R)-1-(4-fluorophenyl)-2-hydroxypropyl]-6-methylmorpholin-3-one

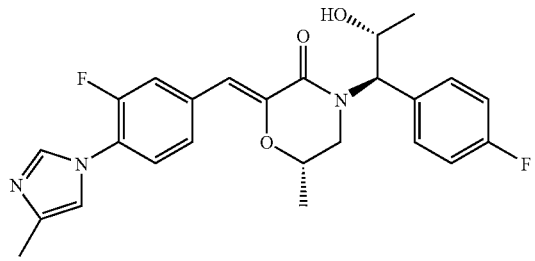

11.0 mg of the title compound was obtained in the same manner as in Example 26 from (S)-4-[(1R,2R)-2-tert-butyl-diphenylsilanyloxy-1-(4-fluorophenyl)propyl]-2-hydroxy- 6-methylmorpholin-3-one prepared from 1-bromo-4-fluorobenzene as a starting material and 3-fluoro-4-(4-methyl-1H-imidazol-1-yl)benzaldehyde.

¹H-NMR (CDCl₃)δ(ppm):
1.31 (d, J=6.0 Hz, 3H), 1.38 (d, J=6.0 Hz, 3H), 2.30 (s, 3H), 3.12 (dd, J=12.8, 9.6 Hz, 1H), 3.57 (dd, J=12.8, 2.4 Hz, 1H), 4.46-4.50 (m, 2H), 5.46 (d, J=8.0 Hz, 1H), 6.79 (s, 1H), 6.97 (s, 1H), 7.05-7.09 (m, 2H), 7.27-7.31 (m, 1H), 7.36-7.39 (m, 2H), 7.43 (dd, J=8.4, 1.6 Hz, 1H), 7.70 (dd, J=13.2, 1.6 Hz, 1H), 7.76 (s, 1H).

EXAMPLE 77

Synthesis of (Z)-2-[1-[3-fluoro-4-(4-methyl-1H-imidazol-1-yl)phenyl]methylidene]-4-[(1R,2R)-2-hydroxy-1-(3,4,5-trifluorophenyl)propyl]-6,6-dimethylmorpholin-3-one

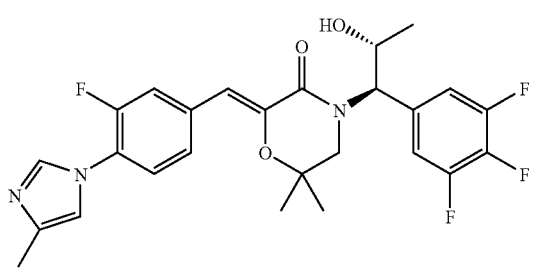

11.6 mg of the title compound was obtained in the same manner as in Example 27 from 4-[(1R,2R)-2-tert-butyldiphenylsilanyloxy-1-(3,4,5-trifluorophenyl)propyl]-2-hydroxy-6,6-dimethylmorpholin-3-one prepared and 3-fluoro-4-(4-methyl-1H-imidazol-1-yl)benzaldehyde.

¹H-NMR (CDCl₃)δ(ppm):
1.28 (s, 3H), 1.34 (d, J=6.0 Hz, 3H), 1.47 (s, 3H), 2.30 (s, 3H), 2.35 (d, J=4.8 Hz, 1H), 3.19 (d, J=12.8 Hz, 1H), 3.60 (d, J=12.8 Hz, 1H), 4.41-4.50 (m, 1H), 5.40 (d, J=7.2 Hz, 1H), 6.84 (s, 1H), 6.97 (s, 1H), 7.12 (dd, J=8.4, 6.4 Hz, 2H), 7.28 (t, J=8.4 Hz, 1H), 7.43 (dd, J=8.4, 2.0 Hz, 1H), 7.71 (dd, J=12.8, 1.2 Hz, 1H), 7.73 (s, 1H).

EXAMPLE 78

Synthesis of (Z)-4-[(1R,2R)-1-(3,4-difluorophenyl)-2-hydroxypropyl]-2-[1-[3-fluoro-4-(4-methyl-1H-imidazol-1-yl)phenyl]methylidene]-6,6-dimethylmorpholin-3-one

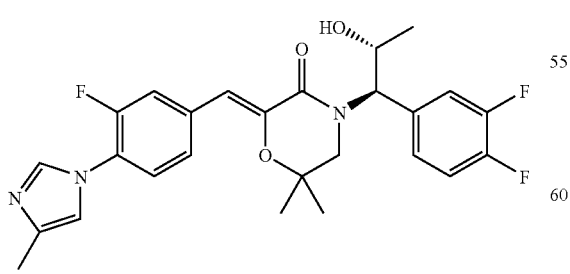

13.9 mg of the title compound was obtained in the same manner as in Example 27 from 4-[(1R,2R)-2-tert-butyldiphenylsilanyloxy-1-(3,4-difluorophenyl)propyl]-2-hydroxy-6, 6-dimethylmorpholin-3-one prepared and 3-fluoro-4-(4-methyl-1H-imidazol-1-yl)benzaldehyde.

¹H-NMR (CDCl₃)δ(ppm):
1.25 (s, 3H), 1.32 (d, J=6.0 Hz, 3H), 1.46 (s, 3H), 2.15 (d, J=6.4 Hz, 1H), 2.30 (s, 3H), 3.17 (d, J=12.8 Hz, 1H), 3.55 (d, J=12.8 Hz, 1H), 4.43-4.48 (m, 1H), 5.42 (d, J=7.6 Hz, 1H), 6.85 (s, 1H), 6.97 (s, 1H), 7.14-7.18 (m, 2H), 7.27-7.30 (m, 2H), 7.43 (dd, J=8.4, 1.6 Hz, 1H), 7.71 (dd, J=13.2, 1.6 Hz, 1H), 7.73 (s, 1H).

EXAMPLE 79

Synthesis of (Z)-2-[1-[3-fluoro-4-(4-methyl-1H-imidazol-1-yl)phenyl]methylidene]-4-[(1R,2R)-1-(4-fluorophenyl)-2-hydroxypropyl]-6,6-dimethylmorpholin-3-one

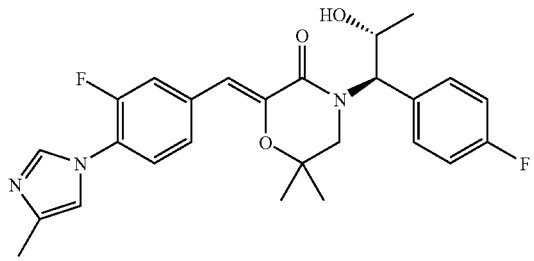

35.1 mg of the title compound was obtained in the same manner as in Example 27 from 4-[(1R,2R)-2-tert-butyldiphenylsilanyloxy-1-(4-fluorophenyl)propyl]-2-hydroxy-6,6-dimethylmorpholin-3-one prepared and 3-fluoro-4-(4-methyl-1H-imidazol-1-yl)benzaldehyde.

¹H-NMR (CDCl₃)δ(ppm):
1.18 (s, 3H), 1.31 (d, J=6.0 Hz, 3H), 1.44 (s, 3H), 2.31 (s, 3H), 3.16 (d, J=12.8 Hz, 1H), 3.56 (d, J=12.8 Hz, 1H), 4.45-4.49 (m, 1H), 5.51 (d, J=8.4 Hz, 1H), 6.84 (s, 1H), 6.97 (s, 1H), 7.03-7.09 (m, 2H), 7.25-7.30 (m, 1H), 7.35-7.44 (m, 3H), 7.70 (d, J=12.8 Hz, 1H), 7.76 (s, 1H).

EXAMPLE 80

Synthesis of (Z)-2-[1-[3-fluoro-4-(4-methyl-1H-imidazol-1-yl)phenyl]methylidene]-4-[(R)-1-(4-fluorophenyl)-2-hydroxyethyl]-6,6-dimethylmorpholin-3-one

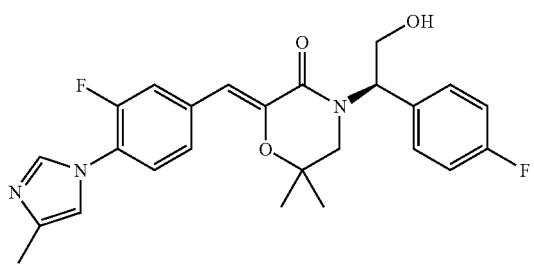

18.6 mg of the title compound was obtained in the same manner as in Example 28 from 4-[(R)-2-tert-butyldiphenylsilanyloxy-1-(4-fluorophenyl)ethyl]-2-hydroxy-6,6-dimethylmorpholin-3-one prepared and 3-fluoro-4-(4-methyl-1H-imidazol-1-yl)benzaldehyde.

$^1$H-NMR (CDCl$_3$)δ(ppm):

1.26 (s, 3H), 1.44 (s, 3H), 2.32 (s, 3H), 3.06 (d, J=12.8 Hz, 1H), 3.40 (d, J=12.8 Hz, 1H), 4.09-4.26 (m, 2H), 5.87 (dd, J=8.0, 5.6 Hz, 1H), 6.85 (s, 1H), 6.98 (s, 1H), 7.04-7.10 (m, 2H), 7.22-7.26 (m, 1H), 7.33-7.39 (m, 3H), 7.69 (d, J=12.8 Hz, 1H), 7.75 (s, 1H).

The compounds in Table 2 were obtained in the same manner.

TABLE 2

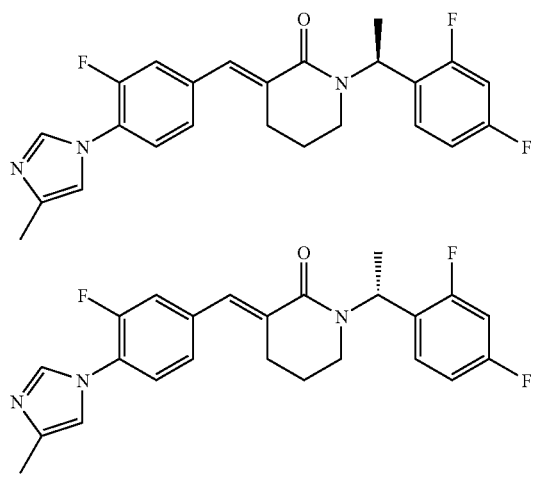

| Example | E$_1$ | DATA: MS m/z | Note |
|---|---|---|---|
| 81 | | M$^+$ + H: 490 (ESI) | Optically active compound |

EXAMPLES 82 AND 83

Synthesis of 1-[1-(2,4-difluorophenyl)ethyl]-3-{1-[3-fluoro-4-(4-methyl-1H-imidazol-1-yl)phenyl]-(E)-methylidene}piperidin-2-one

Synthesis of 3-fluoro-4-(4-methyl-1H-imidazol-1-yl)benzaldehyde 3,4-Difluorobenzaldehyde (30.0 g) was dissolved in DMF (400 mL), and 4-methyl-1H-imidazole (34.8 g) and potassium carbonate (58.5 g) were added to the solution at room temperature. The reaction solution was stirred at 90° C. for six hours. The reaction solution was left to cool to room temperature. Then, ethyl acetate and water were added to the reaction solution, and the organic layer was separated. The resulting organic layer was washed with brine, dried over magnesium sulfate, and then concentrated under reduced pressure. The residue was purified by silica gel column chromatography (elution solvent: heptane-ethyl acetate system), solidified with tert-butyl methyl ether, and separated by filtration to obtain 6.28 g of the title compound. The property values of the compound are as follows.

$^1$H-NMR (CDCl$_3$)δ(ppm):

2.32 (d, J=0.8 Hz, 3H), 7.07 (brs, 1H), 7.57 (dd, J=7.2, 7.2 Hz, 1H), 7.76-7.82 (m, 2H), 7.87 (brs, 1H), 10.01 (d, J=1.6 Hz, 1H).

Synthesis of tert-butyl(E)-5-chloro-2-{1-[3-fluoro-4-(4-methyl-1H-imidazol-1-yl)phenyl]methylidene}valerate 3-Fluoro-4-(4-methyl-1H-imidazol-1-yl)benzaldehyde (2.29 g) and tert-butyl 5-chloro-2-(diethoxyphosphoryl)valerate (3.68 g) were dissolved in a mixed solvent of THF (30 mL) and ethanol (10 mL). Lithium hydroxide monohydrate (1.41 g) was added to the reaction solution at room temperature, and the reaction solution was stirred at room temperature for 18 hours. Saturated sodium bicarbonate water was added to the reaction solution, followed by extraction with ethyl acetate. The resulting extract was dried over magnesium sulfate and then concentrated under reduced pressure. The residue was purified by silica gel column chromatography (elution solvent: heptane-ethyl acetate system), solidified with tert-butyl methyl ether and heptane, and separated by filtration to obtain 1.96 g of the title compound. The property values of the compound are as follows.

$^1$H-NMR (CDCl$_3$)δ(ppm):

1.56 (s, 9H), 1.98-2.07 (m, 2H), 2.31 (d, J=0.8 Hz, 3H), 2.64-2.70 (m, 2H), 3.59 (t, J=6.4 Hz, 2H), 7.01 (brd, J=1.2 Hz, 1H), 7.22-7.31 (m, 2H), 7.39 (dd, J=8.0 Hz, 8.0 Hz, 1H), 7.55 (s, 1H), 7.77-7.80 (m, 1H).

Synthesis of (E)-5-chloro-2-{1-[3-fluoro-4-(4-methyl-1H-imidazol-1-yl)phenyl]methylidene}valeric acid trifluoroacetate chloroform (5 mL) and TFA (10 mL) were added to tert-butyl(E)-5-chloro-2-{1-[3-fluoro-4-(4-methyl-1H-imidazol-1-yl)phenyl]methylidene}valerate (1.96 g), and the reaction solution was stirred at room temperature for one hour. The reaction solution was concentrated under reduced pressure. The residue was solidified with methylene chloride, ethyl acetate, and heptane and separated by filtration to obtain 2.19 g of the title compound. The property value of the compound is as follows.

ESI-MS; m/z 323[M$^+$+H].

Synthesis of (E)-1-[1-(2,4-difluorophenyl)ethyl]-3-{1-[3-fluoro-4-(4-methyl-1H-imidazol-1-yl)phenyl]methylidene}piperidin-2-one DIEA (0.12 mL), WSC (88 mg), and HOBT (62 mg) were added to a solution of (E)-5-chloro-2-{1-[3-fluoro-4-(4-methyl-1H-imidazol-1-yl)phenyl]methylidene}valeric acid trifluoroacetate (100 mg) and 1-(2,4-difluorophenyl)ethylamine (54 mg) in DMF (5 mL) at room temperature, and the reaction solution was stirred at room temperature for one hour. Ethyl acetate was added to the reaction solution, which was then sequentially washed with saturated sodium bicarbonate water, water, a saturated ammonium chloride solution, and brine. The resulting organic layer was dried over magnesium sulfate and then concentrated under reduced pressure. The residue was purified by silica gel column chromatography (carrier: Chromatorex NH; elution solvent: heptane-ethyl acetate system) to obtain 98 mg of (E)-5-chloro-2-{1-[3-fluoro-4-(4-methyl-1H-imidazol-1-yl)phenyl] methylidene}valeric acid [1-(2,4-difluorophenyl)ethyl] amide. (E)-5-chloro-2-{1-[3-fluoro-4-(4-methyl-1H-imidazol-1-yl)phenyl]methylidene}valeric acid [1-(2,4-difluorophenyl)ethyl]amide (98 mg) was dissolved in DMF (3 mL). 60% sodium hydride (10 mg) was added to the reaction solution at room temperature, and the reaction solution was stirred at room temperature for 30 minutes. Saturated sodium bicarbonate water was added to the reaction solution, followed by extraction with ethyl acetate. The resulting extraction layer was dried over magnesium sulfate and then concentrated under reduced pressure. The residue was purified by silica gel column chromatography (carrier: Chromatorex NH; elution solvent: heptane-ethyl acetate system) to obtain 69 mg of the title compound as a racemate. The compound (20 mg) was separated by CHIRALCEL OJ-H manufactured by Daicel Chemical Industries, Ltd. (2 cm×25 cm; mobile phase: ethanol-hexane system) to obtain the title optically active compound with a retention time of 18 minutes (Example 82) (7 mg) and the title optically active compound with a retention time of 24 minutes (Example 83) (4 mg). The property values of the title compound are as follows.

$^1$H-NMR (CDCl$_3$)δ(ppm):
1.59 (d, J=6.8 Hz, 3H), 1.77-1.87 (m, 2H), 2.31 (d, J=0.8 Hz, 3H), 2.69-2.82 (m, 1H), 2.98-3.06 (m, 1H), 3.26-3.33 (m, 1H), 3.69-3.76 (m, 1H), 6.13 (q, J=6.8 Hz, 1H), 6.81 (ddd, J=10.4, 8.8, 2.8 Hz, 1H), 6.85-6.91 (m, 1H), 6.98 (brs, 1H), 7.19-7.28 (m, 2H), 7.31-7.38 (m, 2H), 7.74 (brs, 1H), 7.80 (brs, 1H).

EXAMPLE 84

Synthesis of (E)-(S)-3-{1-[3-fluoro-4-(4-methyl-1H-imidazol-1-yl)phenyl]methylidene}-1-[(1R,2R)-2-hydroxy-1-(3,4,5-trifluorophenyl)propyl]-5-methylpiperidin-2-one

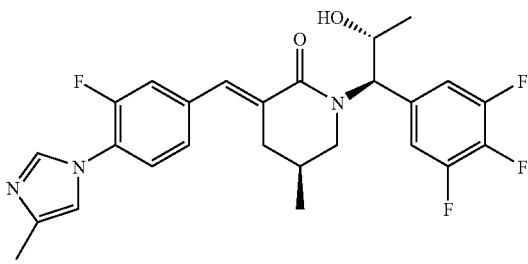

Synthesis of ((R)-3-bromo-2-methylpropoxy)-tert-butyldiphenylsilane tert-Butyldiphenylchlorosilane (83 mL) and imidazole (30 g) were added to a solution of (R)-3-bromo-2-methyl-1-propanol (45 g) in THF (150 mL) under ice-cooling, and the reaction mixture was stirred at room temperature overnight. Water was added to the reaction mixture, followed by extraction with ethyl acetate. The organic layer was washed with brine, dried over anhydrous magnesium sulfate, and then concentrated under reduced pressure. The residue was purified by silica gel column chromatography (carrier: Chromatorex NH; elution solvent: heptane-ethyl acetate system) to obtain 117 g of the title compound. The property values of the compound are as follows.

$^1$H-NMR (CDCl$_3$)δ(ppm):
1.00 (dd, J=0.8 Hz, 6.8 Hz, 3H), 1.06 (s, 9H), 2.00-2.09 (m, 2H), 3.50-3.65 (m, 4H), 7.36-7.46 (m, 6H), 7.65-7.68 (m, 4H).

Synthesis of tert-butyl(S)-5-(tert-butyldiphenylsilanyloxy)-2-(diethoxyphosphoryl)-4-methylvalerate A solution tert-butyl diethylphosphonoacetate (64 g) in THF (100 mL) was added dropwise to a suspension of sodium hydride (containing 40% mineral oil, 13.2 g) in THF (400 mL) under ice-cooling, and the reaction mixture was stirred at room temperature for 75 minutes. A solution of ((R)-3-bromo-2-methylpropoxy)-tert-butyldiphenylsilane (99.4 g) in THF (100 mL) was added dropwise to the reaction mixture, which was then heated under reflux for 23 hours. Ice water was added to the reaction mixture, followed by extraction with ethyl acetate. The organic layer was washed with brine, dried over anhydrous magnesium sulfate, and then concentrated under reduced pressure. The residue was purified by silica gel column chromatography (elution solvent: heptane-ethyl acetate system) to obtain 74.6 g of the title compound. The property values of the compound are as follows.

$^1$H-NMR (CDCl$_3$)δ(ppm):
0.91-0.95 (m, 3H), 1.05 (s, 9H), 1.29-1.35 (m, 6H), 1.45 (s, 9H), 1.68-1.79 (m, 1H), 1.83-2.04 (m, 1H), 2.16-2.26 (m, 1H), 2.95-3.14 (m, 1H), 3.46-3.51 (m, 2H), 4.09-4.17 (m, 4H), 7.35-7.42 (m, 6H), 7.63-7.67 (m, 4H).

tert-Butyl(E)-(S)-5-(tert-butyldiphenylsilanyloxy)-2-[3-fluoro-4-(4-methyl-1H-imidazol-1-yl)phenyl]methylidene]-4-methylvalerate A solution of tert-butyl (4S)-5-(tert-butyldiphenylsilanyloxy)-2-(diethoxyphosphoryl)-4-methylvalerate in THF (50 mL) was added to a solution of tert-butoxy potassium (3.3 g) in THF (50 mL) in a nitrogen atmosphere at −70° C., and the reaction mixture was stirred for 40 minutes. A solution of 3-fluoro-4-(4-methyl-1H-imidazol-1-yl)benzaldehyde (6 g) in THF (50 mL) was added to the reaction mixture at −70° C., and the reaction mixture was stirred for 100 minutes and at room temperature overnight. Water was added to the reaction mixture, followed by extraction with ethyl acetate. The organic layer was washed with brine, dried over anhydrous magnesium sulfate, and then concentrated under reduced pressure. The residue was purified by silica gel column chromatography (elution solvent: heptane-ethyl acetate system) to obtain 9.34 g of the title compound. The property values of the compound are as follows.

$^1$H-NMR (CDCl$_3$)δ(ppm):
1.55 (s, 9H), 1.99-2.08 (m, 2H), 2.30 (s, 3H), 2.63-2.71 (m, 2H), 3.59 (t, J=6.4 Hz, 2H), 3.87 (s, 3H), 6.93 (m, 1H), 7.00 (d, J=1.2 Hz, 1H), 7.09 (dd, J=8.4, 1.2 Hz, 1H), 7.27 (d, J=8.4 Hz, 1H), 7.58 (s, 1H), 7.72 (m, 1H).

Synthesis of tert-butyl(E)-(S)-5-chloro-2-[3-fluoro-4-(4-methylimidazol-1-yl)phenyl]methylidene]-4-methylvalerate TBAF (1 M solution in THF, 22.8 mL) was added to a solution of tert-butyl(E)-(S)-5-(tert-butyldiphenylsilanyloxy)-2-[3-fluoro-4-(4-methyl-1H-imidazol-1-yl)phenyl]methylidene]-4-methylvalerate (9.34 g) in THF (100 mL) under ice-cooling, and the reaction mixture was stirred at room temperature for four hours. Ice water was added to the reaction mixture, followed by extraction with ethyl acetate. The organic layer was washed with brine, dried over anhydrous magnesium sulfate, and then concentrated under reduced pressure. The residue was purified by silica gel column chromatography (elution solvent: heptane-ethyl acetate system), and the target fractions were collected and concentrated to obtain a colorless oil (4.2 g). Triphenylphosphine (3.15 g) was dissolved in a solution of the colorless oil in methylene chloride (50 mL). N-chlorosuccinimide (1.47 g) was added to the reaction solution under ice-cooling, and the reaction mixture was stirred at 0° C. for one hour. Ice water was added to the reaction mixture, followed by extraction with chloroform. The organic layer was washed with brine, dried over anhydrous magnesium sulfate, and then concentrated under reduced pressure. The residue was purified by silica gel column chromatography (carrier: Chromatorex NH; elution solvent: heptane-ethyl acetate system) to obtain 2.84 g of the title compound. The property values of the compound are as follows.

$^1$H-NMR (CDCl$_3$)δ(ppm):
0.96 (d, J=6.8 Hz, 3H), 1.55 (s, 9H), 2.12-2.22 (m, 1H), 2.49 (dd, J=14 Hz, 8 Hz, 1H), 2.74 (dd, J=14 Hz, 6.4 Hz, 1H), 3.37-3.46 (m, 2H), 7.00-7.02 (m, 1H), 7.22-7.29 (m, 1H), 7.38 (t, J=8 Hz, 1H), 7.56 (s, 1H), 7.77 (t, J=1.6 Hz, 1H).

Synthesis of (E)-(S)-5-chloro-2-{1-[3-fluoro-4-(4-methyl-1H-imidazol-1-yl)phenyl]methylidene}-4-methylvaleric acid hydrochloride A solution of tert-butyl(E)-(S)-5-chloro-2-[3-fluoro-4-(4-methylimidazol-1-yl)phenyl]methylidene]-4-methylvalerate (2.84 g) in trifluoroacetic acid (20 mL) was stirred at room temperature for one hour. The reaction mixture was concentrated under reduced pressure, ethyl acetate (10 mL) and a solution of 4 N hydrochloric acid in ethyl acetate (10 mL) were added to the residue, and the reaction solution was concentrated under reduced pressure. This operation was repeated twice. Diethyl ether was added to the residue, and the reaction mixture was rubbed with a spatula. The solidified and precipitated insoluble matter was collected by filtration to obtain 2.05 g of the title compound. The property value of the compound is as follows.
ESI-MS; m/z 337[M$^+$+H].

Synthesis of (E)-(S)-3-{1-[3-fluoro-4-(4-methyl-1H-imidazol-1-yl)phenyl]methylidene}-1-[(1R,2R)-2-hydroxy-1-(3,4,5-trifluorophenyl)propyl]-5-methylpiperidin-2-one DIEA (0.47 mL), WSC (257 mg), and HOBT (181 mg) were added to a suspension of (E)-(S)-5-chloro-2-{1-[3-fluoro-4-(4-methyl-1H-imidazol-1-yl)phenyl]methylidene}-4-methylvaleric acid hydrochloride (250 mg) and (1R,2R)-1-amino-1-(3,4,5-trifluorophenyl)propan-2-ol hydrochloride (243 mg) in DMF (5 mL) at room temperature, and the reaction solution was stirred at room temperature for one hour. Ethyl acetate was added to the reaction solution, which was then sequentially washed with saturated sodium bicarbonate water, water, a saturated ammonium chloride solution, and brine. The resulting organic layer was dried over magnesium sulfate and then concentrated under reduced pressure. The residue was dissolved DMF (8 mL). 60% sodium hydride (32 mg) was added at 0° C., and the reaction solution was stirred at 0° C. for one hour. Ethyl acetate was added to the reaction solution, which was then sequentially washed with saturated sodium bicarbonate water, water, a saturated ammonium chloride solution, and brine. The resulting organic layer was dried over magnesium sulfate and then concentrated under reduced pressure. The residue was purified by silica gel column chromatography (carrier: Chromatorex NH; elution solvent: heptane-ethyl acetate system->ethyl acetate-methanol system) to obtain 176 mg of the title compound. The property values of the compound are as follows.

ESI-MS; m/z 488[M$^+$+H].
$^1$H-NMR (CDCl$_3$)δ(ppm):
1.03 (d, J=6.8 Hz, 3H), 1.32 (d, J=6.4 Hz, 3H), 1.86-2.00 (m, 1H), 2.31 (s, 3H), 2.39 (ddd, J=15.6, 11.6, 2.8 Hz, 1H), 2.65 (brs, 1H), 2.93 (brd, J=15.6, 3.6 Hz, 1H), 3.20-3.29 (m, 2H), 4.44-4.53 (m, 1H), 5.32 (d, J=7.2 Hz, 1H), 6.99-7.02 (m, 1H), 7.05-7.11 (m, 2H), 7.22-7.30 (m, 2H), 7.39 (dd, J=8.0, 8.0 Hz, 1H), 7.75-7.78 (m, 1H), 7.81 (brs, 1H).

EXAMPLE 85

Synthesis of (E)-3-{1-[3-fluoro-4-(4-methyl-1H-imidazol-1-yl)phenyl]methylidene}-1-[(1R,2R)-2-hydroxy-1-(3,4,5-trifluorophenyl)propyl]piperidin-2-one

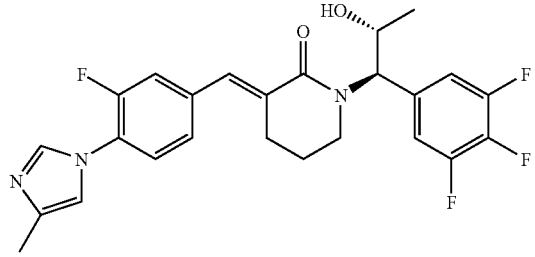

A solution of 4 N hydrogen chloride in dioxane (10 mL) was added to a solution of tert-butyl [(1R,2R)-2-hydroxy-1-(3,4,5-trifluorophenyl)propyl]carbamate (2.85 g) in dioxane (10 mL) at room temperature, and the reaction solution was stirred at room temperature for five hours. Hexane (80 mL) was added to the reaction solution at room temperature, and the reaction solution was stirred at room temperature for 20 minutes. The resulting solid was separated by filtration to obtain (1R,2R)-1-amino-1-(3,4,5-trifluorophenyl)propane-2-ol hydrochloride (2.16 g). DIEA (1.59 mL), WSC (880 mg), and HOBT (620 mg) were added to a solution of (E)-5-chloro-2-{1-[3-fluoro-4-(4-methyl-1H-imidazol-1-yl)phenyl]methylidene}valeric acid trifluoroacetate (1.00 g) and (1R,2R)-1-amino-1-(3,4,5-trifluorophenyl)propan-2-ol hydrochloride (664 mg) in DMF (25 mL) at room temperature, and the reaction solution was stirred at room temperature for one hour. Ethyl acetate was added to the reaction solution, which was then sequentially washed with saturated sodium bicarbonate water, water, a saturated ammonium chloride solution, and brine. The resulting organic layer was dried over magnesium sulfate and then concentrated under reduced pressure. The resulting solid was washed with heptane to obtain (E)-5-chloro-2-{1-[3-fluoro-4-(4-methyl-1H-imidazol-1-yl)phenyl]methylidene}valeric acid [(1R,2R)-2-hydroxy-1-(3,4,5-trifluorophenyl)propyl]amide (1.10 g). (E)-5-chloro-2-{1-[3-fluoro-4-(4-methyl-1H-imidazol-1-yl)phenyl]methylidene}valeric acid [(1R,2R)-2-hydroxy-1-(3,4,5-trifluorophenyl)propyl]amide (1.10 g) was dissolved in DMF (25 mL). 60% sodium hydride (104 mg) was added to the reaction solution at room temperature, and the reaction solution was stirred at room temperature for one hour. Ethyl acetate was added to the reaction solution, which was then sequentially washed with saturated sodium bicarbonate water, water, a saturated ammonium chloride solution, and brine. The resulting organic layer was dried over magnesium sulfate and then concentrated under reduced pressure. The residue was purified by silica gel column chromatography (carrier: Chromatorex NH; elution solvent: heptane-ethyl acetate system->ethyl acetate-methanol system), solidified with ethyl acetate and heptane, and separated by filtration to obtain 780 mg of the title compound. The property values of the compound are as follows.

ESI-MS; m/z 474[M$^+$+H].

$^1$H-NMR (CDCl$_3$)δ(ppm):

1.31 (d, J=6.0 Hz, 3H), 1.77-1.98 (m, 2H), 2.31 (d, J=0.8 Hz, 3H), 2.73 (brd, J=6.4 Hz, 1H), 2.77-2.85 (m, 2H), 3.27 (ddd, J=12.4, 7.2, 4.0 Hz, 1H), 3.54 (ddd, J=12.4, 8.0, 4.0 Hz, 1H), 4.43-4.53 (m, 1H), 5.28 (d, J=7.6 Hz, 1H), 6.99-7.02 (m, 1H), 7.04-7.12 (m, 2H), 7.23-7.31 (m, 2H), 7.38 (dd, J=8.0, 8.0 Hz, 1H), 7.75-7.77 (m, 1H), 7.80-7.83 (m, 1H).

EXAMPLE 86

Synthesis of (E)-1-[(1R,2R)-1-(3,4-difluorophenyl)-2-hydroxypropyl]-3-{1-[3-fluoro-4-(4-methyl-1H-imidazol-1-yl)phenyl]methylidene}piperidin-2-one

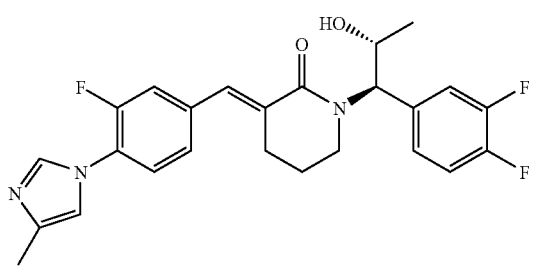

A solution of 4 N hydrogen chloride in ethyl acetate (10 mL) was added to a solution of tert-butyl [(1R,2R)-1-(3,4-difluorophenyl)-2-hydroxypropyl]carbamate (960 mg) in methanol (10 mL) at room temperature, and the reaction solution was stirred at room temperature for 30 minutes. The reaction solution was concentrated under reduced pressure to obtain (1R,2R)-1-amino-1-(3,4-difluorophenyl)propan-2-ol hydrochloride (747 mg). DIEA (1.59 mL), WSC (880 mg), and HOBT (620 mg) were added to a solution of (E)-5-chloro-2-{1-[3-fluoro-4-(4-methyl-1H-imidazol-1-yl)phenyl]methylidene]valeric acid trifluoroacetate (1.00 g) and (1R,2R)-1-amino-1-(3,4-difluorophenyl)propan-2-ol hydrochloride (612 mg) in DMF (20 mL) at room temperature, and the reaction solution was stirred at room temperature for one hour. Ethyl acetate was added to the reaction solution, which was then sequentially washed with saturated sodium bicarbonate water, water, a saturated ammonium chloride solution, and brine. The resulting organic layer was dried over magnesium sulfate and then concentrated under reduced pressure. The resulting solid was washed with heptane to obtain (E)-5-chloro-2-{1-[3-fluoro-4-(4-methyl-1H-imidazol-1-yl)phenyl]methylidene}valeric acid [(1R,2R)-1-(3,4-difluorophenyl)-2-hydroxypropyl]amide (977 mg). (E)-5-chloro-2-{1-[3-fluoro-4-(4-methyl-1H-imidazol-1-yl)phenyl]methylidene}valeric acid [(1R,2R)-1-(3,4-difluorophenyl)-2-hydroxypropyl]amide (977 mg) was dissolved in DMF (25 mL). 60% sodium hydride (95 mg) was added to the reaction solution at room temperature, and the reaction solution was stirred at room temperature for 30 minutes. Water was added to the reaction solution, followed by extraction with ethyl acetate. The resulting extract was dried over magnesium sulfate and then concentrated under reduced pressure. The residue was purified by silica gel column chromatography (carrier: Chromatorex NH; elution solvent: ethyl acetate-methanol system), solidified with ethyl acetate and heptane, and separated by filtration to obtain 740 mg of the title compound. The property values of the compound are as follows.

ESI-MS; m/z 456[M$^+$+H].

$^1$H-NMR (CDCl$_3$)δ(ppm):

1.30 (d, J=6.0 Hz, 3H), 1.74-1.96 (m, 2H), 2.31 (d, J=0.4 Hz, 3H), 2.68-2.85 (m, 3H), 3.19-3.28 (m, 1H), 3.47-3.56 (m, 1H), 4.43-4.52 (m, 1H), 5.36 (d, J=8.0 Hz, 1H), 6.99 (s, 1H), 7.10-7.18 (m, 2H), 7.21-7.29 (m, 3H), 7.36 (dd, J=8.4, 7.6 Hz, 1H), 7.75 (brs, 1H), 7.80 (brs, 1H).

The compounds in Tables 3-1, 3-2, and 3-3 were obtained in the same manner.

TABLE 3-1

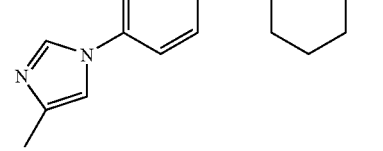

| Example | E$_1$ | DATA: MS m/z | Notes |
|---|---|---|---|
| 87 | 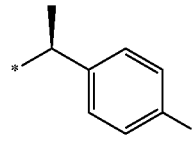 | M$^+$ + H: 408 (ESI) | Optically active compound |
| 88 | 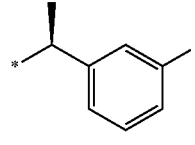 | M$^+$ + H: 408 (ESI) | Optically active compound |
| 89 | 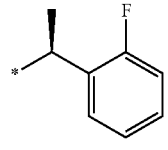 | M$^+$ + H: 408 (ESI) | Optically active compound |
| 90 | 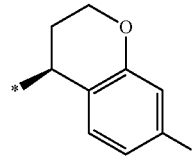 | M$^+$ + H: 436 (ESI) | Optically active compound |

TABLE 3-1-continued

| Example | E₁ | DATA: MS m/z | Notes |
|---|---|---|---|
| 91 | (1-hydroxyethyl)(3,5-difluorophenyl)methyl* | M⁺ + H: 456 (ESI) | Optically active compound (separation column AD-H: retention time 24 minuts) |
| 92 | (1-hydroxyethyl)(3,5-difluorophenyl)methyl* | M⁺ + H: 456 (ESI) | Optically active compound (separation column AD-H: retention time 29 minuts) |
| 93 | (1-hydroxy-3,3-dimethylindan-2-yl)* | M⁺ + H: 446 (ESI) | Optically active compound (separation column AD-H: retention time 8.0 minuts) |
| 94 | (1-hydroxy-3,3-dimethylindan-2-yl)* | M⁺ + H: 446 (ESI) | Optically active compound (separation column AD-H: retention time 34 minuts) |
| 95 | 2-(hydroxymethyl)-2-(3,4,5-trifluorophenyl)propyl* | M⁺ + H: 474 (ESI) | Optically active compound (separation column AD-H: retention time 53 minuts) |
| 96 | 2-(hydroxymethyl)-2-(3,4,5-trifluorophenyl)propyl* | M⁺ + H: 474 (ESI) | Optically active compound (separation column AD-H: retention time 61 minuts) |

TABLE 3-1-continued

| Example | E₁ | DATA: MS m/z | Notes |
|---|---|---|---|
| 97 | (1-hydroxyethyl)(6-chloropyridin-3-yl)methyl* | M⁺ + H: 455 (ESI) | Optically active compound |
| 98 | 2-(4-fluorophenyl)propan-2-yl* | M⁺ + H: 422 (ESI) | |

TABLE 3-2

| Example | E₁ | DATA: MS m/z | Notes |
|---|---|---|---|
| 99 | 1-(2,6-difluoropyridin-3-yl)ethyl* | M⁺ + H: 441 (ESI) | Optically active compound |
| 100 | (1-hydroxyethyl)(4-fluorophenyl)methyl* | M⁺ + H: 452 (ESI) | Optically active compound |
| 101 | (1-hydroxyethyl)(3,4-difluoro-5-methylphenyl)methyl* | M⁺ + H: 488 (ESI) | Optically active compound |

TABLE 3-2-continued

| Example | E₁ | DATA: MS m/z | Notes |
|---|---|---|---|
| 102 | (structure with HO, F, difluorophenyl) | M⁺ + H: 470 (ESI) | Optically active compound |

TABLE 3-3

| Example | E₁ | DATA: MS m/z | Notes |
|---|---|---|---|
| 103 | (structure with difluoropyridine) | M⁺ + H: 441 (ESI) | Optically active compound |
| 104 | (structure with HO, fluorophenyl) | M⁺ + H: 452 (ESI) | Optically active compound |
| 105 | (structure with HO, difluorophenyl) | M⁺ + H: 470 (ESI) | Optically active compound |

EXAMPLE 106

Synthesis of (Z)-(6S,8aR)-3-{1-[3-methoxy-4-(4-methyl-1H-imidazol-1-yl)benzylidene]-6-(3,4,5-trifluorophenyl)tetrahydropyrrolo[2,1-c][1,4]oxazin-4-one

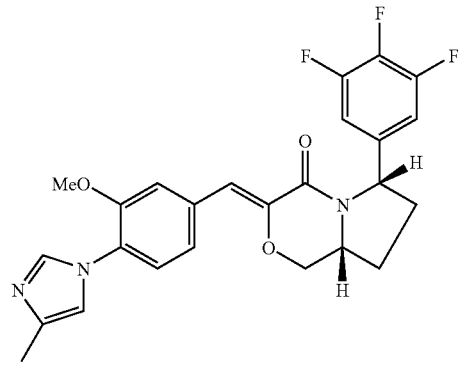

Synthesis of ethyl (2R,5S)-5-(3,4,5-trifluorophenyl)pyrrolidine-2-carboxylate

To a solution of (R)-5-oxopyrrolidine-1,2-dicarboxylic acid 1-tert-butyl ester 2-ethyl ester (CAS No. 128811-48-3; 4.1 g) in tetrahydrofuran (100 mL), 3,4,5-trifluorophenylmagnesium bromide (0.35 M solution in diethyl ether; 55 mL) was added dropwise at −40° C. over 20 minutes, and the reaction solution was stirred at −40° C. for five hours. Saturated aqueous ammonium chloride and ethyl acetate were added to the solution. The reaction solution was heated to room temperature, and the organic layer was separated. The resulting organic layer was washed with brine, dried over anhydrous magnesium sulfate, and then concentrated under reduced pressure. The residue was purified by silica gel column chromatography (heptane->heptane:ethyl acetate=1:1) to obtain 4.8 g of ethyl (R)-2-tert-butoxycarbonylamino-5-oxo-5-(3,4,5-trifluorophenyl)pentanoate. A solution of 4 N hydrochloric acid in ethyl acetate (30 mL) was added to a solution of the resulting ethyl(R)-2-tert-butoxycarbonylamino-5-oxo-5-(3,4,5-trifluorophenyl)pentanoate in ethyl acetate (30 mL), and the solution was stirred for 15 hours. The reaction solution was concentrated under reduced pressure. Ethyl acetate and saturated sodium bicarbonate water were added to the residue, and the organic layer was separated. The resulting organic layer was dried over anhydrous magnesium sulfate and then concentrated under reduced pressure. 10% palladium-carbon (100 mg) was added to a solution of the residue in ethyl acetate (50 mL), and the reaction solution was stirred in a hydrogen stream at 1 atm for six hours. The reaction solution was filtered through celite, and the filtrate was concentrated under reduced pressure to obtain 2.91 g of the title compound. The property value of the compound is as follows.

ESI-MS; m/z 274[M⁺+H].

Synthesis of [(2R,5S)-5-(3,4,5-trifluorophenyl)pyrrolidine-2-yl]methanol

LAH (483 mg) was added to a solution of ethyl (2R,5S)-5-(3,4,5-trifluorophenyl)pyrrolidine-2-carboxylate (2.91 g) in THF (50 mL) at −15° C. over one hour. The reaction solution was stirred at −15° C. for 19 hours. Water (0.5 mL), a 5 N sodium hydroxide solution (0.5 mL), and water (1.5 mL) were sequentially added to the reaction solution, and the mixture was stirred at room temperature for 30 minutes. The reaction solution was filtered through celite, and the filtrate was concentrated under reduced pressure to obtain 2.4 g of the title compound. The property values of the compound are as follows.

ESI-MS; m/z 232[M$^+$+H].
$^1$H-NMR (CDCl$_3$)δ(ppm):
1.51-1.63(m, 1H), 1.66-1.77(m, 1H), 1.89-2.00(m, 1H), 2.10-2.20(m, 1H), 3.43(dd, J=10.0,5.6 Hz, 1H), 3.47-3.55(m, 1H), 3.64(dd, J=10.0,3.6 Hz, 1H), 4.23(t,J=8.0 Hz, 1H), 7.02 (t,J=8.0 Hz, 2H).

Synthesis of (Z)-(6S,8aR)-3-{1-[3-methoxy-4-(4-methyl-1H-imidazol-1-yl)benzylidene]-6-(3,4,5-trifluorophenyl)tetrahydropyrrolo[2,1-c][1,4]oxazin-4-one 521 mg of the title compound was obtained from [(2R,5S)-5-(3,4,5-trifluorophenyl)pyrrolidine-2-yl]methanol as a starting material in the same manner as in Example 41. The property values of the compound are as follows.

ESI-MS; m/z 470[M$^+$+H].
$^1$H-NMR (CDCl$_3$)δ(ppm):
1.71-1.82(m, 1H), 1.92-1.98(m, 1H), 2.10-2.20(m, 2H), 2.30(s, 3H), 2.37-2.48(m, 1H), 3.86(s, 3H), 4.09-4.13(m, 1H), 4.68(d, J=8 Hz, 1H), 5.14(d, J=9.2 Hz, 1H), 6.75(s, 1H), 6.84(dd, J=8.4 Hz, 6.4 Hz, 2H), 6.93-6.94(m, 1H), 7.21(d, J=8 Hz, 1H), 7.37-7.41(m, 2H), 7.72(d, J=1.2 Hz, 1H).

EXAMPLE 107

Synthesis of (6S,9aR)-6-(4-chlorophenyl)-3-{1-[3-methoxy-4-(4-methyl-1H-imidazol-1-yl)phenyl]-(Z)-methylidene}hexahydropyrido[2,1-c][1,4]oxazin-4-one

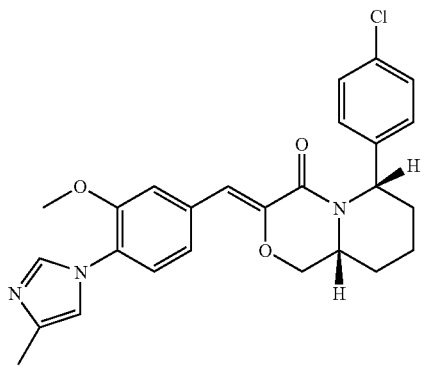

Synthesis of methyl(2R,6S)-6-(4-chlorophenyl)piperidine-2-carboxylate

To a solution of 1-tert-butyl(R)-6-oxopiperidine-1,2-dicarboxylate (CAS No. 183890-36-0, 9.00 g) in THF (120 ml), 4-chlorophenylmagnesium bromide (1.0 M solution in diethyl ether, 42 ml) was added in a nitrogen atmosphere at −78° C. over 20 minutes. The reaction solution was stirred at −78° C. to −40° C. for 1.5 hours, and then quenched with a saturated ammonium chloride solution at −40° C. Water was added to the reaction solution, followed by extraction with ethyl acetate. The resulting extract was dried over magnesium sulfate and then concentrated under reduced pressure. The residue was purified by silica gel column chromatography (elution solvent: heptane-ethyl acetate system) to obtain methyl(R)-2-tert-butoxycarbonylamino-6-(4-chlorophenyl)-6-oxohexanoate (9.53 g). A solution of 4 N hydrogen chloride in ethyl acetate (90 ml) was added to a solution of methyl(R)-2-tert-butoxycarbonylamino-6-(4-chlorophenyl)-6-oxohexanoate (9.53 g) in ethyl acetate (90 ml) at room temperature, and the reaction solution was stirred at room temperature for 12 hours. The reaction solution was concentrated under reduced pressure, and the residue was made basic with a saturated sodium bicarbonate solution. Then, chloroform was added to the residue, and the mixture was stirred at room temperature for two hours. The organic layer was separated, dried over magnesium sulfate, and then concentrated under reduced pressure. Sodium cyanoborohydride (3.29 g) and then acetic acid (4.27 ml) were added to a solution of the residue in methanol (150 ml) at 0° C., and the reaction solution was stirred at 0° C. for one hour and at room temperature for one hour. A saturated sodium bicarbonate solution was added to the reaction solution, followed by extraction with chloroform. The resulting extract was dried over magnesium sulfate and then concentrated under reduced pressure. The residue was purified by silica gel column chromatography (elution solvent: heptane-ethyl acetate system) and solidified with a heptane-diisopropyl ether system to obtain 2.47 g of the title compound. The property values of the compound are as follows.

ESI-MS; m/z 254 [M$^+$+H].
$^1$H-NMR (CDCl$_3$)δ(ppm):
1.38-1.60(m, 3H), 1.72-1.78(m, 1H), 1.96-2.03(m, 1H), 2.05-2.12(m, 1H), 2.17(brs, 1H), 3.49(dd, J=10.8, 2.8 Hz, 1H), 3.63(d d, J=11.2, 2.8 Hz, 1H), 3.73(s, 3H), 7.25-7.34(m, 4H).

Synthesis of [(2R,6S)-6-(4-chlorophenyl)piperidin-2-yl]methanol

Lithium aluminum hydride (508 mg) was suspended in THF (50 mL) in a nitrogen atmosphere. Methyl (2R,6S)-6-(4-chlorophenyl)piperidine-2-carboxylate (2.47 g) was added to the suspension at −20° C., and the reaction solution was stirred at −20° C. for one hour. Water (0.51 ml), a 5 N sodium hydroxide solution (0.51 ml), and water (1.53 ml) were sequentially added to the reaction solution at −20° C., and the reaction solution was stirred at room temperature for 15 minutes. Ethyl acetate was added to the reaction solution. Then, the reaction solution was filtered through celite, and the filtrate was concentrated under reduced pressure. The residue was purified by silica gel column chromatography (carrier: Chromatorex NH; elution solvent: heptane-ethyl acetate system) to obtain 1.90 g of the title compound. The property value of the compound is as follows.

ESI-MS; m/z 226[M$^+$+H].

Synthesis of (6S,9aR)-6-(4-chlorophenyl)-3-{1-[3-methoxy-4-(4-methyl-1H-imidazol-1-yl)phenyl]-(Z)-methylidene}hexahydropyrido[2,1-c][1,4]oxazin-4-one 199 mg of the title compound was obtained from [(2R,6S)-6-(4-chlorophenyl)piperidin-2-yl]methanol (270 mg) in the same manner as in Example 40. The property values of the compound are as follows.

ESI-MS; m/z 464 [M$^+$+H].
$^1$H-NMR(CDCl$_3$)δ(ppm):

1.39-1.54(m, 2H), 1.66-1.77(m, 2H), 2.14-2.25(m, 2H), 2.30(s, 3H), 3.86(s, 3H), 4.03-4.13(m, 2H), 4.35(dd, J=10.4, 2.4 Hz, 1H), 5.37(t,J=4.0 Hz, 1H), 6.83(s, 1H), 6.93(s, 1H), 7.20-7.23(m, 3H), 7.30-7.33(m, 2H), 7.36-7.40(m, 2H), 7.73 (s, 1H).

EXAMPLE 108

Synthesis of (6R,9aR)-3-{1-[3-methoxy-4-(4-methyl-1H-imidazol-1-yl)phenyl]-(Z)-methylidene}-6-(3,4,5-trifluorophenyl)tetrahydro[1,4]oxazino[3,4-c][1,4]oxazin-4-one

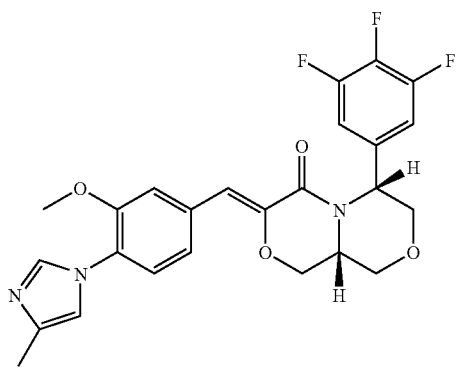

Synthesis of (S)-5-benzyloxymethylmorpholin-3-one

Bromoacetyl chloride (5.06 mL) was added to a mixed solution of (R)-(+)-2-amino-3-benzyloxy-1-propanol (10 g) in toluene (100 mL) and a 2 N sodium hydroxide solution (100 mL) under ice-cooling. The reaction solution was stirred at 0° C. for 30 minutes and then at 60° C. for one hour. The reaction solution was returned to room temperature. Then, a toluene-THF (1:1) mixed solution was added to the reaction solution, and the organic layer was separated. The resulting organic layer was dried over anhydrous magnesium sulfate and then concentrated under reduced pressure. The residue was purified by silica gel column chromatography (elution solvent: heptane-ethyl acetate system) to obtain 1.36 g of the title compound. The property values of the compound are as follows.

¹H-NMR (CDCl₃)δ(ppm):
3.42(t,J=9.2 Hz, 1H), 3.54(dd, J=9.2, 5.2 Hz, 1H), 3.62(dd, J=12.0, 6.0 Hz, 1H), 3.75(m, 1H), 3.86(dd, J=12.0, 4.0 Hz, 1H), 4.12(d, J=16.8 Hz, 1H), 4.18(d, J=16.8 Hz, 1H), 4.53(s, 2H), 6.29(brs, 1H), 7.28-7.40(m, 5H).

Synthesis of tert-butyl(S)-3-benzyloxymethyl-5-oxomorpholine-4-carboxylate

TEA (1.72 mL), 4-dimethylaminopyridine (189 mg), and di-tert-butyl dicarbonate (2.02 g) were added to a solution of (S)-5-benzyloxymethylmorpholin-3-one (1.36 g) in acetonitrile (25 mL). The reaction solution was stirred at room temperature for two hours. Then, brine and ethyl acetate were added to the reaction solution, and the organic layer was separated. The resulting organic layer was dried over anhydrous magnesium sulfate and then concentrated under reduced pressure. The residue was purified by silica gel column chromatography (elution solvent: heptane-ethyl acetate system) to obtain 1.65 g of the title compound. The property values of the compound are as follows.

¹H-NMR (CDCl₃)(ppm):
1.50(s, 9H), 3.57(dd, J=8.8, 4.8 Hz, 1H), 3.68-3.75(m, 2H), 4.08-4.28(m, 4H), 4.53(d, J=12.0 Hz, 1H), 4.58(d, J=12.0 Hz, 1H), 7.25-7.36(m, 5H).

Synthesis of tert-butyl {(S)-1-benzyloxymethyl-2-[2-oxo-2-(3,4,5-trifluorophenyl)ethoxy]ethyl}carbamate To a suspension of magnesium (249 mg) in diethyl ether (5 mL), 1-bromo-3,4,5-trifluorobenzene (446 μL) was added dropwise at 40° C. over 10 minutes, and the reaction solution was stirred at 40° C. for one hour. This solution was added dropwise to a solution of tert-butyl (S)-3-benzyloxymethyl-5-oxomorpholine-4-carboxylate (1.1 g) in tetrahydrofuran (30 mL) at −40° C. over 10 minutes, and the reaction solution was stirred at −40° C. for one hour. A saturated ammonium chloride solution was added to the solution in small portions at −40° C., and the reaction solution was returned to room temperature. Ethyl acetate was added to the reaction solution, and the organic layer was separated. The resulting organic layer was washed with brine, and then dried over anhydrous magnesium sulfate and concentrated under reduced pressure. The residue was purified by silica gel column chromatography (heptane-ethyl acetate system) to obtain 952 mg of the title compound. The property values of the compound are as follows.

¹H-NMR (CDCl₃)δ(ppm):
1.43(s, 9H), 3.54(dd, J=9.2, 6.0 Hz, 1H), 3.61-3.71(m, 3H), 3.96(m, 1H), 4.51(s, 2H), 4.61(s, 2H), 5.02(m, 1H), 7.21-7.35 (m, 5H), 7.50-7.62(m, 2H).

Synthesis of [(3S,5R)-5-(3,4,5-trifluorophenyl)morpholine-3-yl]methanol

A solution of 4 N hydrochloric acid in ethyl acetate (30 mL) was added to a solution of tert-butyl {(S)-1-benzyloxymethyl-2-[2-oxo-2-(3,4,5-trifluorophenyl)ethoxy]ethyl}carbamate (3.55 g) in ethyl acetate (30 mL) at room temperature. The reaction solution was stirred at room temperature for one hour and then concentrated under reduced pressure. 10% palladium-carbon (containing 50% water, 167 mg) was added to a solution of the resulting residue in methanol (50 mL), and the reaction solution was stirred in a hydrogen atmosphere at room temperature for 18 hours. Palladium-carbon in the reaction solution was removed by filtration, and then the filtrate was concentrated under reduced pressure. A saturated sodium bicarbonate solution and ethyl acetate were added to the resulting residue, and the organic layer was separated. The organic layer was washed with brine. The resulting organic layer was dried over anhydrous magnesium sulfate and then concentrated under reduced pressure. The residue was purified by silica gel column chromatography (elution solvent: heptane-ethyl acetate system) to obtain 1.52 g of the title compound. The property values of the compound are as follows.

¹H-NMR (CDCl₃)δ(ppm):
3.13-3.22(m, 2H), 3.34(dd, J=10.8, 10.4 Hz, 1H), 3.53(dd, J=10.8, 6.4 Hz, 1H), 3.67(dd, J=10.8, 4.0 Hz, 1H), 3.77(dd, J=10.8, 3.2 Hz, 1H), 3.85(dd, J=10.8, 3.2 Hz, 1H), 3.96(dd, J=10.4,3.2 Hz, 1H), 7.02-7.25(m, 2H).

Synthesis of (6R,9aR)-3-{1-[3-methoxy-4-(4-methyl-1H-imidazol-1-yl)phenyl]-(Z)-methylidene}-6-(3,4,5-trifluorophenyl)tetrahydro[1,4]oxazino[3,4-c][1,4]oxazin-4-one The title compound (110 mg) was obtained from [(3S,5R)-5-(3,4,5-trifluorophenyl)morpholine-3-yl]methanol (250 mg) in the same manner as in Example 40. The property values of the compound are as follows.

ESI-MS; m/z 486[M$^+$+H].

$^1$H-NMR (CDCl$_3$)δ(ppm):
2.28(s, 3H), 3.46-3.55(m, 1H), 3.64(dd, J=7.6, 12.4 Hz, 1H), 3.83(s, 3H), 4.06-4.26(m, 3H), 4.30(m, 1H), 4.36(dd, J=2.4, 10.4 Hz, 1H), 4.74(dd, J=4.4, 7.2 Hz, 1H), 6.77(s, 1H), 6.91(brs, 1H), 6.95-6.99(m, 2H), 7.19(d, J=8.8 Hz, 1H), 7.31-7.34(m, 2H), 7.70(d, J=0.8 Hz, 1H).

EXAMPLE 109

Synthesis of (6R,9aR)-6-(3,4-difluorophenyl)-3-{1-[3-methoxy-4-(4-methyl-1H-imidazol-1-yl)phenyl]-(Z)-methylidene}tetrahydro[1,4]oxazino[3,4-c][1,4]oxazin-4-one

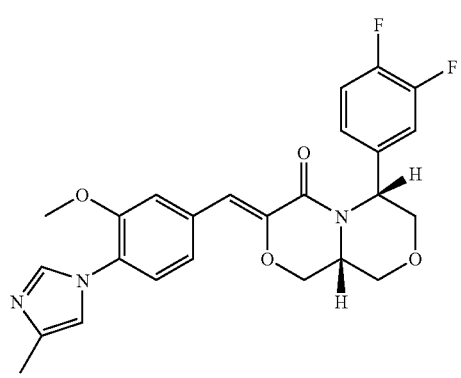

185 mg of the title compound was obtained from [(3S,5R)-5-(3,4-difluorophenyl)morpholine-3-yl]methanol (338 mg) in the same manner as in Example 108. The property values of the 6compound are as follows.

ESI-MS; m/z 468[M$^+$+H].

$^1$H-NMR (CDCl$_3$)δ(ppm):
2.29(s, 3H), 3.53(dd, J=11.2, 11.2 Hz, 1H), 3.68(dd, J=12.0, 7.2 Hz, 1H), 3.84(s, 3H), 4.04-4.21(m, 3H), 4.27-4.31(m, 2H), 4.80(dd, J=7.2, 4.4 Hz, 1H), 6.78(s, 1H), 6.91(s, 1H), 7.06-7.20(m, 4H), 7.31-7.34(m, 2H), 7.70(s, 1H).

EXAMPLE 110

Synthesis of (6R,9aR)-6-(4-fluorophenyl)-3-{1-[3-methoxy-4-(4-methyl-1H-imidazol-1-yl)phenyl]-(Z)-methylidene}tetrahydro[1,4]oxazino[3,4-c][1,4]oxazin-4-one

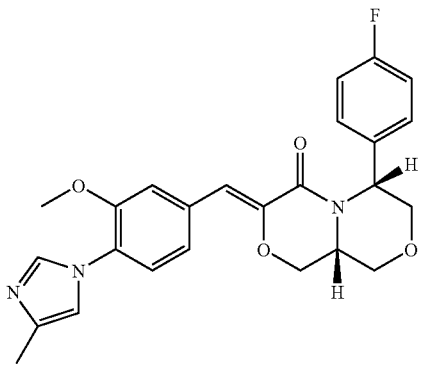

242 mg of the title compound was obtained from [(3S,5R)-5-(4-fluorophenyl)morpholine-3-yl]methanol (311 mg) in the same manner as in Example 108. The property values of the compound are as follows.

ESI-MS; m/z 450[M$^+$+H].

$^1$H-NMR (CDCl$_3$)δ(ppm):
2.29(s, 3H), 3.55(dd, J=11.6, 11.6 Hz, 1H), 3.72(dd, J=12.0, 7.6 Hz, 1H), 3.83(s, 3H), 4.02-4.21(m, 3H), 4.30-4.36(m, 2H), 4.85(dd, J=7.6, 4.0 Hz, 1H), 6.79(s, 1H), 6.91(s, 1H), 7.03-7.07(m, 2H), 7.19(d, J=8.8 Hz, 1H), 7.30-7.34(m, 4H), 7.70(s, 1H).

EXAMPLE 111

Synthesis of (6R,9aR)-6-(4-chlorophenyl)-3-[1-[3-methoxy-4-(4-methyl-1H-imidazol-1-yl)phenyl]-(Z)-methylidene]tetrahydro[1,4]oxadino[3,4-c]oxadine-4-one

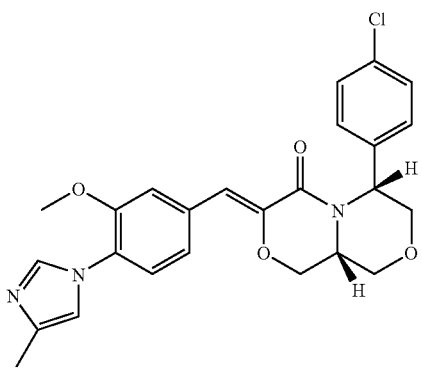

The title compound (357 mg) was obtained from [(3S,5R)-5-(4-chlorophenyl)morpholine-3-yl]methanol (470 mg) in the same manner as in Example 108. The property values of the compound are as follows.

ESI-MS; m/z 466[M$^+$+H].

$^1$H-NMR (CDCl$_3$)δ(ppm):

2.29(s, 3H), 2.52(t,J=11.2 Hz, 1H), 3.68(dd, J=12.4,8.0 Hz, 1H), 3.83(s, 3H), 4.04(dd, J=11.2, 4.4 Hz, 1H), 4.09-4.20 (m, 2H), 4.26-4.36(m, 2H), 4.81(dd, J=7.6, 4.4 Hz, 1H), 6.78(s, 1H), 6.91(s, 1H), 7.19(d, J=8.4 Hz, 1H), 7.23-7.34(m, 6H), 7.70(s, 1H).

The present inventors performed the following tests in order to exhibit utility of the compound of the general formula (I) of the present invention.

TEST EXAMPLE 1

Quantification of Aβ Peptide in Culture of Neurons from Rat Fetus Brain (1) Rat Primary Neuronal Culture Primary neuronal cultures were prepared from the cerebral cortex of embryonic day 18 Wistar rats (Charles River Japan, Yokohama, Japan). Specifically, the embryos were aseptically removed from pregnant rats under ether anesthesia. The brain was isolated from the embryo and immersed in an ice-cold L-15 medium (Invitrogen Corp. Cat #11415-064, Carlsbad, Calif., USA, or SIGMA L1518, for example). The cerebral cortex was collected from the isolated brain under a stereoscopic microscope. The cerebral cortex fragments collected were enzymatically treated in an enzyme solution containing 0.25% trypsin (Invitrogen Corp. Cat #15050-065, Carlsbad, Calif., USA) and 0.01% DNase (Sigma D5025, St. Louis, Mo., USA) at 37° C. for 30 minutes to disperse the cells. Here, the enzymatic reaction was stopped by adding inactivated horse serum to the solution. The enzymatically treated solution was centrifuged at 1,500 rpm for five minutes to remove the supernatant. 5 to 10 ml of a medium was added to the resulting cell mass. Neurobasal medium (Invitrogen Corp. Cat #21103-049, Carlsbad, Calif., USA) supplemented with 2% B27 supplement (Invitrogen Corp. Cat #17504-044, Carlsbad, Calif., USA), 25 μM 2-mercaptoethanol (2-ME, WAKO Cat #139-06861, Osaka, Japan), 0.5 mM L-glutamine (Invitrogen Corp. Cat #25030-081, Carlsbad, Calif., USA), and Antibiotics-Antimycotics (Invitrogen Corp. Cat #15240-062, Carlsbad, Calif., USA) was used as the medium (Neurobasal/B27/2-ME). However, the above Neurobasal medium not supplemented with 2-ME (Neurobasal/B27) was used for the assay. The cells were redispersed by mild pipetting of the cell mass to which the medium was added. The cell dispersion was filtered through a 40-μm nylon mesh (Cell Strainer, Cat #35-2340, Becton Dickinson Labware, Franklin Lakes, N.J., USA) to remove the remaining cell mass, and thus a neuronal cell suspension was obtained. The neuronal cell suspension was diluted with the medium and then plated in a volume of 100 μl/well at an initial cell density of $5 \times 10^5$ cells/cm$^2$ in a 96-well polystyrene culture plate pre-coated with poly-L or D-lysine (Falcon Cat #35-3075, Becton Dickinson Labware, Franklin Lakes, N.J., USA coated with poly-L-lysine using the method shown below, or BIOCOAT™ cell environments Poly-D-lysine cell ware 96-well plate, Cat #35-6461, Becton Dickinson Labware, Franklin Lakes, N.J., USA). Poly-L-lysine coating was carried out as follows. 100 μg/ml of a poly-L-lysine (SIGMA P2636, St. Louis, Mo., USA) solution was aseptically prepared with a 0.15 M borate buffer (pH 8.5). 100 μl/well of the solution was added to the 96-well polystyrene culture plate and incubated at room temperature for one or more hours or at 4° C. overnight or longer. The coated 96-well polystyrene culture plate was washed with sterile water four or more times, and then dried or rinsed with, for example, sterile PBS or medium, and used for cell plating. The plated cells were cultured in the culture plate at 37° C. in 5% $Cb_2$-95% air for one day. Then, the total amount of the medium was replaced with a fresh Neurobasal™/B27/2-ME medium, and then the cells were cultured for further three days.

(2) Addition of Compound

The drug was added to the culture plate on Day 4 of culture as follows. The total amount of the medium was removed from the wells, and 180 μl/well of Neurobasal medium not containing 2-ME and containing 2% B-27 (Neurobasal/B27) was added thereto. A solution of the test compound in dimethyl sulfoxide (hereinafter abbreviated as DMSO) was diluted with Neurobasal/B27 so that the initial concentration was at 10-fold of the final concentration. 20 μl/well of the dilution was added to and sufficiently mixed with the medium. The final DMSO concentration was 1% or less. Only DMSO was added to the control group.

(3) Sampling

The cells were cultured for three days after addition of the compound, and the total amount of the medium was collected. The resulting medium was used as an ELISA sample. The sample was not diluted for ELISA measurement of Aβx-42 and diluted to 5-fold with a diluent supplied with an ELISA kit for ELISA measurement of Aβx-40.

(4) Evaluation of Cell Survival

Cell survival was evaluated by an MTT assay according to the following procedure. After collecting the medium, 100 μl/well of a pre-warmed medium was added to the wells. Further, 8 μl/well of a solution of 8 mg/ml of MTT (SIGMA M2128, St. Louis, Mo., USA) in D-PBS(–) (Dulbecco's phosphate buffered Saline, SIGMA D8537, St. Louis, Mo., USA) was added to the wells. The 96-well polystyrene culture plate was incubated in an incubator at 37° C. in 5% $CO_2$-95% air for 20 minutes. 100 μl/well of an MTT lysis buffer was added thereto, and MTT formazan crystals were sufficiently dissolved in the buffer in the incubator at 37° C. in 5% $CO_2$-95% air. Then, the absorbance at 550 nm in each well was measured. The MTT lysis buffer was prepared as follows. 100 g of SDS (sodium dodecyl sulfate (sodium lauryl sulfate), WAKO 191-07145, Osaka, Japan) was dissolved in a mixed solution of 250 mL of N,N'-dimethylformamide (WAKO 045-02916, Osaka, Japan) with 250 mL of distilled water. 350 μl each of concentrated hydrochloric acid and concentrated acetic acid were further added to the solution to allow the solution to have a final pH of about 4.7.

Upon measurement, wells having no cells plated and containing only the medium and MTT solution were set as background (bkg). The measured values were respectively applied to the following formula including subtracting bkg values from them. Thus, the proportion against the control group (group not treated with the drug, CTRL) (% of CTRL) was calculated to compare and evaluate cell survival activities.

% of CTRL=($A550\_sample–A550\_bkg$)/($A550\_CTRL–bkg$)×100

(A550_sample: absorbance at 550 nm of sample well, A550_bkg: absorbance at 550 nm of background well, A550_CTRL: absorbance at 550 nm of control group well)

(5) AD ELISA

For Aβ ELISA, Human/Rat β Amyloid (42) ELISA Kit Wako (#290-62601) and Human/Rat β Amyloid (40) ELISA Kit Wako (#294-62501) from Wako Pure Chemical Industries, Ltd., or Human Amyloid beta (1-42) Assay Kit (#27711) and Human Amyloid beta (1-40) Assay Kit (#27713) from Immuno-Biological Laboratories, Co., Ltd. (IBL Co., Ltd.) were used. Aβ ELISA was carried out according to the protocols recommended by the manufacturers (methods described in the attached documents). However, the Aβ calibration curve was created using beta-amyloid peptide 1-42, rat and beta-amyloid peptide 1-40, rat (Calbiochem, #171596 [Aβ$_{42}$], #171593 [Aβ$_{40}$]).

(6) Results

The results are shown in Tables 4-1, 4-2 and 4-3 as percentage to the Aβ concentration in the medium of the control group (% of CTRL).

TABLE 4-1

| Test Compound | Activity for reducing Aβ42 production IC50 (nM) |
|---|---|
| Example 1 | 77 |
| Example 2 | 187 |
| Example 3 | 41 |
| Example 4 | 69 |
| Example 5 | 125 |
| Example 6 | 156 |
| Example 7 | 76 |
| Example 8 | 113 |
| Example 9 | 60 |
| Example 10 | 84 |
| Example 12 | 101 |
| Example 13 | 129 |
| Example 14 | 146 |
| Example 16 | 201 |
| Example 18 | 183 |
| Example 19 | 54 |
| Example 20 | 82 |
| Example 21 | 195 |
| Example 22 | 30 |
| Example 23 | 130 |
| Example 24 | 36 |
| Example 25 | 141 |
| Example 26 | 6 |
| Example 27 | 5 |
| Example 28 | 16 |

TABLE 4-2

| Test Compound | Activity for reducing Aβ42 production IC50 (nM) |
|---|---|
| Example 29 | 23 |
| Example 30 | 54 |
| Example 31 | 31 |
| Example 32 | 41 |
| Example 33 | 63 |
| Example 34 | 23 |
| Example 35 | 23 |
| Example 36 | 109 |
| Example 37 | 20 |
| Example 38 | 52 |
| Example 39 | 130 |
| Example 40 | 100 |
| Example 41 | 141 |
| Example 51 | 67 |
| Example 52 | 86 |
| Example 53 | 40 |
| Example 54 | 74 |
| Example 55 | 111 |
| Example 58 | 67 |
| Example 60 | 96 |
| Example 63 | 103 |
| Example 74 | 140 |
| Example 75 | 146 |
| Example 77 | 141 |
| Example 84 | 37 |
| Example 85 | 64 |
| Example 96 | 89 |

TABLE 4-2-continued

| Test Compound | Activity for reducing Aβ42 production IC50 (nM) |
|---|---|
| Example 101 | 88 |
| Example 105 | 61 |

TABLE 4-3

| Test Compound | Activity for reducing Aβ42 production IC50 (nM) |
|---|---|
| Example 107 | 78 |
| Example 108 | 60 |
| Example 109 | 100 |
| Example 111 | 129 |

The results in Tables 4-1, 4-2 and 4-3 confirmed that the compound of the present invention has an effect of reducing Aβ42 production.

TEST EXAMPLE 2

Effect on Amyloid β Production in Cerebrospinal Fluid, Brain, and Plasma of Rats Animals were moved to a laboratory on the previous day of the start of experiment (Day 0). Provisional individual numbers were assigned to the tail of animals with an oil pen. Their body weights were measured, and allocation of treatment was performed. Thereafter, individual numbers were assigned to the animals again. A vehicle or sample was forcibly orally administered to the rats once a day over three days since the start of experiment (Day 1) (5 mL/kg). Six hours after the final oral administration, Nembutal (Dainippon Pharmaceutical Co., Ltd., Osaka) was intraperitoneally administered to the rats (50 mg/kg). Under anesthesia, the posterior region of neck was incised, and a 25G needle was inserted into the cerebellomedullary cistern to collect about 100 μL of cerebrospinal fluid. The collected cerebrospinal fluid was put in a tube containing 1 μL of 100 mmol/L p-ABSF and preserved in ice in order to prevent decomposition of Aβ. Thereafter, the abdominal cavity was opened, and about 2.5 mL of blood was collected from the abdominal aorta using a heparin syringe and preserved in ice. Finally, the rats were decapitated, the brain was removed and lightly washed with brine, the wet weight of each half of the brain was then measured, and each half of the brain was put in a 15 mL tube and frozen with liquid nitrogen. The removed brain sample was cryopreserved until measurement. The cerebrospinal fluid was centrifuged at 4° C. at 7,000 rpm for five minutes, and then the supernatant was collected to measure Aβ. The blood was centrifuged at 4° C. at 3,000 rpm for five minutes, and then the plasma was collected to measure Aβ.

For Aβ40 and Aβ42 measurement, the cerebrospinal fluid or plasma was diluted with a diluent supplied with an Aβ measurement kit. 70% formic acid was added to the brain tissue (right brain) at 1 mL per 100 mg (wet weight) of the tissue, and the brain tissue was sonicated. Immediately after the sonication, the mixture was 20-fold diluted with a 0.9 mol/L Tris buffer (pH 12) and neutralized. The neutralized liquid was directly used for Aβ measurement.

Aβ was measured according to the instruction attached to the measurement kit. Specifically, 100 μL each of the diluted cerebrospinal fluid, the diluted plasma sample, or the original brain liquid before neutralization were added to a microplate having Aβ40 and Aβ42 antibodies solid-phased. 100 μL each of various concentrations of Aβ standard solutions were added to the microplate, and reaction was carried out at 4° C. overnight. The microplate was washed with a wash solution supplied with the measurement kit five times. Then, an HRP-labeled secondary antibody was added to the microplate, and reaction was carried out at 4° C. for one hour. After this reaction, the microplate was washed with the same wash solution five times and colored with a TMB solution, and the coloring reaction was stopped by a stop solution. Then, the absorbance at 450 nm was measured by SPECTRA MAX 190 (Molecular Devices, Sunnyvale, Calif., USA). The Aβ40 and Aβ42 concentrations in each sample were calculated from the standard curve.

The compound of the general formula (I) or pharmacologically acceptable salt thereof according to the present invention has an effect of reducing production of Aβ42 or the like. Accordingly, the present invention can particularly provide a therapeutic or prophylactic agent for a neurodegenerative disease caused by Aβ such as Alzheimer's disease or Down's syndrome.

The compound of the general formula (I) of the present invention has an effect of reducing Aβ40 and Aβ42 production, and thus is particularly useful as a prophylactic or therapeutic agent for a neurodegenerative disease caused by Aβ such as Alzheimer's disease or Down's syndrome.

The invention claimed is:

1. A compound represented by the formula (I):

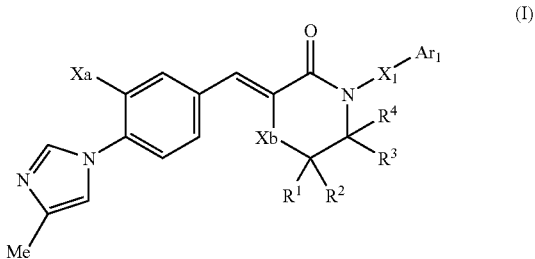

or a pharmacologically acceptable salt thereof, wherein
(a) $R^1$, $R^2$, $R^3$, and $R^4$ are the same or different and each represent a hydrogen atom or a C1-6 alkyl group;
$X_1$ represents a C1-6 alkylene group, wherein the C1-6 alkylene group may be substituted with 1 to 3 hydroxyl groups or C1-6 alkyl groups, wherein the C1-6 alkyl groups may be substituted with 1 to 3 hydroxyl groups, or a C3-13 cycloalkyl group formed by two C1-6 alkyl groups together bonded to the same carbon atom of the C1-6 alkylene group;
$X_a$ represents a methoxy group or a fluorine atom;
$X_b$ represents an oxygen atom; and
$Ar_1$ represents an aryl group, pyridinyl group, aryloxy group, or pyridinyloxy group that may be substituted with 1 to 3 substituents selected from Substituent Group A1;
(b) $Ar_1$-$X_1$- represents a C3-8 cycloalkyl group condensed with a benzene ring, wherein one methylene group on the C3-8 cycloalkyl group may be substituted with an oxygen atom, the C3-8 cycloalkyl group may be substituted with 1 to 3 hydroxyl groups and/or C1-6 alkyl groups, and the benzene ring may be substituted with 1 to 3 substituents selected from Substituent Group A1; and $R^1$, $R^2$, $R^3$, $R^4$, $X_a$, and $X_b$ are as defined in (a);
(c) one of $R^1$ and $R^2$ and one of $R^3$ and $R^4$ are the same or different and each represent a hydrogen atom or a C1-6 alkyl group; the other of $R^1$ and $R^2$ and the other of $R^3$ and $R^4$, together with the carbon atoms to which they are respectively bonded, form a C3-8 cycloalkyl group, wherein the C3-8 cycloalkyl group may be substituted with 1 to 3 substituents selected from Substituent Group A1; and $X_1$, $X_a$, $X_b$, and $Ar_1$ are as defined in (a) or (b);
(d) $Ar_1$-$X_1$- and $R^4$, together with the nitrogen atom to which $Ar_1$-$X_1$- is bonded and the carbon atom to which $R^4$ is bonded, form a 4- to 8-membered nitrogen-containing heterocyclic group that may be substituted with an aryl group or pyridinyl group, wherein one methylene group on the 4- to 8-membered nitrogen-containing heterocyclic group may be substituted with a methylene group substituted with 1 or 2 substituents selected from Substituent Group A1, a vinylene group that may be substituted with 1 or 2 substituents selected from Substituent Group A1, an oxygen atom, or an imino group that may be substituted with a substituent selected from Substituent Group A1, and the aryl group or pyridinyl group may be substituted with 1 to 3 substituents selected from Substituent Group A1; $X_b$ represents an oxygen atom; and $R^1$, $R^2$, $R^3$, and $X_a$ are as defined in (a) and (b);
(e) $R^1$ and $R^2$, together with the carbon atom to which they are bonded, form a C3-8 cycloalkyl group; and $R^3$, $R^4$, $X_1$, $X_a$, $X_b$, and $Ar_1$ are as defined in (a) and (b); or
(f) $R^3$ and $R^4$, together with the carbon atom to which they are bonded, form a C3-8 cycloalkyl group; and $R^1$, $R^2$, $X_1$, $X_a$, $X_b$, and $Ar_1$ are as defined in (a) and (b);

(Substituent Group A1: (1) a halogen atom, (2) a hydroxyl group, (3) a cyano group, (4) a C3-8 cycloalkyl group, (5) a C3-8 cycloalkoxy group, (6) a C1-6 alkyl group, wherein the C1-6 alkyl group may be substituted with 1 to 5 halogen atoms or one to three C1-6 alkoxy groups, (7) an amino group that may be substituted with one or two C1-6 alkyl groups, wherein the C1-6 alkyl groups may be substituted with 1 to 5 halogen atoms, (8) a C1-6 alkoxy group, wherein the C1-6 alkoxy group may be substituted with 1 to 5 halogen atoms, and (9) a carbamoyl group that may be substituted with one or two C1-6 alkyl groups, wherein the C1-6 alkyl groups may be substituted with 1 to 3 halogen atoms).

2. The compound or pharmacologically acceptable salt thereof according to claim 1, wherein the compound is represented by the formula (I-a):

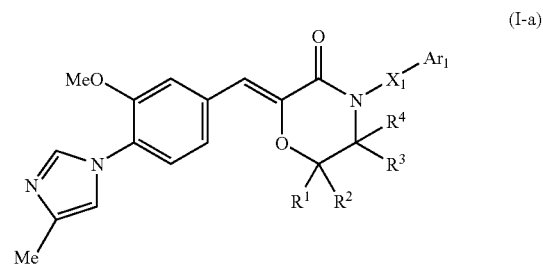

wherein $R^1$, $R^2$, $R^3$, $R^4$, $X_1$, and $Ar_1$ are as defined in claim 1.

3. The compound or pharmacologically acceptable salt thereof according to claim 1, wherein the compound is represented by the formula (II):

(II)

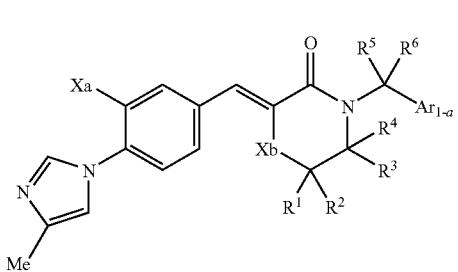

wherein $R^1$, $R^2$, $R^3$, $R^4$, $X_a$, and $X_b$ are as defined in claim 1; $R^5$ and $R^6$ are the same or different and each represent a hydrogen atom or a C1-6 alkyl group, wherein the C1-6 alkyl group may be substituted with 1 to 3 hydroxyl groups; and $Ar_{1-a}$ represent a phenyl group or pyridinyl group that may be substituted with 1 to 3 substituents selected from Substituent Group A1 as defined in claim 1.

4. The compound or pharmacologically acceptable salt thereof according to claim 3, wherein the compound is represented by the formula (II-a):

(II-a)

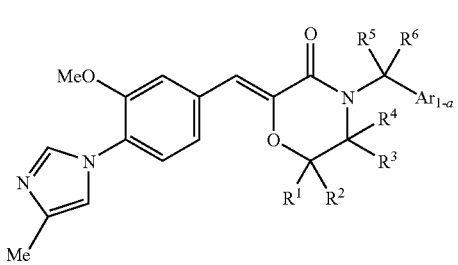

wherein $R^1$, $R^2$, $R^3$, and $R^4$, and $R^5$, $R^6$, and $Ar_{1-a}$ are as defined in claim 3.

5. The compound or pharmacologically acceptable salt thereof according to claim 3, wherein the compound is represented by the formula (II-b):

(II-b)

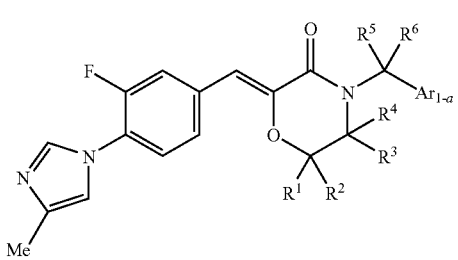

wherein $R^1$, $R^2$, $R^3$, and $R^4$ and $R^5$, $R^6$, and $Ar_{1-a}$ are as defined in claim 3.

6. The compound or pharmacologically acceptable salt thereof according to claim 3, wherein the compound is represented by the formula (II-c):

(II-c)

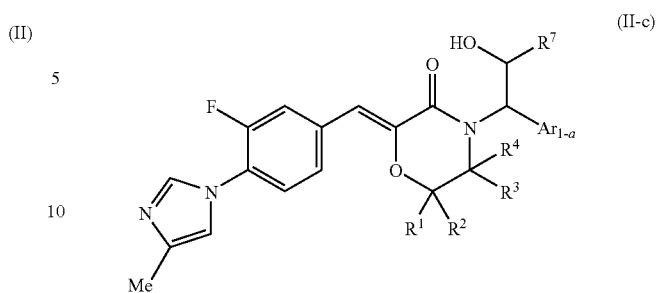

wherein $R^1$, $R^2$, $R^3$, and $R^4$ are as defined in claim 3; $R^7$ represents a hydrogen atom or a C1-6 alkyl group; and $Ar_{1-a}$ is as defined in claim 3.

7. The compound or pharmacologically acceptable salt thereof according to claim 1, wherein the compound is represented by the formula (I-b):

(I-b)

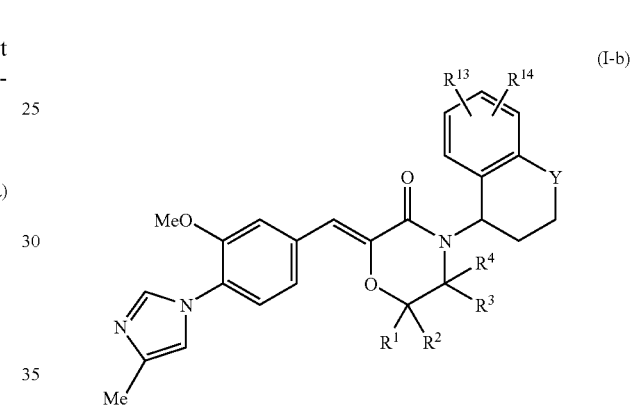

wherein $R^1$, $R^2$, $R^3$, and $R^4$ are as defined in claim 1; $R^{13}$ and $R^{14}$ are the same or different and each represent a hydrogen atom or a substituent selected from Substituent Group A1 as defined in claim 1; and Y represents a methylene group or an oxygen atom.

8. The compound or pharmacologically acceptable salt thereof according to claim 7, wherein $R^{13}$ and $R^{14}$ are the same or different and each represent a hydrogen atom, a halogen atom, or a C1-6 alkoxy group.

9. The compound or pharmacologically acceptable salt thereof according to claim 1, wherein the compound is represented by the formula (I-c):

(I-c)

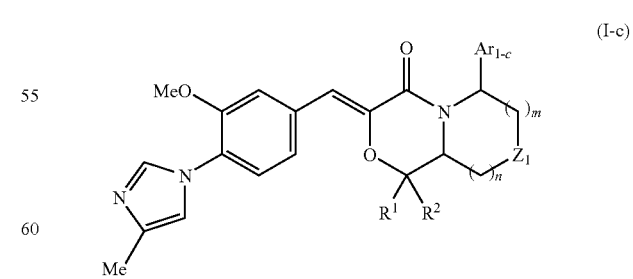

wherein $R^1$ and $R^2$ are as defined in claim 1; $Ar_{1-c}$ represents a phenyl group or pyridinyl group that may be substituted with 1 to 3 subsitutents which are the same or different and selected from Substituent Group A1; $Z_1$ represents a methylene group or vinylene group that may be substituted with 1 or 2 substituents selected from Substituent Group A1 as defined in claim 1, an oxygen atom, or an imino group that may be substituted with a substituent selected from Substituent Group A1; and n and m are the same or different and each represent an integer of 0 to 2.

10. The compound or pharmacologically acceptable salt thereof according to claim 9, wherein $Z_1$ represents a methylene group, wherein the methylene group may be substituted with 1 or 2 substituents which are the same or different and selected from the group consisting of a C1-6 alkyl group and a hydroxyl group; and n and m each represent 1.

11. The compound or pharmacologically acceptable salt thereof according to claim 9, wherein $Z_1$ represents an oxygen atom, and n and m represent an integer of 1.

12. The compound or pharmacologically acceptable salt thereof according to claim 1, wherein $Ar_1$ represents an aryl group or pyridinyl group, or an aryl group or pyridinyl group substituted with 1 to 3 halogen atoms.

13. The compound or pharmacologically acceptable salt thereof according to claim 1, wherein $Ar_1$ represents a phenyl group or pyridinyl group, or a phenyl group or pyridinyl group substituted with 1 to 3 halogen atoms.

14. The compound or pharmacologically acceptable salt thereof according to claim 1, wherein the compound is selected from the following group:
1) (Z)-2-[1-[3-methoxy-4-(4-methyl-1H-imidazol-1-yl) phenyl]methylidene]-4-(3,4,5-trifluorobenzyl)morpholin-3-one,
2) (Z)-2-[1-[3-methoxy-4-(4-methyl-1H-imidazol-1-yl) phenyl]methylidene]-4-(2,3,4-trifluorobenzyl)morpholin-3-one,
3) (Z)-(S)-2-[1-[3-methoxy-4-(4-methyl-1H-imidazol-1-yl)phenyl]methylidene]-6-methyl-4-(3,4,5-trifluorobenzyl)morpholin-3-one,
4) (Z)-(R)-2-[1-[3-methoxy-4-(4-methyl-1H-imidazol-1-yl)phenyl]methylidene]-6-methyl-4-(3,4,5-trifluorobenzyl)morpholin-3-one,
5) (Z)-(S)-2-[1-[3-methoxy-4-(4-methyl-1H-imidazol-1-yl)phenyl]methylidene]-6-methyl-4-(2,3 ,4-trifluorobenzyl)morpholin-3-one,
6) (Z)-(R)-2-[1-[3-methoxy-4-(4-methyl-1H-imidazol-1-yl)phenyl]methylidene]-6-methyl-4-(2,3,4-trifluorobenzyl)morpholin-3-one,
7) (Z)-4-[(S)-1-(4-fluorophenyl)ethyl]-2-[1-[3-methoxy-4-(4-methyl-1H-imidazol-1-yl)phenyl]methylidene]-6,6-dimethylmorpholin-3-one,
8) (Z)-(R)-4-[(S)-1-(4-fluorophenyl)ethyl]-2-[1-[3-methoxy-4-(4-methyl-1H-imidazol-1-yl)phenyl]methylidene]-6-methylmorpholin-3-one,
9) (Z)-(S)-4-[(S)-1-(4-fluorophenyl)ethyl]-2-[1-[3-methoxy-4-(4-methyl-1H-imidazol-1-yl)phenyl]methylidene]-6-methylmorpholin-3-one,
10) (Z)-2-[1-[3-methoxy-4-(4-methyl-1H-imidazol-1-yl) phenyl]methylidene]-4-[(S)-1-(3,4,5-trifluorophenyl) ethyl]morpholin-3-one,
11) (Z)-2-[1-[3-methoxy-4-(4-methyl-1H-imidazol-1-yl) phenyl]methylidene]-4-[(R)-1-(3,4,5-trifluorophenyl) ethyl]morpholin-3-one,
12) (Z)-4-[(S)-chroman-4-yl]-2-[1-[3-methoxy-4-(4-methyl-1H-imidazol-1-yl)phenyl]methylidene]-6,6-dimethylmorpholin-3-one,
13) (Z)-(S)-4-[(S)-chroman-4-yl]-2-[1-[3-methoxy-4-(4-methyl-1H-imidazol-1-yl)phenyl]methylidene]-6-methylmorpholin-3-one,
14) (Z)-(R)-4-[(S)-chroman-4-yl]-2-[1-[3-methoxy-4-(4-methyl-1H-imidazol-1-yl)phenyl]methylidene]-6-methylmorpholin-3-one,
15) (Z)-(6S, 9aR)-6-(4-fluorophenyl)-3-{1-[3-methoxy-4-(4-methyl-1H-imidazol-1-yl)benzylidene]hexahydropyrido[2,1-c][1,4]oxazin-4-one,
16) (Z)-(6R, 9aS)-6-(4-fluorophenyl)-3-{1-[3-methoxy-4-(4-methyl-1H-imidazol-1-yl)benzylidene]hexahydropyrido[2,1-c][1,4]oxazin-4-one,
17) (Z)-(S)-4-[(S)-1-(6-chloropyridin-3-yl)ethyl]-2-[1-[3-methoxy-4-(4-methyl-1H-imidazol-1-yl)phenyl]methylidene]-6-methylmorpholin-3-one,
18) (Z)-(S)-4-[(R)-1-(6-chloropyridin-3-yl)ethyl]-2-[1-[3-methoxy-4-(4-methyl-1H-imidazol-1-yl)phenyl] methylidene]-6-methylmorpholin-3-one,
19) (Z)-(S)-4-[(S)-1-(5-chloropyridin-2-yl)ethyl]-2-[1-[3-methoxy-4-(4-methyl-1H-imidazol-1-yl)phenyl]methylidene]-6-methylmorpholin-3-one,
20) (Z)-(S)-4-[(R)-1-(5-chloropyridin-2-yl)ethyl]-2-[1-[3-methoxy-4-(4-methyl-1H-imidazol-1-yl)phenyl] methylidene]-6-methylmorpholin-3-one,
21) (Z)-(S)-4-[(S)-1-(2,6-difluoropyridin-3-yl)ethyl]-2-[1-[3-methoxy-4-(4-methyl-1H-imidazol-1-yl)phenyl] methylidene]-6-methylmorpholin-3-one,
22) (Z)-(S)-4-[(R)-1-(2,6-difluoropyridin-3-yl)ethyl]-2-[2-[3-methoxy-4-(4-methyl-1H-imidazol-1-yl)phenyl] methylidene]-6-methylmorpholin-3-one,
23) (Z)-(S)-4-[(S)-1-(2,3-difluoropyridin-4-yl)ethyl]-2-[1-[3-methoxy-4-(4-methyl-1H-imidazol-1-yl)phenyl] methylidene]-6-methylmorpholin-3-one,
24) (Z)-(S)-4-[(R)-1-(2,3-difluoropyridin-4-yl)ethyl]-2-[1-[3-methoxy-4-(4-methyl-1H-imidazol-1-y1) pheny1]methylidene]-6-methylmorpholin-3-one,
25) (Z)-(S)-4-[(1R, 2R)-2-hydroxy-1-(3,4,5-trifluorophenyl)propyl]-2-[1-[3-methoxy-4-(4-methyl-1H-imidazol-1-yl)phenyl]methylidene]-6-methylmorpholin-3-one,
26) (Z)-4-[(1R, 2R)-2-hydroxy-1-(3,4,5-trifluorophenyl) propyl]-2-[1-[3-methoxy-4-(4-methyl-1H-imidazol-1-yl)phenyl]methylidene]-6,6-dimethylmorpholin-3-one,
27) (Z)-4-[(R)-1-(4-fluorophenyl)-2-hydroxyethyl]-2-[1-[3-methoxy-4-(4-methyl-1H-imidazol-1-yl)phenyl] methylidene]-6,6-dimethylmorpholin-3-one,
28) (Z)-(6R)-4-[(1R, 2R)-2-hydroxy-1-(3,4,5-trifluorophenyl)propyl]-2-[1-[3-methoxy-4-(4-methyl-1H-imidazol-1-yl)phenyl]methylidene]-6-methylmorpholin-3-one,
29) (Z)-4-[(1R, 2R)-2-hydroxy-1-(3,4,5-trifluorophenyl) propyl]-2-[1-[3-methoxy-4-(4-methyl-1H-imidazol-1-yl)phenyl]methylidene]morpholin-3-one,
30) (Z)-4-[(1R, 2R)-1-(3,4-difluorophenyl)-2-hydroxypropyl]-2-[1-[3-methoxy-4-(4-methyl-1H-imidazol-1-yl)phenyl]methylidene]morpholin-3-one,
31) (Z)-(S)-4-[(1R, 2R)-1-(4-fluorophenyl)-2-hydroxypropyl]-2-[1-[3-methoxy-4-(4-methyl-1H-imidazol-1-yl)phenyl]methylidene]-6-methylmorpholin-3-one,
32) (Z)-4-[(1R, 2R)-1-(4-fluorophenyl)-2-hydroxypropyl]-2-[1-[3-methoxy-4-(4-methyl-1H-imidazol-1-yl) phenyl]methylidene]-6,6-dimethylmorpholin-3-one,
33) (Z)-(S)-4-[(1R, 2R)-1-(3,4-difluorophenyl)-2-hydroxypropyl]-2-[1-[3-methoxy-4-(4-methyl -1H-imidazol-1-yl)phenyl]methylidene]-6-methylmorpholin-3-one,
34) (Z)-4-[(1R, 2R)-1-(3,4-difluorophenyl)-2-hydroxypropyl]-2-[1-[3-methoxy-4-(methylimidazol-1-yl) phenyl]methylidene]-6,6-dimethylmorpholin-3-one, 35) (Z)-(S)-4-[(S)-2-hydroxy-1-methyl-1-(3,4,5-trifluorophenyl)ethyl]-2-[1-[3-methoxy-4-(4-methyl-1H-imidazol-1-yl)phenyl]methylidene]-6-methylmorpholin-3-one, 36) (Z)-(6S)-2-[1-[3-methoxy-4-(4-methyl-1H-imidazol-1-yl)phenyl]methylidene]-6-methyl-4-[(S)-1-(3,4,5-trifluorophenyl)ethyl]morpholin-3-one, 37) (Z)-(6S)-4-[1-(4-fluorophenyl)-1-methylethyl]-2-[1-[3-methoxy-4-(4-methyl-1H-imidazol-1-yl)phenyl]methylidene]-6-methylmorpholin-3-one, 38) (Z)-(6S)-4-[1-(4-fluorophenyl)cyclopropyl]-2-[1-[3-methoxy-4-(4-methyl-1H-imidazol-1-yl)phenyl]methylidene]-6-methylmorpholin-3-one, 39) (Z)-(6S, 9aR)-3-{1-[3-methoxy-4-(4-methyl-1H-imidazol-1-yl)benzylidene]-6-(3,4,5-trifluorophenyl)hexahydropyrido[2,1-c][1,4]oxazin-4-one, 40) (Z)-(6S, 9aR)-6-(3,4-difluorophenyl)-3-{1-[3-methoxy-4-(4-methyl-1H-imidazol-1-yl)benzylidene]hexahydropyrido[2,1-c][1,4]oxazin-4-one, 41) (Z)-(6S,9aR)-6-(2,6-difluoropyridin-3-yl)-3-{1-[3-methoxy-4-(4-methyl-1H-imidazol-1-yl)benzylidene]hexahydropyrido[2,1-c][1,4]oxazin-4-one, 42) (Z)-(S)-4-[(S)-1-(5-fluoropyridin-2-yl)ethyl]-2-[1-[3-methoxy-4-(4-methyl-1 H-imidazol-1-yl)phenyl]methylidene]-6-methylmorpholin-3-one, 43) (Z)-(S)-4-[(S)-1-(2-chloropyridin-4-yl)ethyl]-2-[1-[3-methoxy-4-(4-methyl-1H-imidazol-1-yl)phenyl]methylidene]-6-methylmorpholin-3-one, 44) (Z)-(S)-4-[(S)-1-(2-chloro-3-fluoropyridin-4-yl)ethyl]-2-[1-[3-methoxy-4-(4-methyl-1H-imidazol-1-yl)phenyl]methylidene]-6-methylmorpholin-3-one, 45) (Z)-(S)-4-[(S)-1-(2,6-difluoropyridin-4-yl)ethyl]-2-[1-[3-methoxy-4-(4-methyl-1H-imidazol-1-yl)phenyl]methylidene]-6-methylmorpholin-3-one, 46) (Z)-4-[(S)-1-(2-chloropyridin-4-yl)ethyl]-2-[1-[3-methoxy-4-(4-methyl-1H-imidazol-1-yl)phenyl]methylidene]-6,6-dimethylmorpholin-3-one, 47) (Z)-4-[(S)-1-(2,6-difluoropyridin-3-yl)ethyl]-2-[1-[3-methoxy-4-(4-methyl-1H-imidazol-1-yl)phenyl]methylidene]-6,6-dimethylmorpholin-3-one, 48) (Z)-4-[(S)-1-(6-fluoropyridin-3-yl)ethyl]-2-[1-[3-methoxy-4-(4-methyl-1H-imidazol-1-yl)phenyl]methylidene]-6,6-dimethylmorpholin-3-one 49) (Z)-4-[(S)-1-(6-chloropyridin-3-yl)ethyl]-2-[1-[3-methoxy-4-(4-methyl-1H-imidazol-1-yl)phenyl]methylidene]-6,6-dimethylmorpholin-3-one, 50) (Z)-4-[(S)-1-(2,3-difluoropyridin-4-yl)ethyl]-2-[1-[3-methoxy-4-(4-methyl-1H-imidazol-1-yl)phenyl]methylidene]-6,6-dimethylmorpholin-3-one, 51) (Z)-4-[(S)-1-(5-chloropyridin-2-yl)ethyl]-2-[1-[3-methoxy-4-(4-methyl-1H-imidazol-1-yl)phenyl]methylidene]-6,6-dimethylmorpholin-3-one, 52) (Z)-(R)-4-[(S)-1-(2,6-difluoropyridin-3-yl)ethyl]-2-[1-[3-methoxy-4-(4-methyl-1H-imidazol-1-yl)phenyl]methylidene]-6-methylmorpholin-3-one, 53) (Z)-(S)-4-(4-fluorobenzyl)-2-[1-[3-fluoro-4-(4-methyl-1H-imidazol-1-yl)phenyl]methylidene]-6-methylmorpholin-3-one, 54) (Z)-2-[1-[3-fluoro-4-(4-methyl-1H-imidazol-1-yl)phenyl]methylidene]-4-[(S)-1-(4-trifluorophenyl)ethyl]-6,6-dimethylmorpholin-3-one, 55) (Z)-4-[(S)-chroman-4-yl]-2-[1-[3-fluoro-4-(4-methyl-1H-imidazol-1 -yl)phenyl]methylidene]-6,6-dimethylmorpholin-3-one, 56) (Z)-(S)-4-[(S)-chroman-4-yl]-2-[1-[3-fluoro-4-(4-methyl-1H-imidazol-1 -yl)phenyl]methylidene]-6-methylmorpholin-3-one, 57) (Z)-(S)-2-[1-[3-fluoro-4-(4-methyl-1H-imidazol-1-yl)phenyl]methylidene]-4-[(1R, 2R)-2-hydroxy-1-(3,4,5-trifluorophenyl)propyl]-6-methylmorpholin-3-one, 58) (Z)-(S)-4-[(1R,2R)-1-(3,4-difluorophenyl)-2-hydroxypropyl]-2-[1-[3-fluoro-4-(4-methyl-1H-imidazol-1-yl)phenyl]methylidene]-6-methylmorpholin-3-one, 59) (Z)-(S)-2-[1-[3-fluoro-4-(4-methyl-1H-imidazol-1-yl)phenyl]methylidene]-4-[(1R, 2R)-1-(4-fluorophenyl)-2-hydroxypropyl]-6-methylmorpholin-3-one, 60) (Z)-2-[1-[3-fluoro-4-(4-methyl-1H-imidazol-1-yl)phenyl]methylidene]-4-[(1R,2R)-2-hydroxy-1-(3,4,5-trifluorophenyl)propyl]-6,6-dimethylmorpholin-3-one, 61) (Z)-4-[(1R,2R)-1-(3,4-difluorophenyl)-2-hydroxypropyl]-2-[-/3-fluoro-4-(4-methyl-1H-imidazol-1-yl)phenyl]methylidene]-6,6-dimethylmorpholin-3-one, 62) (Z)-(6S,8aR)-3-{1-[3-methoxy-4-(4-methyl-1H-imidazol-1-yl)benzylidene]-6-(3,4,5-trifluorophenyl)tetrahydropyrrolo[2,1-c][1,4]oxazin-4-one, 63) (6S, 9aR)-6-(4-chlorophenyl)-3-{1-[3-methoxy-4-(4-methyl-1H-imidazol-1-yl)phenyl]-(Z)-methylidene}hexahydropyrido[2,1-c][1,4]oxazin-4-one, 64) (6R,9aR)-3-{1-[3-methoxy-4-(4-methyl-1H-imidazol-1-yl)phenyl]-(Z)-methylidene}-6-(3,4,5-trifluorophenyl)-tetrahydro[1,4]oxazino[3,4-c][1,4]oxazin-4-one, 65) (6R,9aR)-6-(3,4-difluorophenyl)-3-{1-[3-methoxy-4-(4-methyl-1H-imidazol-1-yl)phenyl]-(Z)-methylidene}-tetrahydro[1,4]oxazino[3,4-c][1,4]oxazin-4-one, 66) (6R,9aR)-6-(4-fluorophenyl)-3-{1-[3-methoxy-4-(4-methyl-1H-imidazol-1-yl)phenyl]-(Z)-methylidene}-tetrahydro[1,4]oxazino[3,4-c][1,4]oxazin-4-one and 67) (6R,9aR)-6-(4-chlorophenyl)-3-{1-[3-methoxy-4-(4-methyl-1H-imidazol-1-yl)phenyl]-(Z)-methylidene}-tetrahydro[1,4]oxazino[3,4-c]oxazin-4-one.

15. A pharmaceutical composition comprising:
the compound or pharmacologically acceptable salt thereof according to claim 1 as an active ingredient; and
a pharmaceutically acceptable carrier.

16. A method of treating senile dementia, Down's syndrome, or amyloidosis, said method comprising:
administering the compound or pharmacologically acceptable salt thereof according to claim 1 to a patient in need thereof.

* * * * *

UNITED STATES PATENT AND TRADEMARK OFFICE
CERTIFICATE OF CORRECTION

| | | |
|---|---|---|
| PATENT NO. | : 7,618,960 B2 | Page 1 of 1 |
| APPLICATION NO. | : 11/594130 | |
| DATED | : November 17, 2009 | |
| INVENTOR(S) | : Teiji Kimura et al. | |

It is certified that error appears in the above-identified patent and that said Letters Patent is hereby corrected as shown below:

ON THE TITLE PAGE:

Insert the following:

-- Related U.S. Application Data

(60) Provisional application No. 60/833,769, filed on Jul. 28, 2006. --

Signed and Sealed this
Twenty-sixth Day of April, 2011

David J. Kappos
*Director of the United States Patent and Trademark Office*